United States Patent
King et al.

(10) Patent No.: US 9,572,788 B2
(45) Date of Patent: Feb. 21, 2017

(54) CELL PERMEABLE INHIBITORS OF ANAPHASE PROMOTING COMPLEX

(71) Applicant: President and Fellows of Harvard College, Cambridge, MA (US)

(72) Inventors: Randall King, Newton, MA (US); Xing Zeng, Brookline, MA (US); Katharine L. Sackton, Somerville, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 0 days.

(21) Appl. No.: 14/276,994

(22) Filed: May 13, 2014

(65) Prior Publication Data
US 2015/0328214 A1  Nov. 19, 2015

(51) Int. Cl.
| | |
|---|---|
| A61K 31/27 | (2006.01) |
| A61K 31/506 | (2006.01) |
| A61P 35/00 | (2006.01) |
| A61N 5/10 | (2006.01) |
| A61K 45/06 | (2006.01) |
| A61K 31/436 | (2006.01) |
| A61K 31/138 | (2006.01) |
| A61K 31/337 | (2006.01) |
| A61K 31/4196 | (2006.01) |
| A61K 31/496 | (2006.01) |
| A61K 31/555 | (2006.01) |
| A61K 47/48 | (2006.01) |

(52) U.S. Cl.
CPC ............ *A61K 31/27* (2013.01); *A61K 31/138* (2013.01); *A61K 31/337* (2013.01); *A61K 31/4196* (2013.01); *A61K 31/436* (2013.01); *A61K 31/496* (2013.01); *A61K 31/506* (2013.01); *A61K 31/555* (2013.01); *A61K 45/06* (2013.01); *A61K 47/48038* (2013.01); *A61N 5/1001* (2013.01); *A61N 2005/109* (2013.01); *A61N 2005/1021* (2013.01)

(58) Field of Classification Search
CPC .............................. A61K 31/27; A61K 31/506
USPC ................................ 514/482, 483, 275, 397
See application file for complete search history.

(56) References Cited

U.S. PATENT DOCUMENTS

| | | | |
|---|---|---|---|
| 5,380,713 A | 1/1995 | Balasubramanian et al. | |
| 6,951,730 B2 | 10/2005 | Small et al. | |
| 7,317,029 B2 | 1/2008 | Cai et al. | |
| 2004/0235829 A1 | 11/2004 | Scott et al. | |
| 2005/0203063 A1* | 9/2005 | Deshaies | A61K 31/795 514/63 |
| 2013/0230458 A1* | 9/2013 | King | A61K 31/155 424/1.61 |

FOREIGN PATENT DOCUMENTS

| | | | |
|---|---|---|---|
| EP | 1469082 A1 | 10/2004 | |
| WO | WO-9719672 A1 | 6/1997 | |
| WO | WO 2012/031118 | * 3/2012 | ........... A61K 31/155 |

OTHER PUBLICATIONS

DiStefano et al., Pharmacological studies of the mechanism of tumor-induced bone marrow cytolysis. Cancer Res. Apr. 1979;39(4):1193-8.
Eisen, Effect of Hexadimethrine Bromide on Plasma Kinin formation, Hydrolysis of P-Tosyl-L-Arginine Methyl Ester and Fibrinolysis. Br J Pharmacol Chemother. Feb. 1964;22:87-103.
Ettmayer et al., Lessons learned from marketed and investigational prodrugs. J Med Chem. May 6, 2004;47(10):2393-404.
Fang et al., The checkpoint protein MAD2 and the mitotic regulator CDC20 form a ternary complex with the anaphase-promoting complex to control anaphase initiation. Genes Dev. Jun. 15, 1998;12(12):1871-83.
Fiedler et al., Activation, inhibition, and pH-dependence of the hydrolysis of alpha-N-benzoyl-L-arginine ethyl ester catalyzed by kallikrein from porcine pancreas. Eur J Biochem. Dec. 1968;7(1):27-33.
Fry et al., APC/C-mediated degradation in early mitosis: how to avoid spindle assembly checkpoint inhibition. Cell Cycle. Jul. 2006;5(14):1487-91.
Jessop et al., Effects of serine protease inhibitor, TAME, on IL-1 beta in LPS-stimulated human monocytes: relationship between synthesis and release of a 33-kDa precursor and the 17-kDa biologically active species. Inflammation. Oct. 1993;17(5):613-31.
Kallio et al., Mammalian p55CDC mediates association of the spindle checkpoint protein Mad2 with the cyclosome/anaphase-promoting complex, and is involved in regulating anaphase onset and late mitotic events. J Cell Biol. Jun. 15, 1998;141(6):1393-406.
Keyes et al., Differential regulation of anaphase promoting complex/cyclosome substrates by the spindle assembly checkpoint in Saccharomyces cerevisiae. Genetics. Jan. 2008;178(1):589-91.
Kraft et al., Mitotic regulation of the human anaphase-promoting complex by phosphorylation. EMBO J. Dec. 15, 2003;22(24):6598-609.
Kramer ER, Gieffers C, Hölzl G, Hengstschläger M, Peters JM. Activation of the human anaphase-promoting complex by proteins of the CDC20/Fizzy family. Curr Biol. Nov. 5, 1998;8(22)1207-10.
Kramer et al., Mitotic regulation of the APC activator proteins CDC20 and CDH1. Mol Biol Cell. May 2000;11(5):1555-69.
NCBI Accession No. AAF05754, dated Nov. 3, 1999.
NCBI Accession No. AAF05755, dated Nov. 3, 1999.
NCBI Accession No. AAH02941, dated Jan. 27, 2004.
NCBI Accession No. AAH05258, dated Nov. 17, 2006.
NCBI Accession No. AAH09498, dated Jan. 27, 2004.
NCBI Accession No. AAH10875, dated Nov. 17, 2006.
NCBI Accession No. AAH10944, dated Nov. 17, 2006.
NCBI Accession No. AAH11656, dated Nov. 17, 2006.

(Continued)

*Primary Examiner* — Sreeni Padmanabhan
*Assistant Examiner* — Irina Neagu
(74) *Attorney, Agent, or Firm* — Mintz Levin Cohn Ferris Glovsky and Popeo, P.C.; Ingrid A. Beattie

(57) ABSTRACT

The disclosure provides compositions and methods for treating cell cycle disorders. Compositions of the disclosure include proTAME, a prodrug analog of TAME and apcin, the combination of which inhibits an activity or function of the anaphase promoting complex (APC) by a synergistic mechanism.

20 Claims, 114 Drawing Sheets

(56) References Cited

OTHER PUBLICATIONS

NCBI Accession No. AAH17713, dated Dec. 2, 2006.
NCBI Accession No. AAH98264, dated Jul. 18, 2005.
NCBI Accession No. AAH98295, dated Jul. 18, 2005.
NCBI Accession No. AAH98362, dated Jul. 15, 2005.
NCBI Accession No. AAH99732, dated Aug. 3, 2005.
NCBI Accession No. AAI11799, dated Jan. 17, 2006.
NCBI Accession No. AAI41849, dated May 8, 2007.
NCBI Accession No. AAI48237, dated Oct. 12, 2007.
NCBI Accession No. NP_001072113, dated Jan. 28, 2012.
NCBI Accession No. NP_001247, dated Jan. 29, 2012.
NCBI Accession No. NP_003894, dated Jan. 28, 2012.
NCBI Accession No. NP_004652, dated Nov. 21, 2011.
NCBI Accession No. NP_057322, dated Nov. 27, 2011.
NCBI Accession No. NP001107563, dated Jan. 29, 2012.
NCBI Accession No. Q13042, dated Feb. 22, 2012.
NCBI Accession No. Q9UJX2, dated Feb. 22, 2012.
NCBI Accession No. Q9UJX3, dated Feb. 22, 2012.
Ricard et al., Proliferation and agglutinability of primary and transformed human epithelial cells in culture. J Cell Sci. Aug. 1976;21(3):553-61.
SciFinder Abstract from Troll, Fundam. Cancer Prev., Proc Int. Symp Princess Takamatsu Cancer Res. Fund, 6th, pp. 41-55, Conference, 1976.
Verma et al., Ubistatins inhibit proteasome-dependent degradation by binding the ubiquitin chain. Science. Oct. 1, 2004;306(5693):117-20.
Vodermaier et al., TPR subunits of the anaphase-promoting complex mediate binding to the activator protein CDH1. Curr Biol. Sep. 2, 2003;13(17):1459-68.

* cited by examiner

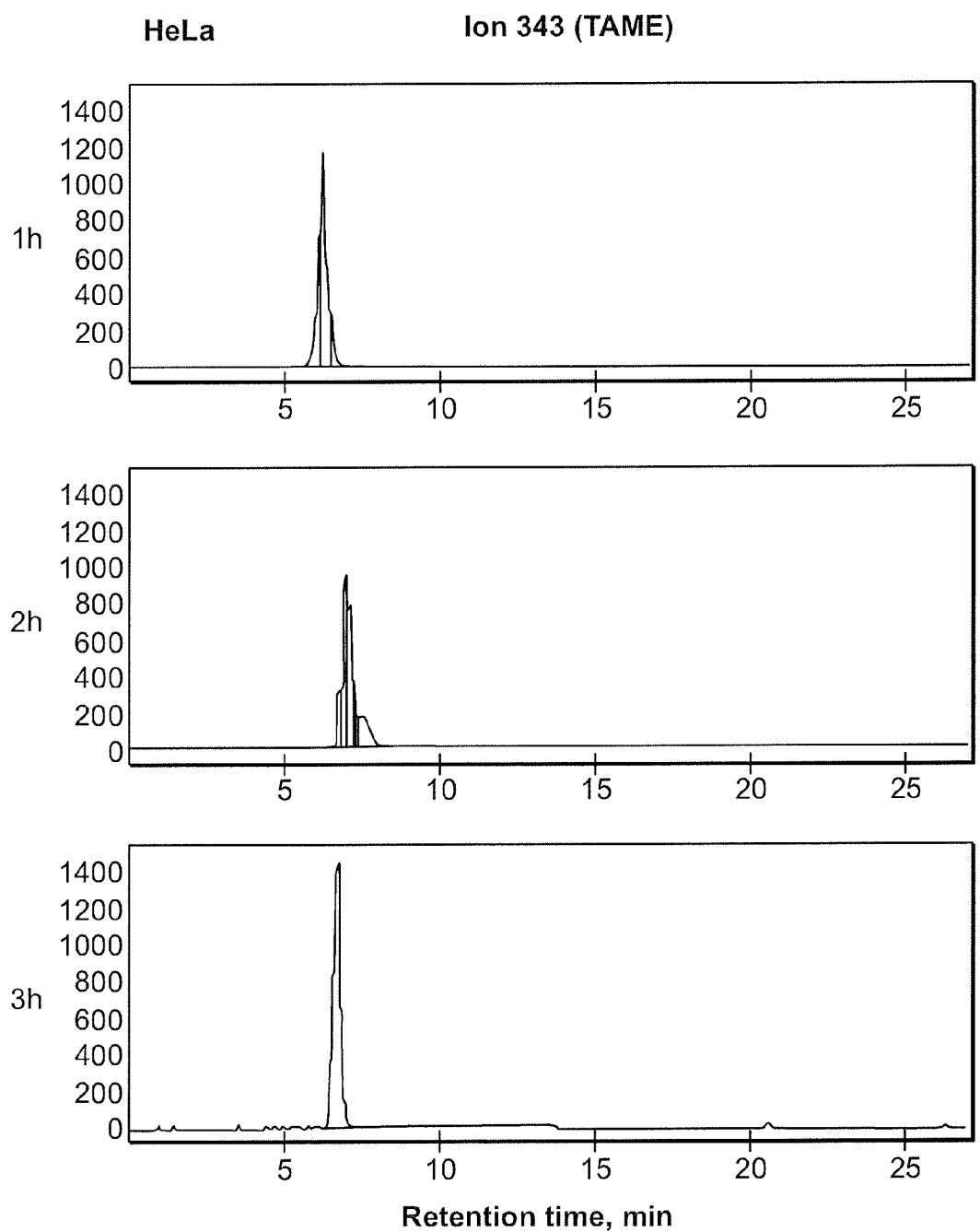

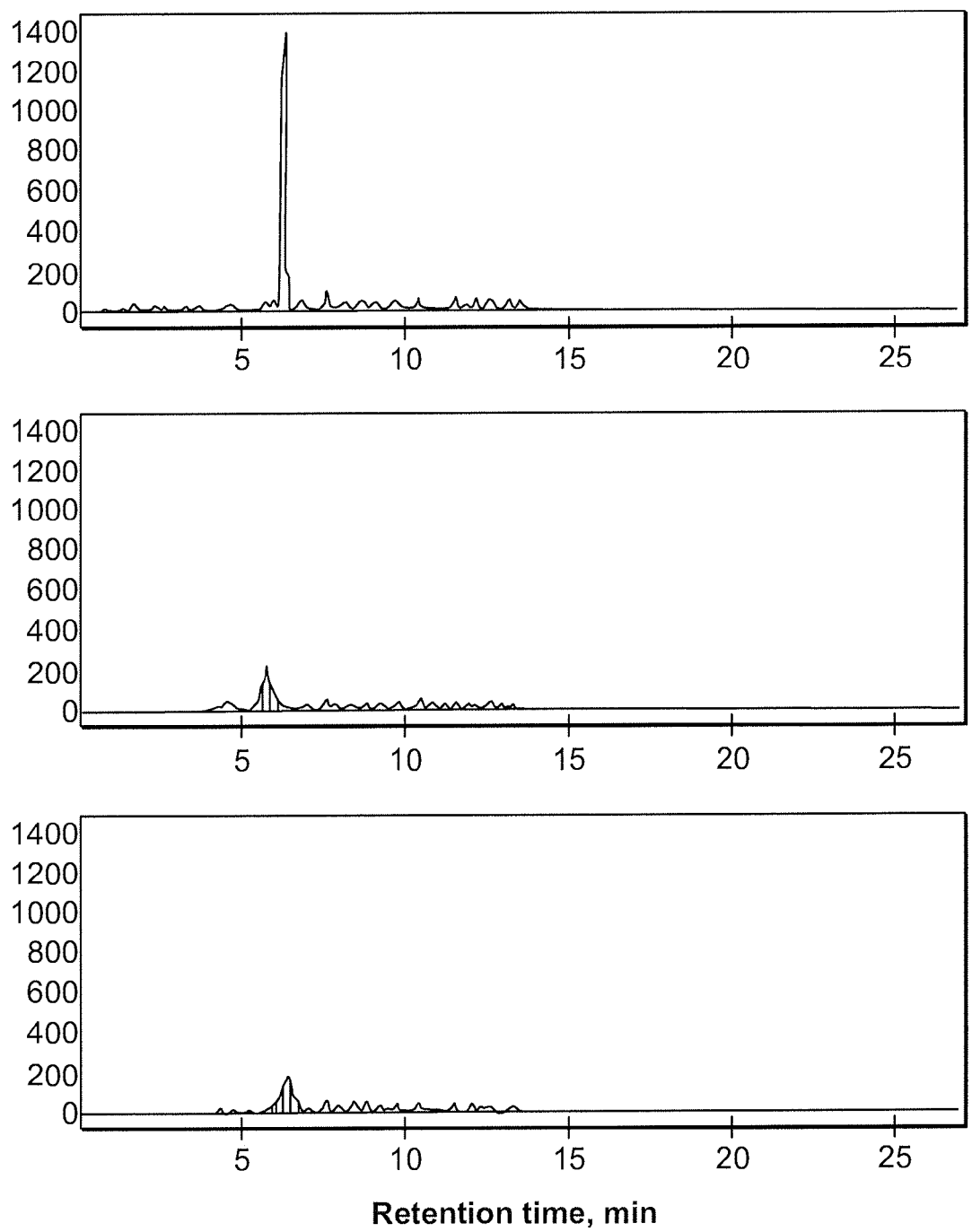

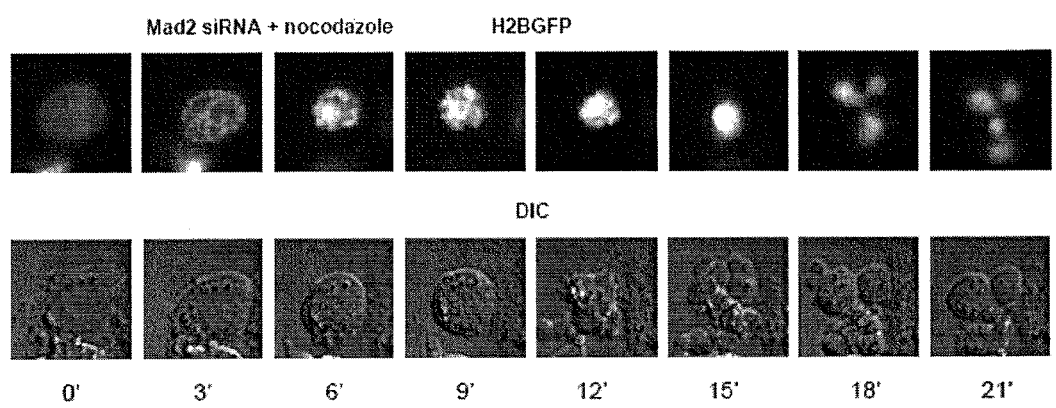

FIGURE 7
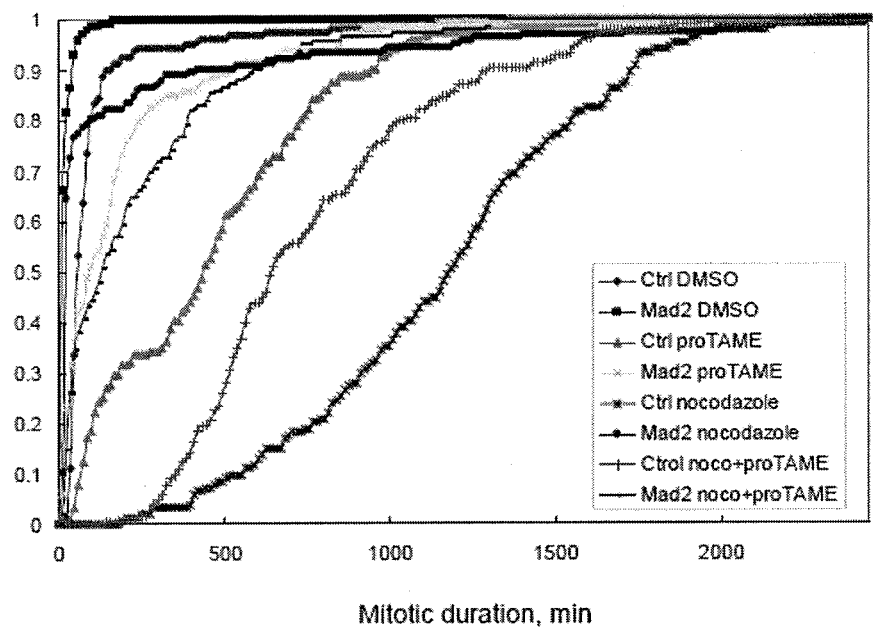
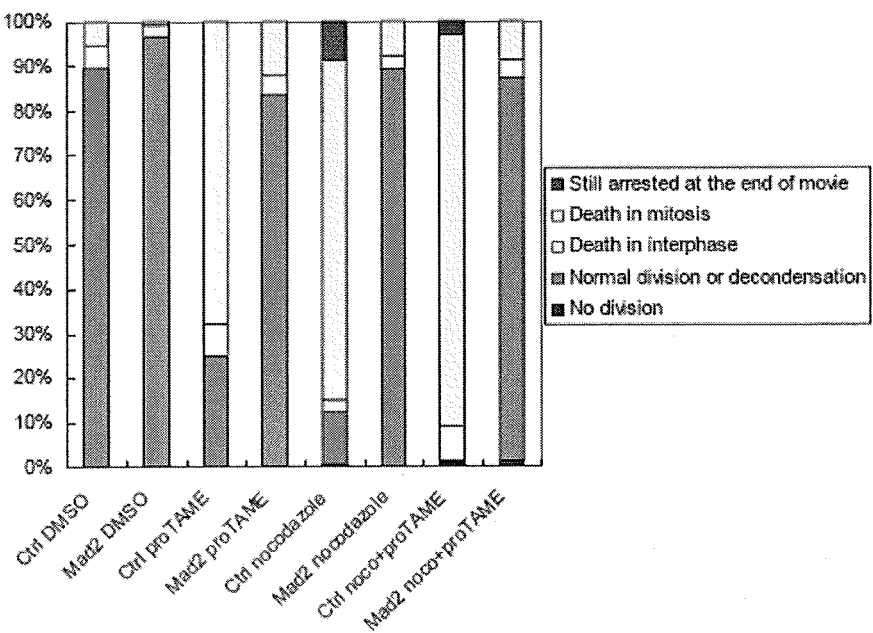

FIGURE 9
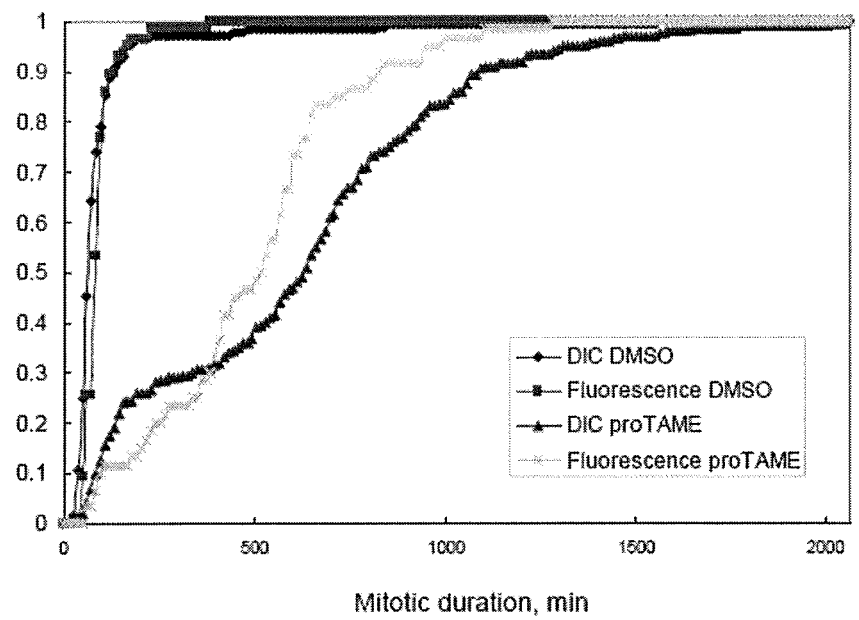
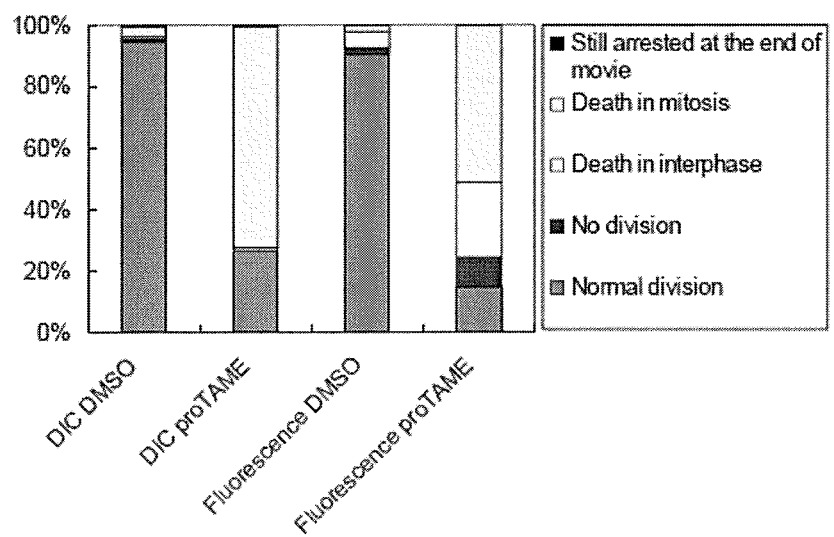

FIGURE 10
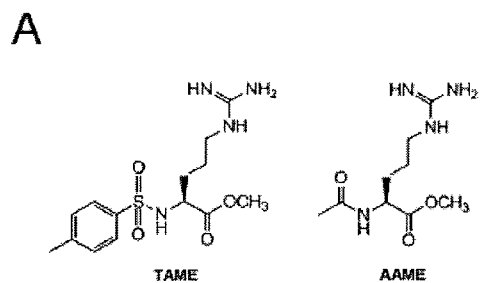
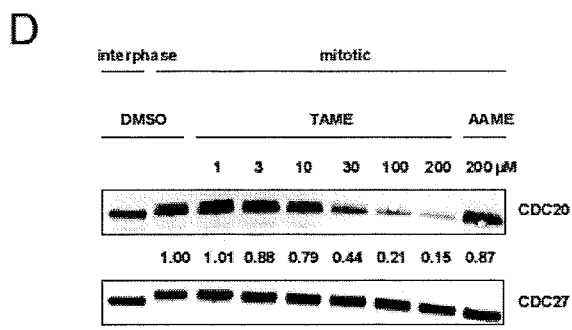
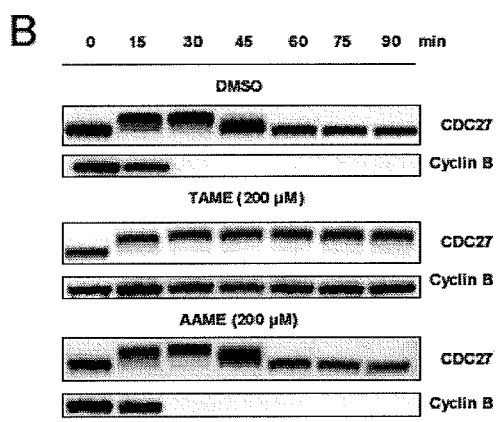
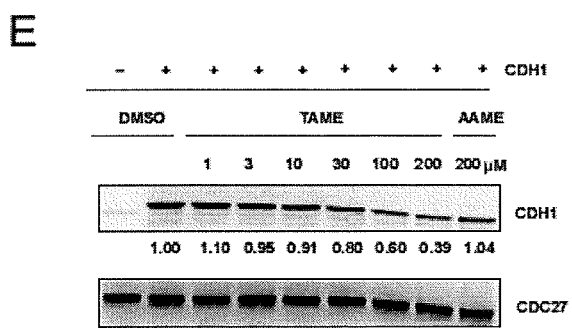
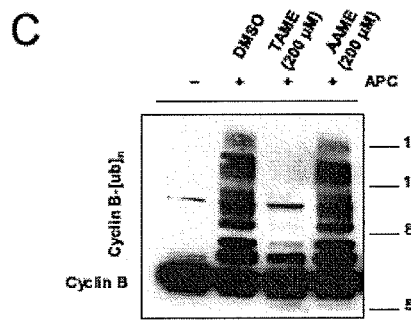
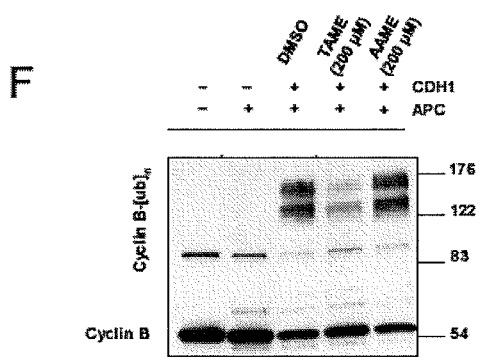

FIG. 12D
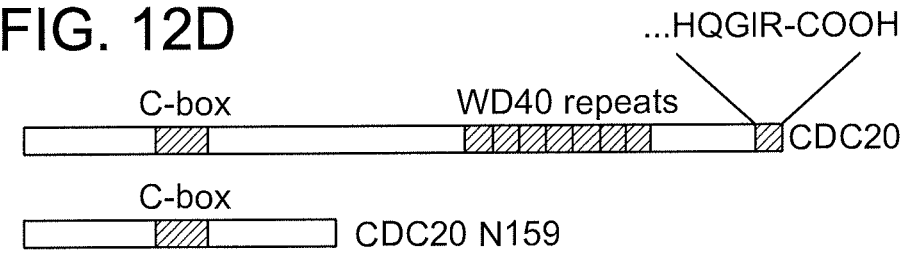
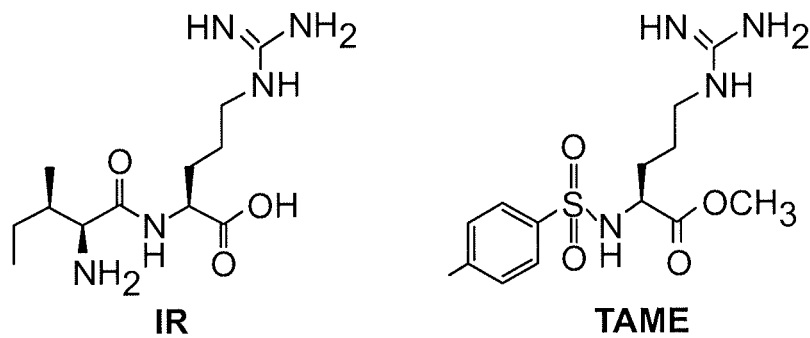
FIG. 12E
FIG. 12F
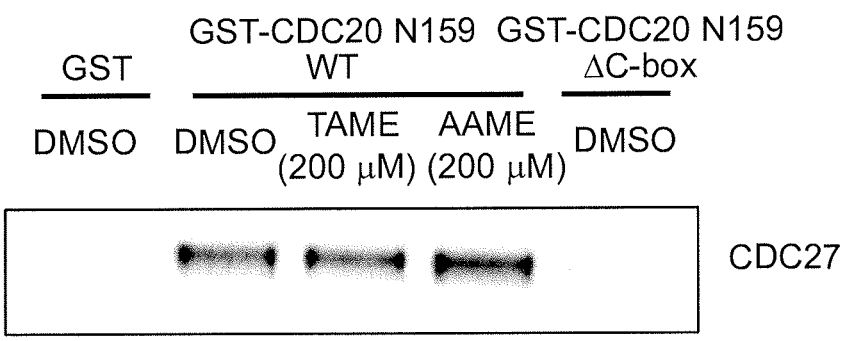

FIGURE 13
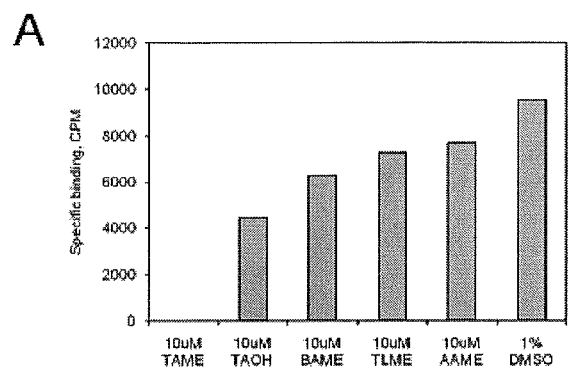
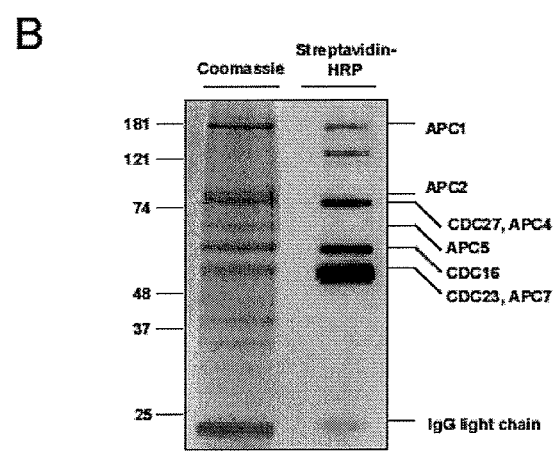
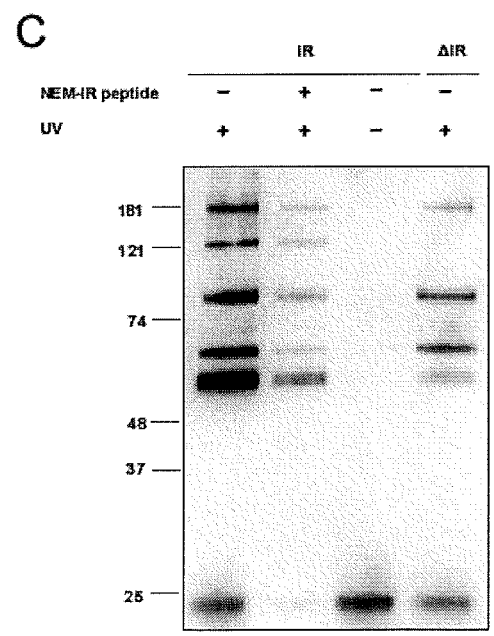

FIG. 15A
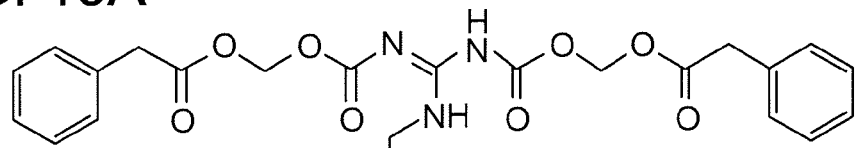
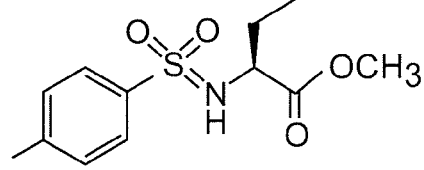
TAME prodrug (proTAME)
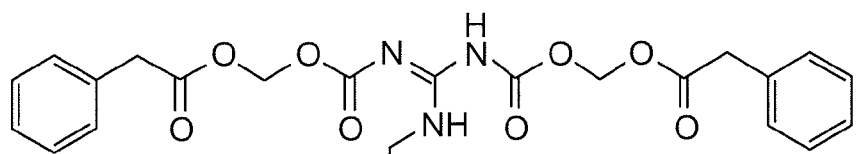
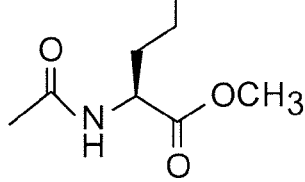
AAME prodrug (proAAME)
FIG. 15B
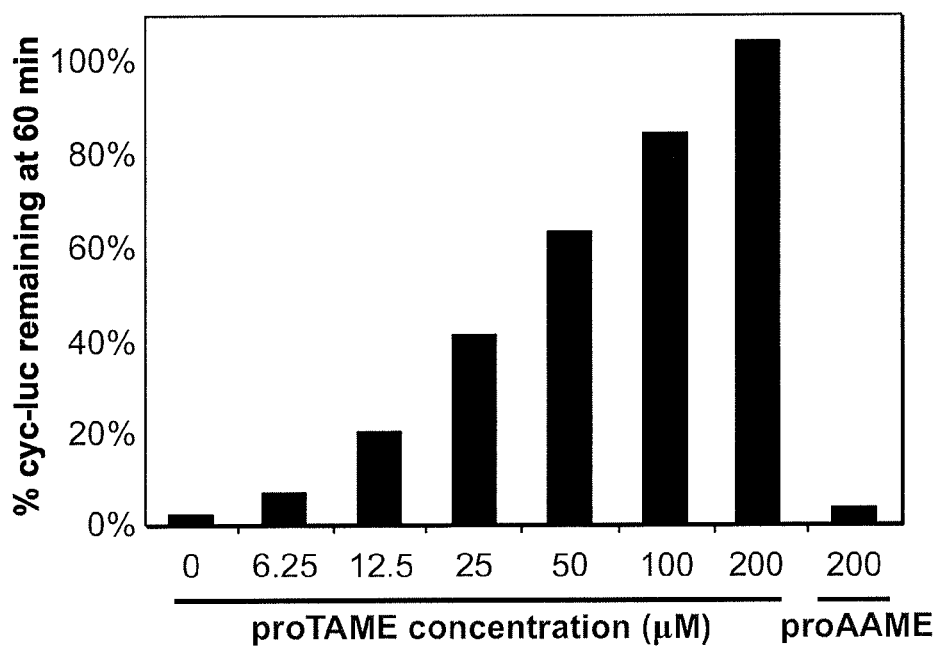

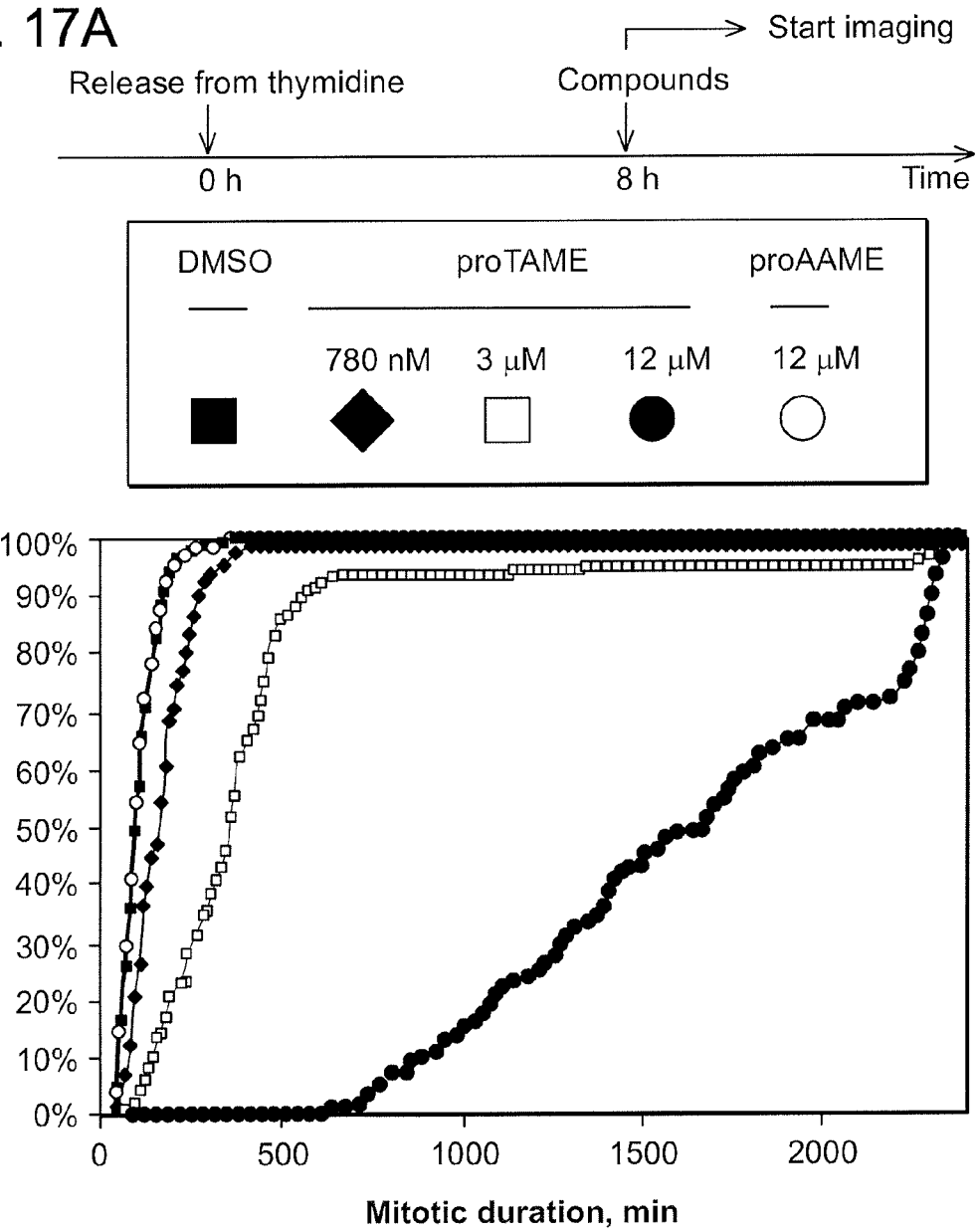

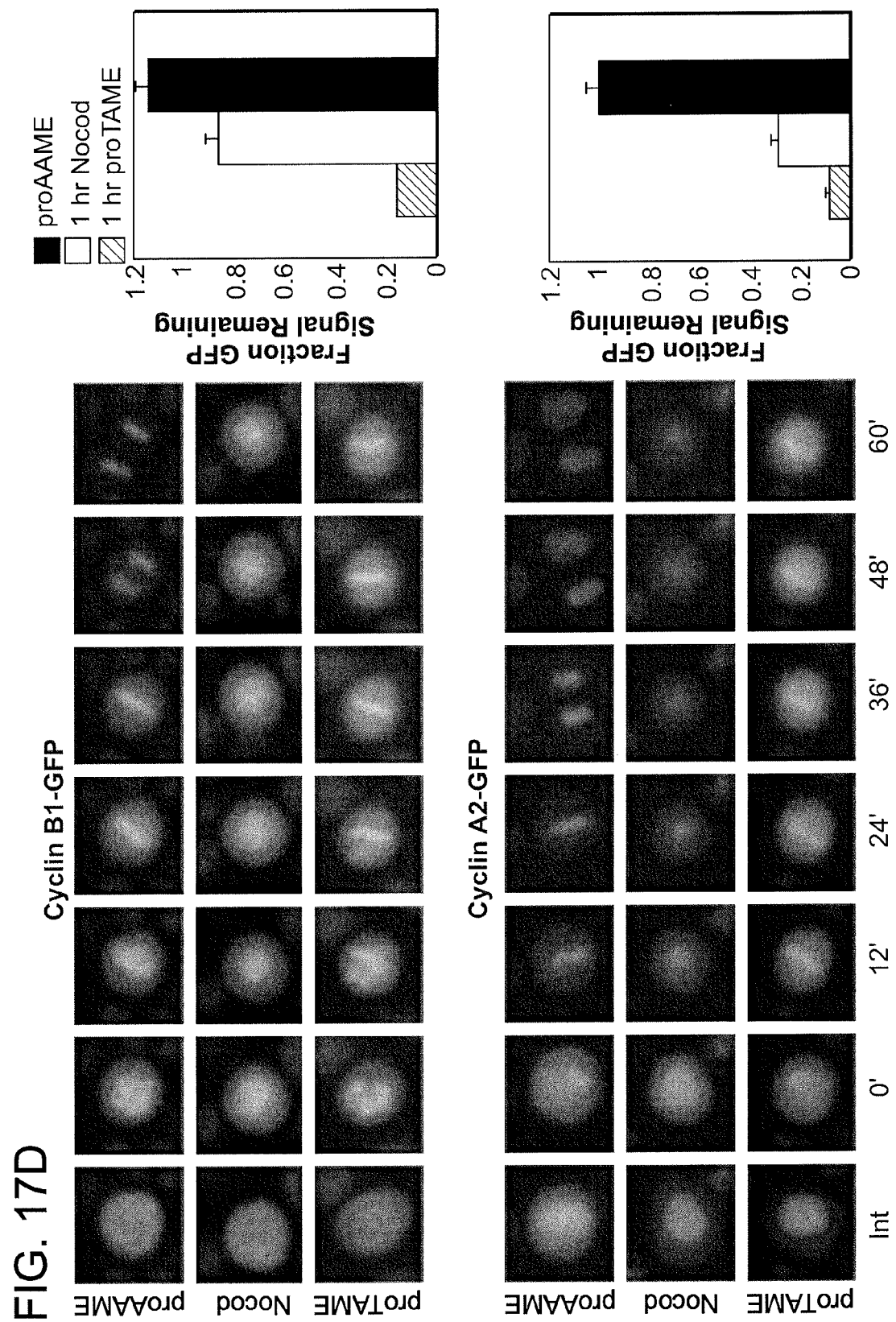

FIG. 17E
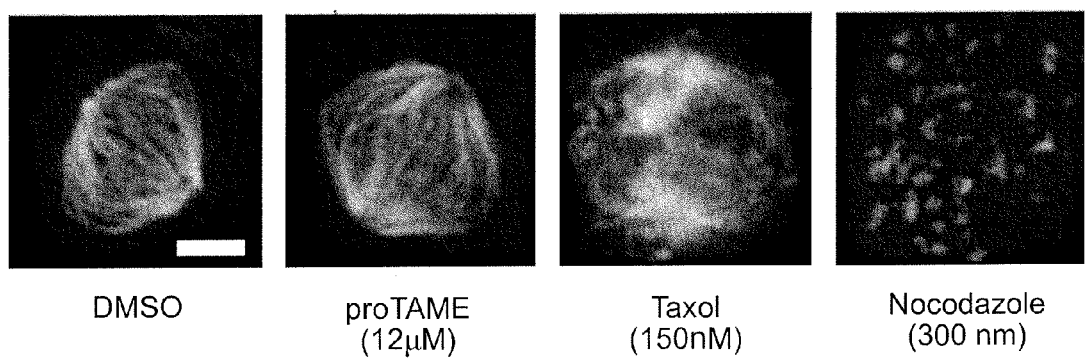
DMSO | proTAME (12μM) | Taxol (150nM) | Nocodazole (300 nm)
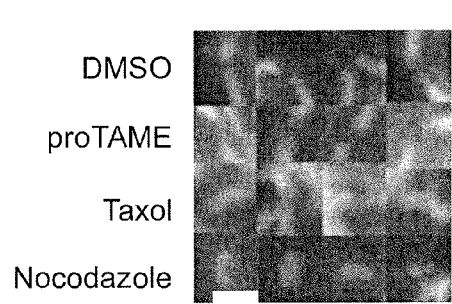
DMSO
proTAME
Taxol
Nocodazole
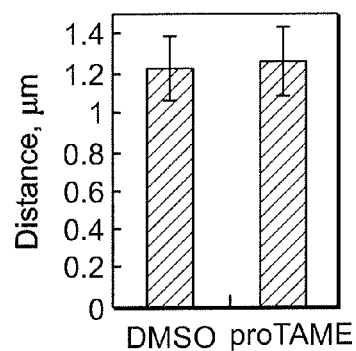

FIGURE 18
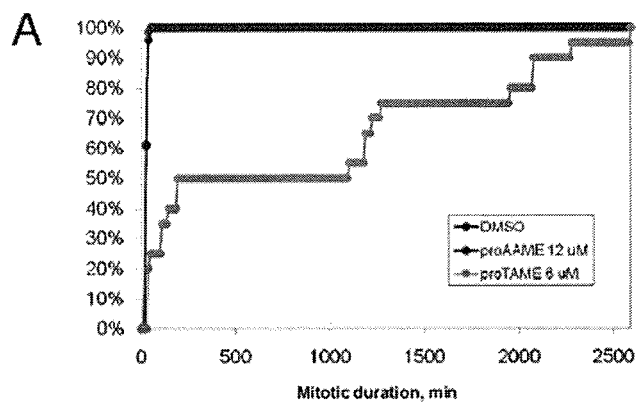
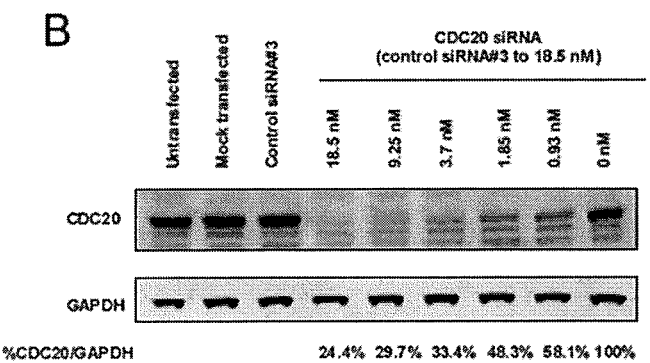
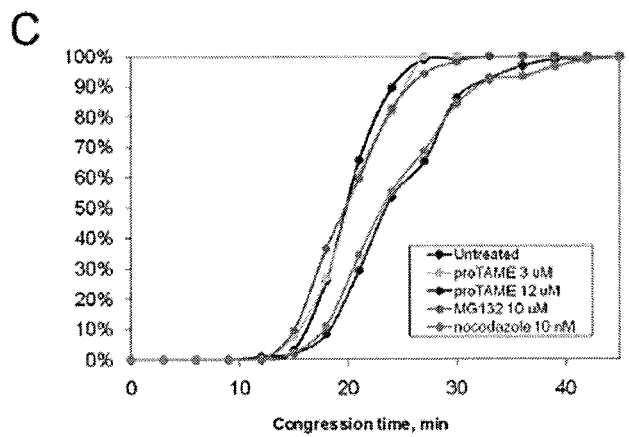

FIG. 19C
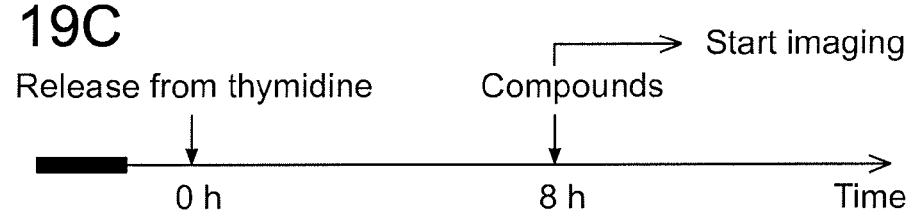
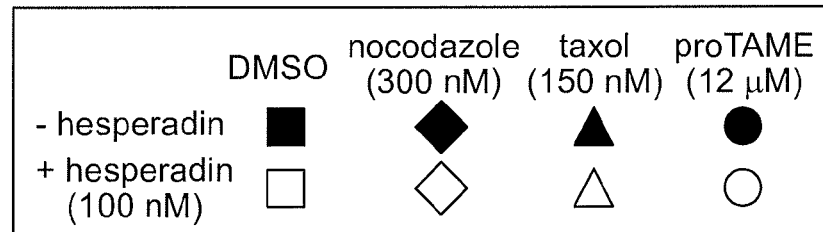
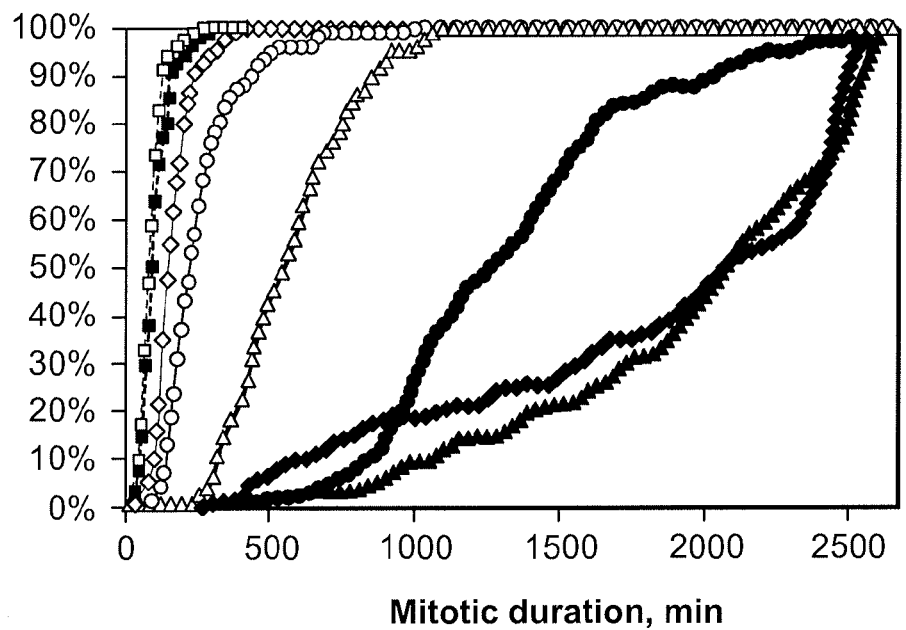
Mitotic duration, min
| Treatment | ■ | ◆ | ▲ | ● |
|---|---|---|---|---|
| Mitotic exit, % | 100.0 | 20.7 | 5.3 | 4.0 |
| Mitotic arrest, % | 0.0 | 34.7 | 30.0 | 1.3 |
| Mitotic death, % | 0.0 | 44.6 | 64.7 | 94.7 |
| Treatment | □ | ◇ | △ | ○ |
| Mitotic exit, % | 100.0 | 100.0 | 100.0 | 100.0 |
| Mitotic arrest, % | 0.0 | 0.0 | 0.0 | 0.0 |
| Mitotic death, % | 0.0 | 0.0 | 0.0 | 0.0 |

| Condition | N | Median mitotic duration (min) | Mean mitotic duration (min) |
|---|---|---|---|
| Control treatment | 153 | 60 | 72.8 |
| Taxol 10nM | 114 | 414 | 595.1 |
| proTAME 3μM | 112 | 132 | 340.2 |
| Taxol 10nM + proTAME 3μM | 130 | 768 | 944.8 |

*8.8hrs in mitosis = point of no return
for proTAME 3μM treated mitotic HeLaHG cells FIGURE 28
A
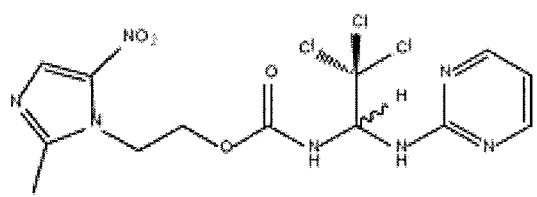
B
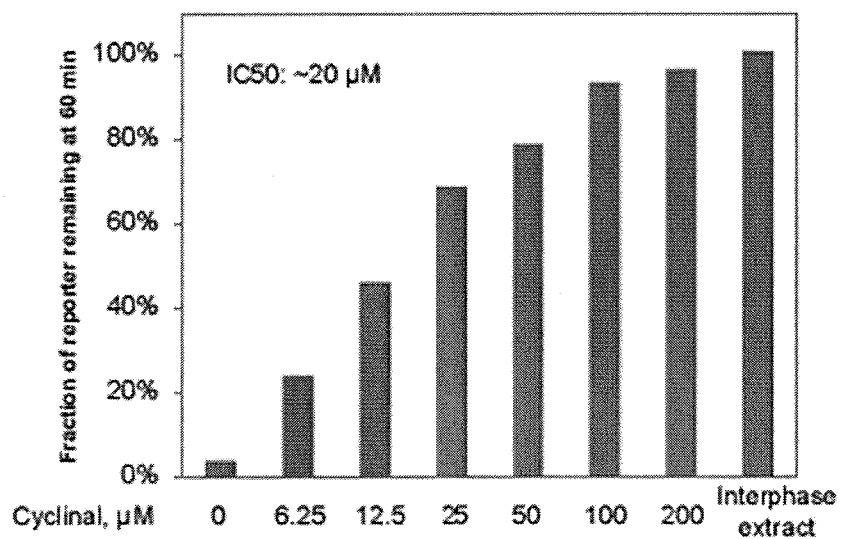

FIGURE 28
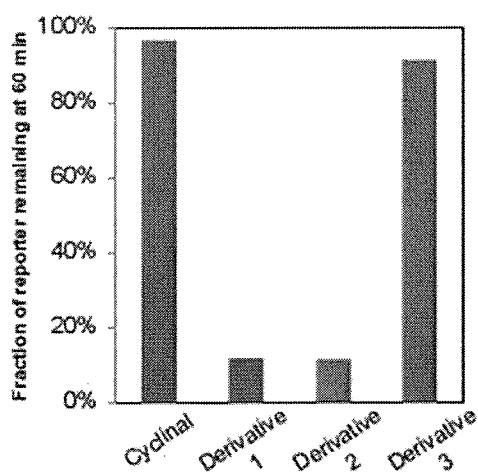
Derivative 1
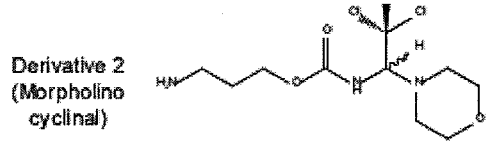
Derivative 2
(Morpholino cyclinal)
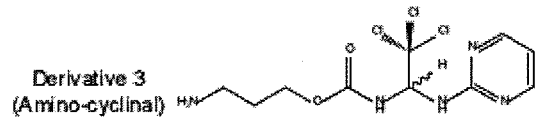
Derivative 3
(Amino-cyclinal)
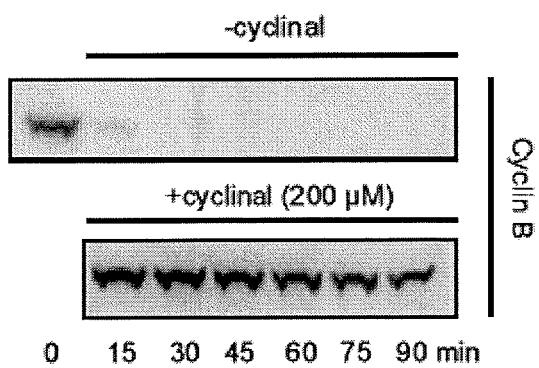

FIGURE 28
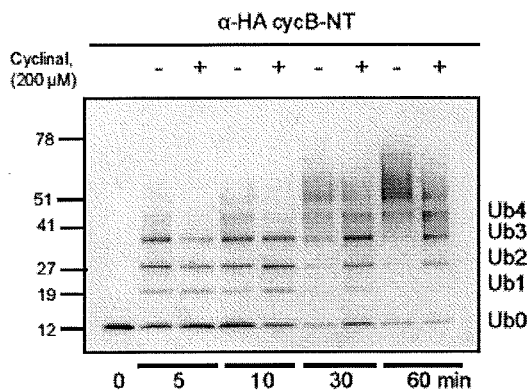
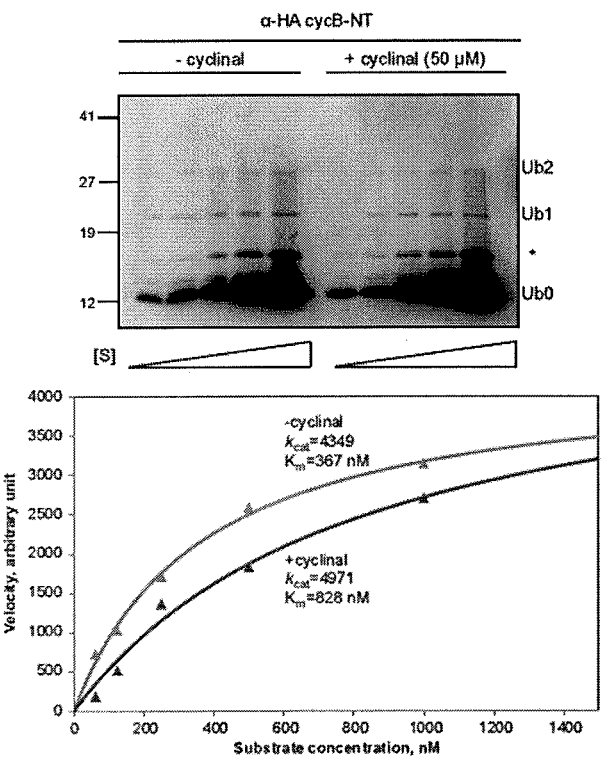
Summary of kinetics data
|  | Exp 1 | Exp 2 | Exp 3 | AVG ± SEM |
|---|---|---|---|---|
| $K_m$ -cyclinal, nM | 367 | 170 | 197 | 245 ± 61 |
| $K_m$ +cyclinal, nM | 828 | 787 | 704 | 773 ± 36 |
| $k_{cat}$ +cyclinal/$k_{cat}$ -cyclinal | 1.14 | 1.43 | 0.98 | 1.18 ± 0.13 |

FIGURE 29
A
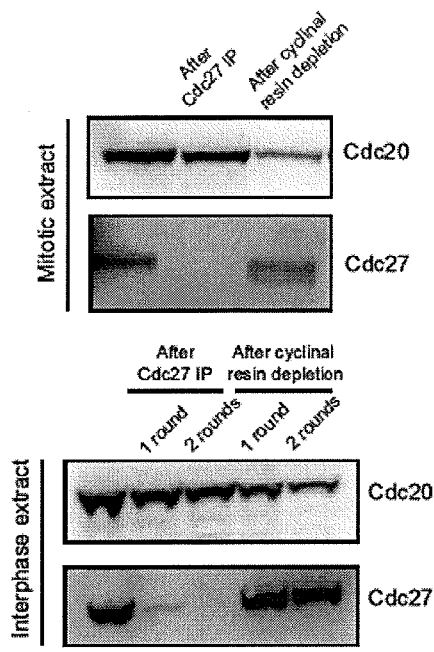
B
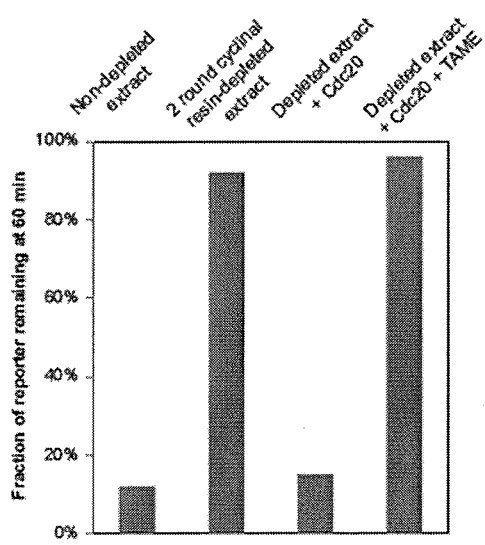

FIGURE 29
C
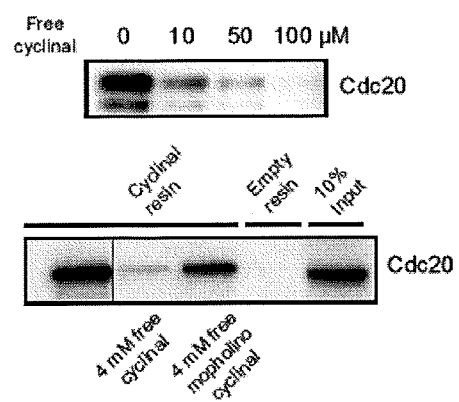
D
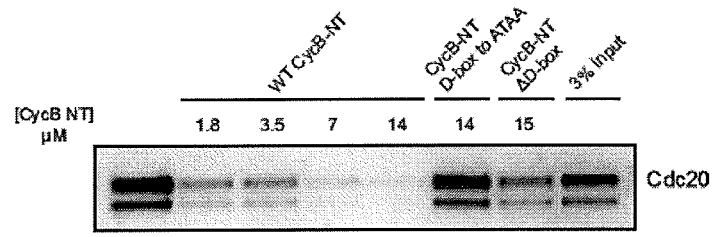
E
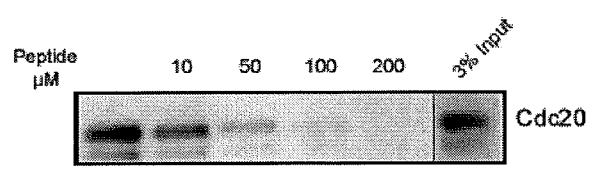

FIGURE 29
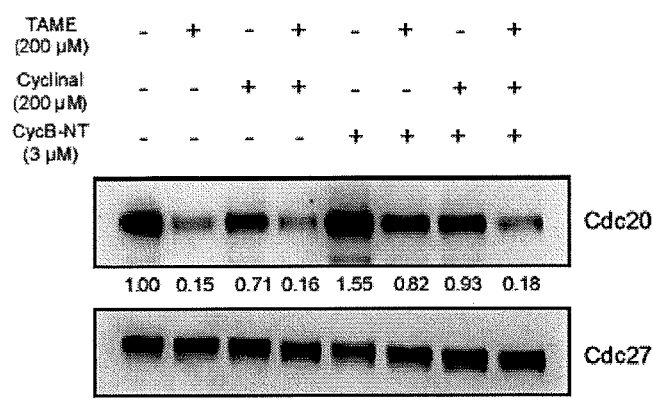
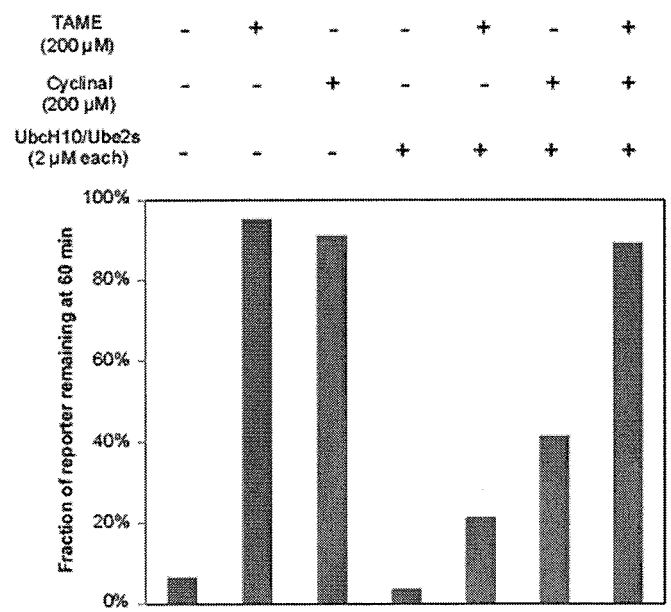

FIGURE 30
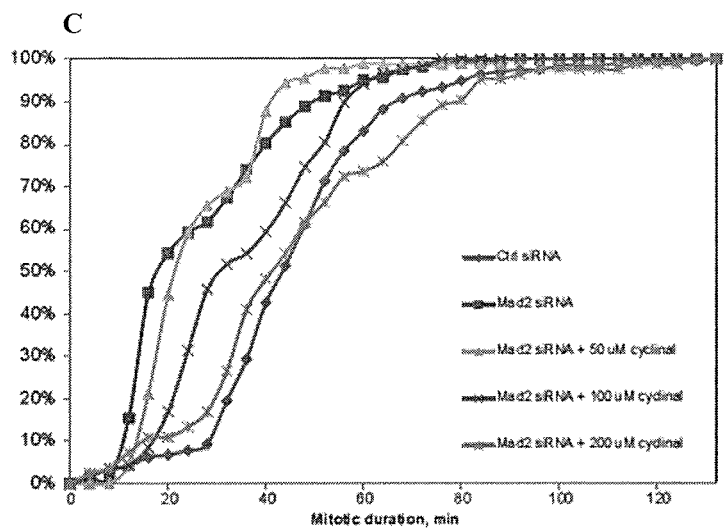
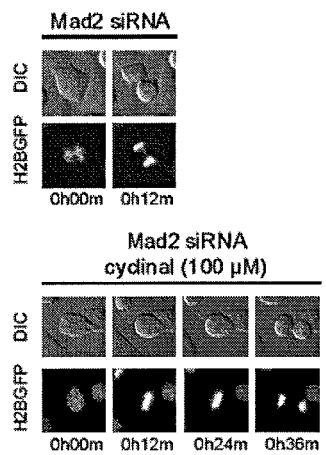
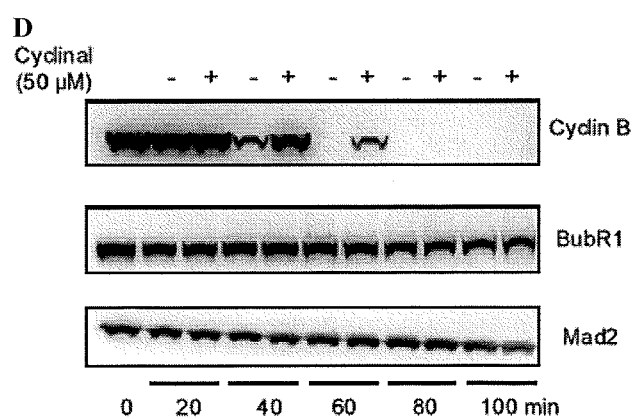

FIGURE 31
A
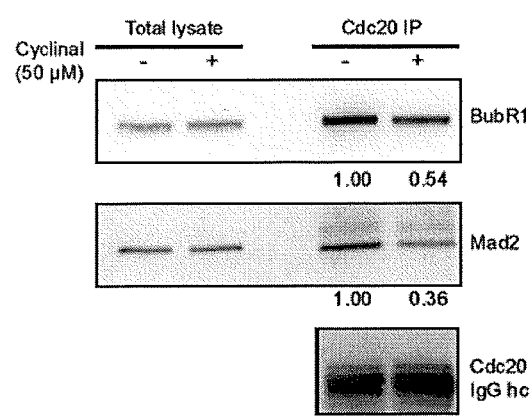
B
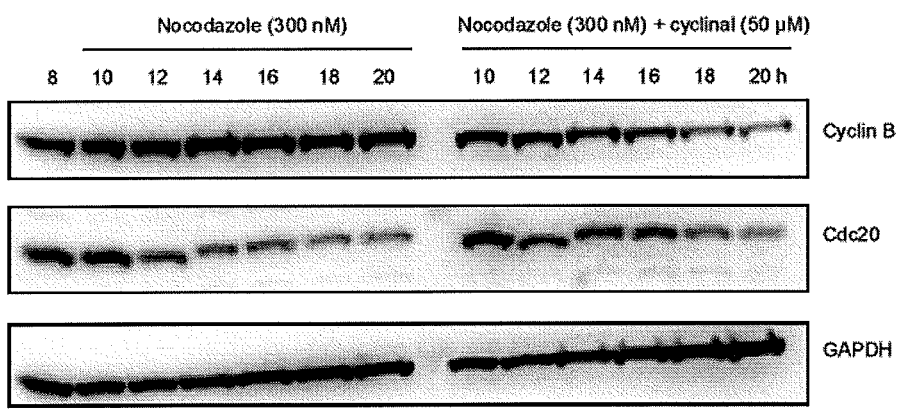

Cell fate distribution

|  | DMSO | proTAME | cyclinal | proTAME + cyclinal |
|---|---|---|---|---|
| Mitotic exit, % | 100 | 9 | 100 | 2 |
| Mitotic arrest, % | 0 | 3 | 0 | 2 |
| Mitotic death, % | 0 | 88 | 0 | 96 |
|  | Hesp | proTAME + Hesp | cyclinal + Hesp | proTAME + cyclinal + Hesp |
| Mitotic exit, % | 100 | 99 | 100 | 4 |
| Mitotic arrest, % | 0 | 0 | 0 | 4 |
| Mitotic death, % | 0 | 1 | 0 | 92 |

Hesperadin (100 nM), proTAME (12µM) + cyclinal (100µM)

FIGURE 35
A
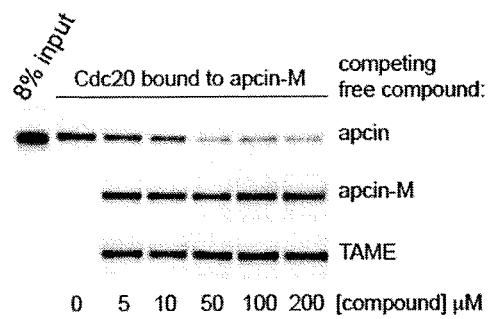
B
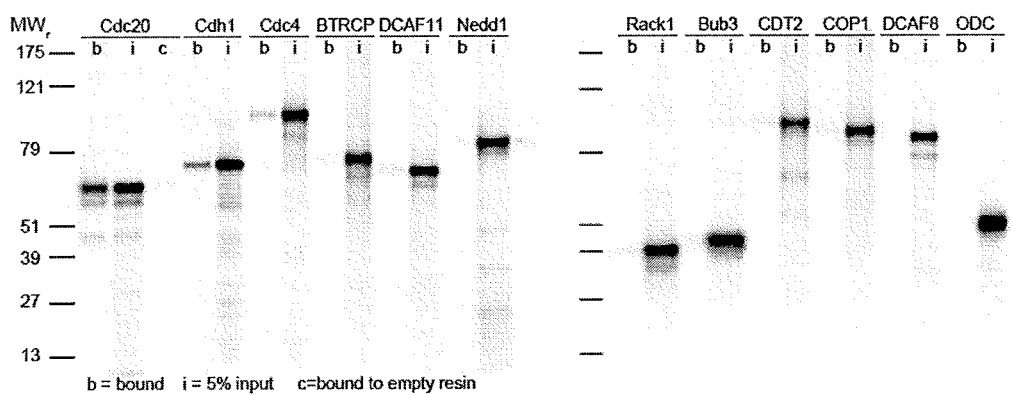
C
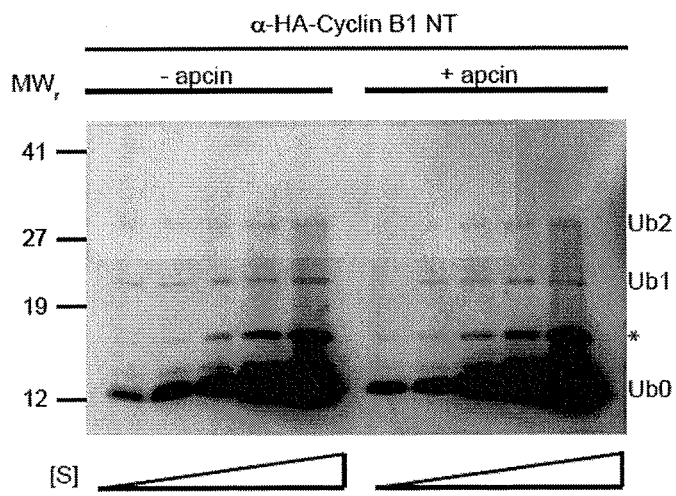

FIGURE 36
A
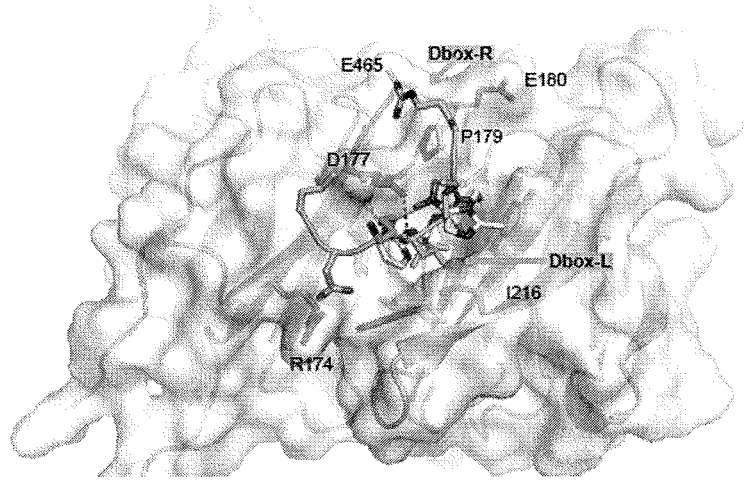
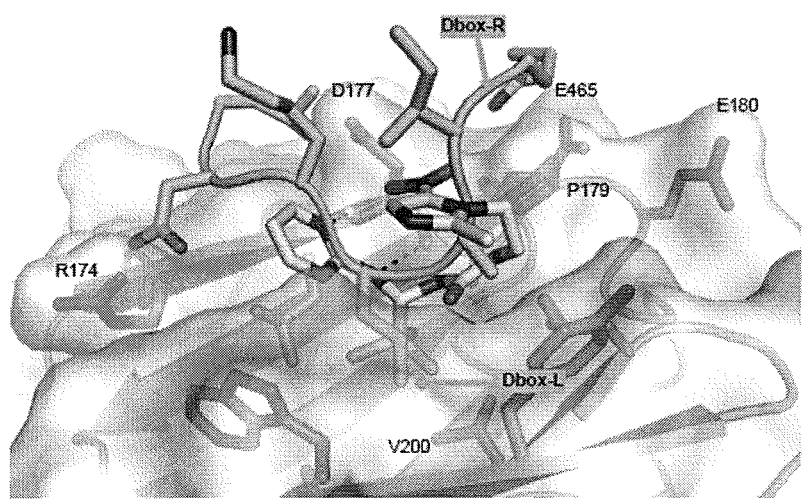
B
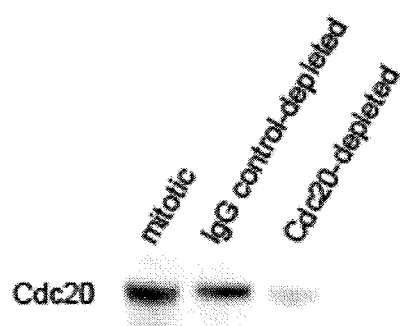

FIGURE 37
D
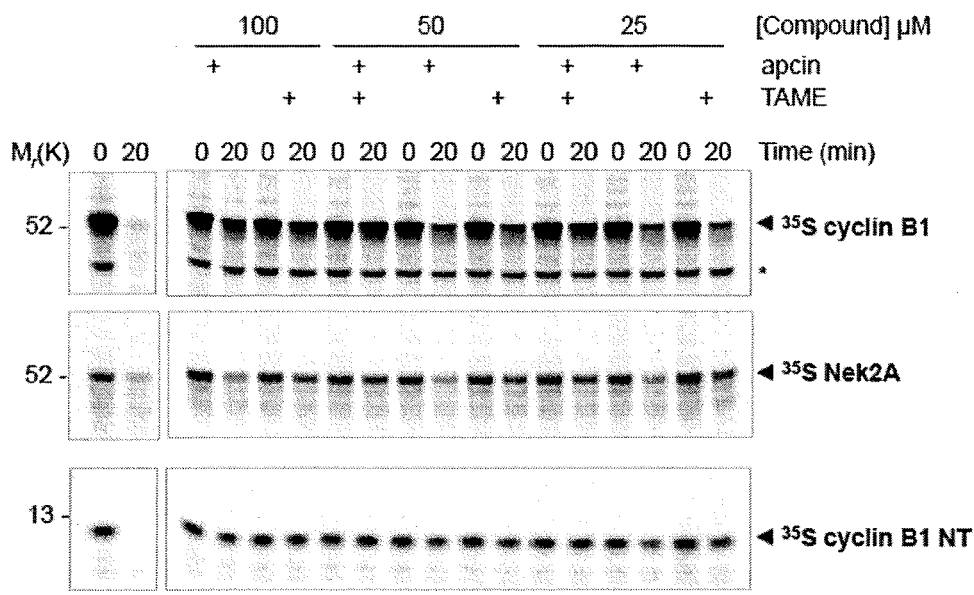
E
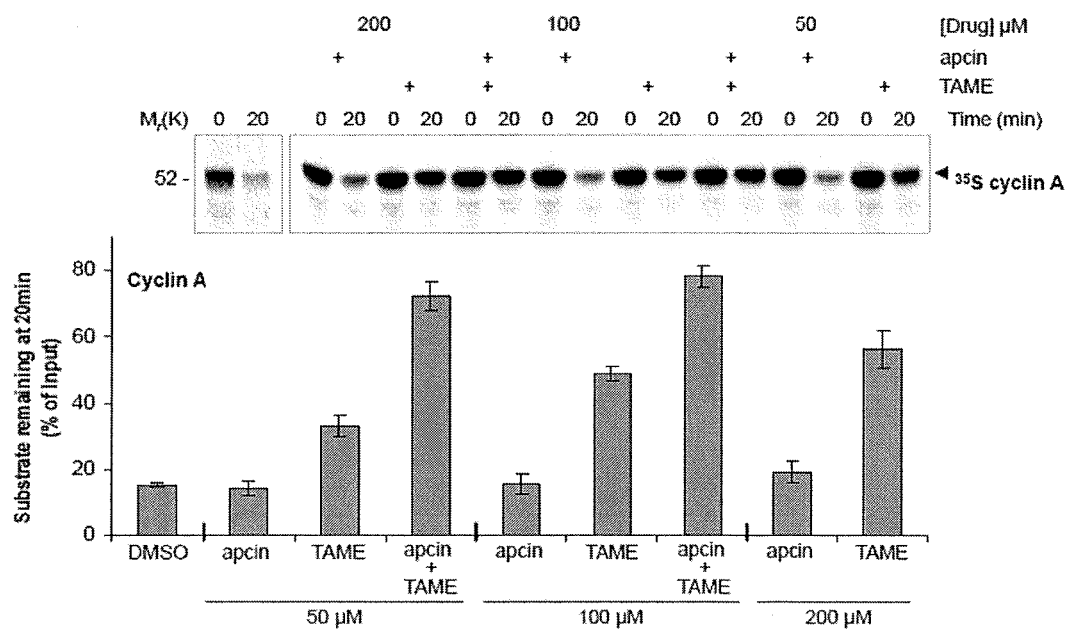

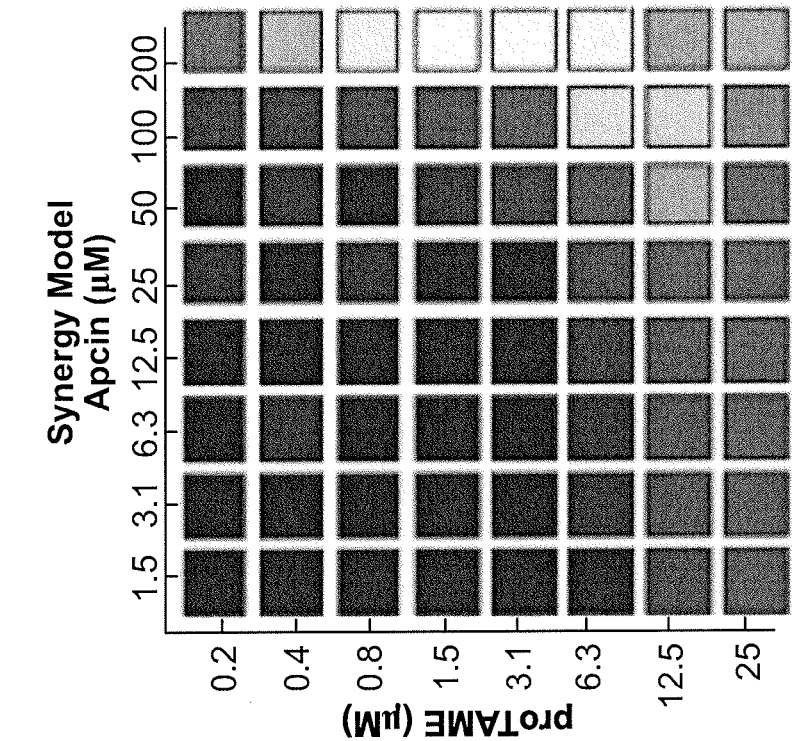
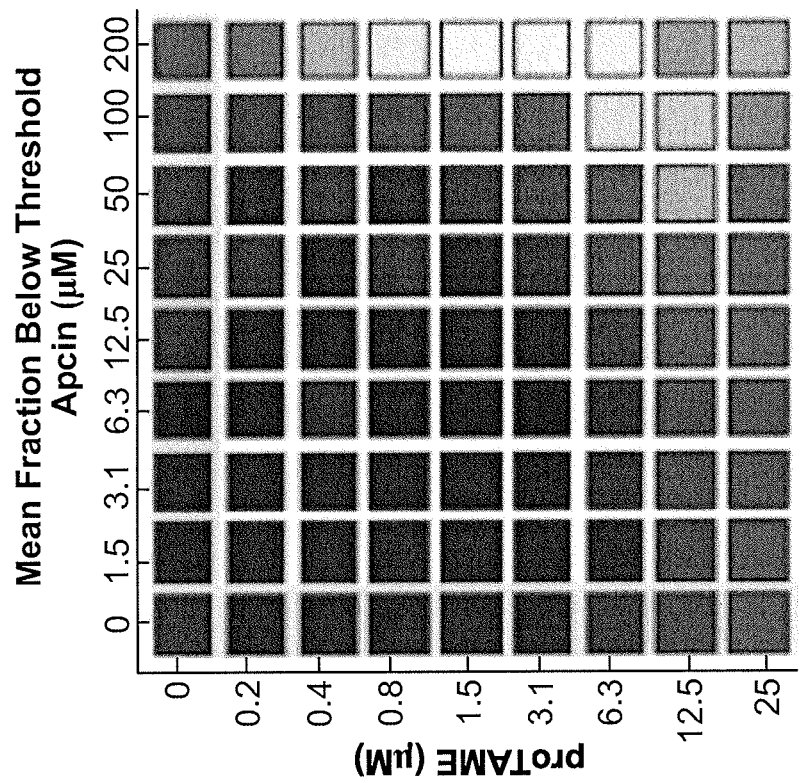
FIG. 38B

SEQUENCE LISTING

<160> NUMBER OF SEQ ID NOS: 14

<210> SEQ ID NO 1
<211> LENGTH: 8
<212> TYPE: PRT
<213> ORGANISM: Artificial Sequence
<220> FEATURE:
<223> OTHER INFORMATION: Chemically synthesized
<220> FEATURE:
<221> NAME/KEY: misc_feature
<222> LOCATION: (7)..(7)
<223> OTHER INFORMATION: Xaa can be any naturally occurring amino acid

<400> SEQUENCE: 1

Asp Arg Phe Tyr Ile Pro Xaa Arg
1               5

<210> SEQ ID NO 2
<211> LENGTH: 22
<212> TYPE: PRT
<213> ORGANISM: Artificial Sequence
<220> FEATURE:
<223> OTHER INFORMATION: Chemically synthesized

<400> SEQUENCE: 2

Cys Phe Ser Lys Thr Arg Ser Thr Lys Glu Ser Val Ser Val Leu Asn
1               5                   10                  15

Leu Phe Thr Arg Ile Arg
            20

<210> SEQ ID NO 3
<211> LENGTH: 20
<212> TYPE: PRT
<213> ORGANISM: Artificial Sequence
<220> FEATURE:
<223> OTHER INFORMATION: Chemically synthesized

<400> SEQUENCE: 3

Cys Phe Ser Lys Thr Arg Ser Thr Lys Glu Ser Val Ser Val Leu Asn
1               5                   10                  15

Leu Phe Thr Arg
            20

<210> SEQ ID NO 4
<211> LENGTH: 19
<212> TYPE: RNA
<213> ORGANISM: Artificial Sequence
<220> FEATURE:
<223> OTHER INFORMATION: Chemically synthesized

<400> SEQUENCE: 4
gaaaggcugu cauguauug                                              19

<210> SEQ ID NO 5
<211> LENGTH: 19
<212> TYPE: RNA
<213> ORGANISM: Artificial Sequence
<220> FEATURE:
<223> OTHER INFORMATION: Chemically synthesized

<400> SEQUENCE: 5
caacagacac uuaauagua                                              19

<210> SEQ ID NO 6
<211> LENGTH: 19
<212> TYPE: RNA

```
<213> ORGANISM: Artificial Sequence
<220> FEATURE:
<223> OTHER INFORMATION: Chemically synthesized

<400> SEQUENCE: 6
cgaagugucu cuguaauua                                                  19

<210> SEQ ID NO 7
<211> LENGTH: 19
<212> TYPE: RNA
<213> ORGANISM: Artificial Sequence
<220> FEATURE:
<223> OTHER INFORMATION: Chemcially synthesized

<400> SEQUENCE: 7
guacgaagug ucucuguaa                                                  19

<210> SEQ ID NO 8
<211> LENGTH: 21
<212> TYPE: DNA
<213> ORGANISM: Artificial Sequence
<220> FEATURE:
<223> OTHER INFORMATION: Chemically synthesized
<220> FEATURE:
<221> NAME/KEY: misc_feature
<222> LOCATION: (20)..(21)
<223> OTHER INFORMATION: 3' termini dTdT overhang, wherein  T is
      actually dT (deoxythymidine)

<400> SEQUENCE: 8
ggaacaacug aaagauuggt t                                               21

<210> SEQ ID NO 9
<211> LENGTH: 21
<212> TYPE: RNA
<213> ORGANISM: Artificial Sequence
<220> FEATURE:
<223> OTHER INFORMATION: Chemically synthesized
<220> FEATURE:
<221> NAME/KEY: misc_feature
<222> LOCATION: (20)..(21)
<223> OTHER INFORMATION: 3' termini UU

<400> SEQUENCE: 9
uaaauuaagc cucgguugau u                                               21

<210> SEQ ID NO 10
<211> LENGTH: 21
<212> TYPE: RNA
<213> ORGANISM: Artificial Sequence
<220> FEATURE:
<223> OTHER INFORMATION: Chemically synthesized
<220> FEATURE:
<221> NAME/KEY: misc_feature
<222> LOCATION: (20)..(21)
<223> OTHER INFORMATION: 3' termini UU

<400> SEQUENCE: 10
ggaaauagcc gagagguaau u                                               21

<210> SEQ ID NO 11
<211> LENGTH: 21
<212> TYPE: RNA
<213> ORGANISM: Artificial Sequence
<220> FEATURE:
<223> OTHER INFORMATION: Chemically synthesized
<220> FEATURE:
<221> NAME/KEY: misc_feature
<222> LOCATION: (20)..(21)
```

<223> OTHER INFORMATION: 3' termini uu

<400> SEQUENCE: 11
ggaagaagau cuagauguau u                                         21

<210> SEQ ID NO 12
<211> LENGTH: 618
<212> TYPE: DNA
<213> ORGANISM: Homo sapiens

<400> SEQUENCE: 12
atggcgctgc agctctcccg ggagcaggga atcaccctgc gcgggagcgc cgaaatcgtg    60
gccgagttct tctcattcgg catcaacagc attttatatc agcgtggcat atatccatct   120 gaaacctta ctcgagtgca gaaatacgga ctcaccttgc ttgtaactac tgatcttgag   180
ctcataaaat acctaaataa tgtggtggaa caactgaaag attggttata caagtgttca   240
gttcagaaac tggttgtagt tatctcaaat attgaaagtg gtgaggtcct ggaaagatgg   300
cagtttgata ttgagtgtga caagactgca aaagatgaca gtgcacccag agaaaagtct   360
cagaaagcta tccaggatga aatccgttca gtgatcagac agatcacagc tacggtgaca   420
tttctgccac tgttggaagt ttcttgttca tttgatctgc tgatttatac agacaaagat   480
ttggttgtac ctgaaaaatg ggaagagtcg ggaccacagt ttattaccaa ttctgaggaa   540 gtccgcttc gttcatttac tactacaatc cacaaagtaa atagcatggt ggcctacaaa   600
attcctgtca atgactga                                                 618

<210> SEQ ID NO 13
<211> LENGTH: 21
<212> TYPE: DNA
<213> ORGANISM: Artificial Sequence
<220> FEATURE:
<223> OTHER INFORMATION: Chemically synthesized
<220> FEATURE:
<221> NAME/KEY: misc_feature
<222> LOCATION: (20)..(21)
<223> OTHER INFORMATION: 3' termini dTdT overhang, wherein TT is
      actually dTdT (dT is dexoythymidine)

<400> SEQUENCE: 13
ggaacaacug aaagauuggt t                                         21

<210> SEQ ID NO 14
<211> LENGTH: 205
<212> TYPE: PRT
<213> ORGANISM: Homo sapiens

<400> SEQUENCE: 14

Met Ala Leu Gln Leu Ser Arg Glu Gln Gly Ile Thr Leu Arg Gly Ser
1               5                   10                  15

Ala Glu Ile Val Ala Glu Phe Phe Ser Phe Gly Ile Asn Ser Ile Leu
            20                  25                  30

Tyr Gln Arg Gly Ile Tyr Pro Ser Glu Thr Phe Thr Arg Val Gln Lys
        35                  40                  45

Tyr Gly Leu Thr Leu Leu Val Thr Thr Asp Leu Glu Leu Ile Lys Tyr
    50                  55                  60

Leu Asn Asn Val Val Glu Gln Leu Lys Asp Trp Leu Tyr Lys Cys Ser
65                  70                  75                  80

Val Gln Lys Leu Val Val Ile Ser Asn Ile Glu Ser Gly Glu Val
            85                  90                  95

```
Leu Glu Arg Trp Gln Phe Asp Ile Glu Cys Asp Lys Thr Ala Lys Asp
            100             105                 110

Asp Ser Ala Pro Arg Glu Lys Ser Gln Lys Ala Ile Gln Asp Glu Ile
        115             120                 125

Arg Ser Val Ile Arg Gln Ile Thr Ala Thr Val Thr Phe Leu Pro Leu
        130             135             140

Leu Glu Val Ser Cys Ser Phe Asp Leu Leu Ile Tyr Thr Asp Lys Asp
145                     150             155                 160

Leu Val Val Pro Glu Lys Trp Glu Glu Ser Gly Pro Gln Phe Ile Thr
                165             170             175

Asn Ser Glu Glu Val Arg Leu Arg Ser Phe Thr Thr Thr Ile His Lys
            180             185             190

Val Asn Ser Met Val Ala Tyr Lys Ile Pro Val Asn Asp
        195             200             205
```

CELL PERMEABLE INHIBITORS OF ANAPHASE PROMOTING COMPLEX

GOVERNMENT SUPPORT

This invention was made with U.S. Government support under National Institutes of Health grant RO1 GM66492. The Government has certain rights in the invention.

FIELD OF THE DISCLOSURE

This disclosure relates generally to the fields of oncology and disorders associated with cell division.

INCORPORATION BY REFERENCE OF SEQUENCE LISTING

The contents of the text file named "29297-094F01USSeqList.txt", which was created on Jul. 18, 2014 and is 7 KB in size, are thereby incorporated by reference in their entirety.

BACKGROUND

Conventional antiproliferative agents used in the treatment of cancer are generally grouped as compounds which affect the integrity of nucleic acid polymers, e.g., by binding, alkylating, inducing strand breaks, intercalating between base pairs or affecting enzymes which maintain the integrity and function of DNA and RNA, and compounds that bind to proteins to inhibit enzymatic action (e.g., antimetabolites) or the function of structural proteins necessary for cellular integrity (e.g., antitubulin agents). Other antiproliferative drugs include those that block steroid hormone action for the treatment of hormone-dependent cancer, photochemically activated agents, radiation sensitizers, and protectors. Many of these agents are associated with adverse side effects.

SUMMARY

The disclosure encompasses Anaphase-Promoting Complex/Cyclosome (APC) inhibitors as anticancer agents and improves upon the success of known anti-cancer agents, such as taxanes, in treating a wide variety of different cancers. A prodrug of TAME (proTAME) and an apcin act synergistically to inhibit the APC by two different mechanisms. The compositions and methods are useful to treat a subject, who is diagnosed as comprising a tumor, having comprised a tumor, or at risk of developing a primary tumor, or a metastasis from a primary tumor. The subject is a human patient, a companion animal such as a dog or cat, a performance animal such as a race horse, or livestock animal such as a cow, goat, or fowl.

The synergism of, for instance, proTAME and apcin is unexpected. Provided the individual activities of proTAME and apcin when individually contacted to cells, it was anticipated that the combination of TAME/proTAME and apcin would be ineffective to induce a mitotic arrest because, in cells, apcin inactivates the SAC, which TAME/proTAME requires to inhibit the APC. The disclosure provides the first evidence that the combination of proTAME and apcin induces cell cycle arrest by superior and unexpected means.

Protein machines are multi-subunit protein complexes that orchestrate highly regulated biochemical tasks. An example is the Anaphase-Promoting Complex/Cyclosome (APC/C), a thirteen-subunit ubiquitin ligase that initiates the metaphase-anaphase transition and mitotic exit by targeting proteins such as securin and cyclin B1 for ubiquitin-dependent destruction by the proteasome. The APC/C represents a target for cancer therapy because blocking mitotic exit is an effective approach for inducing tumor cell death. APC/C activation in mitosis requires binding of Cdc20, which forms a co-receptor with the APC/C to recognize substrates containing a Destruction box (D-box). The data provided in this disclosure demonstrate that APC/C-dependent proteolysis and mitotic exit can be inhibited, synergistically, by simultaneously disrupting two protein-protein interactions within the APC/C-Cdc20-substrate ternary complex. The studies described in this disclosure identified a small molecule, called apcin (APC inhibitor) (also known as cyclinal and R7), which binds to Cdc20 and competitively inhibits the association of D-box-containing substrates. Analysis of the crystal structure of the apcin-Cdc20 complex indicates that apcin occupies the D-box-binding pocket on the side face of the WD40-domain. The ability of apcin to block mitotic exit is amplified, synergistically, by co-addition of TAME, a small molecule that blocks the interaction between Cdc20 and the APC/C. Thus, simultaneous disruption of multiple, weak protein-protein interactions is an effective approach for inactivating a protein machine.

Taxanes bind microtubules and activate the spindle checkpoint, which can arrest cells in mitosis and induce cell death. However, taxane-treated cells can exit mitosis before dying, through a process of "mitotic slippage" that results from incomplete inhibition of the APC by the Spindle Assembly Checkpoint (SAC). Variability in the relative rates of mitotic slippage compared to mitotic cell death may explain the variability in sensitivity of cell lines and tumors to taxanes and mitotic kinesin inhibitors.

Direct inhibition of APC is a more effective way of inducing mitotic arrest than stimulating the SAC. For example, knockdown of Cdc20, which is an activator of APC, by RNAi induces prolongs mitotic arrest and cell death, but only if Cdc20 is reduced to very low levels. This approach to inducing cell death shows much less variability across different cancer cell lines, compared to taxane treatment. Furthermore, studies in mice demonstrate that elimination of Cdc20 function can lead to very effective tumor regression in animals.

The small molecules of the disclosure, and combinations thereof, inhibit $APC^{Cdc20}$ by pharmacologic approaches to recapitulate the effects of Cdc20 knockdown or knockout. The cell-permeable prodrug of TAME, proTAME is unexpectedly effective at inducing mitotic arrest in cells. One explanation for the effectiveness of proTAME is that proTAME interferes with the process of SAC inactivation. Together, proTAME and the SAC synergize to produce very strong inhibition of APC activity. For example, mitotic arrest induced by taxol requires ongoing protein synthesis in mitosis, because APC-dependent proteolysis is not fully inhibited by the SAC. In contrast, proTAME causes more profound APC inhibition, such that mitotic arrest is independent of protein synthesis. These discoveries explain why direct APC inhibition is more effective at inducing prolonged mitotic arrest and cell death than microtubule inhibition.

Importantly, although proTAME induces mitotic arrest in cell lines with a strong SAC, TAME and proTAME are less effective in cells with a weak SAC. While cyclinal (also known as apcin and R7) is sufficient to inhibit the APC and induce mitotic arrest in *Xenopus* extracts, cyclinal has an unexpectedly opposite effect in cells. In cells, cyclinal on its own only weakly inhibits APC, and surprisingly inactivates the SAC. For this reason, it was anticipated that the combination of TAME/proTAME and cyclinal would be ineffective to induce a mitotic arrest because, in cells, cyclinal inactivates the SAC, which TAME/proTAME requires to inhibit the APC. Stated differently, in cells, because cyclinal inactivates the SAC, the co-administration of cyclinal with TAME/proTAME was expected to create an environment in which the TAME/proTAME molecule would be ineffective. Moreover, when cyclinal is administered to cells alone, cyclinal actually accelerates progression through mitosis. Therefore, unexpectedly, when cells are treated with the combination of TAME/proTAME and cyclinal, a profound mitotic arrest is induced. Data provided herein show that this synergistic effect occurs because TAME/proTAME and cyclinal both inhibit binding of Cdc20 to the APC, and, therefore, inhibit APC activity. TAME/proTAME and cyclinal interfere with APC/Cdc20 binding at two independent points: TAME/proTAME blocks the IR tail/Apc3 interaction whereas cyclinal blocks the WD40/D-box interaction (FIG. 33). Thus, the combination inhibits multiple redundant interactions between APC and Cdc20, leading to a complete inhibition of APC activation.

The combination of TAME/proTAME and cyclinal induces a mitotic arrest that is independent of the SAC. Therefore, when TAME/proTAME is provided in combination with cyclinal, the dependence of TAME/proTAME on the SAC is eliminated. This is also in contrast to taxane-based therapies, which directly activate the SAC, but not the underlying machinery of the cell cycle. Agents that inactivate the SAC do not release the mitotic arrest induced by the synergistic combination of TAME/proTAME and cyclinal. Therefore, the disclosure identifies a direct method of inhibiting APC that does not depend on the SAC.

One of the most substantial obstacles to developing the APC-inhibitory combination of the disclosure (TAME/proTAME and cyclinal) was the desire to pharmacologically recapitulate the reduction of Cdc20 required to induce mitotic arrest and cell death, but which had previously only been demonstrated using RNAi technology. In part, because the APC inhibitory combination of the disclosure recapitulates this knockdown of Cdc20 expression pharmacologically, the disclosure provides an exciting break-through. Moreover, in sharp contrast to the most relied-upon anticancer drugs currently available, including taxane derivatives, the combination of TAME/proTAME and cyclinal induces a mitotic arrest that is independent of any cell-cycle checkpoint. The effectiveness of a taxane-based treatment is dependent upon the status of the mitotic checkpoint in the cell, which cannot be empirically-determined prior to treatment. Accordingly, if the aberrant cell proliferation observed by any given cell or cancer cell does not result from a checkpoint malfunction, or if the checkpoint is perturbed in an unexpected or taxane-independent manner, then a taxane-based treatment would be ineffective. Furthermore, the efficacy of a therapy that is dependent upon check point or SAC status is unpredictable. Critically, the APC inhibitory combination of proTAME and cyclinal produces a profound mitotic arrest that does not require the SAC or any other checkpoint. By inhibiting Cdc20 binding to the APC with TAME, while simultaneously suppressing substrate binding to Cdc20 with cyclinal, the synergistic combination of TAME/proTAME and cyclinal completely disables APC-$^{Cdc20}$ function, producing the pharmacologic equivalent of a Cdc20 knockout. The efficacy of the mitotic arrest induced by the combination of TAME/proTAME and cyclinal does not depend upon the mechanism within the cell that caused proliferation to become misregulated or unregulated, because cell proliferation, whether it occurs at an appropriate or inappropriate time, requires entry into the cell cycle, which is the target of the combination of TAME/proTAME and cyclinal.

This discovery provides an entirely new approach to treating cancer: induction of a true cell cycle arrest by directly disabling the cell cycle machinery. Mitosis is an inherently pro-apoptotic state, and cell death in mitosis occurs independently of p53 status, suggesting that induction of mitotic arrest may be an effective mechanism for killing all tumor cells. Because the combined use of proTAME and cyclinal can induce mitotic arrest independent of checkpoint response, it is more effective at inducing cell death than other strategies that arrest cells indirectly by damaging DNA or the mitotic spindle. By combining APC inhibitors with drugs, including but not limited to, a nutlin or rapamycin, that induce cell cycle arrest of normal cells in interphase, tumor cells are selectively arrested in mitosis while sparing normal cells.

Compositions of the disclosure include proTAME or the combination of proTAME and apcin. These compositions are both effective for inducing mitotic arrest in cells, however, the mechanisms by which this arrest occurs differ. Importantly, proTAME and apcin have apparently opposite effects when they are provided alone, compared to a condition in which they are provided in combination. This apparent contradiction provides the basis for the unexpected and synergistic effects observed when proTAME and apcin are administered in combination.

The disclosure provides a composition including a prodrug of tosyl-L-arginine methylester (TAME) and apcin. The prodrug diffuses across the plasma membrane of a cell and decreases cell proliferation by inhibiting mitosis. Once inside the cell, the prodrug is processed to yield the active agent, TAME. The prodrug is formulated into a pharmaceutical composition which includes the prodrug and a physiologically acceptable excipient. Preferably, the prodrug is a TAME derivative in which a guanidino group is linked to a protecting group. The protecting group is an enzyme-cleavable group such as a carbamate group that is cleaved by an intracellular enzyme. The guianidino substituent of TAME occurs in the arginine residue. An exemplary prodrug is an esterase-activatable N,N'-bis(acyloxymethyl carbamate) derivative of the parent molecule, TAME.

In certain embodiments, proTAME, and its parent molecule, once inside the cell, TAME, contact a component of a tetratricopeptide repeats (TPR) subcomplex of an APC. Exemplary components of a TPR subcomplex include, but are not limited to, APC3/Cdc27, APC6, APC7, or APC8. In a preferred embodiment proTAME/TAME blocks the interaction of Cdc20 with APC through the interaction of the IR tail of Cdc20 with APC3.

The phospholipid membrane of cells limits the permeation of molecules into a cell. The membrane acts as a barrier to passive diffusion of water-soluble molecules, and substances that dissolve in lipids pass more easily into the cell. The prodrugs described herein are lipophilic, uncharged, esterase-activatable prodrugs of guanidine containing molecules. The prodrug has improved cell permeability, and once inside the cell, is converted to active TAME by esterase(s). The prodrug is characterized as at least 10%, 20%, 50%, 2-fold, 5-fold, 20-fold or more membrane-permeable (e.g., eukaryotic cell membrane permeable) compared to the parent drug.

A "prodrug" is a molecule which is converted to a therapeutically active molecule after administration. For example, prodrug (e.g., proTAME) converted to TAME after gaining access into a mammalian cell. Conversion of the prodrug to the active drug may occur by hydrolysis of an ester group or some other biologically labile group. Generally, but not necessarily, a prodrug is inactive or less active than the therapeutically active molecule to which it is converted. The prodrug is characterized by a protecting group that is associated with or linked to an inhibitor of the anaphase promoting complex (APC). The presence of the group, e.g., a carbamate group on a guanidine substituent of arginine increases cellular uptake or transport across a cellular membrane (e.g. plasma membrane or nuclear membrane). The prodrug has additional advantages such as improved solubility, oral absorption, cellular targeting or specificity, stability, half-life, or blood-brain barrier permeability of the inhibitory molecule. Alternatively, or in addition, prodrugs decrease the degradation, immunogenicity, toxicity, or required dosage compared to the parent molecule.

Also within the disclosure is a method for manufacturing an anti-proliferative agent such as a cell-permeable inhibitor of APC by introducing an amino protecting group, e.g., a carbamate protecting group, onto a guanidino substituent of an arginine residue of TAME. The carbamate protecting group is introduced by contacting said TAME with N,N'-bis(benzyloxycarbonyl)-S-methylisourea.

In a preferred embodiment of the disclosure, the molecule is proTAME:

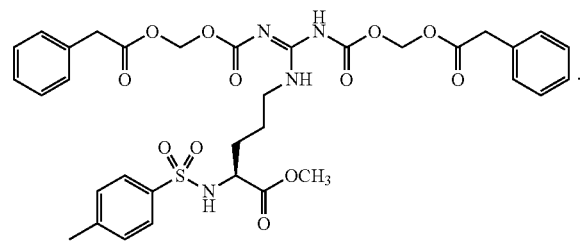 [SMILES: COC(=O)[C@H](CCCN/C(=N\C(=O)OCOC(=O)Cc1ccccc1)NC(=O)OCOC(=O)Cc1ccccc1)NS(=O)(=O)c1ccc(C)cc1]

In all aspects of the disclosure, apcin is:

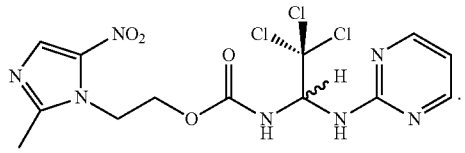

The phrase "pharmaceutically acceptable" refers to those compounds, materials, compositions, carriers, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

"Pharmaceutically acceptable salt" of a compound means a salt that is pharmaceutically acceptable and that possesses the desired pharmacological activity of the parent compound.

"Pharmaceutically acceptable salts" refers to derivatives of the disclosed compounds wherein the parent compound is modified by making acid or base salts thereof. Examples of pharmaceutically acceptable salts include, but are not limited to, mineral or organic acid salts of basic residues such as amines, alkali or organic salts of acidic residues such as carboxylic acids, and the like. The pharmaceutically acceptable salts include the conventional non-toxic salts or the quaternary ammonium salts of the parent compound formed, for example, from non-toxic inorganic or organic acids. For example, such conventional non-toxic salts include, but are not limited to, those derived from inorganic and organic acids selected from 2-acetoxybenzoic, 2-hydroxyethane sulfonic, acetic, ascorbic, benzene sulfonic, benzoic, bicarbonic, carbonic, citric, edetic, ethane disulfonic, 1,2-ethane sulfonic, fumaric, glucoheptonic, gluconic, glutamic, glycolic, glycollyarsanilic, hexylresorcinic, hydrabamic, hydrobromic, hydrochloric, hydroiodic, hydroxymaleic, hydroxynaphthoic, isethionic, lactic, lactobionic, lauryl sulfonic, maleic, malic, mandelic, methane sulfonic, napsylic, nitric, oxalic, pamoic, pantothenic, phenylacetic, phosphoric, polygalacturonic, propionic, salicyclic, stearic, subacetic, succinic, sulfamic, sulfanilic, sulfuric, tannic, tartaric, toluene sulfonic, and the commonly occurring amine acids, e.g., glycine, alanine, phenylalanine, arginine, etc.

Other examples include hexanoic acid, cyclopentane propionic acid, pyruvic acid, malonic acid, 3-(4-hydroxybenzoyl)benzoic acid, cinnamic acid, 4-chlorobenzenesulfonic acid, 2-naphthalenesulfonic acid, 4-toluenesulfonic acid, camphorsulfonic acid, 4-methylbicyclo-[2.2.2]-oct-2-ene-1-carboxylic acid, 3-phenylpropionic acid, trimethylacetic acid, tertiary butylacetic acid, muconic acid, and the like. The disclosure also encompasses salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, tromethamine, N-methylglucamine, and the like.

All references to pharmaceutically acceptable salts include solvent addition forms (solvates) or crystal forms (polymorphs) as defined herein, of the same salt.

Pharmaceutically acceptable salts of the present disclosure can be synthesized from a parent compound that contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; non-aqueous media like ether, ethyl acetate, ethanol, isopropanol, or acetonitrile can be used. Lists of suitable salts are found in *Remington's Pharmaceutical Sciences*, 18th ed. (Mack Publishing Company, 1990). For example, salts can include, but are not limited to, the hydrochloride and acetate salts of the aliphatic amine-containing, hydroxyl amine-containing, and imine-containing compounds of the present disclosure.

Apcin blocks the interaction of the WD40 region on Cdc20 with the D-box sequence on potential APC substrates (e.g. cyclin B1, securin), and, therefore, competes with substrates for binding to the WD40 region. Thus, apcin blocks Cdc20-mediated activation of the APC by an independent, yet functionally redundant pathway, to the IR tail/APC3 interaction that is blocked by proTAME/TAME.

The combination of TAME/proTAME and apcin inhibits an activity of an anaphase promoting complex/cyclosome (APC). In some embodiments, the combination of TAME/proTAME and apcin inhibits the ability of Cdc20 to activate APC, and, therefore, the ability of APC to degrade substrates. Blockade of APC activity causes a profound mitotic arrest.

The disclosure provides a pharmaceutical composition comprising, consisting essentially of, or consisting of, one or more of the molecules described herein, including, but not limited to, TAME/proTAME, apcin, or a combination thereof. Furthermore, the pharmaceutical composition includes a pharmaceutical carrier.

Compositions and formulations of the disclosure are administered to a cell. The cell is optionally eukaryotic, mammalian, or, preferably, human. In certain aspects of the disclosure, the compositions and formulations of the disclosure are administered to the cell in vitro, in vivo, ex vivo, or any combination thereof.

The compositions and molecules of the disclosure inhibit an activity of an anaphase promoting complex (APC) to arrest mitosis and reduce proliferation of cells such as cancer cells or other aberrantly proliferating cells. The compositions are useful to treat cellular proliferative disorders such as cancers, e.g., skin cancer, virally induced hyperproliferative HPV-papilloma, HSV-shingles, colon cancer, bladder cancer, breast cancer, melanoma, ovarian carcinoma, prostate carcinoma, or lung cancer as well as psoriasis and eczema. The compositions may be also useful in the context of in vitro fertilization, because they enhance the ability of these early embryos to properly segregate DNA during mitosis.

The disclosure provides a formulation comprising an amount of a prodrug of tosyl-L-arginine methylester (TAME) that is sufficient to inhibit the degradation of a substrate of an anaphase-promoting complex/cyclosome (APC) for arresting the mitotic cycle of a cell.

Moreover, the disclosure provides a formulation comprising an amount of a prodrug of tosyl-L-arginine methylester (TAME) that is sufficient to inhibit the degradation of a substrate of an anaphase-promoting complex/cyclosome (APC) for arresting the mitotic cycle of a cell, for use in the treatment of a cell proliferative disorder. A preferred cell proliferative disorder is cancer.

The disclosure provides a method treating a cell proliferative disorder in a subject, comprising administering to the subject an amount of a composition comprising a prodrug of tosyl-L-arginine methylester (TAME) that is sufficient to inhibit the degradation of a substrate of an anaphase-promoting complex/cyclosome (APC), thereby arresting the mitotic cycle of one or more cells in the subject. A preferred cell proliferative disorder is cancer.

The disclosure also provides a formulation comprising, an amount of: a) a prodrug of tosyl-L-arginine methylester (TAME), and b) a apcin molecule that is sufficient to inhibit the degradation of a substrate of an anaphase-promoting complex/cyclosome (APC) for arresting the mitotic cycle of a cell.

Moreover, the disclosure provides a formulation comprising, an amount of: a) a prodrug of tosyl-L-arginine methylester (TAME), and b) a apcin molecule that is sufficient to inhibit the degradation of a substrate of an anaphase-promoting complex/cyclosome (APC) for arresting the mitotic cycle of a cell, for use in the treatment of a cell proliferative disorder. A preferred cell proliferative disorder is cancer.

The disclosure provides a method treating a cell proliferative disorder in a subject, comprising administering to the subject an amount of a composition comprising: a) a prodrug of tosyl-L-arginine methylester (TAME), and b) a apcin molecule that is sufficient to inhibit the degradation of a substrate of an anaphase-promoting complex/cyclosome (APC), thereby arresting the mitotic cycle of one or more cells in the subject. A preferred cell proliferative disorder is cancer.

These formulations and compositions further include a pharmaceutical carrier.

Optionally, these formulations and compositions include a therapeutic agent. An exemplary therapeutic agent includes, but is not limited to, a chemotherapy, a radiation therapy, an immunotherapy, or a hormone therapy.

Radiation therapy is a radioactive isotope that is either administered alone or conjugated to another molecule, such as a carrier, to administration, and removal of the isotope from a cell, tissue, organ or subject. Exemplary radiation therapies include, but are not limited to, actinium-225 ($Ac^{225}$), bismuth-213 ($Bi^{213}$), boron-10 ($B^{10}$)+neutron therapy, holmium-166 ($Ho^{166}$), iodine-125 ($I^{125}$), iodine-131 ($I^{133}$), iridium-192 ($Ir^{192}$), lead-212 ($Pb^{212}$), lutetium-177 ($Lu^{177}$), rhenium-186 ($Re^{186}$), samarium-153 ($Sm^{153}$), strontium-89 ($Sr^{89}$), or yttrium-90 ($Y^{90}$).

Immunotherapy is based upon the development of human monoclonal antibody therapies that are either themselves therapeutic, or, alternatively, capable of selectively targeting a cell of interest to aid in the administration of another therapy. For instance, a cell of interest is characterized by a proliferation disorder. Exemplary immunotherapies of the disclosure include, but are not limited to, rituximab (Rituxan®), trastuzumab (Herceptin®), gemtuzumab ozogamicin (Mylotarg®), alemtuzumab (Campath®), ibritumomab tiuxetan (Zevalin®), tositumomab (Bexxar®), cetuximab (Erbitux®), bevacizumab (Avastin®), panitumumab (Vectibix®), ofatumumab (Arzerra®), denosumab (Xgeva™), ipilimumab (Yervoy™), and brentuximab vedotin (Adcetris™). The hormone therapy is tamoxifen (Nolvadex®), an aromatase inhibitor, anastrozole (Arimidex®), letrozole (Femara®), or fulvestrant (Faslodex®).

Chemotherapy includes any pharmacological molecule or composition that mitigates that harm incurred when a normal cell undergoes a transformation into a disease state characterized by aberrant proliferation. Typically, the proliferation of the transformed cell is increased compared to a normal or healthy cell, and, therefore, the chemotherapy is designed to inhibit or prevent cell division. Exemplary chemotherapy agents include, but are not limited to, carboplatin (Paraplatin®), cisplatin (Platinol, Platinol-AQ®), cyclophosphamide (Cytoxan, Neosar®), doxorubicin (Adriamycin®), etoposide (VePesid®), fluorouracil (5-FU), gemcitabine (Gemzar®), irinotecan (Camptosar®), methotrexate, (Folex®, Mexate, Amethopterin), paclitaxel (Taxol®), topotecan (Hycamtin®), vincristine, (Oncovin, Vincasar PFS®), or vinblastine (Velban®).

In certain embodiments, the formulations described herein contain a chemotherapy that specifically targets either a cell cycle checkpoint or, specifically, the spindle assembly checkpoint. The chemotherapy may target the APC complex itself.

Alternatively, or in addition, the chemotherapy may confer selectivity for cancer cells upon the combination of TAME/proTAME and apcin. Selectivity may be achieved by providing a chemotherapeutic agent that protects the normal cells surrounding the target cell by inducing a state of scenescence (or non-division), which allows the combination of TAME/proTAME and apcin to target only dividing cells. In these embodiments, the chemotherapeutic agent includes, but is not limited to, a nutlin (nutlin-1, nutlin-2, nutlin-3), and sirolimus (rapamycin).

The formulations of the disclosure are administered to any cell, including a eukaryotic, mammalian, or, preferably, human cell. In certain aspects, the cell is characterized by a proliferative disorder. The cell proliferative disorder is, for example, cancer, Castleman Disease, Gestational Trophoblastic Disease, or myelodysplastic syndrome. Nonlimiting examples of cancer include, but are not limited to, adrenal cortical cancer, anal cancer, bile duct cancer, bladder cancer, bone cancer, brain or a nervous system cancer, breast cancer, cervical cancer, colon cancer, rectral cancer, colorectal cancer, endometrial cancer, esophageal cancer, Ewing family of tumor, eye cancer, gallbladder cancer, gastrointestinal carcinoid cancer, gastrointestinal stromal cancer, Hodgkin Disease, intestinal cancer, Kaposi Sarcoma, kidney cancer, large intestine cancer, laryngeal cancer, hypopharyngeal cancer, laryngeal and hypopharyngeal cancer, leukemia, acute lymphocytic leukemia (ALL), acute myeloid leukemia (AML), chronic lymphocytic leukemia (CLL), chronic myeloid leukemia (CML), chronic myelomonocytic leukemia (CMML), liver cancer, lung cancer, non-small cell lung cancer, small cell lung cancer, lung carcinoid tumor, lymphoma, lymphoma of the skin, malignant mesothelioma, multiple myeloma, nasal cavity cancer, paranasal sinus cancer, nasal cavity and paranasal sinus cancer, nasopharyngeal cancer, neuroblastoma, non-Hodgkin lymphoma, oral cavity cancer, oropharyngeal cancer, oral cavity and oropharyngeal cancer, osteosarcoma, ovarian cancer, pancreatic cancer, penile cancer, pituitary tumor, prostate cancer, retinoblastoma, rhabdomyosarcoma, salivary gland cancer, sarcoma, adult soft tissue sarcoma, skin cancer, basal cell skin cancer, squamous cell skin cancer, basal and squamous cell skin cancer, melanoma, stomach cancer, small intestine cancer, testicular cancer, thymus cancer, thyroid cancer, uterine sarcoma, uterine cancer, vaginal cancer, vulvar cancer, Waldenstrom Macroglobulinemia, or Wilms Tumor. These cancers may be either primary or metastatic cancer. Moreover, these cancers may occur in either a child or an adult.

The composition containing proTAME, apcin, or a combination thereof, and a therapeutic agent are provided to treat a cell proliferative disorder, including cancer. The therapeutic agent may be administered to a cell simultaneously or sequentially with the proTAME or proTAME/apcin combination. In certain embodiments, the composition containing proTAME, apcin, or a combination thereof, is provided, contacted, or administered to the cancer cell prior to the therapeutic agent. In other embodiments, the composition containing proTAME, apcin, or a combination thereof, is provided, contacted, or administered to the cancer cell at substantially the same time as the therapeutic agent. Substantially the same time may describe a period of 24 hours. In alternative embodiments, the composition containing proTAME, apcin, or a combination thereof, is provided, contacted, or administered to the cancer cell at after the therapeutic agent. In all embodiments of these methods, it is understood that when the therapeutic agent is a spindle assembly checkpoint activator or an inhibitor of proteasome-dependent degradation, the therapeutic agent acts in a synergistic manner or demonstrates synergy with the proTAME composition.

Exemplary compositions of the methods described herein optionally include a Mad-2 composition. Mad-2 compositions include a Mad-2 polynucleotide or a Mad-2 polypeptide and a pharmaceutically acceptable carrier. Alternatively, or in addition, exemplary compositions of the above methods of treating a cell cycle disorder include a chemotherapeutic agent.

The following polynucleotide sequence comprises, consists essentially of or consists of the coding region of the human Mad2 mRNA sequence:

(SEQ ID NO: 12)
ATGGCGCTGCAGCTCTCCCGGGAGCAGGGAATCACCCTGCGCGGGAGCGC

CGAAATCGTGGCCGAGTTCTTCTCATTCGGCATCAACAGCATTTTATATC

AGCGTGGCATATATCCATCTGAAACCTTTACTCGAGTGCAGAAATACGGA

CTCACCTTGCTTGTAACTACTGATCTTGAGCTCATAAAATACCTAAATAA

TGTGGTGGAACAACTGAAAGATTGGTTATACAAGTGTTCAGTTCAGAAAC

TGGTTGTAGTTATCTCAAATATTGAAAGTGGTGAGGTCCTGGAAAGATGG

CAGTTTGATATTGAGTGTGACAAGACTGCAAAAGATGACAGTGCACCCAG

AGAAAAGTCTCAGAAAGCTATCCAGGATGAAATCCGTTCAGTGATCAGAC

AGATCACAGCTACGGTGACATTTCTGCCACTGTTGGAAGTTTCTTGTTCA

TTTGATCTGCTGATTTATACAGACAAAGATTTGGTTGTACCTGAAAAATG

GGAAGAGTCGGGACCACAGTTTATTACCAATTCTGAGGAAGTCCGCCTTC

GTTCATTTACTACTACAATCCACAAAGTAAATAGCATGGTGGCCTACAAA

ATTCCTGTCAATGACTGA.

The following polynucleotide sequence comprises, consists essentially of or consists of an siRNA molecule that binds to and silences expression of one or more human Mad2 mRNA sequence(s):

(SEQ ID NO: 13)
GGAACAACUGAAAGAUUGGdTdT.

The following amino acid sequence comprises, consists essentially of or consists of the sequence of the human Mad2 protein:

(SEQ ID NO: 14)
MALQLSREQGITLRGSAEIVAEFFSFGINSILYQRGIYPSETFTRVQKYG

LTLLVTTDLELIKYLNNVVEQLKDWLYKCSVQKLVVVISNIESGEVLERW

QFDIECDKTAKDDSAPREKSQKAIQDEIRSVIRQITATVTFLPLLEVSCS

FDLLIYTDKDLVVPEKWEESGPQFITNSEEVRLRSFTTTIHKVNSMVAYK

IPVND.

Exemplary compositions of the methods described herein optionally include a therapeutic agent. ProTAME enhances mitotic arrest and the amount of cell death induced by a taxane molecule, compound, or drug, e.g. paclitaxel or Taxol™, or by a proteasome inhibitor. Based on the synergistic effect of proTAME and these agents (e.g. taxanes and/or proteasome inhibitors), combination therapies using proTAME together with either a taxane or a proteosome inhibitor (or both) is used to treat or reduce the severity of the cell cycle disorders described herein (e.g. cancer). In one aspect, the second therapeutic agent is a spindle assembly checkpoint activator. A preferred spindle assembly checkpoint activator is paclitaxel or Taxol™. Alternatively, or in addition, the second therapeutic agent is an inhibitor of proteasome-dependent degradation. A preferred inhibitor of proteasome-dependent degradation is MG132.

Taxanes are a family of naturally-occurring or synthetically-produced diterpene compounds that inhibit cell growth and/or division. Exemplary taxanes include paclitaxel (Taxol™), docetaxel (Taxotere®), albumin-bound paclitaxel (Abraxane®), docosahexaenoic acid (DHA)-paclitaxel (Taxoprexin®), and paclitaxel poliglumex (Xyotax®).

The disclosure provides a method of treating a cell proliferative disorder in a subject in need thereof, including administering a composition described herein to the subject.

The disclosure provides a method of inducing cell death of a target cell, including contacting a composition described herein to the cell. According to this method, the target cell is in vivo, in vitro, ex vivo, or in situ. The target cell may represent a cell proliferative disorder.

The disclosure provides a method of inhibiting proliferation of a target cell, comprising contacting a composition described herein to the cell. According to this method, the target cell is in vivo, in vitro, ex vivo, or in situ. The target cell may represent a cell proliferative disorder.

Exemplary, but nonlimiting examples of cell proliferative disorders include cancer, Castleman Disease, Gestational Trophoblastic Disease, or myelodysplastic syndrome. In a preferred embodiment, the cell proliferative disease is cancer. Exemplary, but nonlimiting varieties of cancer include, adrenal cortical cancer, anal cancer, bile duct cancer, bladder cancer, bone cancer, brain or a nervous system cancer, breast cancer, cervical cancer, colon cancer, rectal cancer, colorectal cancer, endometrial cancer, esophageal cancer, Ewing family of tumor, eye cancer, gallbladder cancer, gastrointestinal carcinoid cancer, gastrointestinal stromal cancer, Hodgkin Disease, intestinal cancer, Kaposi Sarcoma, kidney cancer, large intestine cancer, laryngeal cancer, hypopharyngeal cancer, laryngeal and hypopharyngeal cancer, leukemia, acute lymphocytic leukemia (ALL), acute myeloid leukemia (AML), chronic lymphocytic leukemia (CLL), chronic myeloid leukemia (CML), chronic myelomonocytic leukemia (CMML), liver cancer, lung cancer, non-small cell lung cancer, small cell lung cancer, lung carcinoid tumor, lymphoma, lymphoma of the skin, malignant mesothelioma, multiple myeloma, nasal cavity cancer, paranasal sinus cancer, nasal cavity and paranasal sinus cancer, nasopharyngeal cancer, neuroblastoma, non-Hodgkin lymphoma, oral cavity cancer, oropharyngeal cancer, oral cavity and oropharyngeal cancer, osteosarcoma, ovarian cancer, pancreatic cancer, penile cancer, pituitary tumor, prostate cancer, retinoblastoma, rhabdomyosarcoma, salivary gland cancer, sarcoma, adult soft tissue sarcoma, skin cancer, basal cell skin cancer, squamous cell skin cancer, basal and squamous cell skin cancer, melanoma, stomach cancer, small intestine cancer, testicular cancer, thymus cancer, thyroid cancer, uterine sarcoma, uterine cancer, vaginal cancer, vulvar cancer, Waldenstrom Macroglobulinemia, or Wilms Tumor. The cancer or tumor may be primary or metastatic. Alternatively, or in addition, the cancer or tumor may occur in a child or an adult.

Formulations, compositions, compounds, and molecules (drugs, prodrugs) disclosed herein may be mixed or formulated with pharmaceutically acceptable excipients for administration to human or animal subjects. For example, a drug to be administered systemically is formulated as a powder, pill, tablet or the like, or as a solution, emulsion, suspension, aerosol, syrup or elixir suitable for oral or parenteral administration or for inhalation. The compositions or compounds are purified, i.e. isolated from natural sources or chemically synthesized. A purified composition or compound comprises at least 75%, 80%, 90%, or 100% (w/w) of the desired molecule.

Formulations, compositions, compounds, and molecules (drugs, prodrugs) disclosed herein may be administered to a subject locally or systemically by any one of the following routes: topical, intravenous, intraocular, subcutaneous, intraparitoneal, intramuscular, intraspinal, or surgical administration.

The pharmaceutically effective dose depends on the type of disease, the composition used, the route of administration, the individual and physical characteristics of the subject under consideration (for example, age, gender, weight, diet, smoking-habit, exercise-routine, genetic background, medical history, hydration, blood chemistry), concurrent medication, and other factors that those skilled in the medical arts will recognize.

Generally, an amount from about 0.01 mg/kg and 25 mg/kg body weight/day of active ingredients is administered dependent upon potency of the composition containing proTAME or a combination of proTAME and apcin. In alternative embodiments dosage ranges include, but are not limited to, 0.01-0.1 mg/kg, 0.01-1 mg/kg, 0.01-10 mg/kg, 0.01-20 mg/kg, 0.01-30 mg/kg, 0.01-40 mg/kg, 0.01-50 mg/kg, 0.01-60 mg/kg, 0.01-70 mg/kg, 0.01-80 mg/kg, 0.01-90 mg/kg, 0.01-100 mg/kg, 0.01-150 mg/kg, 0.01-200 mg/kg, 0.01-250 mg/kg, 0.01-300 mg/kg, 0.01-500 mg/kg, and all ranges and points in between. In alternative embodiments dosage ranges include, but are not limited to, 0.01-1 mg/kg, 1-10 mg/kg, 10-20 mg/kg, 20-30 mg/kg, 30-40 mg/kg, 40-50 mg/kg, 50-60 mg/kg, 60-70 mg/kg, 70-80 mg/kg, 80-90 mg/kg, 90-100 mg/kg, 100-150 mg/kg, 150-200 mg/kg, 200-300 mg/kg, 300-500 mg/kg, and all ranges and points in between.

The blood plasma concentration of proTAME, TAME, apcin, or the composition containing proTAME or a combination of proTAME and apcin can be about 0.1 $\mu M$ to about 1000 $\mu M$, about 0.1 $\mu M$ to about 1 $\mu M$; about 0.1 $\mu M$ to about 10 LM; about 10 $\mu M$ to about 100 $\mu M$; about 100 $\mu M$ to about 500 $\mu M$, about 500 $\mu M$ to about 1000 $\mu M$, and any micromolar concentration in between. Alternatively, or in addition, the cerebral spinal fluid concentration of proTAME, TAME, apcin, or the composition containing proTAME or a combination of proTAME and apcin can be about 0.1 $\mu M$ to about 1000 $\mu M$, about 0.1 $\mu M$ to about 1 LM; about 0.1 $\mu M$ to about 10 $\mu M$; about 10 $\mu M$ to about 100 $\mu M$; about 100 $\mu M$ to about 500 $\mu M$, about 500 $\mu M$ to about 1000 $\mu M$, or any micromolar concentration in between.

The pharmaceutical composition can be administered at a dosage from about 1 mg/m$^2$ to 5000 mg/m$^2$ per day, about 1 mg/m$^2$ to 10 mg/m$^2$ per day, about 10 mg/m$^2$ to 100 mg/m$^2$ per day, about 100 to 1000 mg/m$^2$ per day, about 1000 to 2500 mg/m$^2$ per day, about 2500 to 5000 mg/m$^2$ per day, or any daily mg/m$^2$ dosage in between. Preferably, 1 mg/m$^2$ to 5000 mg/m$^2$ per day is the administered dosage for a human.

Subjects of the disclosure either present a sign or symptom of a cell proliferative disease and/or have been diagnosed with a cell proliferative disease. A sign is an external and visible indication that something is not right in the body. Signs are signals that can be observed by family members, colleagues, and medical professionals. For instance, a fever, abnormal or labored breathing, or abnormal lung sounds heard through a stethoscope are examples of signs. A symptom is a different kind of signal of disease, illness, injury, or that something is not right in the body. Symptoms are only felt or noticed by the person who has them, but are not usually obvious to the outside observer. For example, fatigue, pain, and feeling short of breath are examples of symptoms.

Typical signs or symptoms include, but are not limited to, tumors (benign or malignant), pain (for instance, as a tumor grows and exerts pressure on surrounding vasculature and organs), fever, fatigue, weight loss (as the proliferating cells drain energy resources from the body), changes to immune system function (decreased immune function or autoimmune episodes), presence of secreted factors in the bloodstream (from a cell mass or the metastasis thereof), weakness, dizziness, and blood clots (particularly in the legs), unexplained bleeding, the appearance of wounds or sores and, optionally, the inability of these wounds to heal, and visible changes to the skin (e.g., melanoma).

Preferably, subjects are human; however, subjects of all animal species are contemplated. In particular, preferred animal species include, worm (e.g., C. elegans), frog (e.g., Xenopus), mouse, rat, guinea pig, ferret, bird, feline/cat (domestic and wild), canine/dog (domestic and wild), livestock (cattle, goats, sheep, swine), horse, and non-human primates (e.g. macaque, marmoset, tamarin, spider monkey, owl monkey, vervet monkey, squirrel monkey, baboon as well as great apes (gorillas, chimpanzees, and orangutans)). Subjects encompass both males and females. Subjects are of any age, including, but not limited to, neonatal, infant, child, adult, and elderly populations. Subjects may receive other therapies prior to, concurrently with, or following administration of the compositions and formulations of the disclosure.

All references cited herein are hereby incorporated by reference.

BRIEF DESCRIPTION OF THE DRAWINGS

FIG. 6 is a series of photographs showing that Mad2 knockdown efficiently overrides the spindle assembly checkpoint in the presence of nocodazole. Asynchronous HeLa H2B-GFP cells were transfected with Mad2 siRNA 24 h prior to treatment with 300 nM nocodazole. Live imaging was done at 40× magnification and 3 min interval.

FIG. 7A is a graph showing the effects of Mad2 knockdown on proTAME-induced mitotic arrest determined by DIC imaging. Asynchronous HeLa cells were transfected with Mad2 or control siRNA. 24 h after transfection, the cells were treated with 0.06% DMSO, 12 μM proTAME, 300 nM nocodazole or 12 μM proTAME plus 300 nM nocodazole. DIC imaging was performed for 48 h at 15 min interval.

FIG. 7B is a graph of cumulative frequency and cell fate distribution based on the results of FIG. 7A. The mitotic duration of each division was determined and cumulative frequency curves and cell fate distributions were plotted.

FIG. 9A is a graph showing that fluorescence imaging accelerates proTAME-induced cell death. HeLa H2B-GFP cells were treated with 12 μM proTAME or 0.06% DMSO. Live cell imaging was performed using differential interference contrast (DIC) optics for 48 h at 15 min intervals. For comparison, the curves obtained in H2B-GFP fluorescent imaging experiment shown in FIG. 1B were plotted on the same graph.

FIG. 9B is a graph of cumulative frequency and cell fate distribution based on the results of FIG. 9A. Mitotic duration of each division was determined and cumulative frequency curves and cell fate distributions were plotted.

FIG. 10A is a series of schematic diagrams depicting the structures of TAME and AAME.

FIGS. 10B-F are a series of immunoblots showing that TAME inhibits APC activation by perturbing binding of Cdc20 or Cdh1. (B) TAME induces mitotic arrest in *Xenopus* extract. Recombinant cyclin B1/Cdk1 was added to interphase extract in the presence of compounds. Cdc27 phosphorylation and cyclin B1 levels were examined by immunoblot. (C) TAME inhibits APC activation. Compounds were added to mitotic *Xenopus* extract immediately before APC immunoprecipitation. The activity of the isolated APC was measured in a reconstituted assay. (D) TAME inhibits Cdc20 association with mitotic APC. Compounds were added to mitotic *Xenopus* extract prior to APC immunoprecipitation. Numbers represent CCD-imaging based-intensity quantitation of the immunoblot, and show the relative amount of Cdc20 normalized to Cdc27. (E) TAME inhibits Cdh1 association with interphase APC. Interphase *Xenopus* extract was pre-incubated with compounds for 30 min prior to adding recombinant Cdh1 and APC immunoprecipitation. (F) TAME inhibits APC activation by Cdh1. Interphase *Xenopus* extract was pre-incubated with compound for 30 min prior to adding recombinant Cdh1 and APC immunoprecipitation. The activity of the isolated APC was measured in a reconstituted assay.

FIG. 12D is a series of schematic diagrams of Cdc20, the C-box containing fragment, and structures of the IR tail and TAME.

FIG. 12E is a pair of immunoblots showing that TAME inhibits the interaction between the Cdh1 C-terminal IR peptide and the APC. Left: Resin coupled with cysteine (Ctrl resin), Cdh1 C-terminal peptide (WT), or the peptide lacking the C-terminal isoleucine and arginine (ΔIR) was incubated with interphase *Xenopus* extract, washed, and the amount of bound Cdc27 was analyzed by immunoblot. Right: Cdh1 C-terminal resin was incubated with interphase extract in the presence of compounds and the amount of Cdc27 was analyzed as above.

FIG. 12F is an immunoblot showing that TAME does not inhibit the interaction between the C-box and the APC. A 159-amino acid N-terminal fragment of Cdc20 containing the C-box fused to GST (GST-CDC20 N159 WT) or the same fragment lacking the C-box (GST-CDC20 N159 ΔC-box) were bound to glutathione resin and incubated with mitotic *Xenopus* extract in the presence of compounds. Bound Cdc27 was analyzed by immunoblot.

FIG. 13A is a graph depicting the ability of TAME derivatives to compete with $^3$H-TAME for binding to the APC correlates with their ability to inhibit cyclin B-luciferase degradation. Two hundred nM $^3$H-TAME was added into interphase extract with 10 µM of unlabeled TAME derivatives before Cdc27 immunoprecipitation, and the amount of bound radioactivity was determined by scintillation counting. Specific binding was obtained by subtracting the value of mock IP (IP without Cdc27 antibody). The relative levels of competition correlate with the trends seen in the cyclin-luciferase assay as shown in FIG. 11C.

FIG. 13B is an immunoblot showing that Cdh1 C-terminal peptide crosslinks to the TPR subcomplex in an IR-dependent manner. An IR peptide coupled to a photocrosslinker labels a subset of APC subunits. Left: Coomassie stain of APC immunopurified from interphase Xenopus extract. Right: APC subunits crosslinked by the labeled IR peptide. Identity of APC subunits was confirmed by mass spectrometry.

FIG. 13C is an immunoblot showing that crosslinking is IR-dependent. The crosslinking assay was performed in the presence of excess unlabeled IR peptide with the N-terminal cysteine blocked with N-ethyl maleimide (NEM) (lane 2), no UV illumination (lane 3) or with labeled ΔIR peptide (lane 4).

FIG. 15A is a series of schematic diagrams depicting structures of proTAME and proAAME.

FIG. 15B is a graph showing that proTAME inhibits APC activity in Xenopus extract and inhibits Cdh1-dependent APC activity during interphase in HeLa cells. ProTAME inhibits cyclin B-luciferase degradation in mitotic Xenopus extract. Different concentrations of proTAME or proAAME were added to mitotic Xenopus extract containing cyclin B-luciferase reporter. Samples were collected at 60 min and the remaining reporter level was measured by luminescence.

FIG. 17A is a schematic diagram depicting the experimental timeline and a graph showing that proTAME induces mitotic arrest in HeLa cells. Double thymidine synchronized HeLa H2B-GFP cells were treated with compounds and analyzed by time-lapse imaging. Cumulative frequency curves of mitotic duration and cell fate distributions are shown.

FIG. 17D is a series of photographs of immunohistochemistry and accompanying graphs showing that proTAME stabilizes exogenous cyclin B1-GFP and cyclin A2-GFP in HeLa cells. HeLa H2B-RFP cells transduced with cyclin-GFP adenoviruses were treated with 20 µM proTAME or proAAME, or 150 nM nocodazole. Representative cells are shown. For quantitation, the fraction of GFP intensity remaining at 60 min as compared to the onset of mitosis was determined (n≥30 individual cells per treatment). Error bars represent standard error of the mean.

FIG. 17E is a series of photographs of immunohistochemistry and an accompanying graph showing that proTAME does not disrupt mitotic spindles or alter interkinetochore distance. Asynchronous HeLa cells were treated with compounds for 2 h, and then stained with anti-tubulin (green) and CREST (red) antibody. Representative images are shown. Bar: 3 µm. Representative images of kinetochore pairs are shown. Bar: 1.2 µm. Inter-kinetochore distance was measured in DMSO or proTAME treated cells (n=55, P=0.23). Error bars represent standard deviation.

FIG. 18A is a graph and table showing that proTAME induces a mitotic delay in hTERT-RPE1 H2B-GFP cells. Asynchronous hTERT-RPE1 H2B-GFP cells were treated with 0.06% DMSO, 6 μM proTAME or 12 μM proAAME. Cells were imaged at 12 min interval. Cumulative frequency curves of mitotic duration and cell fate distribution are shown.

FIG. 18B is a series of immunoblots showing that partial Cdc20 knockdown sensitizes HeLa H2B-GFP cells to proTAME treatment. HeLa H2B-GFP cells were plated in 24-well plates and transfected with indicated siRNAs. Control siRNA#3 was added to final 18.5 nM siRNA concentration in wells with decreasing Cdc20 siRNA concentration. Cells were lysed 48 h after transfection and lysates were subjected to western blotting to detect Cdc20 and GAPDH. Protein level quantification was performed on a LiCor Odyssey scanner as described in Material and Methods.

FIG. 18C is a graph showing that a high concentration of proTAME induces a mild delay in chromosome congression. HeLa H2B-GFP cells were synchronized by double thymidine block and treated with 0.06% DMSO, 3 μM proTAME, 12 μM proTAME, 10 μM MG132 or 10 nM nocodazole at 8 h after release. Cells were imaged at 3 min interval and 40× magnification. The time between prophase and full metaphase congression was analyzed. Cumulative frequency curves of the congression time were plotted.

FIG. 19C is a schematic diagram depicting the experimental timeline and a graph showing that proTAME-induced mitotic arrest is hesperadin-sensitive. Double thymidine synchronized HeLa H2B-GFP cells were treated with compounds 8 h following release.

FIG. 28A is a diagram depicting the structure of cyclinal.

FIG. 28B is a graph showing that apcin stabilizes a cyclin B1-luciferase reporter in mitotic *Xenopus* extract. Different concentrations of cyclinal were added to the extract and the amount of the reporter remaining at 60 min was measured by luminescence.

FIG. 28C is a graph and corresponding diagrams that depict the structure activity relation of cyclinal. Compounds were added to the extract at 200 μM. The amount of the reporter remaining at 60 min was measured by luminescence.

FIG. 28D is a photograph of Western blot showing that cyclinal stabilizes full length cyclin B1 in *Xenopus* extract. Recombinant human cyclin B1/Cdk1 was added to interphase extract at 200 nM and cyclinal was added to the extract at 200 μM. Samples were collected at indicated time points and the level of cyclin B1 was analyzed by Western blot.

FIG. 28E is a photograph of a Western blot showing that cyclinal reduces the level of APC-ubiquitination in vitro. Cyclinal was added to the reconstituted in vitro APC ubiquitination assay at 200 μM. An HA-tagged cyclin B1 N-terminal fragment (cycB-NT) was added to the reaction at 500 nM. Samples were collected at indicated time points and ubiquitinated cycB-NT was detected by anti-HA blot.

FIG. 28F is a photograph of a Western blot and a corresponding graph showing that cyclinal increases of the $K_m$ of $APC^{Cdc20}$ but does not affect the $k_{cat}$. An APC kinetics assay was run with different concentrations of cycB-NT (from left to right: 62.5, 125, 250, 500 and 1000 nM) and methylated ubiquitin. The reaction was stopped at 45 seconds and the products were detected by anti-HA blot. Band intensity of the mono- and di-ubiquitinated substrate was quantitated and plotted against substrate concentration. Data were fit to a hyperbolic curve by nonlinear regression. *An SDS-resistant aggregated form of substrate.

FIG. 29A is a pair of photographs of Western blots showing that cyclinal resin depletes Cdc20 from mitotic (top) and interphase (bottom) *Xenopus* extracts. Affigel resin coupled with amino-cyclinal was incubated with mitotic or interphase extracts. As a comparison, a Cdc27 IP was performed in parallel. The levels of Cdc27 and Cdc20 before and after depletion were analyzed by Western blot.

FIG. 29B is a graph showing that cyclinal resin-depleted extract cannot degrade the luciferase reporter, which can be rescued by adding in vitro-translated Cdc20. Mitotic extract was subjected to two rounds of cyclinal resin depletion. The depleted extract was divided into 3 parts. Two parts were supplemented with in vitro-translated Cdc20 and 200 μM TAME was added to one of them. The luciferase assay was then run with the 3 parts separately.

FIG. 29C is a pair of photographs of Western blots showing that Cdc20 binding to the cyclinal resin can be competed by free cyclinal. Cyclinal resin was incubated with in vitro-translated Cdc20 and different concentrations of free cyclinal or the inactive morpholino derivative as indicated. The amount of resin bound Cdc20 was analyzed by Western blot.

FIG. 29D is a photograph of a Western blot showing that Cdc20 binding to the cyclinal resin can be competed by cycB-NT in a D-box dependent manner. Cyclinal resin was incubated with in vitro-translated Cdc20 and different concentrations of cycB-NT or the D-box mutants as indicated. The amount of resin bound Cdc20 was analyzed by Western blot.

FIG. 29E is a photograph of a Western blot showing that Cdc20 binding to the cyclinal resin can be competed by a stapled D-box peptide. Cyclinal resin was incubated with in vitro-translated Cdc20 and different concentrations of the stapled D-box peptide. The amount of resin bound Cdc20 was analyzed by Western blot.

FIG. 29F is a pair of photographs of Western blots showing that TAME and cyclinal synergize to induce Cdc20 dissociation from the APC in mitotic extract. The extract was incubated with various components as indicated and the APC was immunoprecipitated by Cdc27 IP. The amount Cdc27 and Cdc20 bound to beads was analyzed by Western blot.

FIG. 29G is a graph showing that TAME and cyclinal synergize to stabilize APC substrates in mitotic extract. The extract was either untreated or supplemented with 2 µM UbcH10, 2 µM Ube2s and 20 µM ubiquitin. TAME (200 µM) and/or cyclinal (200 µM) were added to the extract as indicated. Degradation of the luciferase reporter was then measured.

FIG. 31A is a series of photographs of Western blots showing that cyclinal reduces the binding of BubR1 and Mad2 to Cdc20. Cdc20 was immunoprecipitated from lysates from cells arrested with nocodazole or nocodazole and cyclinal. The amount of BubR1 and Mad2 co-isolated with Cdc20 was measured by Western blot.

FIG. 31B is a series of photographs of Western blots showing that cyclinal partially stabilizes Cdc20 in nocodazole-arrested cells. Double thymidine synchronized HeLa cells were treated with nocodazole and cyclinal at 8 h after release from thymidine. Samples were collected at indicated time points and protein levels were analyzed by Western blot.

FIG. 32C is a series of photographic frames of images of live cells showing that cyclinal and proTAME-induced mitotic arrest is roscovitine-insensitive. Double thymidine synchronized HeLa cells were transfected with Cdc20 siRNA between the two thymidine blocks, or treated with nocodazole or proTAME at 8 h after release from thymidine, or MG132 at 10 h after release. The cells were then treated with 100 µM roscovitine at 12 h after release. Representative frames from live cell imaging are shown.

FIG. 35A is a series of photographs showing that apcin-M and TAME do not inhibit binding of Cdc20 to apcin-A resin. Experiment was performed as shown in FIG. 40e except that the inactive apcin-M or the Cdc20-IR tail antagonist TAME were also tested and Cdc20 was detected by autoradiography.

FIG. 35B is a series of photographs of representative autoradiographs of WD40 proteins corresponding to chart in FIG. 1f. b=bound, i=5% input, c=bound to empty resin (control).

FIG. 35C is a pair of photographs of experiment 1 also shown in FIG. 40h. An APC/C kinetics assay was run with methylated ubiquitin and different concentrations of HA-tagged Cyclin B1 N-terminal fragment (Cyclin B1-NT): from left to right 62.5, 125, 250, 500 and 1000 nM. The reaction was stopped at 45 seconds and the products were detected by anti-HA blot. * indicates an SDS-resistant aggregated form of substrate.

FIG. 36A is a pair of schematic diagrams depicting the overlay of the structure of the Cdc20-apcin structure with the structure of a D-box-substrate bound to Cdh1 (He, J. et al. Mol Cell 50, 649-660, (2013)). The trichloromethyl group of apcin projects into a hydrophobic pocket that is occupied by the leucine of the RXXL motif of the D-box. The position of the arginine from the RXXL motif supports a role for E465 of Cdc20 in a charge-based interaction with the D-box, consistent with data that the E465S mutation disrupts the ability of Cdc20 to promote substrate degradation more than it perturbs apcin binding.

FIG. 36B is a photograph showing that three rounds of depletion with anti-Cdc20 antibody covalently coupled to protein A beads depletes endogenous Xenopus Cdc20 from mitotic extract while depletion with IgG covalently coupled to protein A beads does not reduce endogenous Cdc20 levels.

FIG. 38A is a schematic diagram showing a summary of the assay and data processing methods to determine synergy between apcin and proTAME using a fixed-cell imaging assay.

Figure 38A:
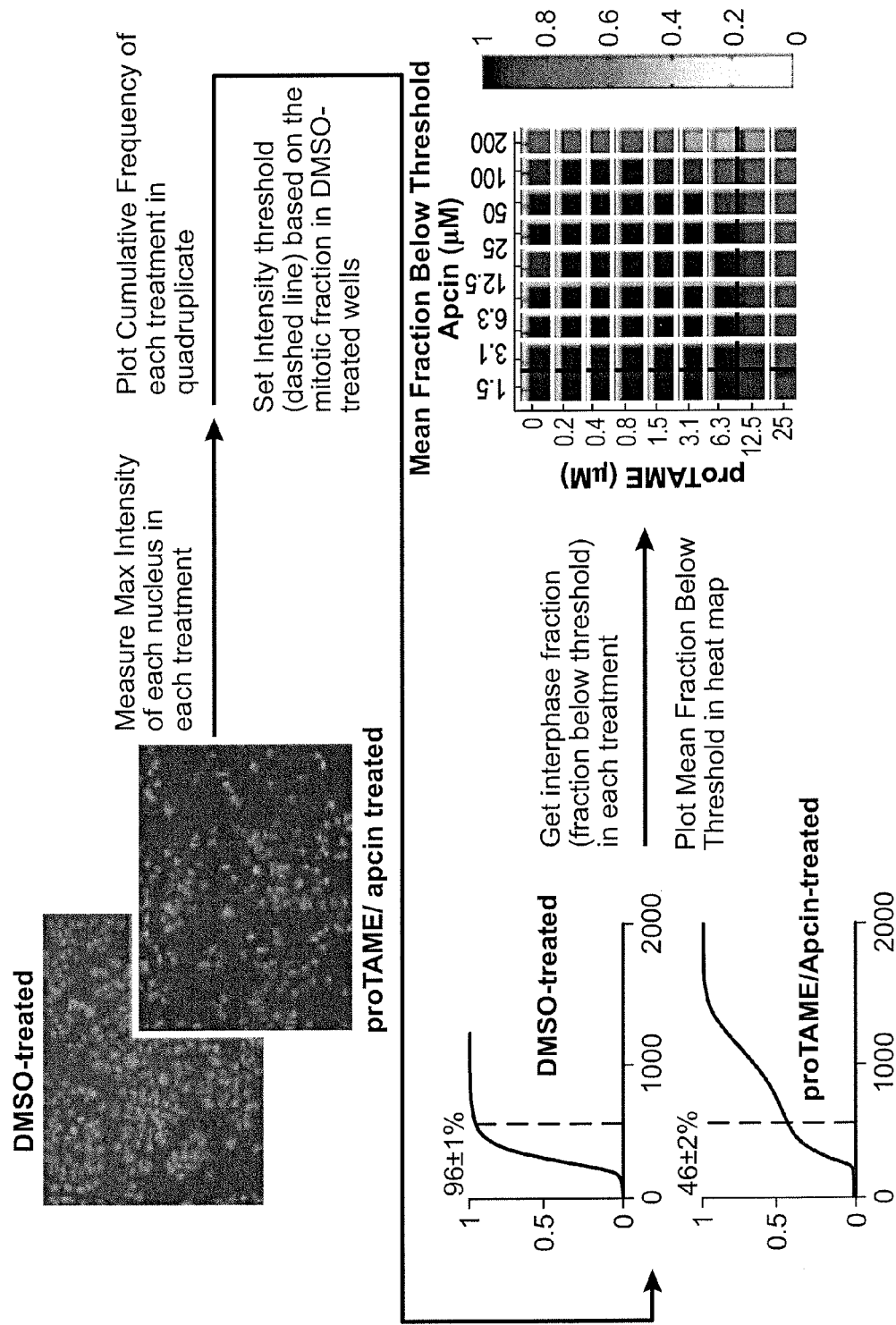
Figure 38A:
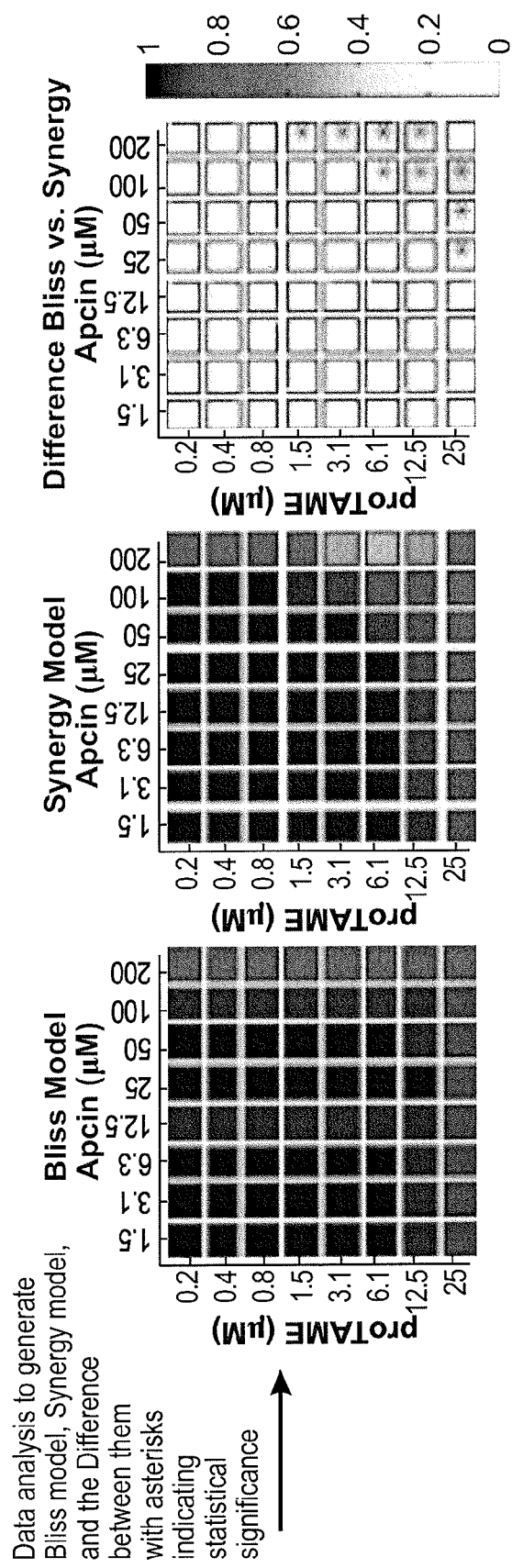
Figure 38B:
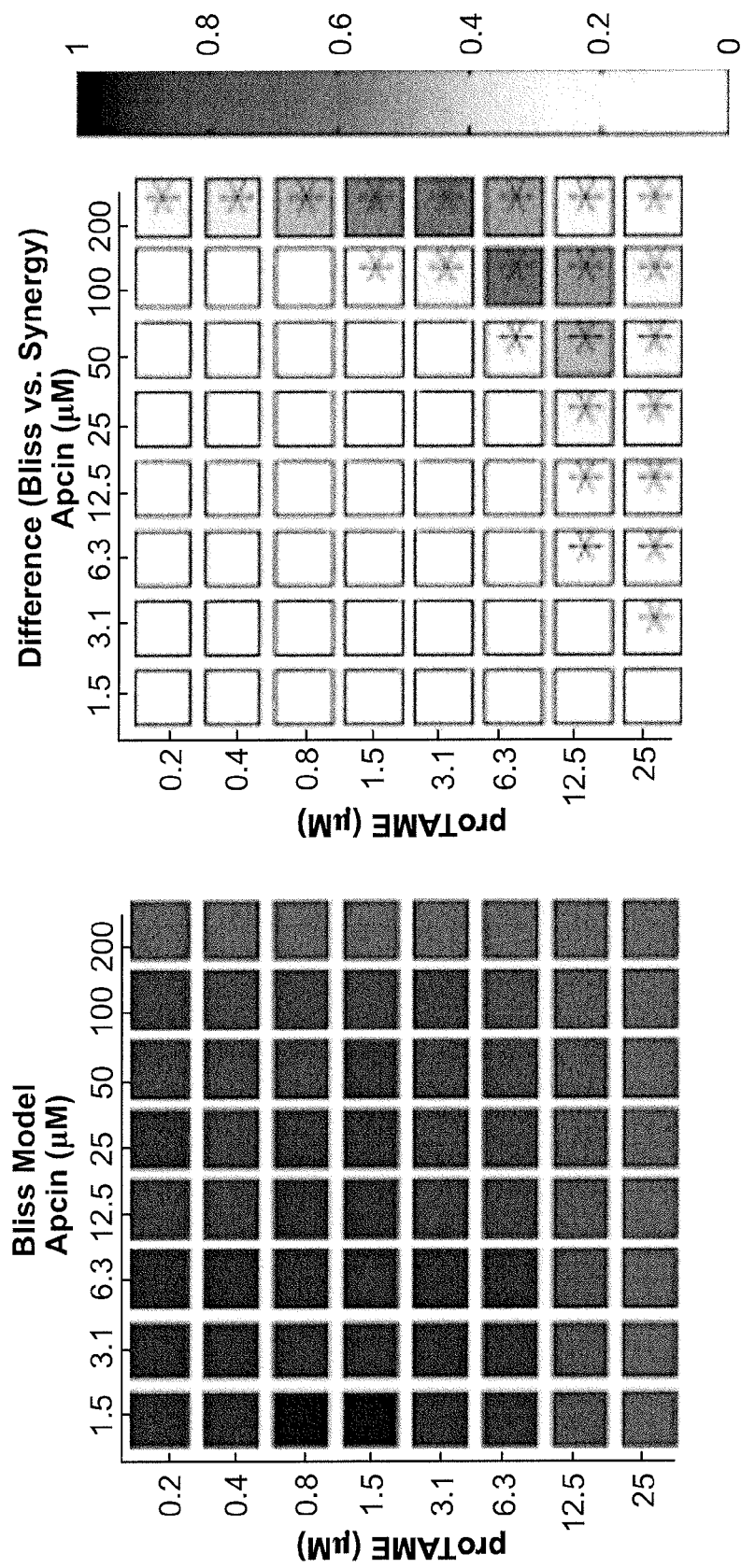
Figure 38B:
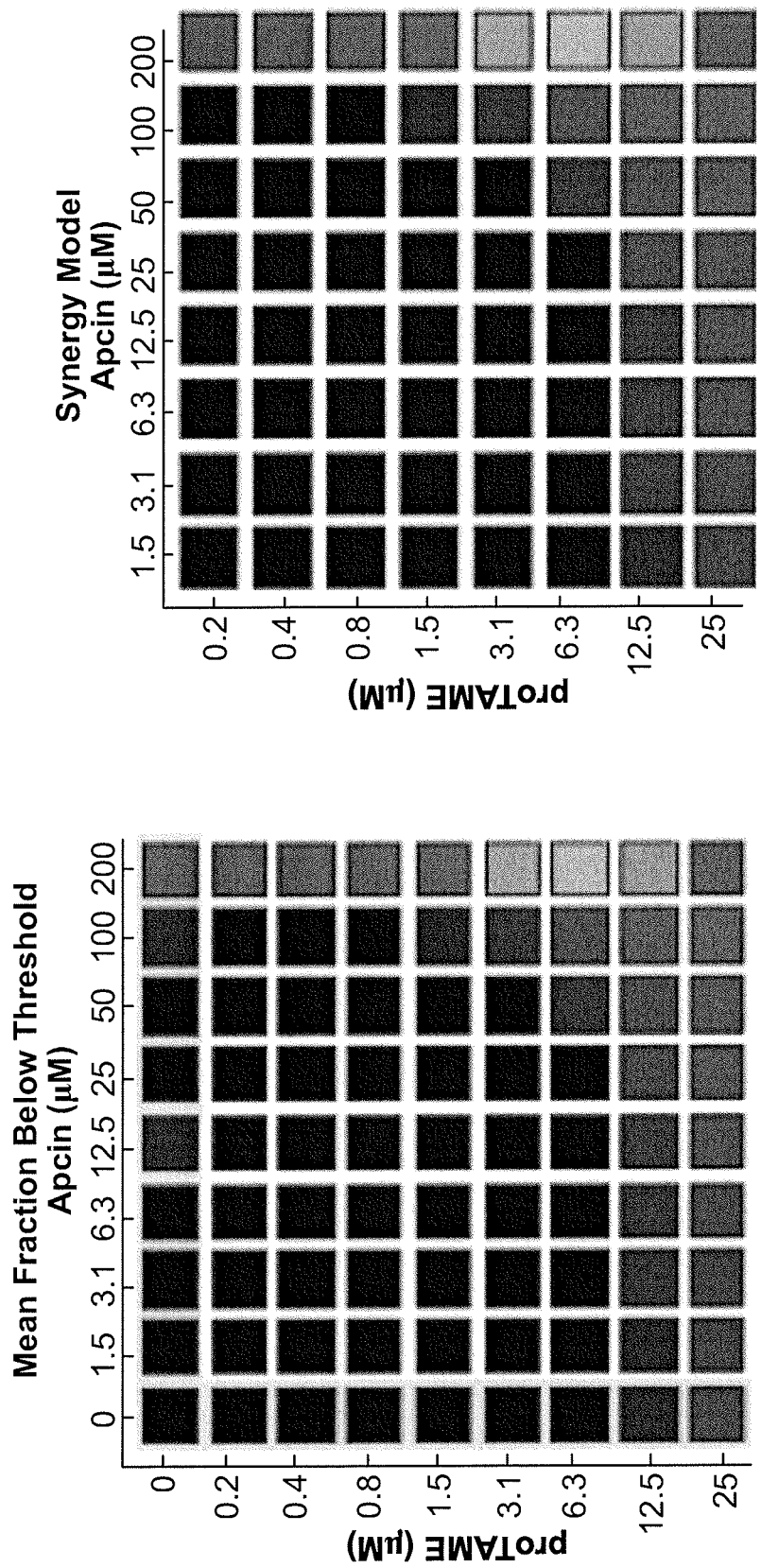
Figure 38B:
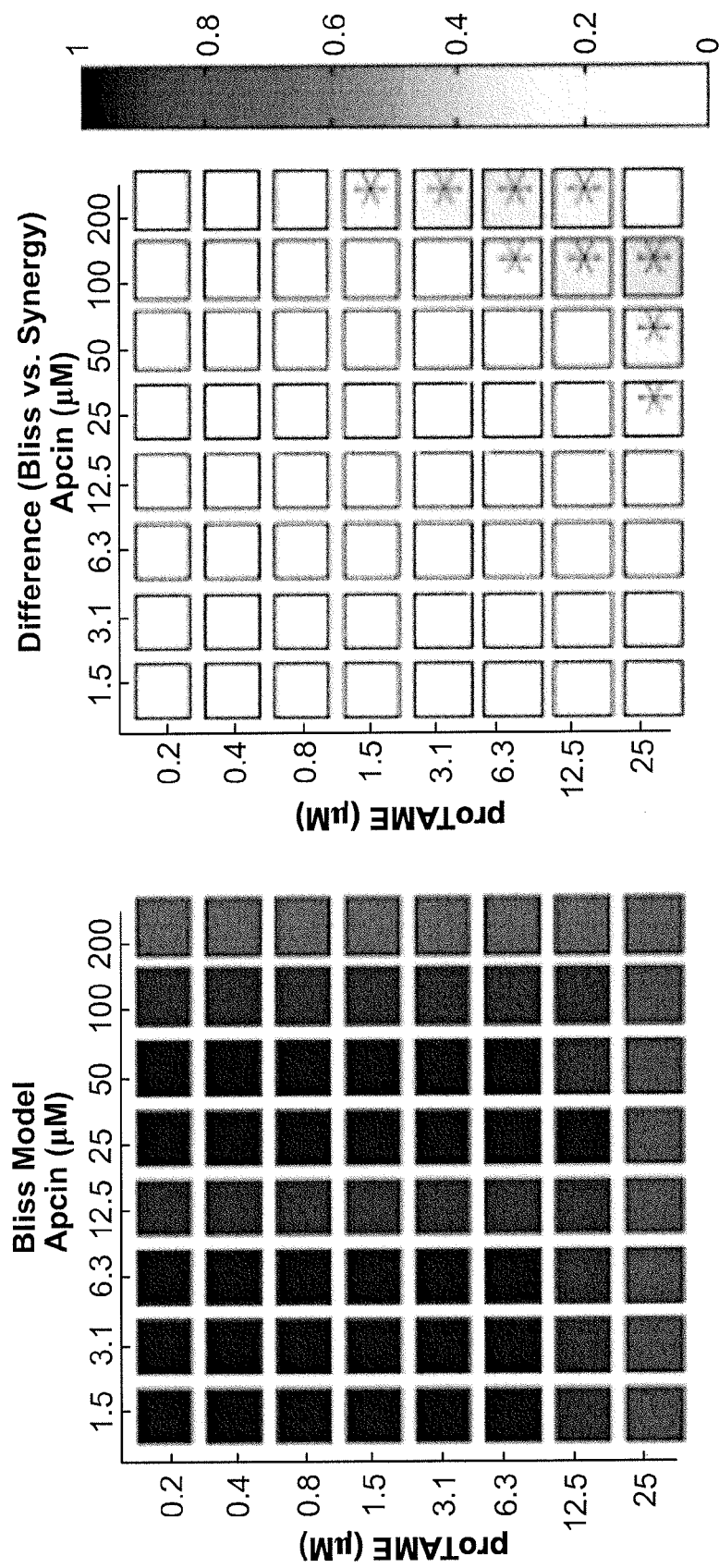
Figure 38B:
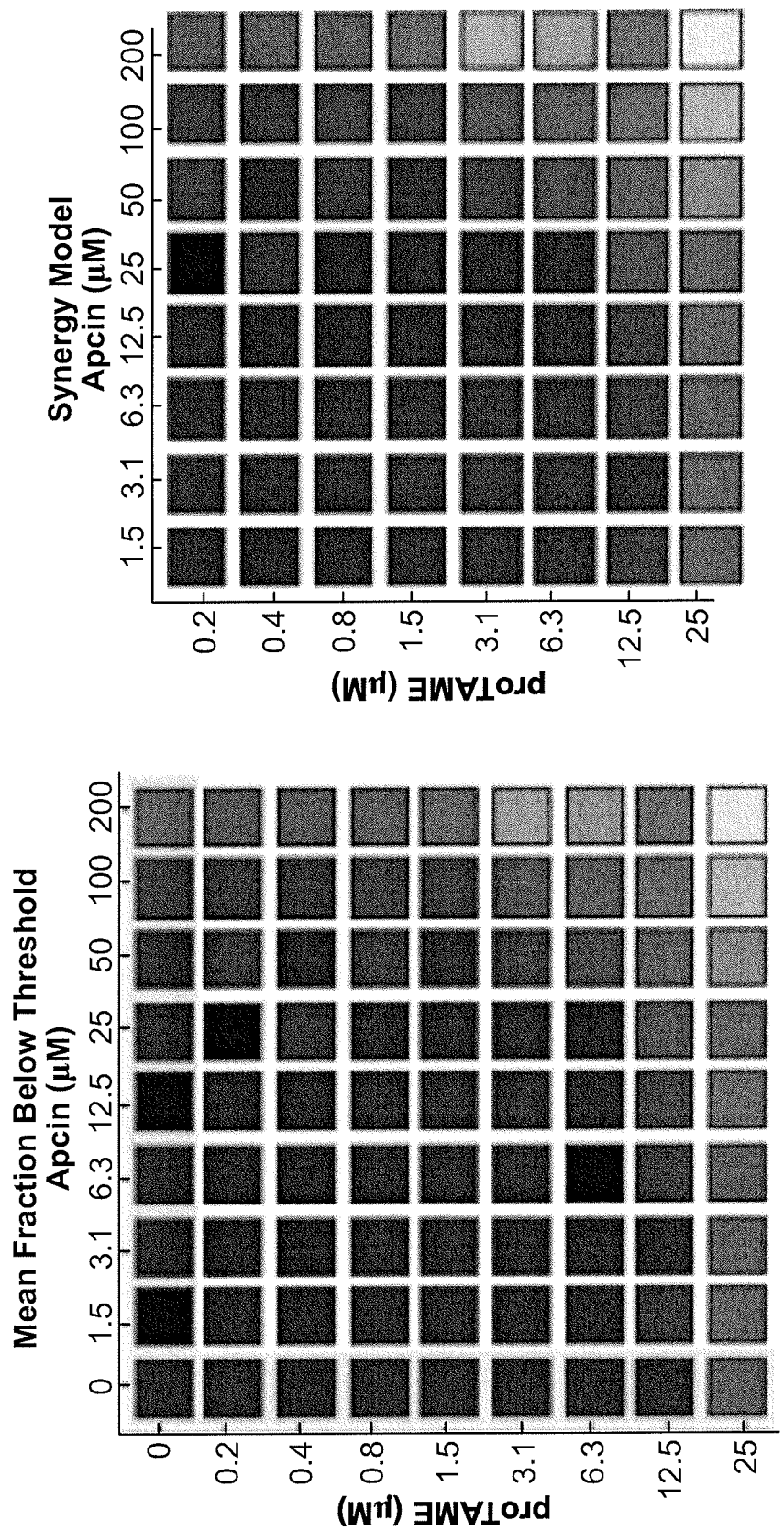
Figure 38B:
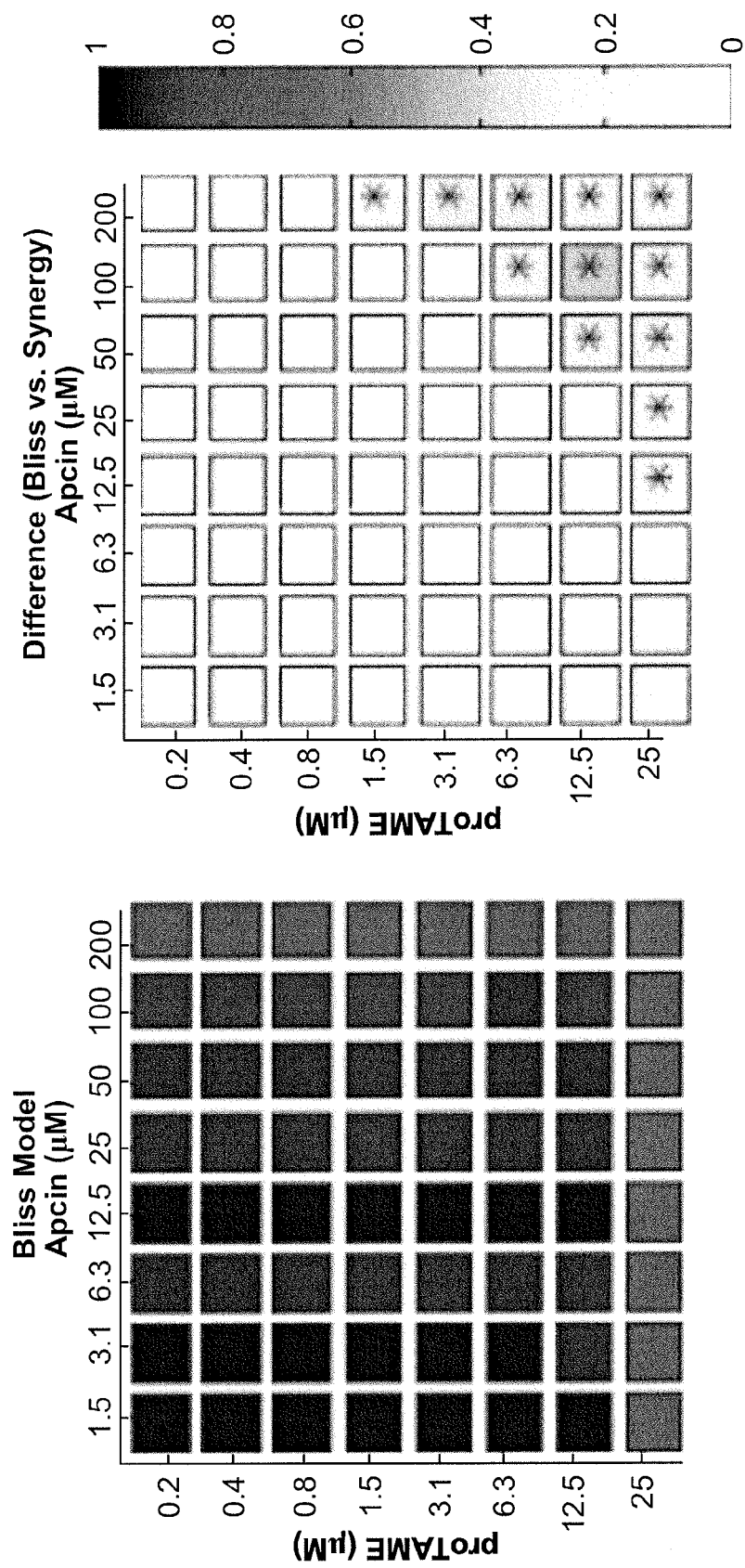
Figure 38B:
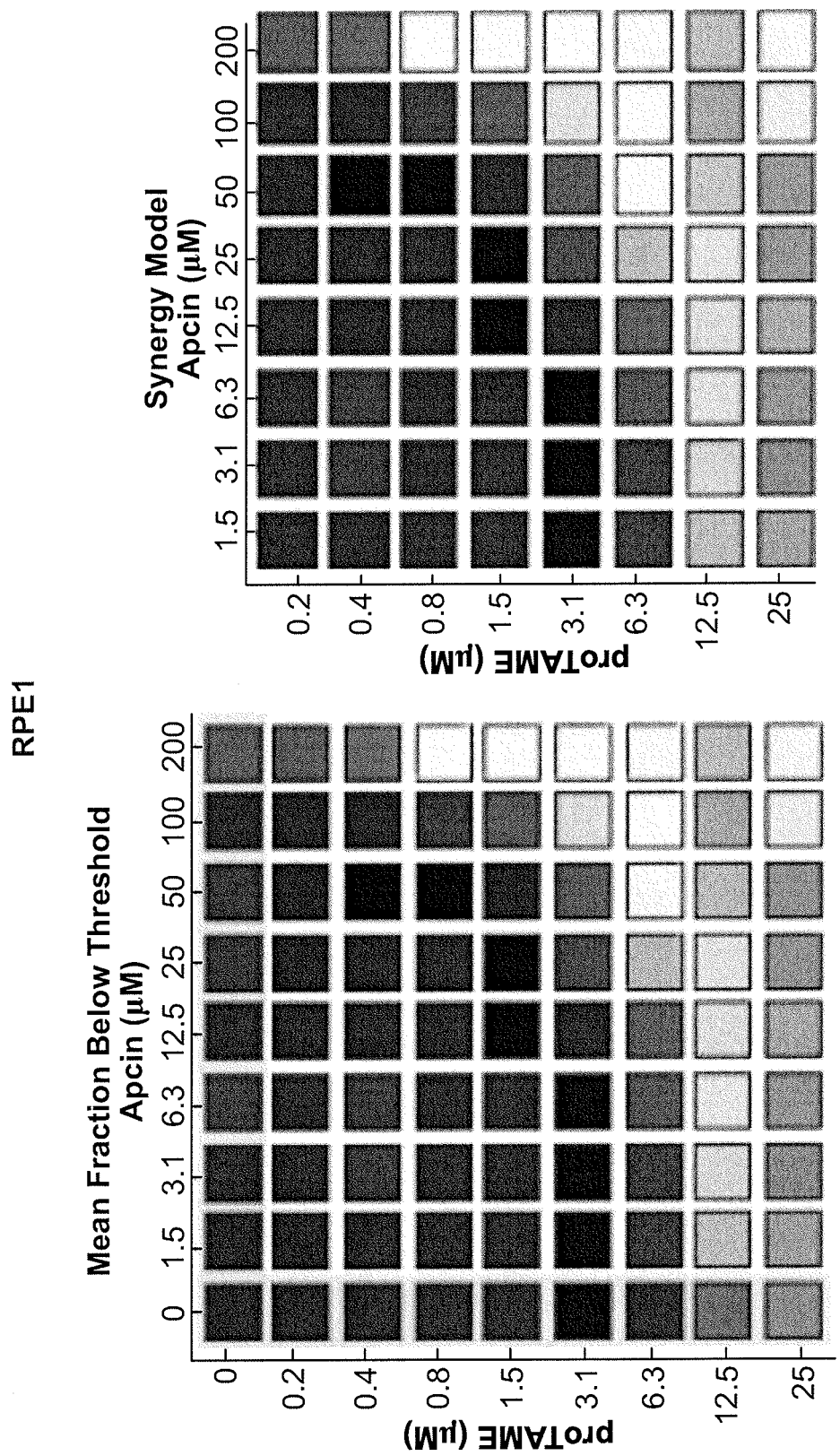
Figure 38B:
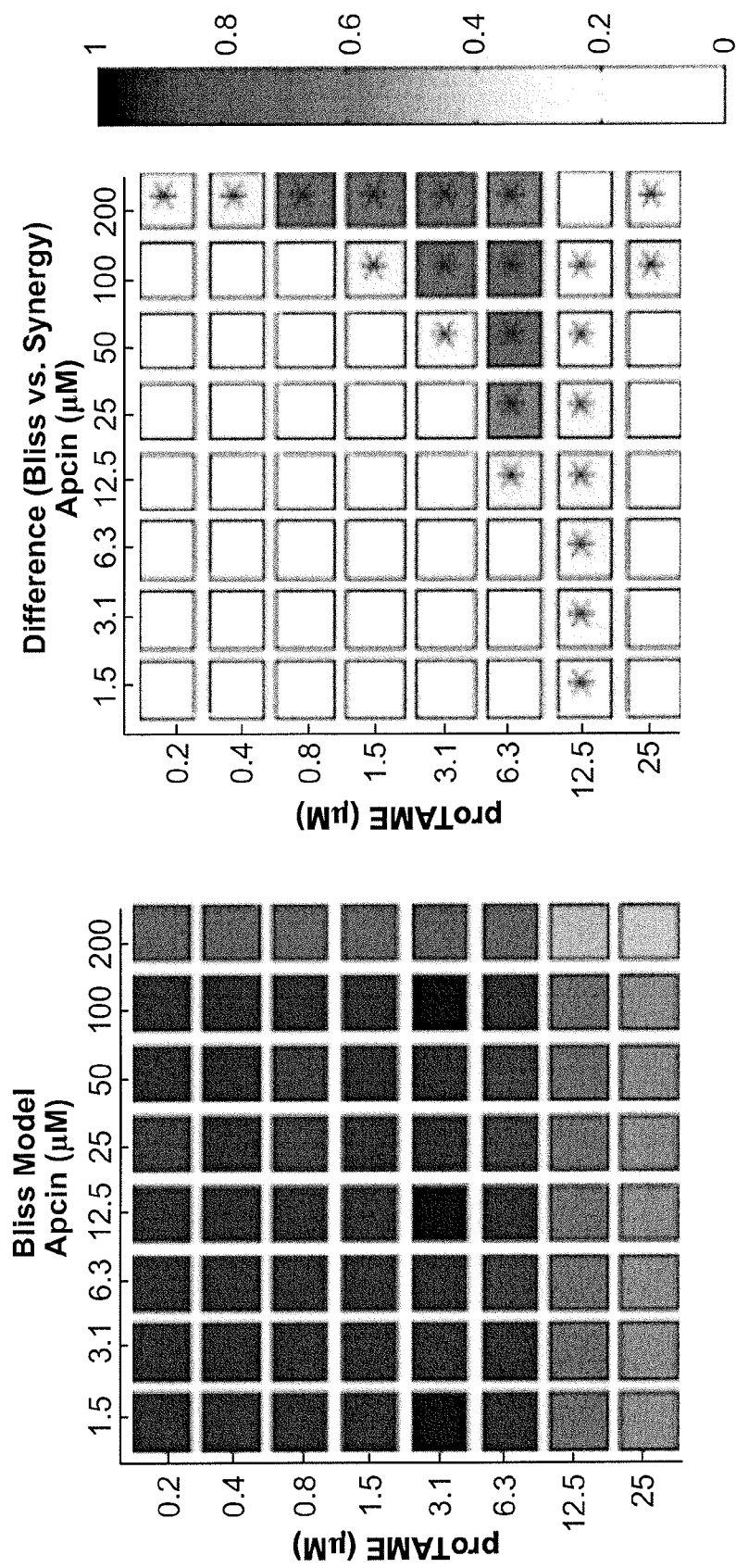

FIG. 38B is a series of heat maps showing multiple methods of analysis. First column (far left vertical column): Primary data plotted as a heat map displaying Mean Fraction Below Threshold for each drug treatment concentration in each of four cell lines. Note that a high value in this column indicates a low mitotic index. Effects of single drugs alone are highlighted in pale purple. Second column (labeled "Synergy Model"): Calculated effect of the combination of drugs based on a model that permits synergistic interaction between proTAME and apcin. Because this panel shows calculated values, the effects of individual drugs are not shown. Note that the synergy model closely parallels the actual data shown in the first column. Third column: Calculated effect of the combination of drugs based on a model that permits only multiplicative interaction between proTAME and apcin (Bliss Model). Because this panel shows calculated values, the effects of individual drugs are not shown. Note that the Bliss model does not closely parallel the actual data shown in the first column. Fourth column: Heatmap of the difference between the Synergy and Bliss model predictions shows the degree of synergy at each drug dose combination (same as FIG. 43a).

Figure 38C:
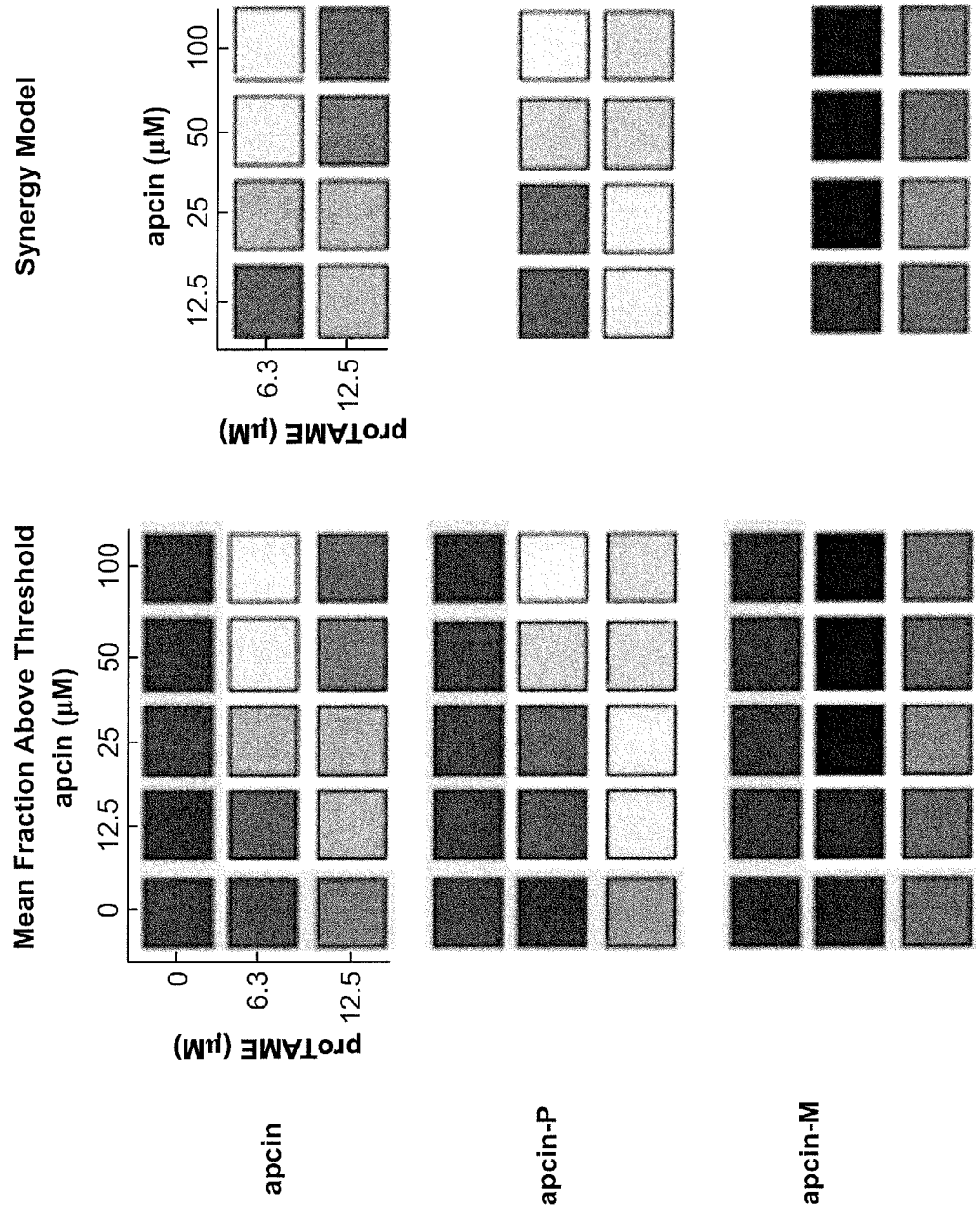
Figure 38C:
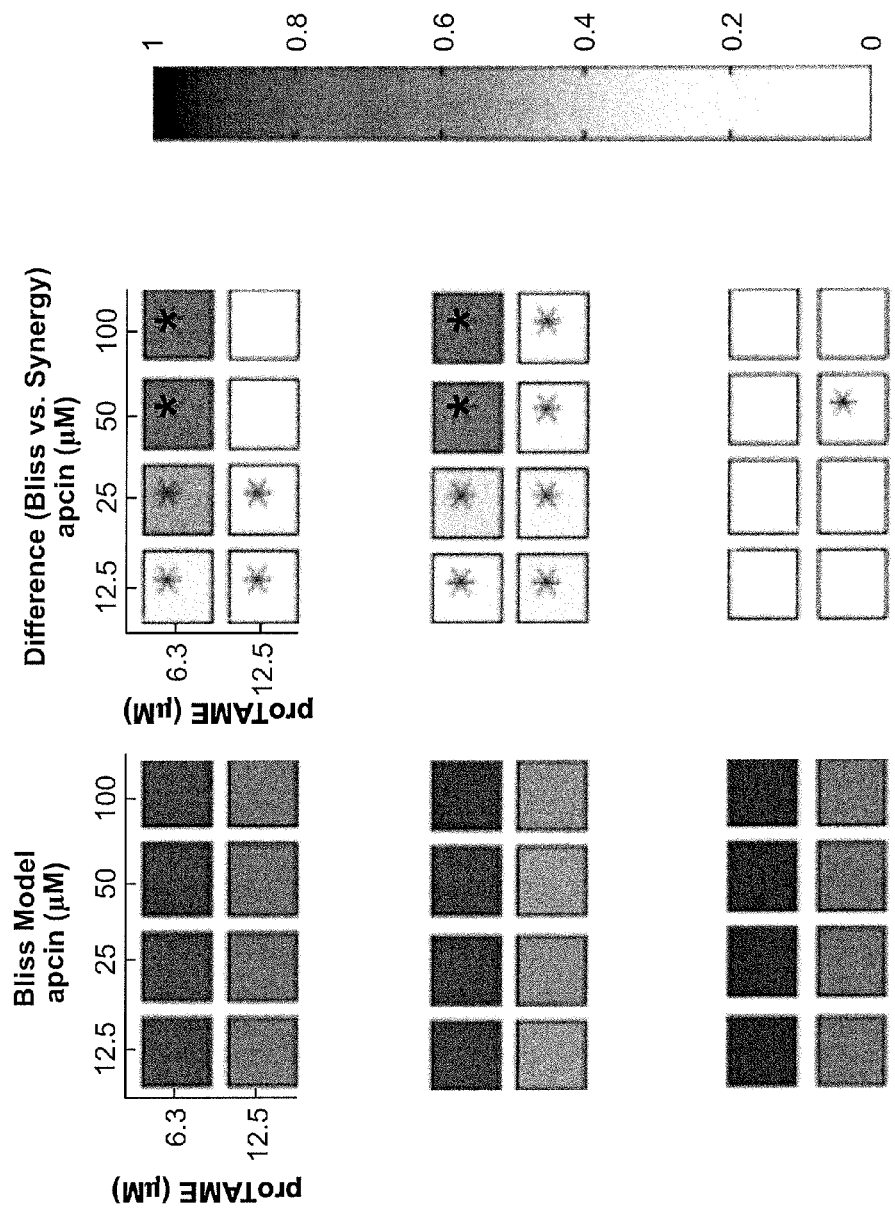
Figure 43A:
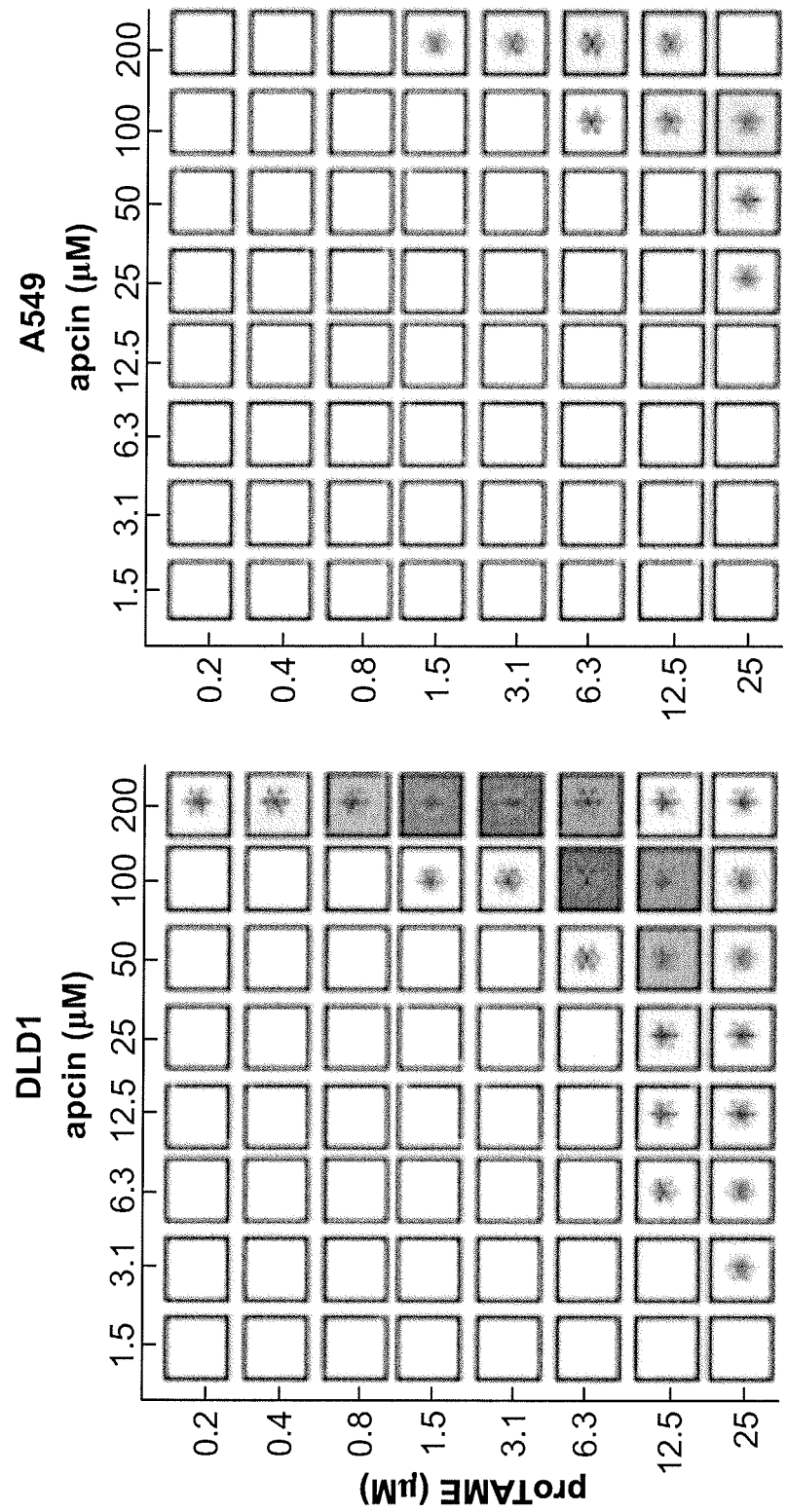
Figure 43A:
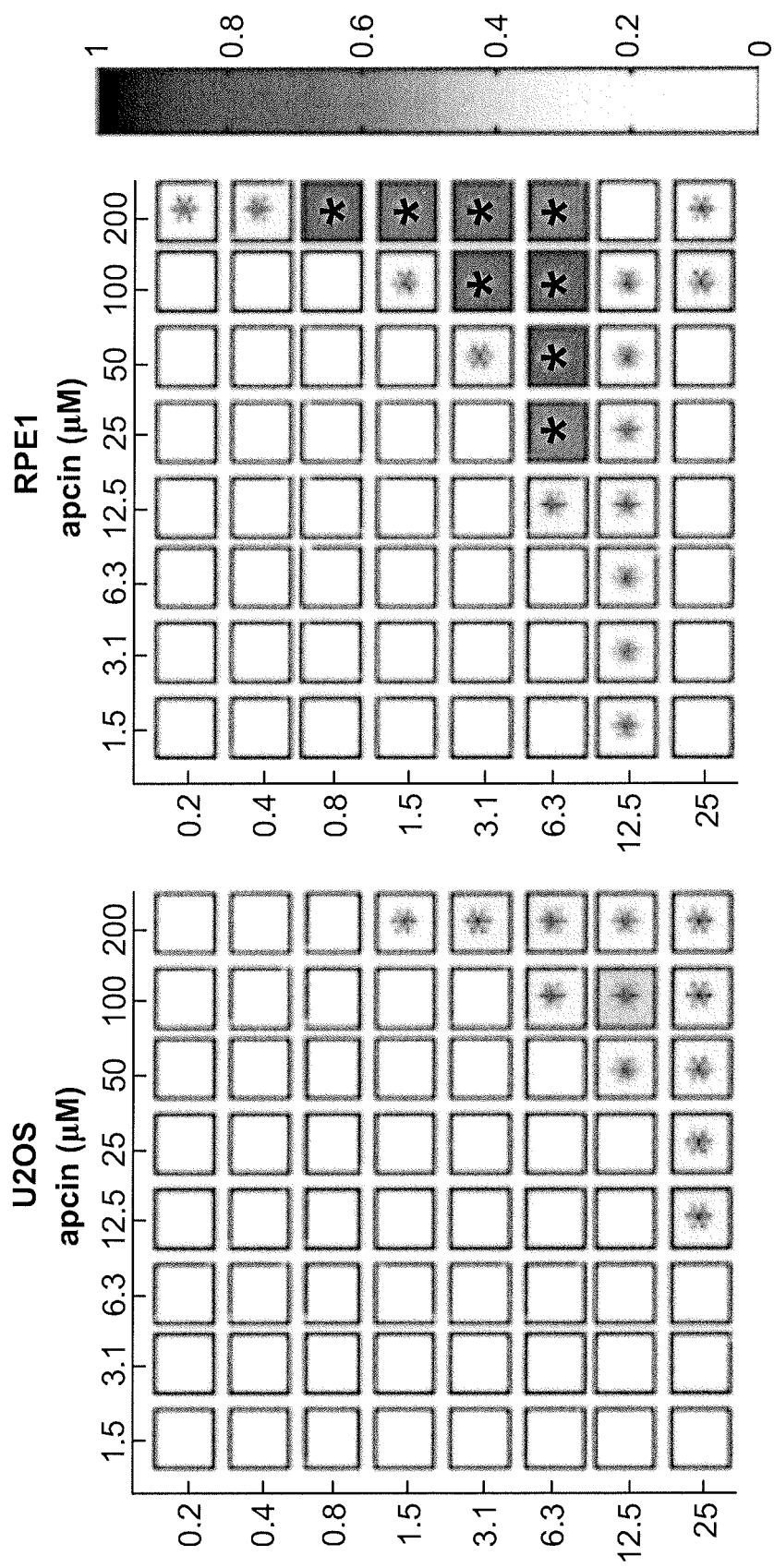
Figure 43B:
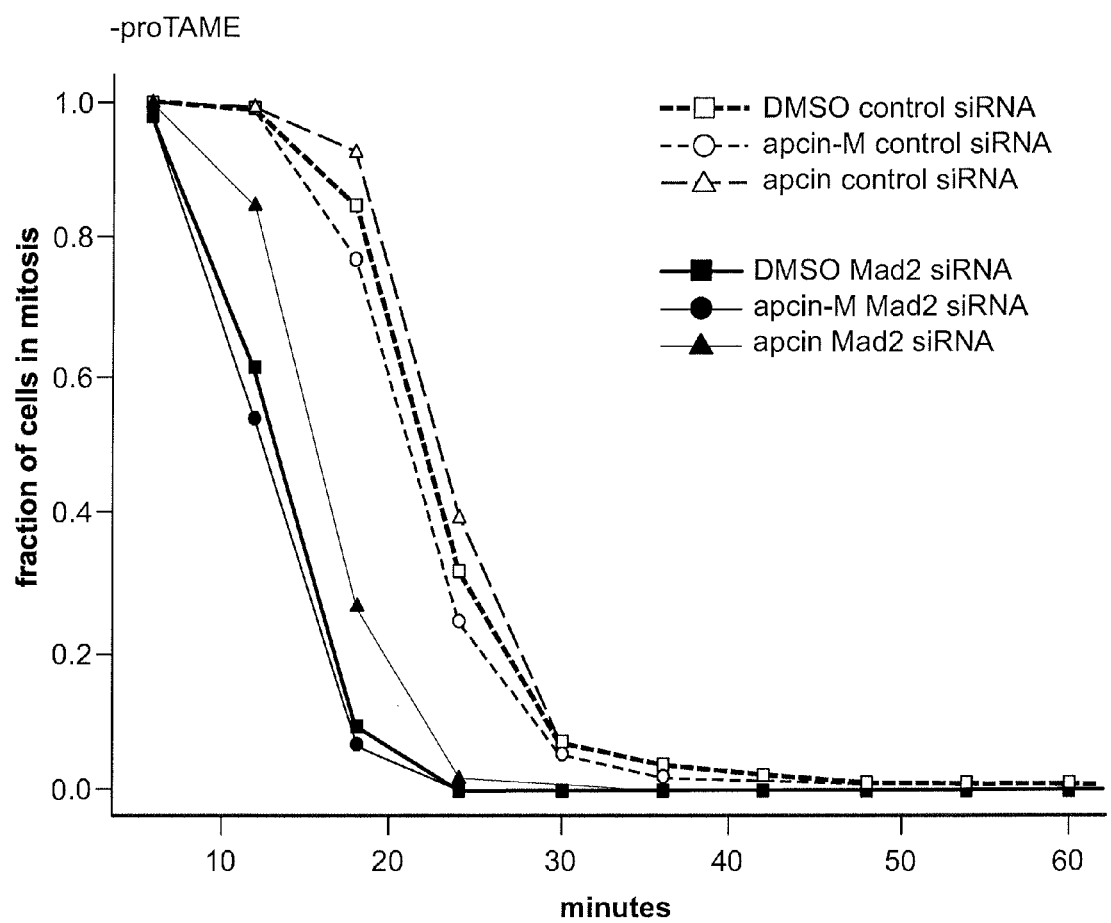
Figure 43B:
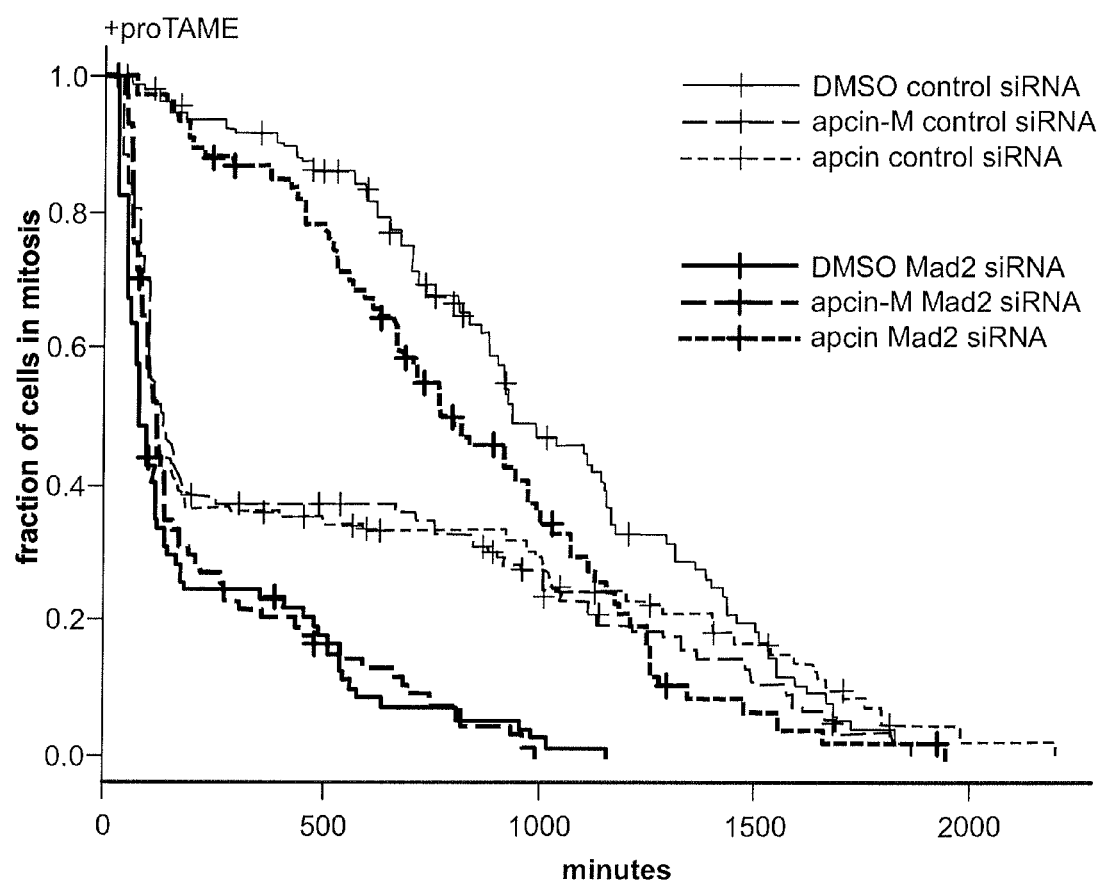
Figure 43B:
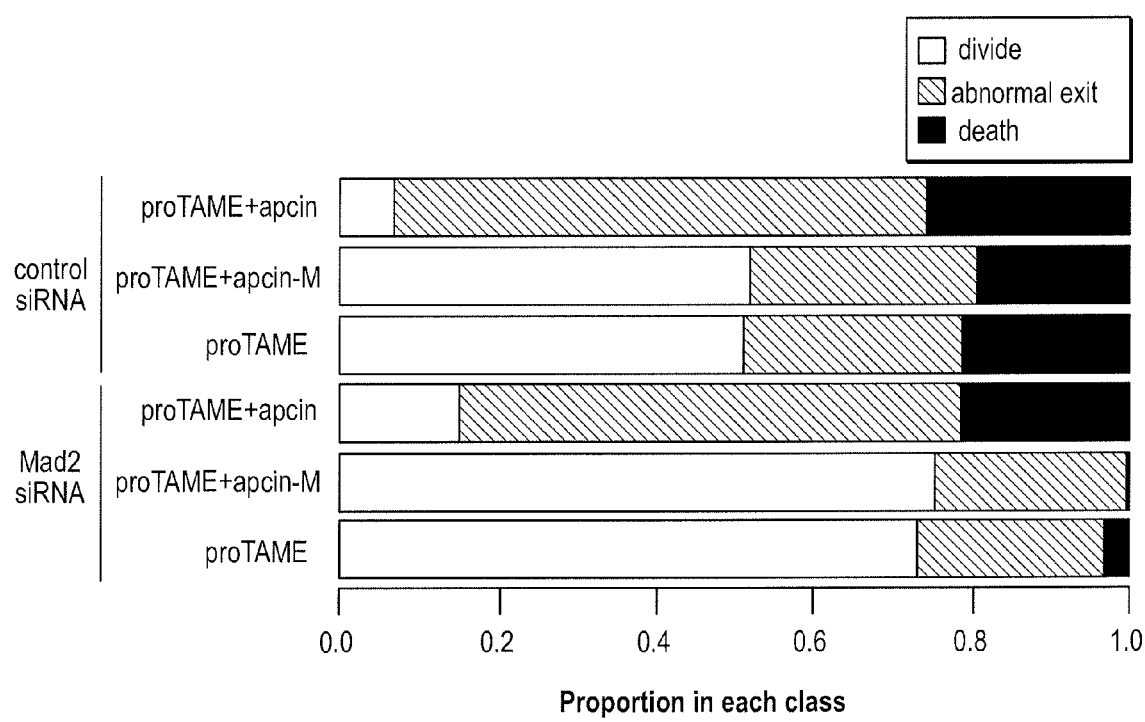

FIG. 38C is a series of heat maps showing the activity of apcin, apcin-P, and apcin-M in the fixed cell assay described in FIG. 43B.

Figure 38D:
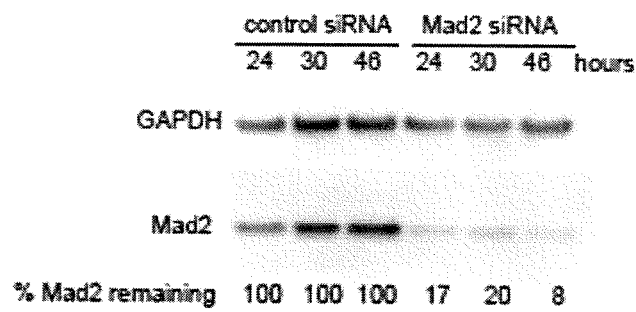

FIG. 38D is a Western blot of Mad2 knockdown by siRNA from one of the experiments shown in FIG. 43B.

Figure 38E:
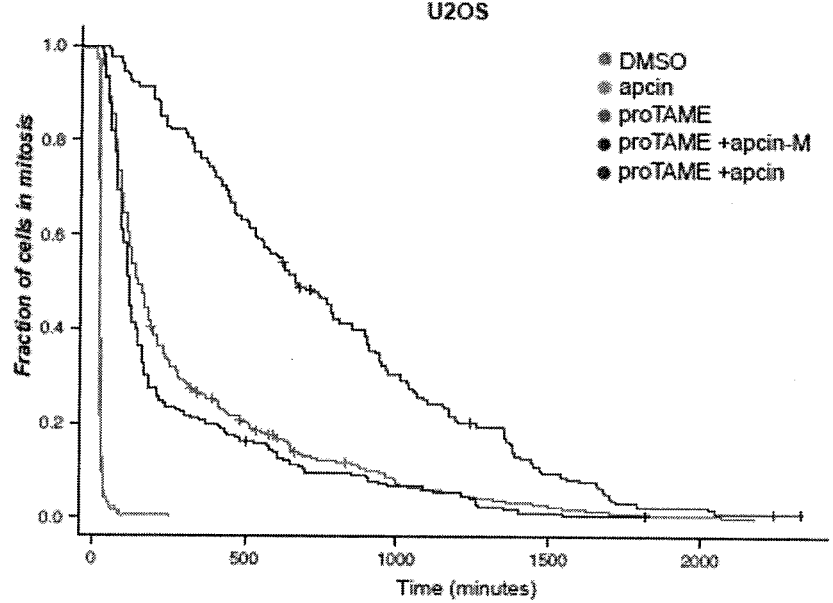

FIG. 38E is a graph showing synchronized U2OS H2B-GFP cells treated with apcin or apcin-M (25 μM) and/or proTAME (12 μM). Cells were then imaged every 6 or 10 minutes for 45 hours. Mitotic duration and cell fate were determined by manual inspection of the movies and plotted as Kaplan-Meier curves. The hatch marks on the Kaplan-Meier curved indicate mitotic duration endpoints of censored cells. Includes the combined results of five independent experiments. U2OS model differs from the model used to test RPE1 data in that the U2OS analysis is not stratified by either date or person, and the U2OS data does not include an effect of apcin-M alone (in the absence of proTAME). Pairwise comparison between proTAME and proTAME+apcin-M tested using a Cox proportional hazards model stratified by date, using data from only the experimental blocks in which both proTAME and proTAME+apcin were tested.

Figure 38F:
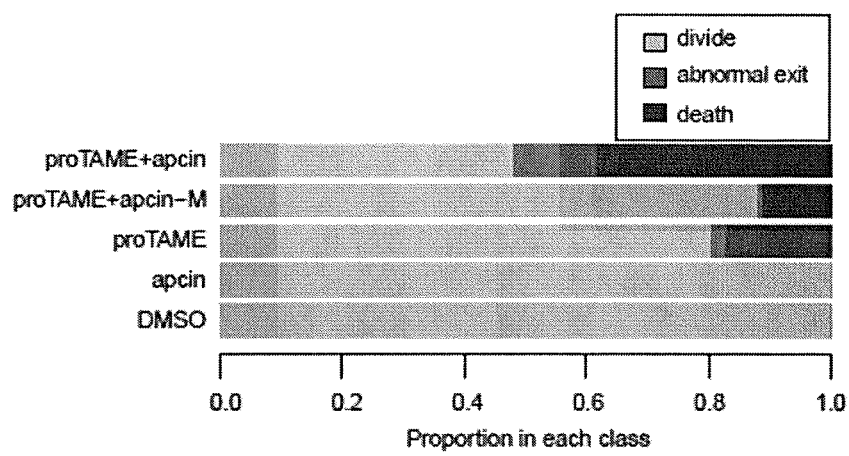

FIG. 38F is a graph further depicting the data shown in FIG. 38E.

FIG. 39A-I is a series of schematic drawings depicting a model of the effects of apcin and TAME on formation of the APC/C-Cdc20-substrate ternary complex. A, Schematic drawing of core APC/C subunits. Not all subunits are indicated, and not all known interactions between subunits are illustrated for sake of simplicity. B, In the absence of substrate, Cdc20 can bind to the APC/C via the C-box, which interacts with APC2, and the IR-tail, which interacts with APC3 (Cdc27). C, Binding of substrates that contain a D-box (DB) can help form a co-receptor interaction between the WD-40 domain of Cdc20 and Apc10. D, The RING-containing subunit APC11 can recruit the E2 enzyme to conjugate ubiquitin to the substrate. E, TAME binds APC3 to interfere with the IR-tail binding site. F, Apcin binds to the leucine pocket of the WD-40 domain of Cdc20. G, In the presence of TAME, the IR-binding site is disrupted, but Cdc20 can still be recruited to the APC/C through the C-box interaction and Co-receptor interaction. Apcin can disrupt the D-box interaction between the substrate and Cdc20, but Cdc20 can still interact through the C-box and IR-tail interactions. I, Combined use of apcin and TAME disrupts both interactions, cooperatively weakening the interaction between APC/C, Cdc20, and substrate.

Figure 40:
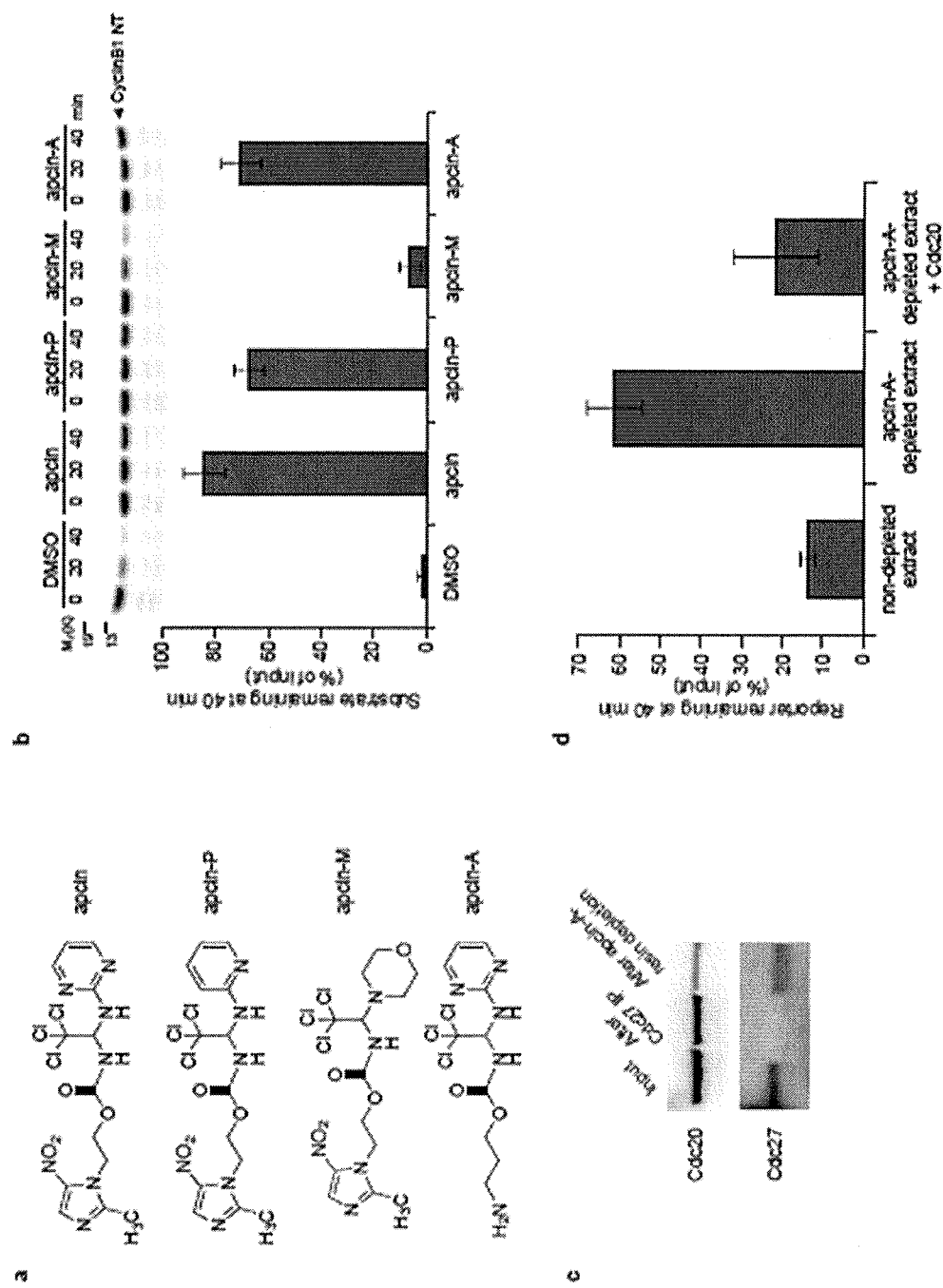

FIG. 40A is a series of chemical structures showing apcin, apcin-P, apcin-M, and apcin-A.

FIG. 40B is a photograph and corresponding graph depicting the effects of the compounds shown in FIG. 40A (200 µM) on proteolysis of an N-terminal $^{35}$S-labeled fragment of cyclin B1 in mitotic Xenopus egg extract. Substrate levels were assessed by SDS-PAGE and quantitated by phosphorimaging, normalizing to value at time 0.

FIG. 40C is a pair of photographs showing that apcin-A resin specifically depletes Cdc20 protein from mitotic Xenopus egg extract. Affigel resin coupled with apcin-A was incubated with mitotic extract. Depletion with Cdc27 antibody-coated beads was performed in parallel for comparison.

FIG. 40D is a graph showing that depletion with Apcin-A resin stabilizes a cyclin-luciferase reporter protein and degradation can be rescued by addition of in-vitro translated Cdc20.

Figure 40E:
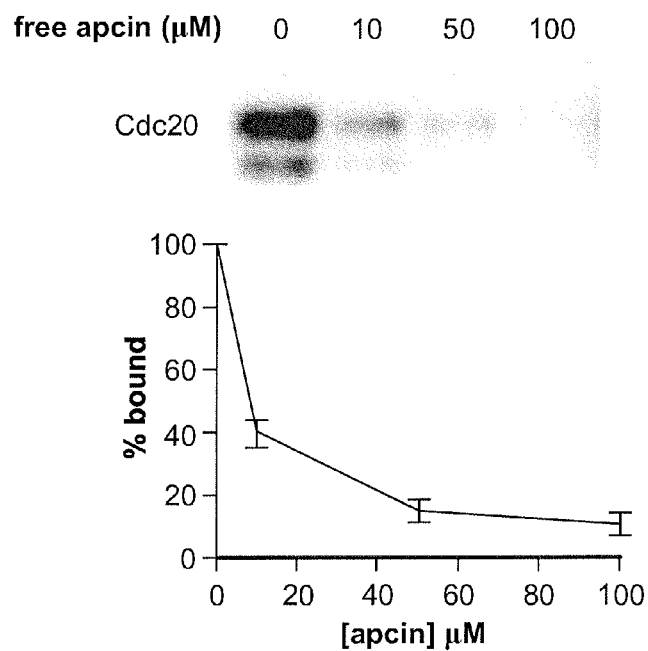

FIG. 40E is a photograph and corresponding graph showing that cdc20 expressed in reticulocyte lysate binds to apcin-A resin and can be competed by free apcin. Cdc20 was detected by western blotting.

Figure 40F:
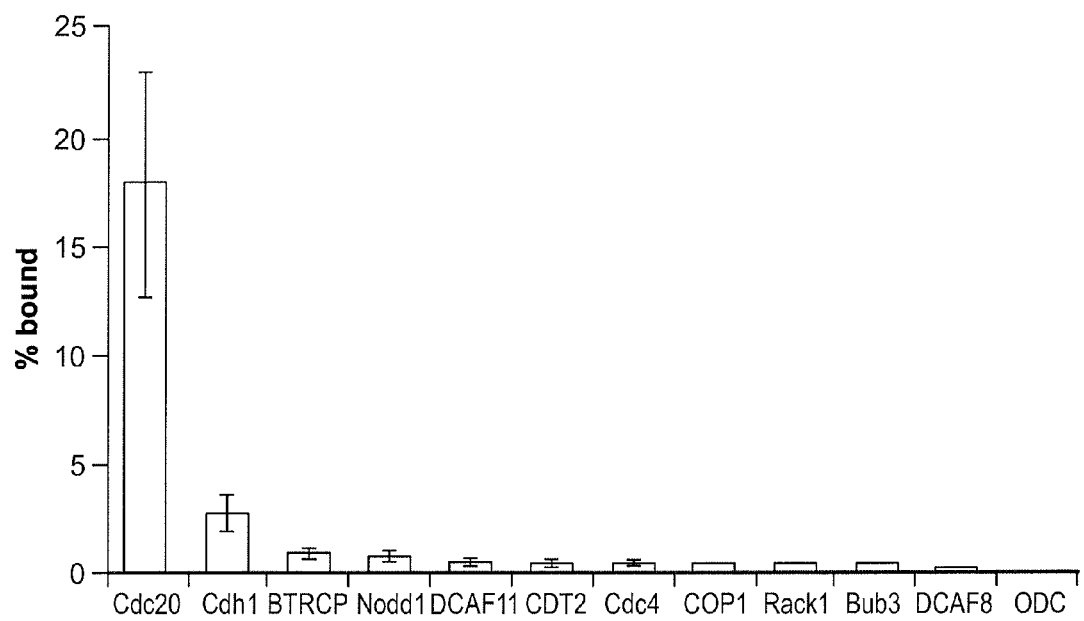

FIG. 40F is a graph showing that Cdc20 binds to apcin-A resin more efficiently than other WD40 proteins. A non-WD40 protein (ODC) is included as a negative control. All proteins were expressed in reticulocyte lysate and labeled with $^{35}$S and detected by autoradiography.

Figure 40G:
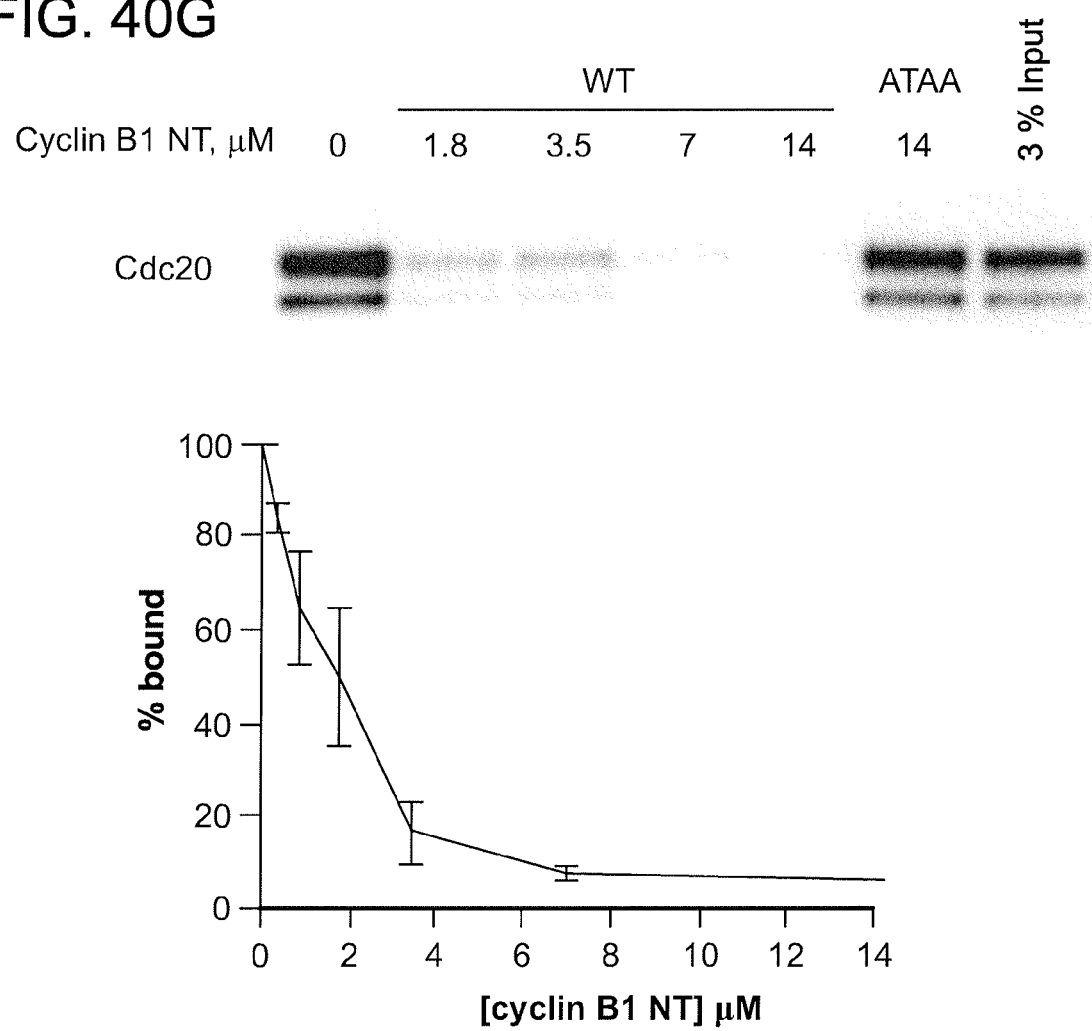

FIG. 40G is a photograph and corresponding graph showing that an N-terminal fragment of cyclin B1, but not a substrate containing a mutation in the D-box (RTAL mutated to ATAA), competes with Cdc20 binding to apcin-A resin. Cdc20 was detected by western blotting.

Figure 40H:
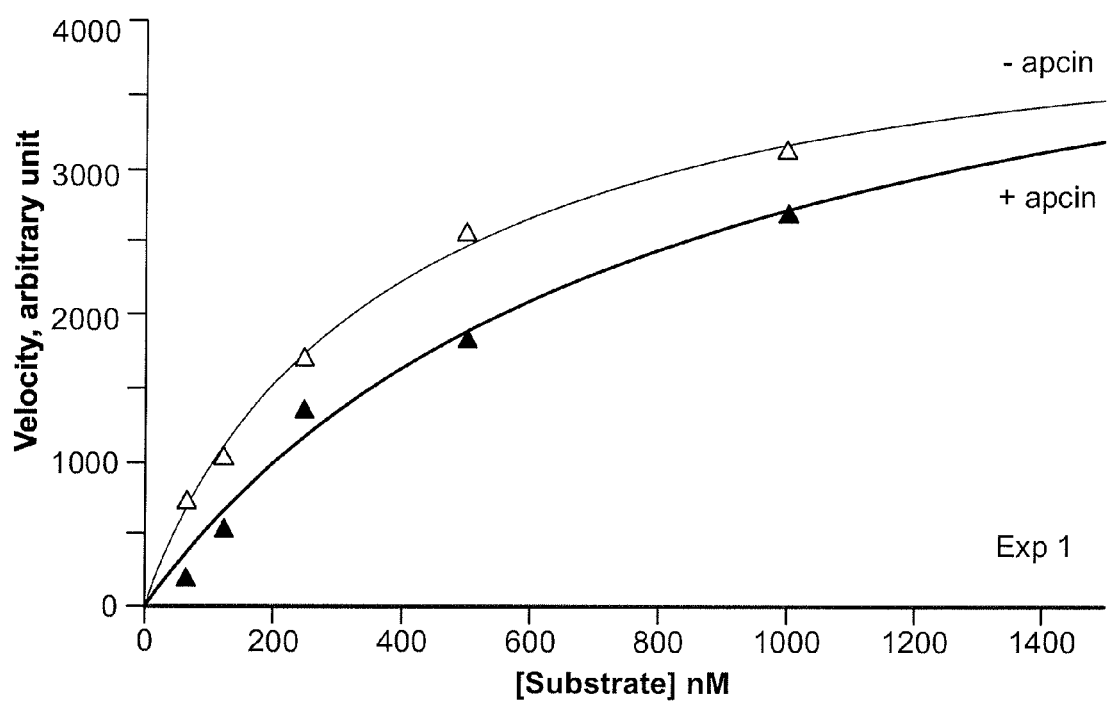

FIG. 40H is a graph and corresponding table showing that apcin increases the apparent $K_m$ of APC/C-Cdc20-dependent ubiquitination of an N-terminal fragment of cyclin B1, but does not decrease $k_{cat}$. Band intensity of the mono- and di-ubiquitinated substrate at 45 seconds (see, FIG. 35c) was quantified and fit to a hyperbolic curve by non-linear regression. The $K_m$, −apcin is significantly different from the $K_m$ +apcin by two-tailed Student's t test (p=0.0039). Error bars represent mean of at least three experiments +/−S.E.M.

Figure 41:
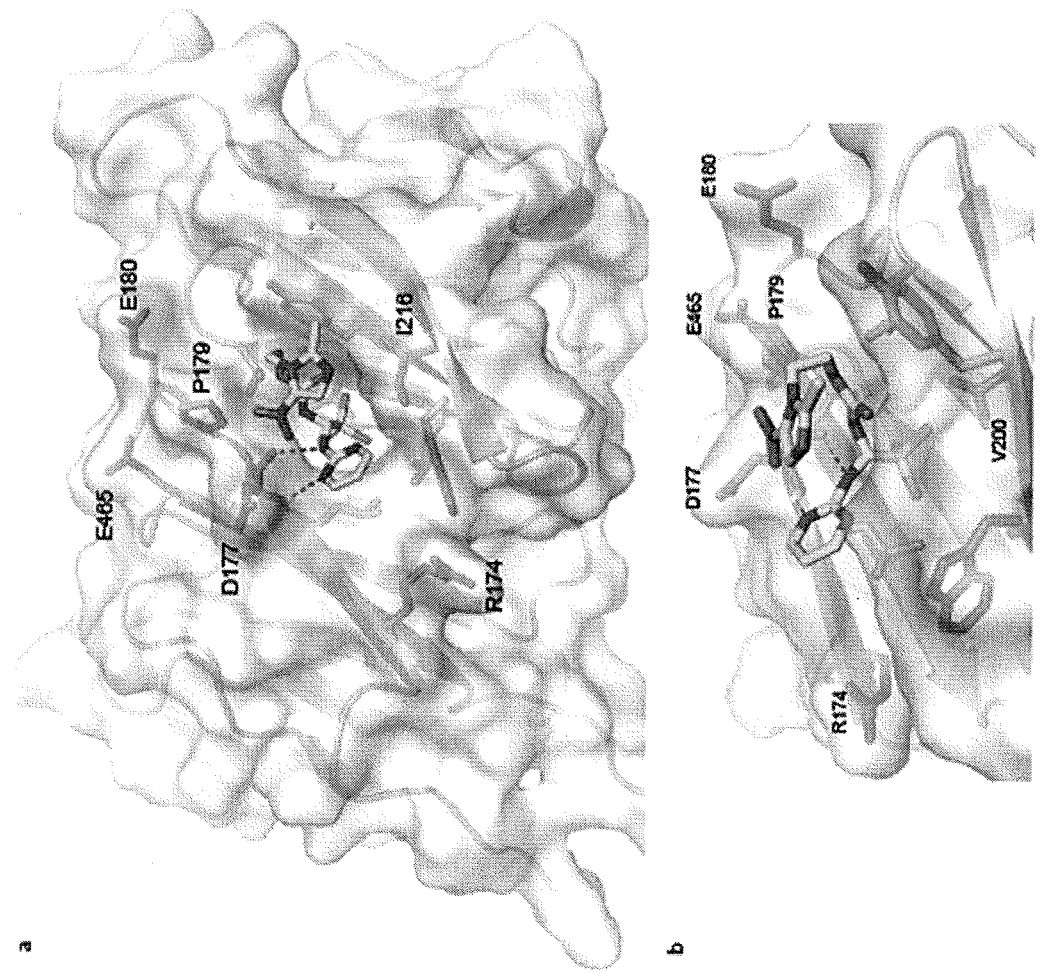
Figure 41:
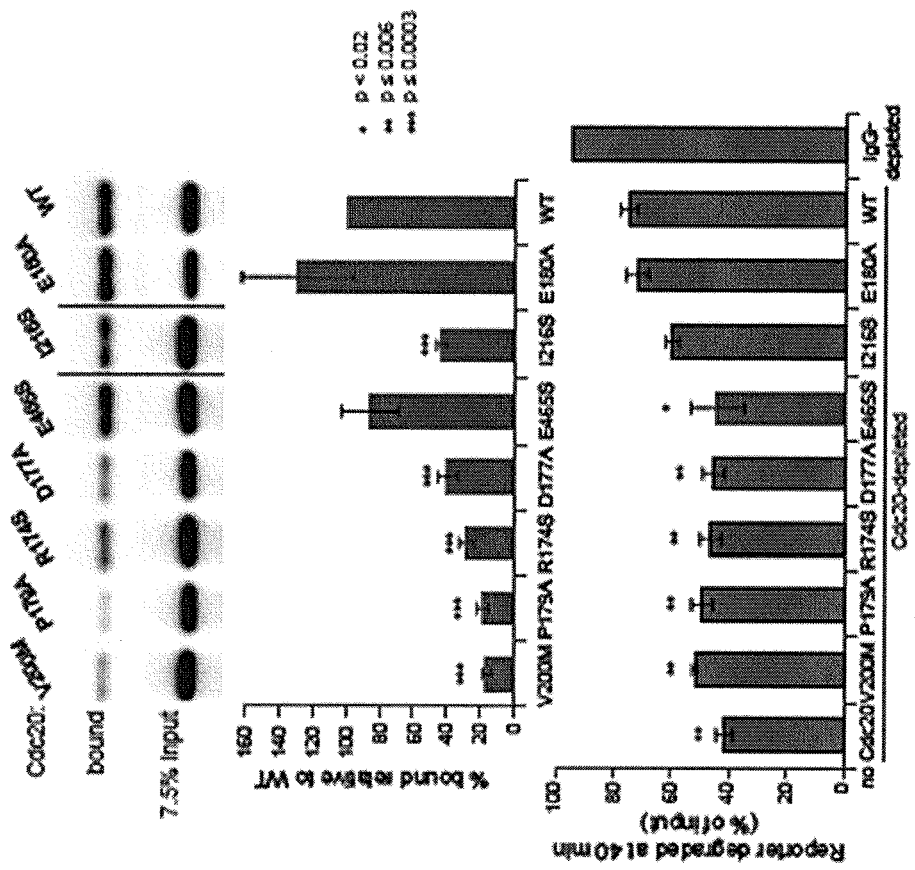

FIG. 41A is a schematic diagram showing that apcin (backbone) binds to side face of WD40 domain of Cdc20; side chains of residues in the binding pocket are shown; residues that are mutated in the experiment in 41C are labeled. See FIG. 36a for overlap of apcin binding pocket with D-box peptide.

FIG. 41B is a schematic diagram showing a view of panel A, rotated to show the position of V200 at the base of hydrophobic binding pocket.

FIG. 41C is a schematic diagram showing the mutation of residues in the binding pocket reduces Cdc20 binding to apcin-A resin (top graph) and the capacity of in vitro-translated Cdc20 protein to rescue cyclin-luciferase degradation in mitotic Xenopus egg extract immunodepleted of Cdc20 (bottom graph). Proteins were labeled with $^{35}$S and levels of mutant Cdc20 bound to resin were assessed by SDS-PAGE and phosphorimaging. Immunodepletion of Cdc20 reduced endogenous Cdc20 by ~80% (see FIG. 36b) which was sufficient to stabilize cyclin-luciferase reporter protein at 40 minutes. Error bars represent mean of three experiments +/−S.E.M.

Figure 42:
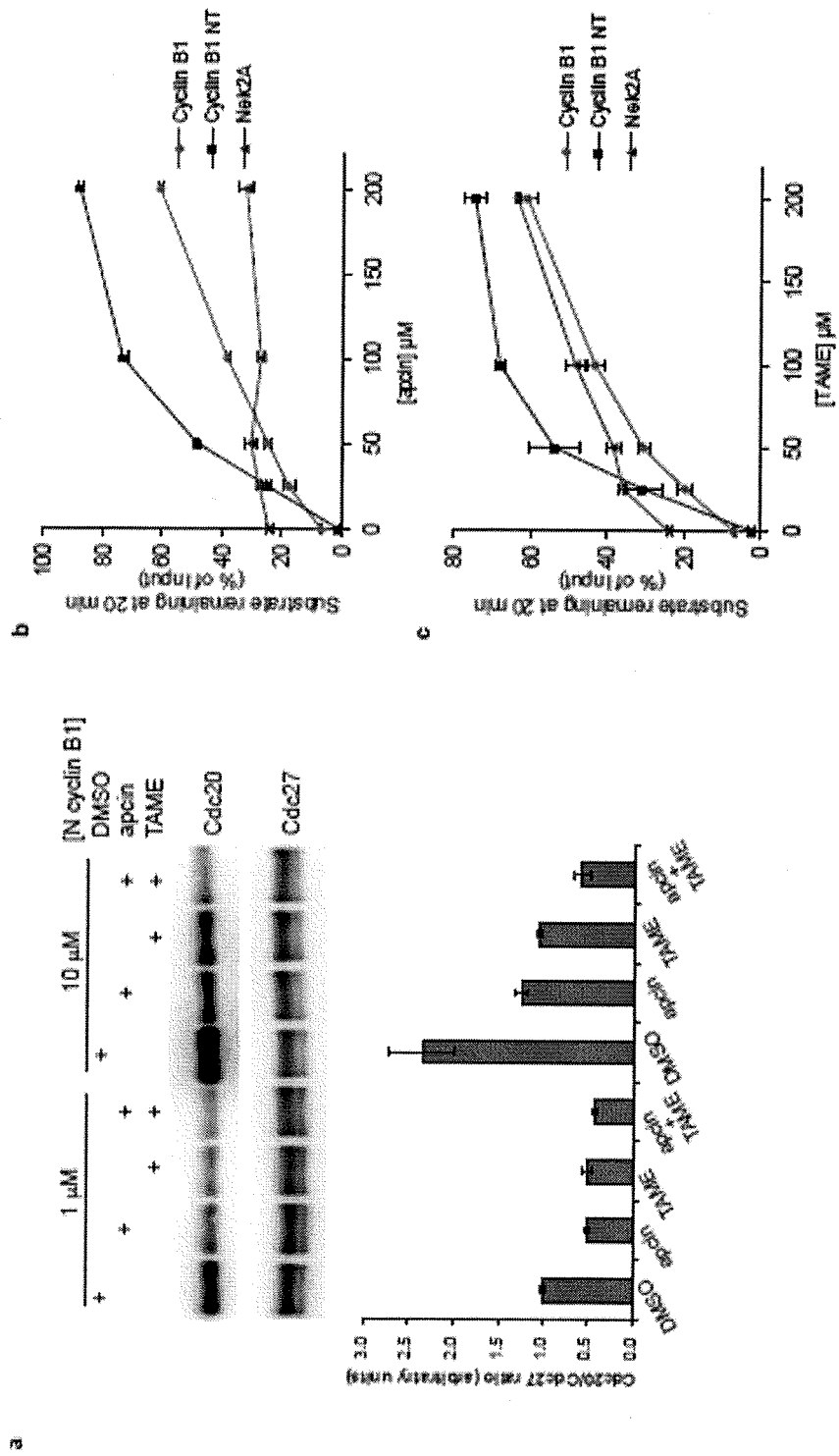
Figure 42:
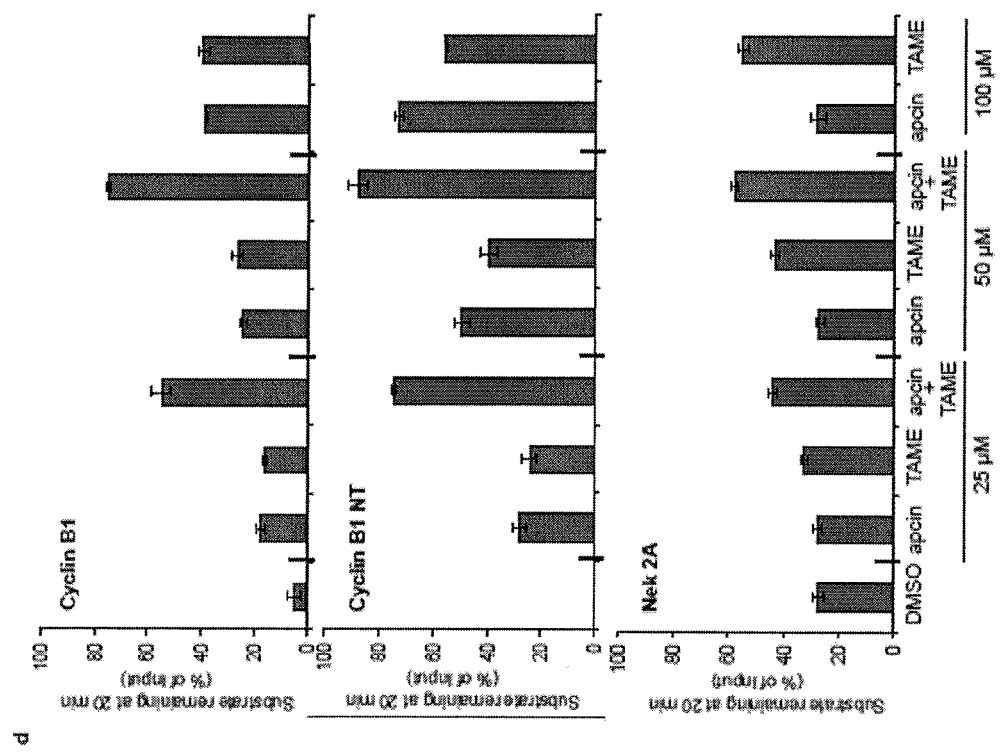

FIG. 42A is a photograph and corresponding graph showing that apcin blocks co-receptor-dependent loading of Cdc20 onto the APC/C. Substrate (cyclin B1 NT, 1 µM or 10 µM), apcin and/or TAME (50 µM each) were added to mitotic Xenopus extract, and the APC/C was isolated with Cdc27 antibodies. Levels of Cdc20 bound to APC/C were assessed by SDS-PAGE and Cdc20 western analysis and normalized to the levels of Cdc27.

FIG. 42B is a graph showing that apcin stabilizes D-box containing substrates cyclin B1 or an N-terminal fragment of cyclin B1, but not Nek2A. $^{35}$S-labeled APC/C substrates expressed in reticulocyte lysate were introduced into mitotically-arrested Xenopus extract that had been pre-treated with apcin for 10 min, at indicated concentrations, or DMSO. Levels of the exogenous substrates were assessed by SDS-PAGE and phosphorimaging (shown in FIG. 37) and plotted as percent remaining.

FIG. 42C is a graph showing that TAME stabilizes D-box containing substrates cyclin B1, an N-terminal fragment of cyclin B1, and Nek2A. $^{35}$S-labeled APC/C substrates expressed in reticulocyte lysate were introduced into mitotically-arrested Xenopus extract that had been pre-treated with apcin for 10 min, at indicated concentrations, or DMSO. Levels of the exogenous substrates were assessed by SDS-PAGE and phosphorimaging (shown in FIG. 37) and plotted as percent remaining.

FIG. 42D is a series of graphs showing that combinations of apcin and TAME stabilize D-box containing substrates cyclin B1, an N-terminal fragment of cyclin B1, and Nek2A. $^{35}$S-labeled APC/C substrates expressed in reticulocyte lysate were introduced into mitotically-arrested Xenopus extract that had been pre-treated with apcin for 10 min, at indicated concentrations, or DMSO. Levels of the exogenous substrates were assessed by SDS-PAGE and phosphorimaging (shown in FIG. 37) and plotted as percent remaining. Error bars represent mean of three experiments +/−S.E.M.

FIG. 43A is a series of models showing that apcin synergizes with proTAME in a fixed cell imaging assay. Asynchronous cells were treated with indicated concentrations of apcin and proTAME. 18 hours later, cells were fixed, stained with Hoechst, and mitotic index determined by intensity of Hoechst staining using automated high-throughput imaging. The data were modeled either assuming Bliss independence (Bliss model) or allowing for synergistic interactions (synergy model). The panel shows the difference between the mitotic index calculated by the Bliss model compared to the synergy model; any positive value indicates synergy. Statistical significance (p<0.05 after correction for multiple testing) is indicated by an asterisk.

FIG. 43B is a series of graphs showing that apcin synergizes with proTAME in a time-lapse imaging assay. Asynchronous RPE1 cells stably expressing H2B-GFP were treated with control siRNA or siRNA targeting Mad2 (see FIG. 38d). Twenty-four hours later, cells were treated with apcin or apcin-M (25 μM) and/or proTAME (6 μM). Cells were then imaged every 6 minutes for 45 hours. Mitotic duration (top and middle panel) and cell fate (bottom panel) were determined by manual inspection of the movies and plotted as inverse cumulative frequency (top panel, −proTAME) or Kaplan-Meier curves (middle panel, +proTAME). The hatch marks on the Kaplan-Meier curves indicate mitotic duration endpoints of cells that were not observed exiting mitosis or dying in mitosis before they migrated out of the field of view or before the end of the movie (censored cells). Graphs include the combined results of two independent experiments. See FIGS. 38e and 38f for quantitative model of data and p-values.

DETAILED DESCRIPTION

The disclosure provides new insights into APC regulation and indicates that the APC is a druggable target amenable to pharmacologic intervention. Most cells that are mitotically arrested following proTAME treatment undergo cell death, as is observed for microtubule inhibitors. The combination of TAME/proTAME and cyclinal induces an unexpected and profound mitotic arrest that is independent of cell checkpoint status or spinal assembly checkpoint (SAC) activity/function. Therefore, the combinatorial therapy of TAME/proTAME and cyclinal is effective in cancer cells, regardless of the mechanism by which cell proliferation became unregulated or misregulated in these cells.

Lower doses of proTAME induce mitotic delay rather than cell death, suggesting that APC inhibitors may be useful for restoring normal chromosome segregation in cases where spindle checkpoint function is compromised. For example, APC inhibitors may be useful for rescuing mitotic failure in preimplantation embryos generated through in vitro fertilization. Given that APC also regulates functions in the central nervous system and controls rates of axon growth, inhibition of Cdh1 association with the APC may also be of therapeutic benefit in the treatment of neurological disease.

The Anaphase-Promoting Complex/Cyclosome (APC) is a multi-subunit ubiquitin E3 ligase that promotes anaphase onset and mitotic exit by ubiquitinating cyclin B and securin to target them for proteolysis by the 26S proteasome (Pines, J. Nat Rev Mol Cell Biol 12, 427-438 (2011)). APC activity requires an activator. In mitosis, Cdc20 is the activator while in interphase, this role is taken by a homologous protein Cdh1 (Pesin, J. A. & Orr-Weaver, T. L. Annu Rev Cell Dev Biol 24, 475-499 (2008)). The activator contains a C-terminal seven WD40-repeats domain that has been shown to interact with a motif known as the Destruction box (D-box), an APC-specific degron on APC substrates (Kraft, C. et al. Mol Cell 18, 543-553 (2005)). The APC recognizes the D-box through a co-receptor formed by the activator and another core APC subunit Apc10 (Buschhorn, B. A., et al. Nat Struct Mol Biol 18, 6-13 (2011); da Fonseca, P. C., et al. Nature 470, 274-278 (2011)). Although additional APC-specific degrons such as the KEN box exist, and might be important for APC activity in late mitosis and interphase (Nguyen, H. G., et al. Mol Cell Biol 25, 4977-4992 (2005); Pfleger, C. M. & Kirschner, M. W. Genes Dev 14, 655-665 (2000)), the D-box is essential for APC Cdc20-driven degradation of cyclin B and securin prior to anaphase onset (Hagting, A., et al. J Cell Biol 157, 1125-1137 (2002); Clute, P. & Pines, J. Nat Cell Biol 1, 82-87 (1999)).

In prometaphase, the APC is activated by Cdc20, leading to ubiquitination and degradation of Nek2A and cyclin A. However, ubiquitination of other APC substrates is inhibited by the Spindle Assembly Checkpoint (SAC) until chromosomes have achieved proper bipolar attachment to the mitotic spindle. Once the SAC is satisfied, ubiquitination and degradation of securin and cyclin B lead to chromosome segregation and mitotic exit. In telophase, another APC activator, Cdh1, replaces Cdc20 and maintains APC activity during G1.

Cdc20 and Cdh1 are important for recruiting substrates to the APC. The activator proteins share several evolutionarily conserved motifs, including an N-terminal C-box (comprising the consensus sequence DRFYIPXR (SEQ ID NO: 1)), seven WD40 repeats (also known as WD or beta-transducin repeats of about 40 amino acids, often terminating in a WD dipeptide and containing 4-16 repeating units that together form a circular beta-propellar structure), and a C-terminal IR tail (a C-terminal region including one or more IR dipeptide motifs). Whereas the WD40 domain may interact simultaneously with substrates and the APC, the C-box and the IR tail are specifically involved in APC binding. The IR tail of Cdh1 interacts with multiple APC subunits, including Cdc27 and Apc7. Deletion of the IR tail of Cdh1 compromises its ability to activate human APC in vitro, and is lethal in budding yeast lacking Sic1. However, deletion of IR tail of Cdc20 does not affect the viability of wild-type budding yeast, and thus, does not seem to be strictly required for APC activation. Instead, the IR tail may be important for regulating Cdc20 abundance, as Cdc20ΔIR accumulates to higher levels than the wild-type protein. Thus while the IR tail seems to be critical for Cdh1 recruitment and activation of the APC, the specific role of Cdc20's IR tail in APC binding and activation remains unclear.

The Spindle Assembly Checkpoint (SAC) ensures that, the replicated sister chromatids faithfully segregate into the two daughter cells during mitosis (Musacchio, A. & Salmon, E. D. Nat Rev Mol Cell Biol 8, 379-393 (2007)). During prometaphase, the kinetochores of each sister chromatid are attached to microtubule fibers emanating from one of the two opposite spindle poles, a configuration known as bi-orientation. Bi-oriented chromosomes then become aligned on an equator plane of the cell in a process named congression and the completion of congression is the hallmark of metaphase. The SAC senses unattached or improperly attached kinetochores and restrains the APC from ubiquitinating securin and cyclin B1 before metaphase is achieved. The effector of SAC-mediated APC inhibition is a complex known as the Mitotic Checkpoint Complex (MCC) that consists of stoichiometric amounts of Mad2, Cdc20, BubR1 and Bub3 (Sudakin, V. et al. J Cell Biol 154, 925-936 (2001)). Although Cdc20 as a component of the MCC can still bind to the APC (Herzog, F., et al. Science 323, 1477-1481 (2009); Zeng, X., et al. Cancer Cell 18, 382-395 (2010)), it is not capable of promoting APC substrate ubiquitination but instead seems to be susceptible to auto-ubiquitination (Reddy, S. K., et al. Nature 446, 921-925 (2007); Stegmeier, F., et al. Nature 446, 876-881 (2007)).

The mechanism of MCC-mediated APC inhibition remains an unanswered question in cell biology. The MCC may alter the way that Cdc20 binds to the APC (Herzog, F., et al. Science 323, 1477-1481 (2009)). Moreover, it has been proposed that budding yeast Mad3 may act as a pseudo-substrate since it contains several APC degrons, including two N-terminal KEN-boxes and one C-terminal D-box, and competes with a canonical substrate for Cdc20 binding (Burton, J. L. & Solomon, M. J. Genes Dev 21, 655-667 (2007)). Interestingly, the roles of these degrons in Mad3 do not seem to be equivalent as KEN-box mutations fully abrogate Mad3 function but the D-box mutation is better tolerated (Burton, J. L. & Solomon, M. J. Genes Dev 21, 655-667 (2007)). The importance of the KEN-box is also confirmed in *Drosophila*, mouse and human cells but the role of the BubR1 D-box has not been evaluated in higher organisms (Elowe, S., et al. J Cell Sci 123, 84-94 (2010); Malureanu, L. A., et al. Dev Cell 16, 118-131 (2009); Rahmani, Z., et al. J Cell Biol 187, 597-605 (2009)).

Microtubule inhibitors are used as anti-mitotic chemotherapy drugs for cancer treatment (Montero, A., et al. Lancet Oncol 6, 229-239 (2005)). They disrupt microtubule functions and activate the SAC to induce mitotic arrest in cells. Direct APC inhibition equally induces mitotic arrest without side effects associated with microtubule inhibition and therefore represents a better route for anti-mitotic drug development (Zeng, X., et al. Cancer Cell 18, 382-395 (2010); Montero, A., et al. Lancet Oncol 6, 229-239 (2005)). To identify potential small molecule APC inhibitors, a high throughput chemical screen was conducted to search for compounds that can stabilize a cyclin B1-luciferase reporter in mitotic *Xenopus* egg extract (Verma, R., et al. Science 306, 117-120 (2004). TAME and cyclinal were among the most potent hits from the screen. TAME acts as a structural analog of the IR tail of Cdc20 and competes for the same binding site on the APC (Zeng, X., et al. Cancer Cell 18, 382-395 (2010)). In the absence of APC substrates such as cyclin B1, TAME strongly inhibits the binding of free Cdc20 to the APC and induces auto-ubiquitination followed by dissociation of Cdc20 pre-bound to the APC. However, APC substrates promote free Cdc20 binding to the APC in the presence of TAME, presumably because forming the D-box co-receptor with Apc10 provides one addition contact point between APC and Cdc20 to render the IR-dependent interaction non-essential. A cell-permeable TAME prodrug (proTAME) induces a prolonged mitotic arrest in cells. However, the arrest is strongly dependent on the SAC, suggesting the major mechanism of proTAME-induced mitotic arrest is prevention of SAC inactivation instead of direct APC inhibition (Zeng, X., et al. Cancer Cell 18, 382-395 (2010)). Because some tumor cells frequently have a defective SAC response (Bharadwaj, R. & Yu, H. Oncogene 23, 2016-2027 (2004), a method of APC inhibition was developed that induces a prolonged mitotic arrest independent on the SAC. TAME's mechanism suggests that complete inhibition of Cdc20 binding to the APC and APC activation may be achieved if the IR-dependent interaction between the APC and Cdc20 and the D-box-dependent interaction between the substrate and Cdc20 are disrupted simultaneously. This synchronous inhibition leads to complete APC inactivation and renders the mitotic arrest independent of the SAC, as shown in cells depleted of Cdc20 by RNAi (Huang, H. C., et al. Cancer Cell 16, 347-358 (2009)).

Cyclinal competes with the D-box for Cdc20 binding. Cyclinal on its own is insufficient to induce a mitotic arrest in cells. Moreover, it overrides prolonged mitotic arrest induced by microtubule inhibitors, which is shown to be a consequence of disruption of the BubR1/Cdc20 interaction. Co-addition of TAME and cyclinal strongly inhibits Cdc20 binding to the APC even in the presence of APC substrates and induces an extremely robust mitotic arrest that is resistant to SAC inactivation and Cdk inhibition.

Figure 33:
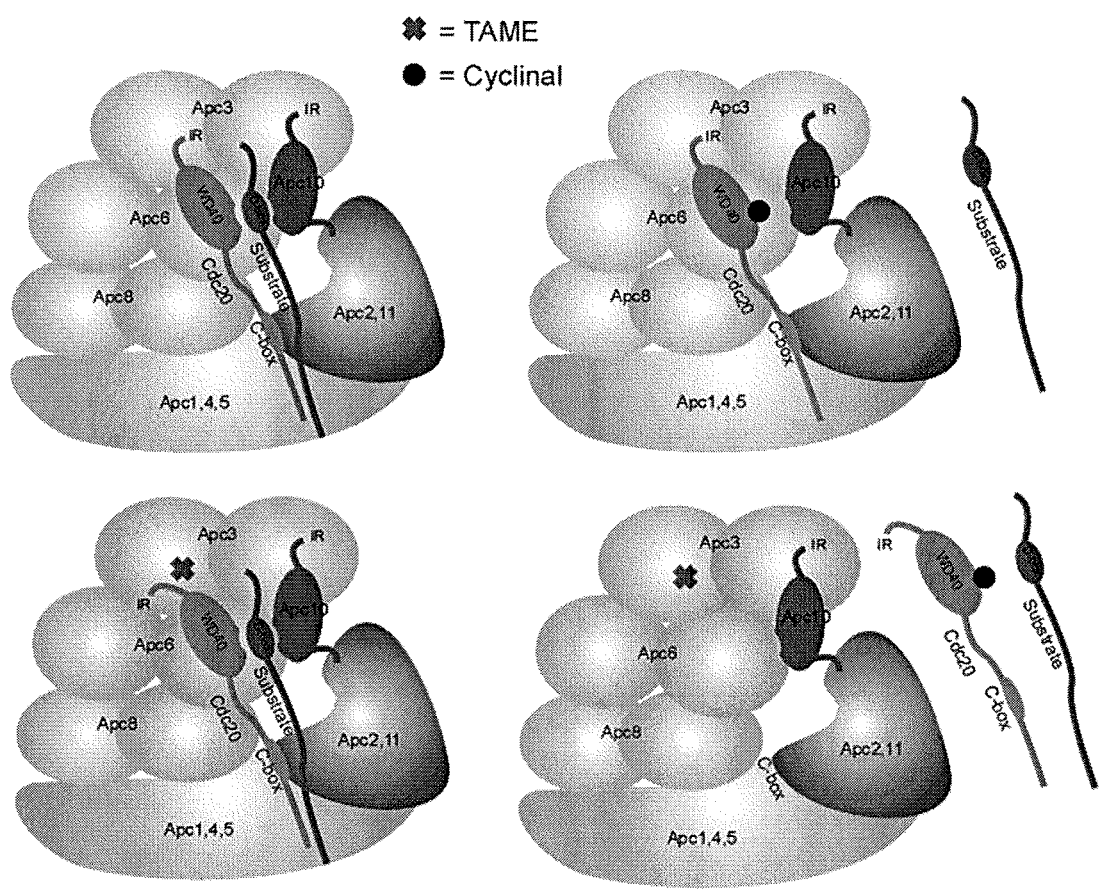
FIG. 33 is a schematic depiction of a model for the synergistic effects of cyclinal and TAME to inhibit binding of Cdc20 to the APC. In an APC/Cdc20/D-box substrate ternary complex, Cdc20 contacts the APC via 3 different interactions, the IR tail/Apc3, the C-box/Apc2, and the WD40/D-box/Apc10. Addition of cyclinal blocks the WD40/D-box interaction, which prevents the D-box substrate binding to APC/Cdc20 but does not affect Cdc20 binding to the APC. Addition of TAME blocks the IR tail/Apc3 interaction, but in the presence of the D-box substrate, the WD40/D-box/Apc10 and the C-box/Apc2 interactions are sufficient to maintain Cdc20 binding to the APC. Addition of both cyclinal and TAME abrogates both the IR tail/Apc3 and the WD40/D-box interactions and strongly inhibits the binding of Cdc20 to the APC.

The examples provided herein delineate the mechanism of action of cyclinal, a small molecule inhibitor of cyclin proteolysis discovered in a phenotypic screen in *Xenopus* extract. Cyclinal competes with the D-box on APC substrates for Cdc20 binding and increases the $K_m$ of the APC in substrate ubiquitination assays. In SAC-deficient cells, cyclinal induces a transient delay in mitotic exit. However, in SAC-proficient cells, cyclinal promotes premature mitotic exit in the presence of microtubule inhibitors but this does not happen after ~5 h into mitosis. Cyclinal compromises the SAC by perturbing a D-box dependent interaction between BubR1 and Cdc20, which results in reduced assembly of the MCC and stabilization of Cdc20. Cyclinal and TAME synergize to inhibit Cdc20 binding to the APC in the presence of APC substrates, which results in complete inhibition of APC activation (FIG. 33). The prolonged mitotic arrest induced by cyclinal/proTAME is therefore fully resistant to methods of inducing mitotic exit such as SAC inactivation or Cdk inhibition.

The D-box and KEN-box are the most commonly found APC degrons. Although the canonical model proposes that Cdc20 specifically recognizes the D-box whereas Cdh1 can recognize both the D-box and the KEN-box (Pfleger, et al. Genes Dev 15, 2396-2407 (2001)), recent evidence suggests that Cdc20 may also interact with the KEN-box. For instance, the KEN-boxes on BubR1 are critical for Cdc20 association and SAC function (Burton, J. L. & Solomon, M. J. Genes Dev 21, 655-667 (2007); Elowe, S., et al. J Cell Sci 123, 84-94 (2010); Malureanu, L. A., et al. Dev Cell 16, 118-131 (2009); Rahmani, Z., et al. J Cell Biol 187, 597-605 (2009); King, E. M., et al. PLoS One 2, e342 (2007)) and the degradation of a KEN-box APC substrate CENP-F seems to be dependent on Cdc20 (Gurden, M. D., et al. J Cell Sci 123, 321-330 (2010)). Structural studies suggest that for Cdh1, the recognition mechanism for the D-box and the KEN-box must be different, since the D-box is bound between the WD40 domain of Cdh1 and Apc10 whereas the KEN-box seems to bind elsewhere (da Fonseca, P. C., et al. Nature 470, 274-278 (2011)). The fact that cyclinal compromises the SAC in a way that is consistent with selective perturbation of the D-box but not the KEN-box interaction between Cdc20 and BubR1 indicates that there are distinct binding sites for the D-box and the KEN-box on Cdc20 and cyclinal selectively blocks the D-box binding site but leaves the KEN-box binding site available.

EXAMPLES

Example 1

Methods

Chemicals and Antibodies

Chemicals. Tosyl-L-arginine methyl ester (T4626), tosyl-L-arginine (S365157), tosyl-L-argininamide (T4501), benzoyl-L-arginine methyl ester (B1007), benzoyl-L-argininamide (B4375) and tosyl-L-lysine methyl ester (T5012) were from Sigma. Acetyl-L-arginine methyl ester was from BACHEM (E-1030). Cdh1 C-terminal peptide and the ΔIR control peptide (sequence: CFSKTRSTKESVSVLNLF-TRIR (SEQ ID NO: 2) and CFSKTRSTKESVSVLNLFTR (SEQ ID NO: 3)) were synthesized by the core facility of Tufts medical school. $^3$H-TAME (15 Ci/mmol, >97% radiochemical purity) was synthesized by AmBios Labs (Newington, Conn.). Hesperadin was a gift from Boehringer Ingelheim. MG132 was from Sigma (C2211). Okadaic acid was from MP Biomedicals (IC15897425). Cycloheximide was from Calbiochem (239764).

Antibodies. Cdc27 antibody for APC immunoprecipitation was from Santa Cruz (sc-9972, AF3.1). Cdc27 antibody for Western blot was from BD Transduction Laboratories (610454). Cyclin B1 antibody was from NeoMarker (RB-008-P). Xenopus Cdc20 antibody was from Abcam (ab18217). Human Cdc20 antibody was from Santa Cruz (sc-8358 H-175). Cdh1 antibody was from Santa Cruz (sc-19398). Streptavidin-HRP was from Invitrogen (SNN1004). Securin antibody was from Abcam (ab3305). Cyclin A antibody was from Santa Cruz (sc H-432). Nek2 antibody was from BD Transduction Laboratories (610593). UbcH10 antibody was from Boston Biochem (A-650). Mad2 antibody was from Bethyl Laboratories (BL1461). GAPDH antibody was from Abcam (ab8245). Anti-α-tubulin-FITC was from Sigma (F2168). CREST antiserum was from Antibodies Incorporated (15-234). Goat anti-human-Alexa 568 was from Invitrogen (A21090). HA antibody was from Santa Cruz (sc-805, Y-11). Apc10 antibody was from Santa Cruz (sc-20989).

Preparation of Xenopus Egg Extract.

Interphase Xenopus egg extract was prepared from eggs laid overnight according to the protocol of Murray (Murray, 1991) with the exception that eggs were activated with 2 µg/ml calcium ionophore (A23187, free acid form, Calbiochem) for 30 minutes prior to the crushing spin. Extract was frozen in liquid nitrogen and stored at −80° C. To make mitotic extract, MBP-cyclin B1Δ90 was added to interphase extract at 20 µg/ml and incubated at 22° C. for 30 min.

Luciferase Assay.

A fusion of the N-terminal domain of cyclin B1 to luciferase (Verma et al., 2004) was added to mitotic extract at 3 µg/ml. The extract was incubated at 23° C. and 3 µl samples were taken at 0, 30, 60, 90 and 120 min. The samples were mixed quickly with 30 µl of luciferin assay buffer (270 µM coenzyme A, 20 mM tricine, 3.67 mM MgSO$_4$, 0.1 mM EDTA, 33.3 mM DTT, 530 µM ATP and 470 µM luciferin, pH 7.8) and the level of luminescence was measured on Wallac 1420 multilabel counter.

TAME Induction of Mitotic Arrest in Xenopus Egg Extract.

Human cyclin B1/cdc2 complex (MPF) was prepared by baculovirus expression and purification and added to interphase extract at 12.5 µg/ml supplemented with 1% DMSO, 200 µM TAME or 200 µM AAME. Extract samples were collected every 15 min following addition of MPF. Cdc27 and cyclin B1 levels were analyzed by Western blot.

In vitro Ubiquitination Assay.

For a single reaction, 5 µl protein A affiprep beads (Bio-Rad 156-0006) were washed with TBST (10 mM Tris, 150 mM NaCl and 0.01% Tween-20, pH 7.5) twice and incubated with 2 µg Cdc27 antibody for 75 min at 4° C. Beads were then washed with TBST twice and XB (100 mM KCl, 0.1 mM CaCl$_2$, 1 mM MgCl$_2$ and 10 mM HEPES, pH 7.7) twice before APC immunoprecipitation. For APC-Cdc20 reaction, MBP-cyclin B1Δ90 was added to interphase extract at 20 µg/ml and incubated at 22° C. for 30 min before immunoprecipitation. To immunoprecipitate APC, 100 µl extract was incubated with 5 µl antibody beads at 4° C. for 1 h. The beads were then washed with XB high salt (XB with 500 mM KCl) twice, XB twice and ubiquitin chain buffer (20 mM Tris, 100 mM KCl, 2 mM ATP and 2.5 mM MgCl$_2$, pH 7.7) three times. A reaction mixture containing 200 µg/ml MBP-E1, 66 µg/ml His$_6$-Ubc4, 25 µg/ml MPF, 1 mg/ml ubiquitin (Sigma) in ubiquitin chain buffer was prepared and 5 µl of this was added to 5 µl antibody beads. Beads were incubated at 22° C. on a Eppendorf Thermomixer with shaking at 1500 rpm for 60 min and the whole mixture was then boiled with 10 µl sample buffer for 5 min. Ubiquitinated cyclin B1 was visualized by cyclin B1 immunoblot.

Degradation of $^{35}$S Labeled Pre-ubiquitinated Cyclin B1.

Human $^{35}$S-cyclin B1/cdc2 complex was prepared by metabolic labeling of SF9 cultures expressing cyclin B1. The labeled lysate containing cyclin B1 was mixed with an unlabeled lysate from cells expressing cdc2, followed by purification of the cyclin B1/cdc2 complex as described above. The labeled complex was ubiquitinated in a reconstituted APC reaction as described above. Interphase Xenopus extract was pre-incubated with 200 µM TAME or control compounds for 22° C. for 30 min. Pre-incubation was performed in the presence of 100 ug/ml cycloheximide to prevent re-incorporation of free labeled amino acid and ½₀th volume of energy mix (150 mM creatine phosphate, 20 mM ATP, 2 mM EGTA and 20 mM MgCl$_2$, pH 7.7). 90 µl of extract was then added to 15 µl of labeled cyclin B1-ubiquitin conjugates and incubated at 22° C. for the indicated amount of time. Reactions were stopped by the addition of an equal volume (105 ul) of chilled 2% perchloric acid. The mixture was incubated on ice for 30 min and centrifuged at 14,000 rpm for 10 min at 4° C. 168 µl of supernatant was mixed with 20 µl 2 M Tris base and 6 ml ultima gold scintillation fluid (Perkin Elmer). Samples were mixed well and counted with a scintillation counter.

Covalent Coupling of Cdc27 Antibody to Protein A Beads.

Protein A affiprep beads were coupled with Cdc27 antibody as described above. After coupling, the beads were washed with TBST for 10 min followed by two additional quick washes with TBST. Dimethyl pimelimidate (DMP, PIERCE, 21666) was freshly dissolved in 100 mM sodium tetraborate decahydrate, pH 9.0 at 20 mM. The beads were mixed with ten beads volume of DMP solution and incubated on a rotating wheel for 45 min in the dark at room temperature. The beads were then washed twice quickly with 200 mM Tris, pH 8.0 twice, followed by a final 1 h wash. Beads were then washed twice in TBST and twice in XB prior to APC immunoprecipitation.

IR Peptide Immobilization on Iodoacetyl Resin.

A 20-aa Cdh1 C-terminal peptide with one cysteine residue added at the N-terminus was synthesized along with a control peptide lacking the C-terminal IR residues. The lyophilized peptide was re-dissolved at 400 µM in 100 mM HEPES, 5 mM EDTA, pH 7.9. To reduce the disulfide bonds, TCEP (Sigma C4706) was dissolved at 10 mM in 100 mM HEPES, 5 mM EDTA, pH 7.9 and added to the peptide solution at a final concentration of 200 µM (stoichiometric amount to reduce disulfide bonds). The peptide was reduced at room temperature for 15 min before mixing with Ultralink iodoacetyl resin (Pierce 53155) that was pre-equilibrated with 100 mM HEPES, 5 mM EDTA, pH 7.9. A ratio of 35 µl resin volume per 110 µl reduced peptide was used. For the negative control, freshly prepared 50 mM cysteine in 100 mM HEPES, 5 mM EDTA, pH 7.9 was used instead of the peptide. The coupling reaction was carried out at room temperature on a rotating wheel for 1 h and unreacted sites on the resin were blocked by further incubation with 50 mM cysteine for 30 min. The resin was then washed with 1 M NaCl followed by two washes with XB and stored at 4° C. before APC pull down.

APC pull down by IR peptide resin. 10 µl of resin coupled with IR peptide, ΔIR peptide or cysteine as described above was mixed with 100 µl interphase *Xenopus* egg extract and incubated on a rotating wheel for 30 min at 4° C. The resin was then washed twice with XB high salt and once with PBS. The resin was boiled with 10 µl sample buffer and the amount of Cdc27 was analyzed by immunoblot.

Conjugation of IR Peptide with Photoactive Crosslinker.

The IR and ΔIR peptides were reduced as described above. The photoactive crosslinker, Profound Mts-Atf-Biotin label transfer reagent (Pierce 33093), was dissolved at 40 mg/ml in DMSO. The crosslinker was added to the reduced peptide at a 1.1 molar excess and the reaction was left at room temperature in the dark for 1 h. The reaction mixture was centrifuged at 12,000 rpm for 1 min and the supernatant was loaded onto HPLC for purification. The purified conjugated peptide showed >99% purity on HPLC. The identity of the conjugated peptide was confirmed by mass spectrometry.

Crosslinking Assay.

Purified conjugated IR or ΔIR peptide was diluted in XB to a final concentration of approximately 2 µM. The following additives were included when necessary: 10 µM of unconjugated IR peptide with the cysteine modified with N-ethyl maleimide to show competition with the conjugated peptide, 20 µM or 200 µM TAME to show inhibition of crosslinking, and 200 µM AAME as a negative control. APC was immunoprecipitated with protein A affiprep beads covalently crosslinked with Cdc27 antibody as described above. After washing, 5 µl aliquot of beads were mixed with 50 µl conjugated peptide and transferred to a 96-well polypropylene clear conical bottom plate. The plate was illuminated at a distance of 10 cm from a 300 watt long wavelength UV lamp for 3 min. The beads were then transferred back to 0.5 ml tubes and mixed with 10 µl sample buffer and boiled for 5 min. APC subunits that were crosslinked were analyzed by streptavidin-HRP blot. To confirm the nature of the crosslinked subunits, APC was immunoprecipitated from interphase extract as described above and run on the same gel of the crosslinked sample and coomassie stained. The bands were subjected to mass spectrometry analysis.

$^3$H-TAME Binding Assay.

$^3$H-TAME (200 nM; 15 Ci/mmol) was added to 100 µl interphase *Xenopus* extract or HeLa cell lysate. APC was immunoprecipitated with Cdc27 antibody (Santa Cruz, AF3.1) coupled to affiprep beads (Bio-Rad). The beads were washed with XB and radioactivity measured by scintillation counting. Alternatively, $^3$H-TAME was added and Cdc27 immunoprecipitation was performed after one or two rounds of APC immunodepletion. Specific binding was calculated as the difference between counts associated with Cdc27 antibody beads compared to beads lacking antibody (mock IP).

$^3$H-TAME Binding Assay in Interphase Extract.

$^3$H-TAME (15 Ci/mmol) was added to interphase extract (100 µl) to a final concentration of 200 nM, and subject to immunoprecipitation (4° C. for 1.5 h) using 5 µl protein A affiprep beads coupled with Cdc27 antibody as described above. Protein A beads without Cdc27 antibody were used as a negative control to measure background level of binding (mock IP). The beads were washed quickly twice with XB high salt and twice with XB. The beads were then transferred to scintillation vials, mixed with scintillation fluid, and counted in a scintillation counter. Alternatively, the extract was subjected to one or two rounds of immunoprecipitation before the addition of $^3$H-TAME. For competition assays, different concentrations of unlabeled TAME were added along with 200 nM $^3$H-TAME into the extract. Specific binding under each condition was obtained by subtracting the value of mock IP.

$^3$H-TAME Binding Assay in HeLa Cell Lysate.

Protein A affiprep beads coupled with Cdc27 antibody were prepared as described above. HeLa cells were harvested in lysis buffer (10 mM potassium phosphate pH 7.5, 0.1 mM EDTA, 0.5 mM EGTA, 50 mM β-glycerophosphate, 1 mM sodium vanadate, 1 mM DTT, 0.5% Triton X-100 and leupeptin, chymostatin and pepstatin each at 10 µg/ml). For 4,000,000 cells, 100 µl lysis buffer was used. The cell lysate was centrifuged at 10,000 rpm for 10 min to remove cell debris. $^3$H-TAME (15 Ci/mmol) was added to cell lysate to a final concentration of 200 nM. For each aliquot of 5 µl beads, 100 µl lysate was used for APC immunoprecipitation at 4° C. for 1 h. Protein A beads without Cdc27 antibody was used as a negative control to measure background level of binding (mock IP). The beads were washed quickly with lysis buffer high salt (500 mM sodium chloride in addition to above components) twice and lysis buffer twice. The beads were then transferred to scintillation vials, mixed with scintillation fluid, and radioactivity measured by scintillation counting. Alternatively, the lysate was subjected to one or two rounds of immunoprecipitation before the addition of $^3$H TAME. For competition assays, 10 µM unlabeled TAME or AAME was added along with 200 nM $^3$H TAME into the lysate. Specific binding under each condition was obtained by subtracting the value of mock IP.

APC Isolation by IR Peptide or C-Box Fragment and Crosslinking.

A cysteine-containing 20 amino acid peptide derived from the C-terminus of Cdh1, or a control peptide lacking the C-terminal isoleucine and arginine residues, was reduced with TCEP at RT for 15 min and coupled to Ultralink iodoacetyl resin (Pierce). Ten µl of resin was mixed with 100 µl interphase *Xenopus* egg extract and incubated on a rotator for 30 min at 4° C. The resin was then washed with XB (100 mM KCl, 0.1 mM CaCl$_2$, 1 mM MgCl$_2$ and 10 mM HEPES, pH 7.7) and bound Cdc27 was analyzed by immunoblot. To investigate the effect of TAME on C-box interactions, a GST fusion protein containing the N-terminal 159 residues of *Xenopus* Cdc20, or the same protein lacking the C-box, were expressed and purified as described previously (Kimata et al., 2008). The proteins (10 µg) were preloaded on 5 µl Glutathione-Sepharose 4B resin (GE Healthcare) and incubated with cyclin B1Δ90-arrested mitotic *Xenopus* extract at RT for 30 min in the presence of 1% DMSO, 200 µM TAME or 200 µM AAME. The resin was then washed with XB and bound Cdc27 was analyzed by immunoblot. For crosslinking studies, the Cdh1-derived C-terminal peptide was conjugated to Profound Mts-Atf-Biotin label transfer reagent (Pierce) and crosslinked as described in the supplemental experimental procedures.

IR Peptide Crosslinking Assay.

The Cdh1-derived C-terminal peptide was conjugated to Profound Mts-Atf-Biotin label transfer reagent (Pierce) as described in the supplemental experimental procedures. APC was immunoprecipitated from interphase extract and the beads (5 µl) were mixed with 50 µl conjugated peptide (2 µM) and transferred to a 96-well polypropylene plate. The plate was illuminated at a distance of 10 cm from a 300 watt long wavelength UV lamp for 3 min. Results were analyzed by streptavidin-HRP blot. Immunopurified APC was run in parallel, and coomassie stained APC subunits were identified by analyzing co-migrating bands by mass spectrometry.

In vitro Ubiquitination Assay.

Human cyclin B1/cdc2 complex was purified and used as the substrate with Ubc4 as the E2 enzyme as previously described (Kirkpatrick et al., 2006).

APC-Cdc20/Cdh1 Association Assay.

APC was immunoprecipitated from cyclin B1Δ90-arrested mitotic *Xenopus* extract or interphase extract supplemented with 0.5 μg/ml recombinant. Compounds were added to mitotic extract immediately before immunoprecipitating the APC. Interphase extracts were pre-incubated with compounds for 30 min before adding recombinant Cdh1 and immunoprecipitating the APC. The beads were washed with XB high salt (XB with 500 mM KCl) and then XB, and bound Cdc27 and Cdc20/Cdh1 were analyzed by immunoblot.

Alternatively, Cdc20 was expressed using an in vitro coupled transcription/translation reticulocyte lysate system following the manufacturer's instruction (Promega L1170). The lysate was diluted with XB so that the concentration of Cdc20 was approximately equal to that of the endogenous Cdc20 in *Xenopus* extract. APC was immunoprecipitated from mitotic extract as described above and the beads were washed with XB high salt and XB. For each binding assay, 5 μl beads were mixed with 50 μl diluted lysate plus 1 μM okadaic acid, 0.05% IPEGAL CA-630 and various competitors as indicated for 30 min with constant shaking. The beads were then washed with XB+0.05% IPEGAL CA-630 and bound Cdc27 and Cdc20 were analyzed by immunoblot.

Live Cell Imaging.

Detailed siRNA transfection and drug treatment schemes are described in supplemental experimental procedures. HeLa H2B-GFP cells were plated in DMEM with 10% FBS at 20% confluence. One day later, cells were synchronized by treatment with 2 mM thymidine for 18 hours, released for 8 hours, and retreated with thymidine for 18 hours prior to release. Live cell imaging was performed at 12 minute intervals on a Nikon TE2000E PFS inverted microscope fitted with an incubation chamber maintained at 37° C. and supplied with 5% $CO_2$. Cell division was tracked by manual inspection of movies, and mitotic duration was measured as the time between the first frame of chromosome condensation and the frame of chromosome segregation (anaphase), decondensation (mitotic exit without anaphase) or cell death (chromosomes shrinking to a small bright dot).

Synthesis of proTAME (14) and proAAME (15)

$N^2$-[(4-methylphenyl)sulfonyl]-$N^5$-[(phenylmethoxy)carbonyl]-L-ornithine 1,2,-dimethylethyl ester (1): A mixture of $N^5$-[(phenylmethoxy)carbonyl]-L-ornithine 1,2,-dimethylethyl ester HCl (718 mg, 2 mmol), acetone (15 mL) and sat. aq. $NaHCO_3$ (15 mL) was treated with p-toluenesulfonyl chloride (420 mg, 2.2 mmole) in acetone (15 mL) at 0° C. and then stirred at room temperature for 16 h. The mixture was diluted with EtOAc, washed with brine, dried over anhydrous sodium sulfate, filtered, concentrated in vacuo to afford an oil, which was purified by silica gel column chromatography using 40% EtOAc in hexane to give compound 1 (910 mg, 95%): $^1$H NMR (500 MHz, $CDCl_3$): δ1.23 (s, 9H), 1.56-1.65 (m, 3H), 1.73-1.77 (m, 1H), 2.39 (s, 3H), 3.21 (q, J=6.0, 2H), 3.72-3.77 (m, 1H), 4.77 (br, 1H), 5.10 (s, 2H), 5.16 (br, 1H), 7.26-7.28 (m, 2H), 7.31-7.36 (m, 5H), 7.70-7.72 (m, 2H).

$N^2$-acetyl-$N^5$-[(phenylmethoxy)carbonyl]-L-ornithine 1,2,-dimethylethyl ester (2) was prepared in a manner similar as 1, with acetyl chloride used in place of p-toluenesulfonyl chloride. $^1$H NMR (500 MHz, $CDCl_3$): δ1.46 (s, 9H), 1.49-1.57 (m, 2H), 1.63-1.69 (m, 1H), 1.81-1.88 (m, 1H), 2.01 (s, 3H), 3.22 (q, J=6.5, 2H), 4.47-4.51 (m, 1H), 4.94 (br, 1H), 5.09 (s, 2H), 6.11 (br d, J=7.5, 1H), 7.30-7.36 (m, 5H).

$N^2$-[(4-methylphenyl)sulfonyl]-L-ornithine 1,2,-dimethylethyl ester (3): A mixture of 1 (500 mg, 1.05 mmole), methanol (1.5 mL), ethanol (15 mL) and 10% Pd—C(200 mg) was stirred under a hydrogen atmosphere at room temperature for 3 h. The mixture was filtered through a pad of Celite, concentrated in vacuo to give crude compound 3 (399 mg, 99%). This material was stored in the freezer and then used without further purification.

$N^2$-acetyl-L-ornithine 1,2,-dimethylethyl ester (4) was prepared in a manner similar as 3.

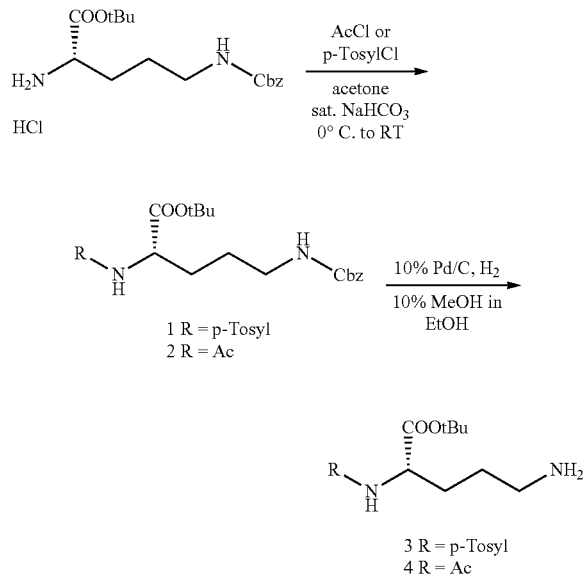

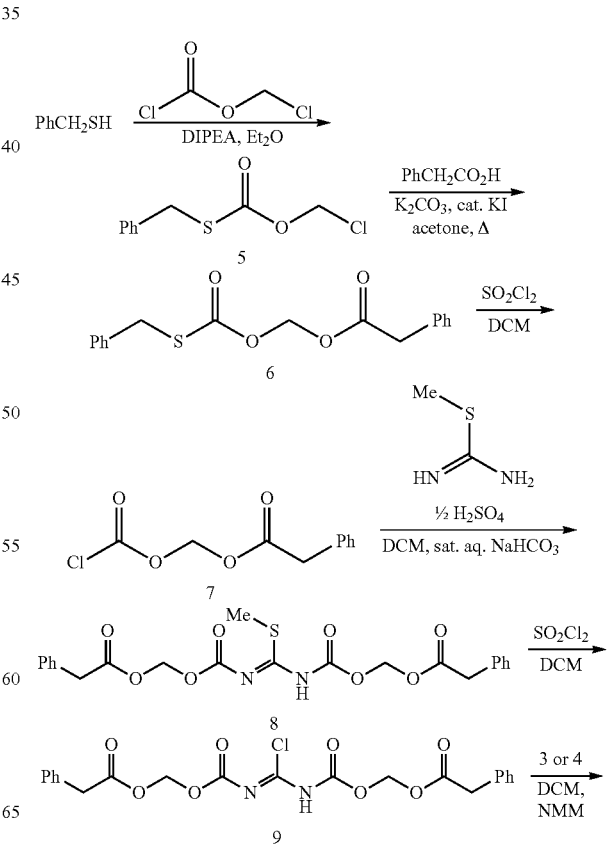

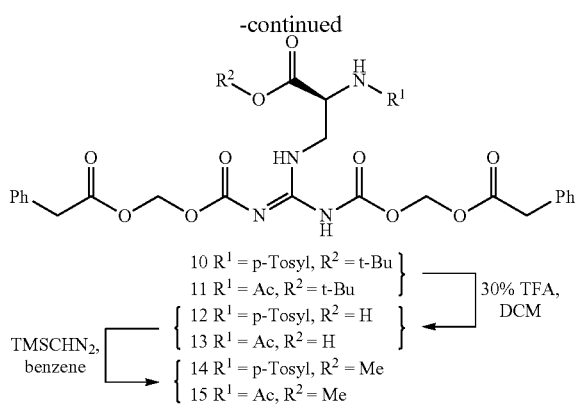

10 R¹ = p-Tosyl, R² = t-Bu
11 R¹ = Ac, R² = t-Bu
12 R¹ = p-Tosyl, R² = H
13 R¹ = Ac, R² = H
14 R¹ = p-Tosyl, R² = Me
15 R¹ = Ac, R² = Me TMSCHN₂, benzene → ; 30% TFA, DCM ←

O-Chloromethyl S-(phenylmethyl)carbothioate (5): was prepared using known methods.

[[(phenylmethylthio)carbonyl]oxy]methyl benzeneacetate (6): A mixture of 5 (6.327 g, 29.2 mmol), phenylacetic acid (3.68 g, 27 mmole), K₂CO₃ (3.74 g, 27 mmole), and cat. KI in acetone (100 mL) was refluxed for 16 h. The mixture was diluted with EtOAc, washed with brine, dried over anhydrous sodium sulfate, filtered, concentrated in vacuo to afford an oil, which was purified by silica gel column chromatography with 5% EtOAc in hexane to give 1 (5.80 g, 92%): ¹H NMR (500 MHz, CDCl₃): δ 3.68 (s, 4H), 4.12 (s, 4H), 5.82 (s, 4H), 7.26-7.33 (m, 10H).

[(chlorocarbonyl)oxy]methyl benzeneacetate (7): was prepared following known methods.

3-(methylthio)-5,9-dioxo-10-phenyl-[(phenylacetyl)oxy] methyl 6,8-dioxa-2,4-diazadec-2-enoate (8): was prepared using known methods. ¹H NMR (500 MHz, CDCl₃): δ 2.44 (s, 3H), 3.70 (s, 4H), 5.84 (s, 4H), 7.26-7.35 (m, 10H).

3-chloro-5,9-dioxo-10-phenyl-[(phenylacetyl)oxy] methyl 6,8-dioxa-2,4-diazadec-2-enoate (9): was prepared using known methods.

1,2,-dimethylethyl (S)-2-[(4-methylphenyl)sulfonyl] amino-4-[[bis[[[[(phenylacetyl)oxy]methoxy]carbonyl] amino]methylene]amino]pentanoate (10) and 1,2,-dimethylethyl (S)-2-(acetyl)amino-4-[[bis[[[[(phenylacetyl)oxy] methoxy]carbonyl]amino]methylene]amino]pentanoate (11): were prepared following known methods.

10: ¹H NMR (500 MHz, CDCl₃): δ 1.23 (s, 9H), 1.57-1.62 (m, 1H), 1.71-1.77 (m, 3H), 2.39 (s, 3H), 3.45 (q, J=6.5, 2H), 3.68 (s, 2H), 3.71 (s, 2H), 3.77-3.79 (m, 1H), 5.23 (d, J=8.5 Hz, 1H), 5.80 (s, 2H), 5.82 (s, 2H), 7.24-7.36 (m, 12H), 7.71-7.73 (m, 2H), 8.29 (br t, J=5.3 Hz, 1H), 11.61 (br s, 1H).

11: ¹H NMR (500 MHz, CDCl₃): δ 1.46 (s, 9H), 1.56-1.71 (m, 3H), 1.86-1.90 (m, 1H), 2.02 (s, 3H), 3.42-3.48 (m, 2H), 3.67 (s, 2H), 3.71 (s, 2H), 4.51-4.54 (m, 1H), 5.80 (s, 2H), 5.82 (s, 2H), 6.19 (d, J=7.5 Hz, 1H), 7.26-7.36 (m, 10H), 8.31 (br t, J=5.5 Hz, 1H), 11.61 (br s, 1H).

(S)-2-[(4-methylphenyl)sulfonyl]amino-4-[[bis[[[[(phenylacetyl)oxy]methoxy]carbonyl]amino]methylene]amino] pentanoic acid (12) and (S)-2-(acetyl)amino-4-[[bis[[[[(phenylacetyl)oxy]methoxy]carbonyl]amino]methylene]amino] pentanoic acid (13): were prepared using known methods (e.g., Bryan, D. B. H., et al. (1977). J Am Chem Soc 99, 2353-2355). Each ester (10 and 11) was deprotected with 30% TFA in DCM at room temperature for 2 h and then purified by silica gel column chromatography with 2.5% MeOH in dichloromethane to give each acid 12 and 13 in 30-40% yield.

12: ¹H NMR (500 MHz, CDCl₃): δ1.66-1.75 (m, 3H), 1.83-1.89 (m, 1H), 2.40 (s, 3H), 3.36-3.46 (m, 2H), 3.68 (s, 2H), 3.71 (s, 2H), 4.01-4.05 (m, 1H), 5.48 (d, J=8.5 Hz, 1H), 5.78 (s, 2H), 5.82 (s, 2H), 7.24-7.35 (m, 12H), 7.72-7.74 (m, 2H), 8.32 (br t, J=5.3 Hz, 1H), 11.55 (br, 1H).

13: ¹H NMR (500 MHz, CDCl₃): δ 1.67-1.77 (m, 3H), 1.93-1.97 (m, 1H), 2.04 (s, 3H), 3.36-3.40 (m, 1H), 3.51-3.55 (m, 1H), 3.67 (s, 2H), 3.70 (s, 2H), 4.54-4.58 (m, 1H), 5.78 (s, 2H), 5.81 (s, 2H), 6.93 (d, J=7.5 Hz, 1H), 7.26-7.35 (m, 10H), 8.41 (br t, J=5.5 Hz, 1H), 11.63 (br, 1H).

Methyl(S)-2-[(4-methylphenyl)sulfonyl]amino-4-[[bis [[[[(phenylacetyl)oxy]methoxy]carbonyl]amino]methylene] amino]pentanoate (14) and methyl (S)-2-(acetyl)amino-4-[[bis[[[[(phenylacetyl)oxy]methoxy]carbonyl]amino] methylene]amino]pentanoate (15): were prepared following a literature procedure (Tangirala, R. S. A., et al. (2006). Bioorg Med Chem 14, 6202-6212). Each acid (12 and 13) was methylated with TMSCHN₂ (2 M solution in hexane) in dry benzene at room temperature and then purified by silica gel column chromatography with 40% EtOAc in hexane for 14, 80% EtOAc in hexane for 15 to give each ester 14 and 15 in 40 to 45% yield, respectively.

14: ¹H NMR (500 MHz, CDCl₃): δ1.65-1.72 (m, 2H), 1.76-1.81 (m, 1H), 2.41 (s, 3H), 3.34 (q, J=6.5, 2H), 3.48 (s, 3H), 3.68 (s, 2H), 3.71 (s, 2H), 3.93-3.97 (m, 1H), 5.28 (d, J=9.0 Hz, 1H), 5.80 (s, 2H), 5.83 (s, 2H), 7.24-7.36 (m, 12H), 7.71-7.72 (m, 2H), 8.28 (br t, J=5.8 Hz, 1H), 11.61 (s, 1H). ¹³C NMR (125 MHz, CDCl₃): δ 21.5, 24.8, 30.2, 40.4, 40.8, 41.0, 52.6, 55.3, 80.5, 81.2, 127.2, 127.3, 127.5, 128.6, 128.7, 129.3, 129.4, 129.7, 132.7, 133.3, 136.5, 143.8, 152.4, 156.3, 162.1, 169.9, 170.3, 171.8, HRMS calcd for C₃₄H₃₉N₄O₁₂S (M+H)⁺727.2285; found 727.2280.

15: ¹H NMR (125 MHz, CDCl₃): δ 1.59-1.73 (m, 3H), 1.88-1.92 (m, 1H), 2.03 (s, 3H), 3.40-3.45 (m, 1H), 3.45-3.52 (m, 1H), 3.68 (s, 2H), 3.71 (s, 2H), 3.75 (s, 3H), 4.63-4.67 (m, 1H), 5.80 (s, 2H), 5.82 (s, 2H), 6.28 (d, J=8.0 Hz, 1H), 7.25-7.36 (m, 10H), 8.32 (br t, J=5.5 Hz, 1H), 11.61 (br s, 1H). ¹³C NMR (500 MHz, CDCl₃): δ 23.4, 25.4, 29.6, 40.6, 41.0, 41.2, 52.1, 52.8, 80.8, 81.4, 127.5, 127.8, 128.8, 129.0, 129.6, 129.7, 132.9, 133.5, 152.7, 156.5, 162.9, 170.2, 170.6, 172.9. HRMS calcd for C₂₉H₃₅N₄O₁₁ (M+H)⁺ 615.2302; found 615.2297.

ProTAME Activation Analysis.

ProTAME was added to interphase *Xenopus* extract at 50 μM or cell growth media at 20 μM. For interphase extract, 800 μl of sample was collected at 0 min, 10 min, 20 min and 30 min after addition of proTAME and diluted to 8 ml with XB. For cell culture, approximately 800,000 cells were collected at 1 h, 2 h and 3 h after addition of proTAME and lysed in 400 μl lysis buffer as described above and subsequently diluted to 4 ml with lysis buffer. The diluted extract or cell lysate was extracted with 1.5 volume of ethyl acetate. The extracts were dried in vacuo and the dry extracts were resuspended in 200 μl of methanol for LC/MS analysis. LC/MS data were obtained using an Agilent series 1200 LC/6130 MS system with a reversed-phase C18 column (Phenomenex Luna C18(2), 4.6 mm×100 mm, 5 μm) and a CH₃CN/H₂O gradient solvent system beginning with 10% aqueous CH₃CN and ending at 100% CH₃CN at 20 min. 10 μl of each sample was injected for each analysis. The collected LC/MS profiles were further analyzed by extracting specific ions such as 343 (TAME) and 727 (proTAME) in the positive ion MS mode.

Odyssey Scanner for Western Signal Quantification.

Secondary antibodies coupled to fluorophores (antimouse Alexa-Fluor 750 and anti-rabbit Alexa-Fluor680, Invitrogen) were used to detect and quantify signals from rabbit anti-Cdc20 (Santa-Cruz, sc-8358) and mouse anti-GAPDH (AbCam, ab8245) antibodies on the same membrane using an Odyssey (Li-Cor Biosciences) scanner. Quantifications are reported as CDC20/GAPDH signal ratio, normalized to control treatment.

Cdc20/Cdh1 Binding Assay in HeLa Cells.

HeLa cells in DMEM 10% FBS were plated in T25 flasks at 20% confluence one day prior to the experiment. They were then synchronized by a double thymidine block (18 h for the first block, 8 h release and another 18 h for the second block, thymidine concentration: 2 mM). For analysis of Cdh1 binding, cells were released into 300 nM from the second thymidine block for 13 h and then washed into fresh medium. Six h later, cells were treated with 12 μM proTAME or proAAME or 0.06% DMSO for 2 h and then collected by trypin digestion. For analysis of Cdc20 binding, cells were transfected with indicated siRNAs during the first release from thymidine block after two washes with DPBS (CellGro 21-030-CV) and addition of 6.3 ml OptiMEM. A volume (79 μl) of 20 μl Control siRNA#3 or a 1:1 mix of 20 μl MAD2 siRNA and BubR1 siRNA (Dharmacon D-004101-01, 5'-GGAAGAAGAUCUAGAUGUA$_{UU}$-3' (SEQ ID NO: 11)) was mixed in 1381 μl OptiMEM in a tube, 23.7 μl OligoFectamine were mixed with 94.1 μl OptiMEM in a second tube. After 5 min incubation at RT, the tubes contents were mixed and siRNA-reagent complexes were allowed to form for 20 min at RT. The transfection mixes were added to cells in OptiMEM and FBS was added to 10% after 5 h transfection. Cyclin B1-Δ107 expressing adenovirus (1:100) was added at the start of the second thymidine block and kept in the medium for all subsequent steps. Cells were treated at 10 h after release with 100 nM okadaic acid, 25 μg/ml cycloheximide and 12 μM proTAME as indicated. After 2 h treatment, cells were collected by mitotic shake-off. Cell pellets were washed twice with DPBS and flash-frozen with liquid nitrogen and stored at −80° C. until use. Cell lysis and APC immunoprecipitation were performed as described above.

Live Cell Imaging.

The imaging plate was mounted onto a motorized stage (Prior ProScan II) on a Nikon TE2000E PFS inverted microscope fitted with an incubation chamber maintained at 37° C. and supplied with 5% $CO_2$. A 20× Plan Apo 0.75 NA or 40× Plan Fluor 0.75 NA objective lens was used as indicated and images were collected with 2×2 binning. DIC or GFP fluorescent images were taken every 12 min (unless otherwise specified) for 36 h with a Hamamatsu ORCA cooled CCD camera and Nikon Elements Software. TIFF files of each image were exported from Elements and used to build stacks and Quicktime movies with Metamorph imaging software (Molecular Devices). For manual analysis, mitotic duration is counted as the time between the first frame of chromosome condensation and the frame of chromosome segregation (anaphase) or decondensation (mitotic exit in the presence of nocodazole) or cell death (chromosomes shrinking to a small bright dot).

Emi1 Knockdown and proTAME Rescue.

HeLa H2B-GFP cells were plated in glass-bottom 24-well plates at 20% confluence one day prior to the experiment. Cells were transfected with a pool of Emi1 siRNA (Dharmacon M-012434-01, 5'-GAAAGGCUGUCAUGUAUUG-3' (SEQ ID NO: 4); 5'-CAACAGACACUUAAUAGUA-3' (SEQ ID NO: 5); 5'-CGAAGUGUCUCUGUAAUUA-3' (SEQ ID NO: 6); 5'-GUACGAAGUGUCUCUGUAA-3' (SEQ ID NO: 7)) or Control#3 siRNA (described above) at 18.5 nM with DharmaFect3. After 24 h, cells were treated with 0.06% DMSO or 12 μM proTAME. Live cell imaging was set up as described above.

ProTAME Dose-response.

HeLa H2B-GFP cells were plated in a 24-well plate in DMEM 10% FBS at 20% confluence one day prior to experiment and synchronized by double thymidine block as described above. ProTAME was added to final concentrations of 780 nM, 3 μM or 12 μM and proAAME was added to a final concentration of 12 μM at 8 h after release from the second thymidine block. 0.06% DMSO was used as the negative control. Live cell imaging was set up as described above.

Exogenous Cyclin-GFP Expression, Live-Cell Imaging, and Quantitation.

HeLa H2B-RFP cells were transduced with cyclin B1-GFP or cyclin A2-GFP adenovirus for 40 h. Phenol Red-Free DMEM (Mediatech) supplemented with 10% FBS and 1:100 Penicillin-Streptomycin-Glutamine (Mediatech) was used as imaging medium. 20 μM proAAME, 20 μM proTAME or 150 nM nocodazole was added 45 min prior to the start of imaging. Live cell imaging was set up as described above except that the cells were plated in an 8-well chambered coverglasses (NUNC Lab-tek 155411). Four positions per treatment group were imaged with DIC transmitted light, red fluorescence, and green fluorescence (Semrock GFP/HcRed "Pinkel" filter set) at 12 min intervals for 24 h. Stacks of red and green fluorescence were merged, saved as AVI video files and analyzed using ImageJ. For quantitation, the first GFP-positive cells that undergo mitosis in three separate movies were chosen, giving at least 30 cells quantitated for each treatment group. Mean intensity values for the green channel were collected for a cytoplasmic region of a cell upon mitotic entry, mitotic exit, or after 1 h of mitotic arrest. At the same time points, background mean green intensity was determined and individually subtracted from the cytoplasmic mean intensity. This background corrected mean intensity value was then used to determine the percentage of the original GFP signal remaining at the completion of division (for the control cells) or after 1 h of mitotic arrest (for the nocodazole and proTAME treated cells). The average values for all quantitated cells were plotted with the error bars representing standard error of the mean.

Immunofluorescence.

HeLa cells grown in DMEM+10% FBS were plated on 25 mm glass coverslips in a E-well dish at a density of 130,000/ml×3 ml 48 h prior to treatment. They were then treated with 0.06% DMSO, 12 μM proTAME, 300 nM nocodazole or 300 nM taxol for 2 h. The cells were washed twice with PBS and fixed with 3% paraformaldehyde for 15 min. The cells were then washed with PBS and permeabilized with PBS plus 0.5% Triton X-100 for 2 min. The cells were then washed with PBS and blocked with PBS plus 5% FBS for 1 h. CREST antisera diluted 1:50 into PBS was added to the cells and incubated at room temperature for 1 h. The cells were washed with PBS and incubated with 1:1000 anti-human-Alexa 568 (Invitrogen, A21090) and 1:100 anti-α-tubulin-FITC for 1 h. The cells were then washed with PBS and the nuclei were stained with 1 μg/ml Hoechst 33342. The cover slips were mounted in 0.1M N-propylgallate in 9:1 glycerol:PBS. Z-series images were taken on a Nikon TE2000 microscope with PerkinElmer spinning disk confocal device. Maximal Z-projection images of individual cells were made by Image J. To measure interkinetochore distances, a straight line was drawn across a kinetochore pair in the same confocal plane and pixel intensities along the line were plotted so that each kinetochore would be represented by a peak on the line. The interkinetochore distance was calculated as the distance between the peaks. Fifty-five kinetochore pairs from 5 cells treated with DMSO or proTAME were measured and the p-value was calculated with a paired student test.

Mad2 Knockdown and Time Point Analysis.

HeLa H2B-GFP cells were plated in a 24-well plate in DMEM+10% FBS at 20% confluence one day prior to the experiment and synchronized by double thymidine block as described above. The cells were released from the first thymidine block into 200 µl OptiMem without FBS. Transfection was performed immediately after the first thymidine release. To prepare the transfection mixture for one well, 40 µl OptiMem was mixed with 2.5 µl of 20 µM Mad2 siRNA stock (GGAACAACUGAAAGAUUGGdTdT (SEQ ID NO: 8), synthesized by DHARMACON) or control (D-001210-01-20, DHARMACON), and 6.5 µl of OptiMem was mixed with 1 µl of Oligofectamine (Invitrogen, 12252-011). The two mixtures were left at room temperature for 5 min before being mixed together and incubated for additional 20 min and then added to the cells to a final volume of 250 µl. 4 h after transfection, 250 µl of DMEM+20% FBS were added to cells. 8 h after the release, 500 µl of 4 mM thymidine in DMEM+10% FBS was added to each well to make the final concentration of 2 mM and the cells were incubated for another 18 h before being released into growth medium. At 8 h after release, cells were treated 0.06% DMSO, 12 µM proTAME, 300 nM nocodazole or 12 µM proTAME plus 300 nM nocodazole in growth medium. Cell samples were collected at 4 h, 8 h, 10 h, 12 h, 14 h, 16 h and 20 h post-release and protein levels were analyzed by Western blot.

Cdc20 Knockdown Sensitization to proTAME Treatment.

HeLa H2B-GFP cells were plated in glass-bottom 24-well plates (Greiner Bio-One 662892) at 20% confluence one day prior to the experiment. Cells were transfected with DharmaFect3, following the manufacturer's protocol at a final concentration of 18.5 nM control siRNA#3 or a mix of 1.85 nM Cdc20 siRNA completed to 18.5 nM with control siRNA#3. After 24 h transfection, cells were treated with DMSO or 4 µM proTAME and live cell imaging was set up immediately as described above.

UbcH10 and Cdc27 Knockdown and Hesperadin Treatment.

HeLa H2B-GFP cells were plated in glass-bottom 24-well plates at 20% confluence one day prior to the experiment and synchronized by double thymidine block as described above. Cells were transfected with UbcH10 siRNA (Dharmacon D-004693-15, 5'-UAAAUUAAGCCUCG-GUUGA$_{UU}$-3' (SEQ ID NO: 9)), Cdc27 siRNA (Dharmacon J-003229-11, 5'-GGAAAUAGCCGAGAGGUAA$_{UU}$-3' (SEQ ID NO: 10)) or Control#3 siRNA (described above) at 18.5 nM with DharmaFect3, during the release from the first thymidine block. Cells were treated with 100 nM Hesperadin or DMSO 8 h after release from the second thymidine block and live cell imaging was set up as described above.

Measuring Cycloheximide-sensitivity of Drug-induced Arrest.

HeLa H2B-GFP cells were plated in a 24-well plate in DMEM+10% FBS at 20% confluence one day prior to experiment and synchronized by double thymidine block as synchronized above. At 8 h after release from the second block, cells were treated with 12 µM proTAME, 300 nM nocodazole or 150 nM taxol and 4 h later, cells were left untreated or treated with an addition of 25 µg/ml cycloheximide. Live cell imaging was set up as described above.

Measuring Hesperadin-sensitivity of Drug-induced Arrest.

HeLa H2B-GFP cells were plated in a 24-well plate in DMEM+10% FBS at 20% confluence one day prior to experiment and synchronized by double thymidine block as described above. At 8 h after release from the second block, 100 nM hesperadin, 12 µM proTAME with or without 100 nM hesperadin, 300 nM nocodazole with or without 100 nM hesperadin or 150 nM taxol with or without 100 nM hesperadin were added to cells. Untreated cells were used as the control. Live cell imaging was set up as described above. For experiments with MG132, at 10 h after release from the second block, 3 µM MG132, or 3 µM MG132 plus 100 nM hesperadin, or 3 µM MG132 plus 100 nM hesperadin and 12 µM proTAME were added to cells. Alternatively, at 10 h after release from the second block, 10 µM MG132 with or without 25 µg/ml cycloheximide was added to the cells. 30 min after, cells were left untreated or treated with 100 nM hesperadin or 100 nM hesperadin and 12 µM proTAME. Live cell imaging was set up as described above.

Measuring Mad2-dependence of MG132-induced Arrest.

HeLa H2B-GFP cells were plated in a 24-well plate in DMEM+10% FBS at 20% confluence one day prior to experiment and synchronized by double thymidine block as described above. Mad2 siRNA transfection was performed as described above. At 10 h after release from the second block, 10 µM MG132 with or without 25 µg/ml cycloheximide was added to the cells. Live cell imaging was set up as described above. Manual analysis was focused only on cells that entered mitosis after MG132 addition.

Chromosome Congression Analysis.

HeLa H2B-GFP cells were plated in 35 mm glass-bottom dishes (MatTek) in DMEM+10% FBS at 20% confluence one day prior to the experiment and synchronized by double thymidine block as described above. Drugs were added as follows to a final volume of 3 ml from 2× concentrated preparation in culture medium. DMSO (0.06%), proTAME (3 and 12 µM) or 10 nM Nocodazole were added 8 h after release from the second block, while MG132 (10 µM) was added at 10 h. H2B-GFP was imaged for 4 hrs every 3 min at 40× magnification as described above.

Click-iT Chemistry Labeling of De Novo-translated Proteins.

HeLa H2B-GFP cells (600,000) were plated in 3 mL DMEM+10% FBS in 6-well plates 24 h prior to synchronization. Cells were arrested in interphase by 2 mM Thymidine treatment for 24 h. To label proteins translated in S/G2 phase, three hours after release from thymidine-block, the cells were washed once with warm DPBS with $Mg^{2+}$/$Ca^{2+}$ and switched to filter-sterilized labeling medium (Methionine-free medium from Sigma, catalog #D0422, supplemented with 10 mL FBS pre-dialyzed against 1 L DPBS, 2 mM Glutamine and 568 µM L-Cysteine). After 30 min pre-incubation to deplete the remaining intracellular pool of Methionine, the methionine analog L-azidohomoalanine (AHA) was added at 250 µM (Invitrogen, catalog #C10102) and the cells were incubated for 3 h in the presence or absence of 25 µg/mL cycloheximide. To label proteins translated in mitosis, cells were treated with 300 nM nocodazole or 12 µM proTAME at 5 h after release from thymidine block and allowed to enter mitosis. Mitotic cells were collected by mitotic shake off, washed once in warm DPBS with $Mg^{2+}$/$Ca^{2+}$ and switched to labeling medium. After 30 min pre-incubation, 250 µM AHA was added. Labeling was allowed to occur for 12 h in the presence or absence of 25 µg/mL cycloheximide. After labeling, the cells were collected by trypsinization (interphase cells) or mitotic shake-off (mitotic cells), washed twice with DPBS with Mg2+/Ca2+ and lysed in 50 μL lysis buffer (Tris-HCl 50 mM pH 8.0, SDS 1% supplemented with 250 U/mL Benzonase, VWR, catalog #80108-806 and EDTA-free protease inhibitors, Roche). After 15 min on ice, cells were vortexed and centrifuged at 15,000 g at 4 C for 5 min. Supernatants were collected and protein concentrations were determined using the BCA assay (Pierce). Proteins (200 μg) were labeled with biotin-azide following the manufacturer's protocol (Invitrogen, catalog #B10184) and the protein reaction buffer kit (catalog #C10276). Labeled proteins were desalted with desalting columns (Thermo Scientific, catalog #89889) pre-washed with incubation buffer (NP-40 1%, SDS 0.1% in DPBS with Ca2+/Mg2+, with protease inhibitors). Ten percent of proteins were kept aside as total protein control for western blots of specific proteins, and another 10% were conserved to run Streptavidin-HRP western blots to detect all labeled proteins. The remaining sample was incubated at room temperature with Neutravidin agarose resin pre-washed with incubation buffer (Thermo scientific, catalog #29200) to purify biotin-labeled proteins. The resin was washed once with incubation buffer and three times with wash buffer (NP-40 1% in DPBS with Ca2+/Mg2+, with protease inhibitors). Purified proteins were boiled in SDS-PAGE loading buffer and tested by western blotting.

Statistical Analysis.

For each indicated figure and conditions, the data sample size (N), median and average values are reported. Statistical analysis was performed using the software Jmp 8.0 (SAS Institute Inc.). Samples were compared two by two using the Mann-Whitney-Wilcoxon non-parametric statistical test. The p values are reported. The samples were considered statistically significantly different when p was inferior to 0.05. Very small p values were reported as zero.

TABLE 1

Statistical Analyses

| Figure | Condition 1 | Ni | Median (min) | Average (min) | Condition 2 | N2 | Median (min) | Average (min) | MW-Wilcoxon Statistical test p value |
|---|---|---|---|---|---|---|---|---|---|
| 4E_ProTAME (12 μM)-induced delay in mitotic entry correlates with the time of addition after release from thymidine block | DMSO | 150 | 612 | 625.0 | proTAME at 0 hr | 150 | 696 | 712.8 | 0 |
| | | | | | proTAME at 2 hrs | 150 | 660 | 669.0 | 3.97E−11 |
| | | | | | proTAME at 4 hrs | 150 | 624 | 636.6 | 0.07 |
| | | | | | proTAME at 6 hrs | 150 | 612 | 619.4 | 0.88 |
| | | | | | proTAME at 8 hrs | 150 | 612 | 622.6 | 0.96 |
| 5A_ProTAME induced mitotic arrest in HeLa cells | DMSO | 150 | 96 | 121.4 | proTAME 780 nM | 150 | 156 | 165.4 | 1.43E−12 |
| | | | | | proTAME 3 μM | 150 | 348 | 444.6 | 0 |
| | | | | | proTAME 12 μM | 150 | 1680 | 1640.5 | 0 |
| | | | | | proAAME 12 μM | 150 | 84 | 100.5 | 0.42 |
| 5B_Partial Cdc20 knockdown and low proTAME concentration synergize in delaying mitosis in HeLa cells | Control siRNA DMSO | 153 | 60 | 72.8 | Cdc20 siRNA DMSO | 150 | 96 | 144.2 | 0 |
| | | | | | Control siRNA proTAME | 114 | 288 | 496.5 | 0 |
| | Cdc20 siRNA DMSO | 150 | 96 | 144.2 | Cdc20 siRNA proTAME | 112 | 1170 | 1235.3 | 0 |

| Figure | Condition 1 | N1 | Median (fraction remaining) | Average (fraction remaining) | Condition 2 | N2 | Median (fraction remaining) | Average (fraction remaining) | MW-Wilcoxon Statistical test p value |
|---|---|---|---|---|---|---|---|---|---|
| 5D_ProTAME stabilizes CyclinB1 | proAAME | 31 | 0.15 | 0.15 | Nocodazole | 34 | 0.83 | 0.87 | 3.87E−08 |
| | Nocodazole | 34 | 0.83 | 0.87 | proTAME | 30 | 1.17 | 1.17 | 2.07E−11 |
| | | | | | proTAME | 30 | 1.17 | 1.17 | 7.86E−12 |
| 5D_ProTAME stabilizes CyclinA2 | proAAME | 40 | 0.06 | 0.08 | Nocodazole | 37 | 0.28 | 0.28 | 4.71E−14 |
| | Nocodazole | 37 | 0.28 | 0.28 | proTAME | 30 | 0.95 | 0.99 | 1.12E−12 |
| | | | | | proTAME | 30 | 0.95 | 0.99 | 7.38E−06 |

| Figure | Condition 1 | N1 | Median (mm) | Average (mm) | Condition 2 | N2 | Median (mm) | Average (mm) | MW-Wilcoxon Statistical test p value |
|---|---|---|---|---|---|---|---|---|---|
| 5E_ProTAME does not alter inter- | DMSO | 55 | 1.22 | 1.23 | proTAME | 55 | 1.28 | 1.26 | 0.23 |

TABLE 1-continued kinetochore distance

| Figure | Condition 1 | N1 | Median (min) | Average (min) | Condition 2 | N2 | Median (min) | Average (min) | MW-Wilcoxon Statistical test p value |
|---|---|---|---|---|---|---|---|---|---|
| 6A_ProTAME arrest is MAD2-dependent | Control siRNA DMSO | 150 | 108 | 121.7 | MAD2 siRNA DMSO | 150 | 12 | 13.2 | 0 |
| | | | | | Control siRNA Nocodazole | 150 | 1812 | 1680.1 | 0 |
| | | | | | Control siRNA proTAME | 150 | 1488 | 1512.4 | 0 |
| | MAD2 siRNA DMSO | 150 | 12 | 13.2 | MAD2 siRNA Nocodazole | 150 | 36 | 98.2 | 0 |
| | | | | | MAD2 siRNA proTAME | 150 | 84 | 121.7 | 0 |
| 6C_ProTAME arrest is hesperadin-sensitive | DMSO | 150 | 102 | 110.9 | DMSO Hesperadin | 150 | 96 | 98.7 | 0.05 |
| | Taxol | 150 | 2070 | 1946.9 | Taxol Hesperadin | 150 | 156 | 168.7 | 0 |
| | proTAME | 150 | 1272 | 1329.3 | proTAME Hesperadin | 151 | 228 | 262.2 | 0 |
| | Nocodazole | 150 | 2094 | 1851.8 | Nocodazole Hesperadin | 150 | 552 | 579.4 | 0 |
| 6D_UbcH10 and Cdc27 siRNA induced mitotic delays are hesperadin-siRNA sensitive | Control siRNA | 150 | 96 | 134.5 | Control siRNA Hesperadin | 150 | 120 | 115.6 | 0.22 |
| | | | | | UbcH10 siRNA | 150 | 156 | 330.5 | 1.51E−10 |
| | | | | | Cdc27 siRNA | 150 | 276 | 575.6 | 0 |
| | UbcH10 siRNA | 150 | 156 | 330.5 | UbcH10 siRNA Hesperadin | 150 | 108 | 115.8 | 5.20E−10 |
| | Cdc27 siRNA | 150 | 276 | 575.6 | Cdc27 siRNA Hesperadin | 150 | 132 | 131.8 | 0 |
| 7A_MG132 arrest is MAD2-dependent | Control siRNA 3 μM MG132 | 169 | 840 | 830.1 | MAD2 siRNA 3 μM MG132 | 150 | 667.5 | 605.3 | 3.81E−05 |
| 7B_Hesperadin overrides MG132 3 μM arrest in HeLa cells | MG132 3 μM Hesperadin | 150 | 174 | 502.2 | MG132 3 μM DMSO | 154 | 1440 | 1549.9 | 0 |
| | | | | | MG132 3 μM Hesperadin proTAME | 150 | 1296 | 1334.0 | 0 |
| 7C_Taxol does not restore mitotic arrest in the presence of MG132 3 μM and hesperadin | MG132 3 μM Hesperadin Taxol | 151 | 420 | 705.3 | MG132 3 μM Hesperadin | 155 | 312 | 511.4 | 0 |
| | | | | | MG132 3 μM Hesperadin proTAME | 150 | 1524 | 1598.9 | 0 |
| 7D_Hesperadin overrides MG132 10 μM arrest in HeLa cells | MG132 10 μM Hesperadin | 149 | 2160 | 2185.3 | MG132 10 μM DMSO | 150 | 2172 | 2169.8 | 0.95 |
| | | | | | MG132 10 μM Hesperadin proTAME | 119 | 2724 | 2657.5 | 1.35E−14 |
| 8A_Cycloheximide sitivity of mitotic arrests. | Nocodazole | 70 | 2160 | 1777.0 | Nocodazole Cycloheximide | 70 | 444 | 442.5 | 0 |
| | Taxol | 100 | 1602 | 1557.6 | Taxol Cycloheximide | 100 | 516 | 538.6 | 0 |
| | proTAME | 100 | 972 | 1052.0 | proTAME Cycloheximide | 100 | 1608 | 1577.9 | 0 |
| 8B_MG132 arrest is MAD2-dependent (see cell fate distribution in figure) | Control siRNA MG132 10 μM | 66 | 1614 | 1715.1 | Control siRNA MG132 10 μM Cycloheximide | 81 | 1788 | 1897.2 | 0.03 |
| | MAD2 siRNA MG132 10 μM | 64 | 1716 | 1755.2 | MAD2 siRNA MG132 10 μM Cycloheximide | 54 | 834 | 1078.0 | 3.11E−05 |
| 8C_Hesperadin rapidly overrides 10 μM MG132 arrest in the presence of cycloheximide | MG132 10 μM Cycloheximide Hesperadin | 133 | 1104 | 1335.9 | MG132 10 μM DMSO Cycloheximide | 151 | 2520 | 2346.4 | 0 |
| | | | | | MG132 10 μM Cycloheximide Hesperadin proTAME | 132 | 2532 | 2383.9 | 0 |
| S4A_ProTAME treatment arrests hTERT-RPE1 cells in mitosis. | DMSO | 26 | 24 | 30.9 | proAAME 12 μM | 31 | 36 | 32.1 | 0.25 |
| | | | | | proTAME 6 μM | 24 | 522 | 819.0 | 8.15E−10 |
| S4C_ProTAME induces a mild delay in chromosome congression | Untreated | 96 | 21 | 21.5 | proTAME 3 μM | 93 | 21 | 21.7 | 0.66 |
| | | | | | proTAME 12 μM | 95 | 24 | 26.0 | 1.37E−09 |

TABLE 1-continued

| | | | | | | | | | |
|---|---|---|---|---|---|---|---|---|---|
| | | | | | MG132 10 µM | 52 | 21 | 21.6 | 0.86 |
| | | | | | Nocodazole 10 nM | 91 | 24 | 26.2 | 7.76E−08 |
| S5G_Hesperadin overrides 12 µM proTAME-induced mitotic arrest after washout from a nocodazole-induced mitotic arrest | Release in medium | 150 | 96 | 124.4 | Release in proTAME 12 µM | 144 | 1410 | 1516.4 | 0 |
| | | | | | Release in proTAME 12 µM Hesperadin 100 nM | 150 | 156 | 202.1 | 1.05E−09 |
| | Release in proTAME 12 µM | 144 | 1410 | 1516.4 | Release in proTAME 12 µM Hesperadin 100 nM | 150 | 156 | 202.1 | 0 |

Substrate Degradation in *Xenopus* Egg Extract:

Mitotic extracts were pretreated with DMSO or compounds for 10 min. Substrates were expressed and $^{35}$S-methionine labeled using the TNT system from Promega and added to the extract at 10% final volume. Extracts were then incubated at 24° C., 1250 RPM, with samples taken at indicated times into SDS sample buffer, separated by SDS gel electrophoresis, and phosphoimaged (Bio-Rad PMI).

Luciferase Assay, Kinetics Assay, and Cdc20-binding to APC/C Assay

Performed using previously published methods (Zeng, X. et al. Cancer Cell 18, 382-395, (2010); Zeng, X. & King, R. W. Nat Chem Biol 8, 383-392, (2012)).

Crystal Structure

Determined as described (Tian, W. et al. *Proc Natl Acad Sci USA* 109, 18419-18424, (2012)) with apcin soaked into crystals at final concentration of 5 mM.

Assay for Cdc20 Binding to Apcin-A Resin:

Five µl of 5 mM apcin-A coupled to Bio-Rad Affigel-10 resin was incubated with in vitro-translated human Cdc20 or other protein (5 µl reticulocyte lysate diluted to 30 µl with XB+0.05% Tween) at 24° C., 1500 RPM, for 30 min. Competitors were pre-incubated with Cdc20 in reticulocyte lysate for 2 minutes at 24° C. before adding to apcin-A resin.

Fixed Cell Imaging Assay:

Asynchronous cells in 384-well plates were treated with indicated concentrations of apcin and proTAME. 18 hours later, cells were fixed and stained. Following automated high-throughput imaging, mitotic index was determined by intensity of Hoechst staining. Maximum intensity of each nucleus in each treatment was plotted as cumulative frequency (intensity vs. fraction of cells below the intensity on the x-axis). An intensity threshold was set based on the mitotic fraction in DMSO-treated wells. The fraction below threshold was calculated for each treatment and used in the statistical models to evaluate synergy.

Fluorescence Live Cell Imaging:

RPE1-H2B-GFP or U2OS-H2B-GFP cells were plated in 24-well glass-bottom plates 18-24 hours prior to siRNA transfection using RNAiMax (Invitrogen). After treatment with compound(s), DIC and GFP images were captured at 6-minute intervals for 45 hours. Movies were manually analyzed using Nikon Elements software or Image J.

Reagents

Commercial antibodies used for western analysis were as follows: anti-Cdc27 (610455, BD Transduction Laboratories™), anti-Cdc20 (BA8)(sc-93399, Santa Cruz Biotechnology and NB 100-2646, Novus Biologicals) to recognize *Xenopus* Cdc20, anti-Cdc20 (H-175)(sc-8358, Santa Cruz Biotechnology) to recognize human Cdc20, anti-HA-Peroxidase (3F10)(12013 819 001, Roche). Secondary antibodies used included anti-rabbit IgG-HRP (NA934; GE Healthcare), and anti-mouse IgG-HRP (NA931; GE Healthcare). For APC/C immunopurification from *Xenopus* extract, anti-Cdc27 (AF3.1; sc-9972, Santa Cruz Biotechnology) was used. For immunodepletion of *Xenopus* Cdc20, a rabbit polyclonal antibody was generated by Yenzym (South San Francisco, Calif.) by immunization with an N-terminal fragment of Cdc20 (residues 1-170; tagged at C-terminus). Chemicals used were cycloheximide (Calbiochem 239764), calcium ionophore (A23187, free acid form, Calbiochem), Tosyl-L-arginine methyl ester (Sigma T4626), proTAME (Boston Biochem I-440), apcin (Enamine T0506-3874), apcin-P (Ambinter Amb2237944), apcin-M (Ambinter Amb1395012).

Preparation of *Xenopus* Egg Extract

Interphase *Xenopus* egg extract was prepared from eggs laid overnight according to the protocol of Murray (Murray, A. W. Methods Cell Biol. 36, 581-605, (1991)) with the exception that eggs were activated with 2 µg/ml calcium ionophore (A23187) for 30 minutes prior to the crushing spin. Extract was frozen in liquid nitrogen and stored at −80° C. Interphase extract was induced to enter mitosis by addition of nondegradable cyclin B (MBP-Δ90) at 20 µg/ml and incubated at 22-24° C. for 30-60 min. Nondegradable cyclin B consisting of a fusion of the maltose-binding protein (MBP) to *Xenopus* cyclin B lacking its N-terminal 90 amino acids (MBP-Δ90) (Salic, A. & King, R. W. Methods Enzymol 399, 567-585, (2005)) was expressed in *E. coli* by inducing cultures at an $OD_{600}$ of 0.6 with 300 µM isopropylthiogalactoside (IPTG) for 5 h at room temperature. Purification was carried out following New England BioLabs (NEB) protocol.

Substrate Degradation Assays in *Xenopus* Egg Extract

Substrates consisted of human full length cyclin B1, cyclin A2, securin, Nek2A, or an N-terminal fragment of human cyclin B1 (residues 1-88). Each substrate was amplified with primers by PCR to allow T7-dependent transcription of the PCR product. Substrates were expressed and labeled with $^{35}$S-methionine (Perkin Elmer NEG709A500UC) using the TNT system from Promega. To measure degradation of substrates, extracts were pretreated with DMSO or test compounds for 10 min as well as 100 µg/ml cycloheximide to prevent re-incorporation of free labeled amino acid. The in vitro-translation reaction was then added to the mitotic *Xenopus* extract at 10% final volume. Extracts were then incubated at 24° C., with shaking at 1250 rpm, with samples taken at indicated times.

Reactions were quenched with SDS sample buffer and processed for SDS-PAGE and phosphoimaging (Bio-Rad PMI) and quantification was performed using Quantity One software (Bio-Rad).

Measuring Cdc20 Binding to APC/C in Xenopus Egg Extract

To examine levels of Cdc20 associated with APC/C, the APC/C was immunopurified from mitotic Xenopus egg extract. For 100 μl extract, 2 μg of anti-Cdc27 antibody (AF3.1, Santa Cruz Biotechnology) was cross-linked to 5 μl of Affiprep Protein A beads (156-0006, Bio-Rad) and incubated for 1 h at 4° C. Apcin, TAME or DMSO was mixed with extract upon addition to anti-Cdc27-Affiprep Protein A beads in the presence or absence of exogenous substrate. Substrate consisted of human cyclin B1 N-terminal fragment (residues 1-88) containing a HA-tag at N-terminus and his tag at C-terminus, as previously described (Dimova, N. V. et al. Nat Cell Biol 14, 168-176, (2012)). Following incubation with extract, beads were washed quickly three times with 20-fold volume of XB (10 mM potassium HEPES, pH 7.7, 100 mM KCl, 0.1 mM $CaCl_2$, 1 mM $MgCl_2$) and combined with SDS sample buffer. For analysis of Cdc20 binding to APC/C, samples were processed for SDS-PAGE and immunoblotting against Cdc20 and APC/C subunit Cdc27. Chemiluminescence was imaged on a Fuji LAS 3000 with Image Reader LAS-3000 software. Levels of Cdc20 were quantified using Image J and data was normalized to respective Cdc27 levels.

Coupling of Apcin-A to Affigel-10 Resin

Affigel-10 resin (Bio-Rad) was washed twice with DMSO and dried. The resin was then mixed with 5 mM or 15 mM apcin-A dissolved in DMSO (2× volume of dry resin). N,N-diisopropylethylamine was diluted 50-fold into the solution. The resin was rotated at RT for 2 h and the reaction was quenched with ⅕ resin volume of ethanolamine. The resin was then washed sequentially with isopropanol, water and XB+0.05% Tween. The resin was stored at 4° C. as a 50% slurry in XB+0.05% Tween.

Cdc20 Depletion by Apcin-A Resin

For a round of depletion of Cdc20 from mitotic Xenopus extract, 15 mM apcin-A resin was incubated with extract at 4° C. rotating for 30 min. The volume of resin used was 40% of the extract volume. Three rounds of depletion were performed. To rescue degradation in the depleted extract, reticulocyte lysate containing in vitro-translated human Cdc20 was added to the extract at 1/10th extract volume.

Assay for Cdc20 Binding to Apcin-A Resin

Human Cdc20 in pCS2 vector was mutated at the various residues described with Quikchange Site-Directed Mutagenesis Kit (Agilent Technologies) and custom primers for each sequence. All mutations were confirmed by sequencing. For a single pull down assay, 5 μl of 5 mM apcin-A resin was incubated with 30 μl diluted in vitro-translated human Cdc20 or other WD40 proteins (5 μl reticulocyte lysate diluted to 30 μl with XB+0.05% Tween) at 24° C. with shaking (1500 RPM) for 30 min. Competitors were pre incubated with Cdc20 in reticulocyte lysate for 2 minutes at room temperature before adding to apcin-A resin. Bound and input Cdc20 in FIGS. 40e and 40g were detected by western blotting. Ccd20, other WD40 proteins, ODC, and Cdc20 mutants in FIGS. 40f and 41c were labeled with $^{35}S$ methionine and detected by phosphorimaging.

Ubiquitination Assay

Measurements of kinetics of ubiquitination were performed using an N-terminal fragment of cyclin B1 and APC/C isolated from Xenopus extract, exactly as previously described (Zeng, X. & King, R. W. Nat Chem Biol 8, 383-392, (2012)).

Antibody-Based Depletion of Cdc20 from Xenopus Extract

Cdc20 antibody, covalently coupled to Affiprep protein-A beads as described (Zeng, X. et al. Cancer Cell 18, 382-395, (2010)), was incubated with mitotic extract at 4° C. with rotation for 30 min. The volume of antibody beads used was 20% of the reaction volume. Three rounds of depletion were performed, with separation of extract from beads after each round by centrifugation in Pierce centrifuge columns (Thermo-Pierce 89868).

Luciferase Assay

A fusion of the N-terminal domain of cyclin B1 to luciferase (Verma, R. et al. Science 306, 117-120, (2004)) was added to mitotic extract at 4 ug/ml (FIG. 30d) or to interphase extract at 250 μg/ml for 10 minutes at room temperature then diluted to a final concentration of 4 ug/ml final in mitotic extract (FIG. 41b). The extract was incubated at room temperature and 3 μL samples were taken at 0, 20, 40 and 60 min. The samples were mixed quickly with 30 μL luciferin assay buffer (270 μM coenzyme A, 20 mM tricine, 3.67 mM MgSO4, 0.1 mM EDTA, 33.3 mM DTT, 530 μM ATP and 470 μM luciferin, pH 7.8), and the level of luminescence was measured on Wallac 1420 multilabel counter.

Protein Purification and Crystallization

The coding region of human Cdc20 containing residues 161-477 (Cdc20-WD40) was amplified by PCR and cloned into the modified pFastBac vector. Recombinant baculovirus encoding the N-terminal His6-tagged Cdc20 protein was constructed using the Bac-to-Bac system (Invitrogen) according to manufacturer's protocols. A tobacco etch virus (TEV) protease cleavage site was introduced into the N-terminus of Cdc20. Sf9 insect cells were infected with the Cdc20 baculovirus and harvested at about 60 hours post-infection. His6-tagged Cdc20-WD40 was purified with $Ni^{2+}$-NTA agarose resin (Qiagen) and cleaved with TEV protease to remove the $His_6$-tag. The Cdc20-WD40 protein was further purified by anion exchange chromatography with a Mono-Q column followed by size exclusion chromatography with a Superdex 200 column (GE Healthcare). Purified Cdc20-WD40 was concentrated to 4-5 mg/ml in the Superdex 200 column buffer containing 25 mM Tris (pH 8.5), 150 mM NaCl, 1 mM $MgCl_2$, 5% glycerol and 5 mM TCEP.

The Cdc20-WD40 protein was crystallized at 20° C. using the sitting-drop vapor-diffusion method with a reservoir solution containing 0.1 M MES (pH 6.5), 15% (w/v) PEG 6000, and 5% MPD. The Cdc20-WD40 crystals were transferred to a new 2 μl sitting drop with a reservoir solution containing 0.1 M MES (pH 6.5) and 20% (w/v) PEG 6000 and soaked for 3-5 hours to get rid of bound MPD. Apcin compound was dissolved into DMSO and added to the same drop at the final concentration of 5 mM. After overnight soaking, the crystals were cryo-protected in a solution containing 0.1 M MES (pH 6.5), 20% (w/v) PEG 6000, 10% glycerol and 5 mM apcin, and then flash-cooled in liquid nitrogen. Crystals diffracted to a minimum Bragg spacing ($d_{min}$) of about 2.1 Å and exhibited the symmetry of space group $P2_1$ with cell dimensions of a=41 Å, b=87 Å, c=48 Å, and β=113° and contained two Cdc20 molecules per asymmetric unit.

Data Collection and Structure Determination

Diffraction data were collected at beamline 19-ID (SBC-CAT) at the Advanced Photon Source (Argonne National Laboratory, Argonne, Ill., USA) and processed with HKL3000[34]. Phases were obtained by molecular replacement with Phaser using the crystal structure of human Cdc20-WD40 (PDB code: 4GGC) as search model (McCoy, A. J. et al. J Appl Crystallogr 40, 658-674, (2007)). Iterative model building and refinements were carried out with COOT and Phenix, respectively (Adams, P. D. et al. Acta crystallographica. Section D, Biological crystallography 66, 213-221, (2010); Emsley, P., et al. Acta crystallographica. Section D, Biological crystallography 66, 486-501, (2010)). The final model for Cdc20-WD40-apcin ($R_{work}$=16.5%, $R_{free}$=21.3%) contains 313 residues, 82 water molecules and one apcin molecule. MolProbity was used for structure validation to show that all models have good geometry, except for one surface residue that is an outlier in a Ramachandran plot (Chen, V. B. et al. Acta crystallographica. Section D, Biological crystallography 66, 12-21, (2010)). Data collection and structure refinement statistics are summarized in Table 2.

High-throughput Image-based Assay to Measure Mitotic Fraction

Parental A549, U2O5, and hTERT-RPE1 cells were purchased from ATCC. DLD-1 cells were purchased from Sigma. For hTERT-RPE1, A549 and U2O5 cells, stable cell lines expressing H2B-GFP were derived using described methods (Sigoillot, F. D. et al. A time-series method for automated determination of changes in mitotic and interphase duration from time-lapse movies. PLoS One 6, e25511, (2011)) and used in the experiments. DLD-1 cells were used without further modification. Cell lines were tested for *mycoplasma* contamination (Lonza kit LT07-218) after they were derived and were found negative. For each cell line, asynchronous cells were resuspended to a density of $3.75 \times 10^4$ cells/ml. A WellMate dispenser (Thermo Scientific) was used to distribute 40 μL of suspension to each well of a black, clear-bottom 384-well plate (Corning 3712). Plates were sealed with breathable white rayon sealing tape (Nunc 241205) during plating and subsequent incubation. After 24 hours incubation, the cells were treated with indicated concentrations of apcin and proTAME dissolved in DMSO. After 18 hours, cells were fixed and stained directly without wash steps to avoid loss of mitotic cells, by adding 10 μl of 6× concentrated fixing/staining reagent (60% Formalin, 0.6% Triton X-100, and 1.5 ug/mL Hoechst 33342 in DPBS). The plates were sealed with aluminum sealing tape (Nunc 276014) and incubated at room temperature for 40 min before imaging. Plates were then imaged at 4 positions per well using an ImageXpress Micro (Molecular Devices) high-throughput microscope, using a 10× objective. Cell images were processed automatically in ImageJ to identify the nuclei and count the number of nuclei and maximum intensity of each nucleus in each image. The output files from ImageJ for each treatment were pooled and the cumulative frequency curve of maximum intensity for the cell population in each treatment was computed using Matlab. An intensity threshold was set based on the mitotic fraction in the wells treated with DMSO to separate mitotic cells from interphase cells. The interphase fraction for each treatment was indicated by the fraction below the threshold on the cumulative frequency plot.

Statistical Analysis of Combined Action of proTAME and Apcin in Fixed Cell Imaging Assay In order to detect departures from Bliss independence across the matrix of proTAME and apcin doses (FIG. 43a), a separate Poisson regression was fit to the count of cells not in mitosis for each dose combination, and it was tested whether a regression model that allows for departures from Bliss independence (the synergy model) is a significantly better fit to the data than a regression model that does not allow departures from Bliss independence (the Bliss model).

A Poisson regression is a natural framework to test Bliss independence for count data. The standard calculation of the predicted effect of a drug combination under Bliss independence, using the fractional product method of Webb (Webb, J. L. Enzyme and metabolic inhibitors. (Academic Press, 1963), is α×Fa×Fb, where α is the null effect, Fa is the proportional reduction in counts attributable to compound A, and Fb is the proportional reduction in counts attributable to compound B. In the Poisson regression model, the following were fit:

$$\log(Y_i/N_i) = B_0 + (B_1 \times A) + (B_2 \times B) + (B_3 \times A{:}B) + \epsilon$$

where $Y_i$ is the count of cells below threshold for each well i, $N_i$ is the total cells for each well I, $B_0$ is the intercept, $B_1$ is the effect of compound A alone (TAME), $B_2$ is the effect of compound B alone (APCIN), and $B_3$ is the parameter that captures departure from Bliss independence. A is an indicator variable for the presence of compound A, and B is an indicator variable for the presence of compound B.

Exponentiating and rearranging, it is easy to see that α in the fractional product method is equivalent to $\exp(B_0)$, Fa is equivalent to $\exp(B_1)$, and Fb is equivalent to $\exp(B_2)$. Thus, it follows that the predicted Bliss independence value in the Poisson regression framework will be $\exp(B_0+B_1+B_2)$, which is equal to the expected value of the model that does not include a $B_3$ term. To test significance, it is possible to compare the likelihood of the data under a model that does not include the $B_3$ term (representing the departure from Bliss independence) to the likelihood of the data under the synergy model, using a standard $\chi^2$ likelihood ratio test. A significant test indicates statistical support for synergy.

The procedure, then, is for each TAME dose ($x_i = x_1 \ldots x_n$, in μM) and each APCIN dose ($y = y_1 \ldots y_n$, in μM), to fit the full (synergy) model and the reduced (Bliss) model to the data from each of four dose/treatment combinations: TAME=0 μM, APCIN=0 μM (no treatment); TAME=$x_i$ μM, APCIN=0 μM (TAME only); TAME=0 μM, APCIN=$y_i$ μM (APCIN only), and TAME=$x_i$ μM, APCIN=$y_i$ μM (combined action). From the model fits, first the significance of the departure from Bliss independence is tested as described above. Then the predicted values for the combined dose under Bliss independence (FIG. 38b, third column) as $\exp(B_0+B_1+B_2)$, and the fitted values under the synergy model (FIG. 38b, second column) for the combined dose as $\exp(B_0+B_1+B_2+B_3)$ (which is simply the expected value of the model when both indicator variables are 1) are generated. The difference between these model fits (FIG. 43a and FIG. 38b fourth column) represents the degree of departure from Bliss independence, with positive values indicating synergy, 0 indicating Bliss independence, and negative values indicating antagonism. Alternately, the value of the parameter $B_3$ may be considered as representing the multiplicative departure from Bliss independence: that is, $B_3$ is what the Bliss independence prediction needs to be multiplied by in order to obtain the expected value of the full model fit.

A separate set of models were fit to each dose combination as described above, so independent estimates of departures from Bliss independence for each combination of doses in the dose matrix were generated, allowing for detection of complicated patterns of non-independence across the dose-response surface. In order to retain proper control of the family-wise Type I error rate, P-values were adjusted for multiple testing using the Holm-Bonferroni method, as implemented in the R function p.adjust. A multiple-test-corrected P-value <0.05 is considered significant.

Fluorescence Live Cell Imaging

RPE1-H2B-GFP or U2OS-H2B-GFP cells were plated in 24-well glass-bottom plates (Greiner BioOne, 662892) 18-24 hours prior to siRNA transfection using RNAiMax (Invitrogen). Plates were inserted into a covered chamber supplied with humidified 5% $CO_2$ and mounted onto a motorized microscope stage (Prior Scientific). DIC and FITC images were captured at 6 minute intervals for 45 hours using a Nikon Ti inverted fluorescence microscope fitted with a 37° C. enclosed incubation chamber and using a 20× Plan Apo 0.75 NA objective lens. A Hamamatsu ORCA cooled CCD camera collected the images with 2×2 binning using Nikon Elements software (version 3.0). Movies were manually analyzed using Nikon Elements software or ImageJ. Mitotic duration was defined as the time from nuclear envelope breakdown until anaphase, in the case of normal mitosis, or until exit from prolonged mitosis as indicated by cytoplasmic blebbing accompanied by changes in chromatin as detected by H2B-GFP.

To measure efficiency of Mad2 knockdown by siRNA, Western blot samples were each prepared from a single well of the 24-well glass-bottom plates. Twenty-four hours after transfection, cells were collected by trypsinization, pelleting, and resuspension in 2× NuPAGE sample buffer (Invitrogen)+50 µM DTT.

Survival Analysis of Live Cell Imaging Data

In order to detect differences in mitotic duration among cells in the live-cell imaging screen, a stratified Cox proportional hazards model (Cox, D. R. Regression models and life tables. J Royal Statistics Soc B34, 187-220, (1972)) was fit to censored mitotic duration times (where cells that are not observed exiting mitosis or dying in mitosis are censored at the last known time in mitosis). The Cox proportional hazards model is a semiparametric approach to modeling time-to-event data, in which covariates are assumed to have constant proportional effects over time relative to a baseline hazard function that can take any form. In this case, stratification on "person" (the individual who analyzed the movie) and "date" (the date the assay was run) allow the baseline hazard function to differ across experimental blocks, but assume a fixed effect of treatment across experimental blocks. The model is thus:

$$h_i(t|Z=j)=h_j(t)\exp(\beta_1 \times apcin_i + \beta_2 \times apcinM_i + \beta_3 \times proTAME_i + \beta_4 \times proTAME_i:apcinM_i + \beta_5 \times proTAME_i:apcin_i), j=1\ldots 4$$

where $h_i(t)$ is the hazard function of cell i at time t, $h_j(t)$ is the baseline hazard for strata j (with 4 levels, one for each person and date combination), $apcin_i$, $proTAME_i$, and $apcinM_i$ are indicator variables for presence or absence of the compounds apcin, proTAME, and apcin-M, respectively in cell i, $proTAME_i$:$apcin_i$ is an indicator variable that is 1 if both proTAME and apcin are present in cell i, and 0 otherwise, and $proTAME_i$:$apcinM_i$ is a similar indicator variable for proTAME+apcin-M. In this model, $\beta_1$, $\beta_2$, $\beta_2$, and $\beta_3$ represent the effects of apcin, apcin-M, and proTAME alone, while $\beta_4$ and $\beta_5$ represent the additional non-additive effect of the compounds beyond what is predicted from the combination of effects of the two compounds alone. This model was fit separately to cells treated with control siRNA or Mad2 siRNA. All statistical analysis was carried out in R 3.0.0 using the functions available as part of the survival package.

In this model, the β coefficients represent the log hazard ratios for exiting mitosis between treated and untreated cells. However, for ease of interpretation the β coefficients are exponentiated to convert them to normal hazard ratios, and then multiplied by 100 to convert to percentages relative to DMSO. These hazard ratios, which are referred to as mitotic exit rate, represent the relative probability that a treated cell in mitosis at time t will exit mitosis in the next time interval compared to an untreated cell. Thus, a treatment that has the effect of reducing mitotic exit rate to 50% of the control indicates that at any time point t, treated cells in mitosis have only half the chance of exiting mitosis in the next time interval as control cells in mitosis do.

The mitotic exit rates relative to DMSO for each treatment predicted by this model are presented in Tables 4-6). For ease of interpretation, the treatment effects are presented relative to DMSO for all individual compounds and compound combinations. Combination compound effects relative to DMSO are easily obtained from the model as the product of the mitotic exit rates for each individual compound and the synergy effect. Also presented is the parameter $\beta_5$, which represents the degree of synergy observed for the proTAME+apcin treatment combination (Table 6). This coefficient can be interpreted as observed mitotic exit rate in the combined compound treatment relative to the mitotic exit rate expected under Bliss independence. Thus, numbers below 100 represent synergy (lower mitotic exit rate compared to expectation) and numbers above 100 represent antagonism.

In order to verify the fit of these data to the proportional hazards assumption of the Cox regression model, the weighted residual test (Grambsch, P. & Therneau, T. Proportional hazards tests and diagnostics based on weighted residuals. Biometrika 91, 515-526, (1994)) implemented in the R function cox.zph was used. While a minor deviation from proportionality was observed only for proTAME in the control siRNA treatment (rho=0.12027, P=0.002697), as expected based on the biphasic nature of the survival curve for proTAME only in this condition, this deviation was eliminated in the Mad2 siRNA trea was found.

Example 2

Figure 1A:
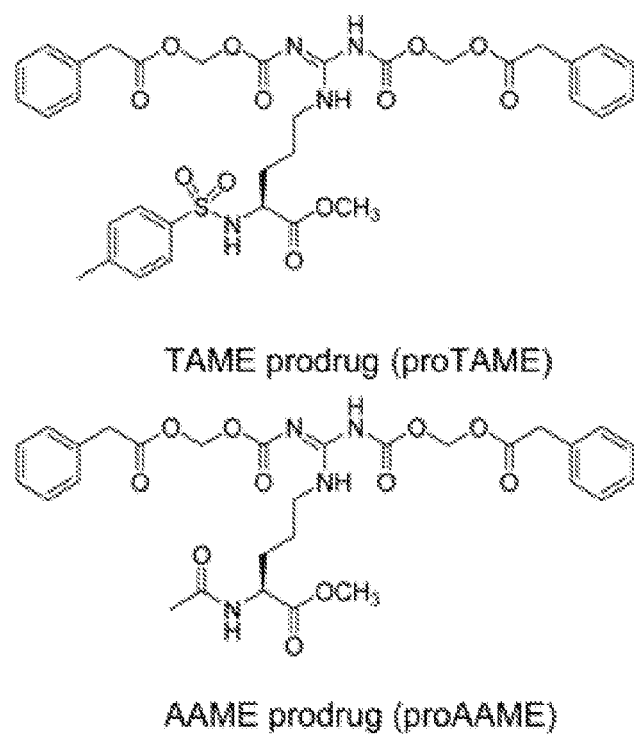
FIG. 1A is a schematic representation of the structure of proTAME and proAAME.

A TAME Prodrug Induces Mitotic Arrest in HeLa Cells by Inhibiting APC Activation Despite the fact that TAME binds to human APC, it did not inhibit mitotic division in human HeLa cells. It was speculated that TAME might not be cell permeable due to its positively charged guanidino group. Therefore a cell-permeable TAME prodrug was synthesized by modification of the guanidino group (Saulnier et al., Bioorgan. & Med. Chem. Let., 1994, 4:1985-1990; hereby incorporated by reference) to produce an N,N'-bis(acyloxymethyl carbamate) derivative 18 (proTAME) (FIG. 1A). Once inside the cell, proTAME is cleaved by cellular esterases, producing an unstable carbamate intermediate that undergoes decarboxylation to restore the original structure of TAME. It was found that proTAME is rapidly converted to TAME in *Xenopus* extract (FIG. 13A) and efficiently inhibits cyclin B-luciferase proteolysis (FIG. 13B). ProTAME is also activated efficiently when added to HeLa cells, but conversion was not efficient in all cell lines tested (FIG. 13C).

Figure 1B:
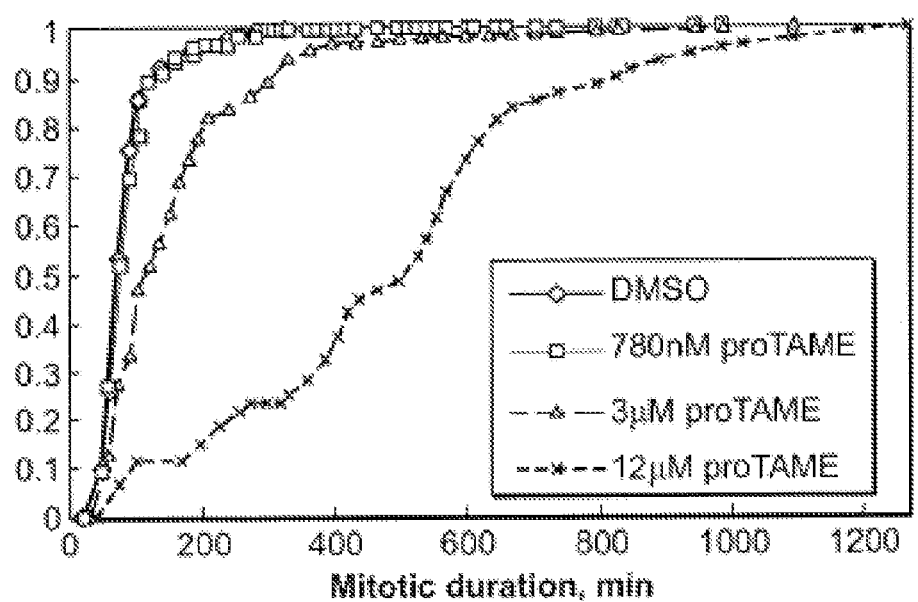
FIG. 1B is a graph showing that proTAME induces mitotic arrest in HeLa cells. HeLa cells expressing H2B-GFP were treated with compounds and imaged for 36 h at 15 min intervals. Cumulative frequency curves of mitotic duration were plotted.
Figure 1C:
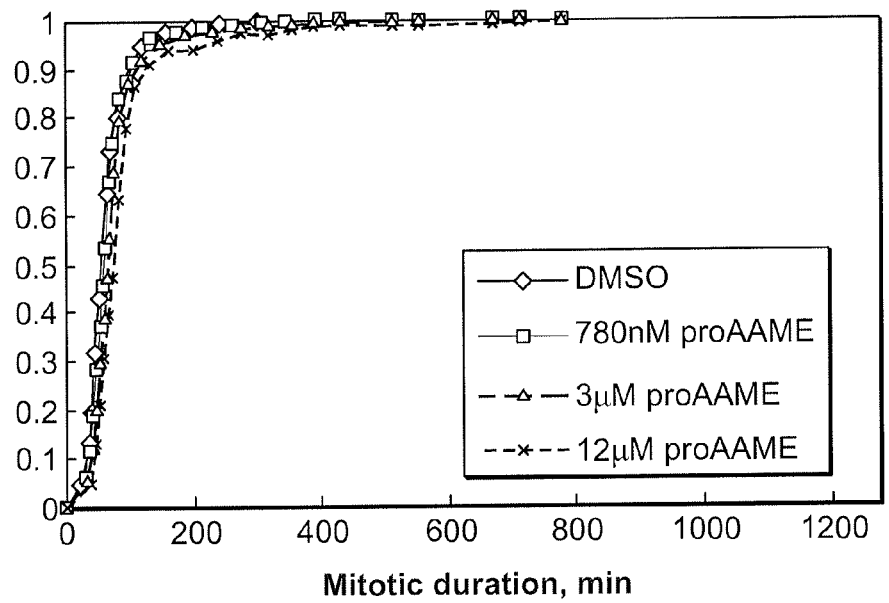
FIG. 1C is a graph showing that proAAME does not induce mitotic arrest in HeLa cell. The same experiment in 1B was done with proAAME.
Figure 1D:
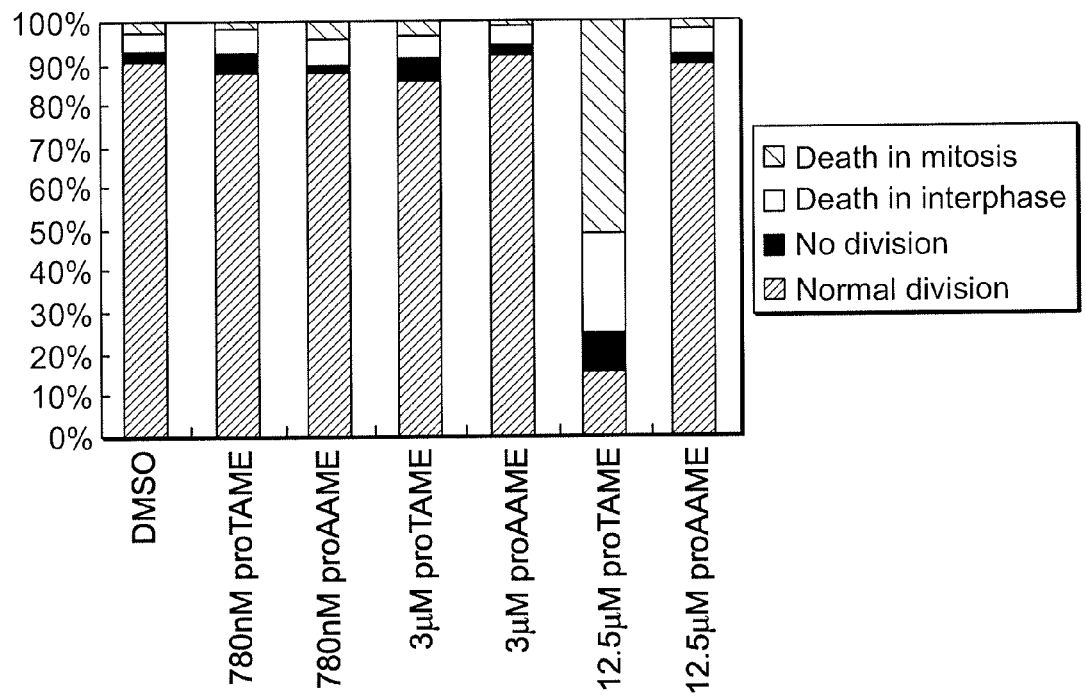
FIG. 1D is a bar graph showing that cell fate distribution for the experiments in 4B and 4C.

The effect of ProTAME on cell division was next determined by live imaging of HeLa cells that express Histone 2B-GFP. As a control, a prodrug version of AAME (proAAME) was synthesized (FIG. 1A). ProTAME induced a dose-dependent increase in mitotic duration, from 75 minutes for DMSO or proAAME treated cells, to 120 minutes for cells treated with 3 µM proTAME (FIGS. 1B and C). At this concentration, proTAME-treated cells formed metaphase plates with normal timing but anaphase onset was delayed. At 12 proTAME-treated cells arrested in metaphase for more than 8 hours, with most cells dying after the prolonged arrest. At this concentration, chromosome congression was also delayed, with cells taking 40 minutes, on average, to achieve metaphase, compared to 15 minutes for DMSO-treated cells. The delay is potentially a consequence of cyclin A stabilization. Some cells showed abnormal segregation of chromosomes after prolonged arrest, suggesting incomplete degradation of securin. At 12 µM, proAAME had no effect on mitosis or cell viability (FIG. 1C). It was noted that fluorescence imaging may artifactually shorten the duration of proTAME-induced mitotic arrest by enhancing cell death, as repeating this experiment by Differential Interference Contrast (DIC) imaging rather than fluorescence imaging increased the duration of mitotic arrest from 8 to over 10 hours (FIG. 9A, B). Under these imaging conditions, late dividing cells (those entering mitosis 16 hours after the initiation of the experiment) did not arrest in mitosis, but rather showed only a modest mitotic delay. Whether this difference reflects proTAME metabolism or whether exposure of cells to proTAME during G1 induces drug resistance is next determined.

Figure 1E:
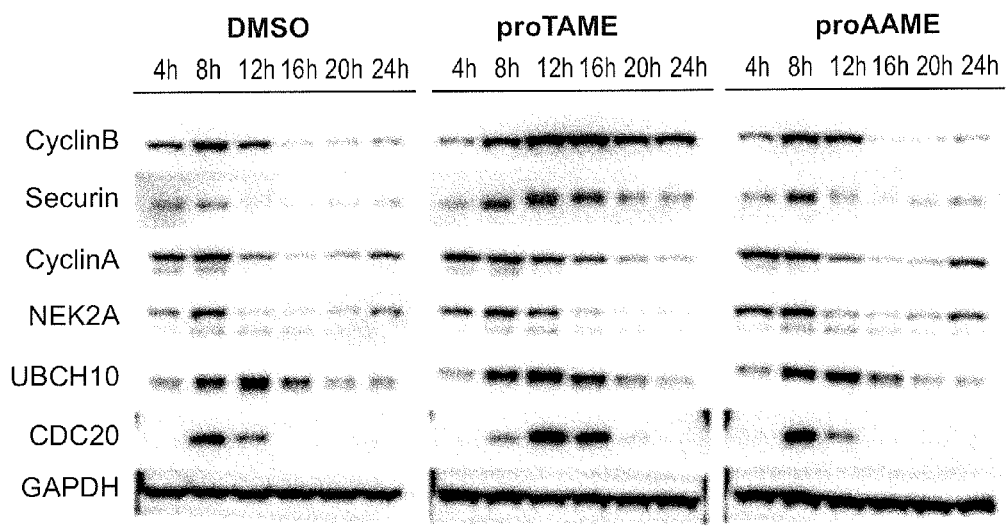
FIG. 1E is a series of photographs of gel electrophoresis analysis showing that proTAME stabilizes endogenous APC substrates. HeLa cells were synchronized by double thymidine procedure and released into compounds (12 μM). Protein levels were measured by immunoblot.
Figure 1F:
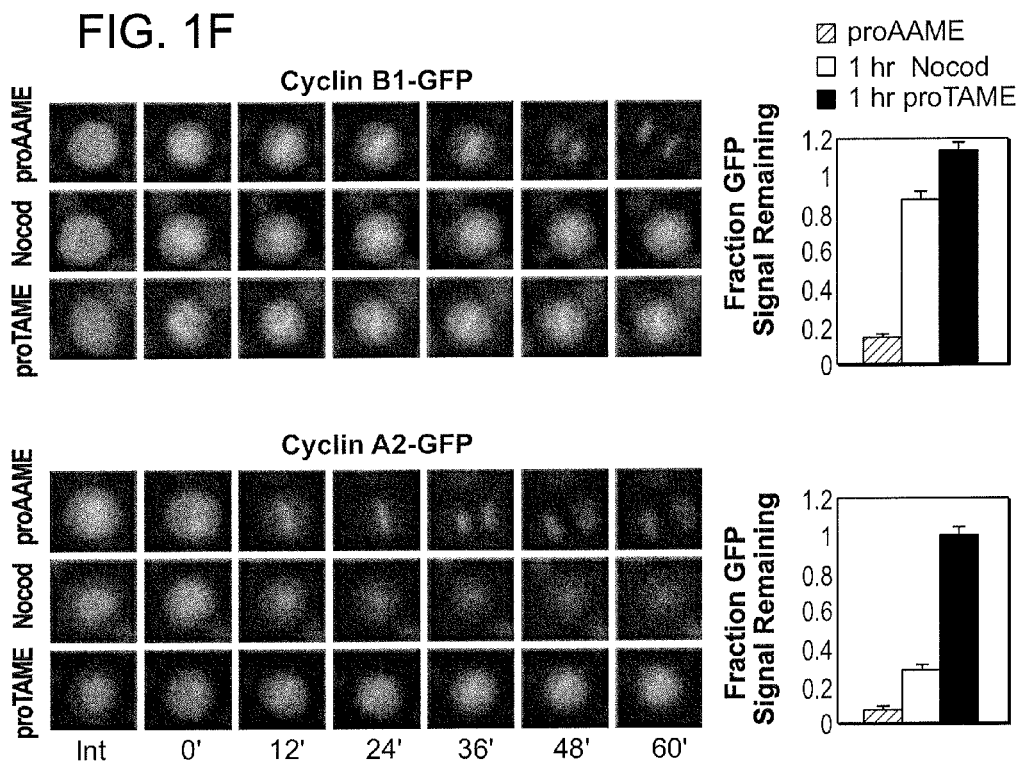
FIG. 1F is a series of photographs and accompanying graphs showing that proTAME stabilizes exogenous cyclin B1-GFP and cyclin A2-GFP in HeLa cells. HeLa H2B-RFP cells transduced with cyclin-GFP adenoviruses were imaged at 12 min intervals after treatment with 20 μM proTAME or proAAME, or 150 nM nocodazole. Representative cells are shown. The fraction of GFP intensity remaining at 60 min as compared to the onset of mitosis was determined for at least 30 individual cells for each group. Error bars represent standard error of the mean.

The effect of proTAME on the degradation of endogenous APC substrates in synchronized HeLa cells was next determined. Cyclin B and securin were dramatically stabilized by proTAME but not by proAAME (FIG. 1E). Cyclin A and Nek2A, which are both degraded in early mitosis, were also stabilized but to a lesser extent. The effects of proTAME on degradation of cyclinB1-GFP or cyclin A2-GFP were also characterized by live cell imaging. In the absence of drug, both proteins were degraded during mitosis, with cyclin A2-GFP degradation preceding that of cyclin B1-GFP. As expected, cyclin B1-GFP was stabilized during nocodazole-induced mitotic arrest, whereas cyclin A2-GFP was degraded, since its degradation is not constrained by the SAC 3 (FIG. 1F). Consistent with the Western blot results, cyclin B1-GFP was stabilized in mitotic cells following proTAME treatment, and in fact accumulated to higher levels than in nocodazole-treated cells. Furthermore, cyclinA2-GFP was robustly stabilized during proTAME-induced mitotic arrest, strongly suggesting that TAME directly inhibits APC activity, and does not stabilize APC substrates simply by activating the SAC.

Figure 1G:
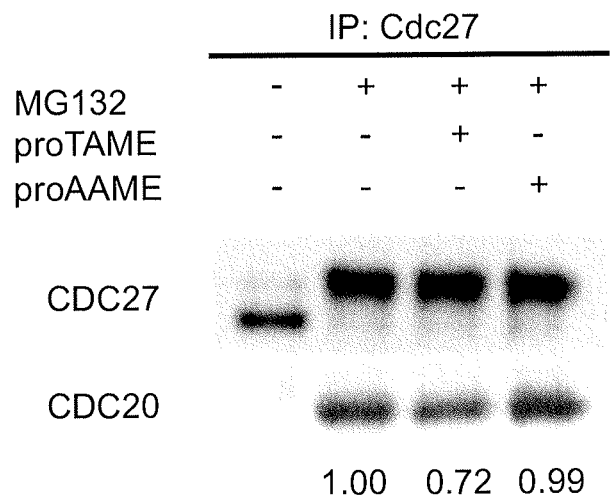
FIG. 1G is a series of photographs and accompanying schematics showing that proTAME partially inhibits Cdc20 binding to human APC. HeLa cells were released from a double thymidine block into growth medium for 10 h, and then treated with 10 μM MG132 plus DMSO, proTAME or proAAME (12 μM) for an additional 2 h. APC was immunoprecipitated with Cdc27 antibody, and the amount of Cdc27 and Cdc20 was analyzed by immunoblot.
Figure 1H:
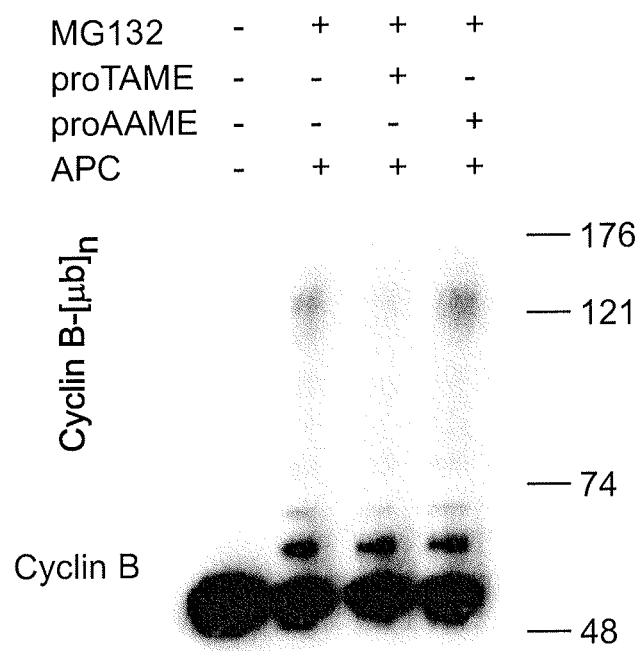
FIG. 1H is a series of photographs and accompanying schematics showing that proTAME inhibits APC-Cdc20 activity. APC from Hela cells treated as in 4G was tested in an in vitro ubiquitination assay.
Figure 2A:
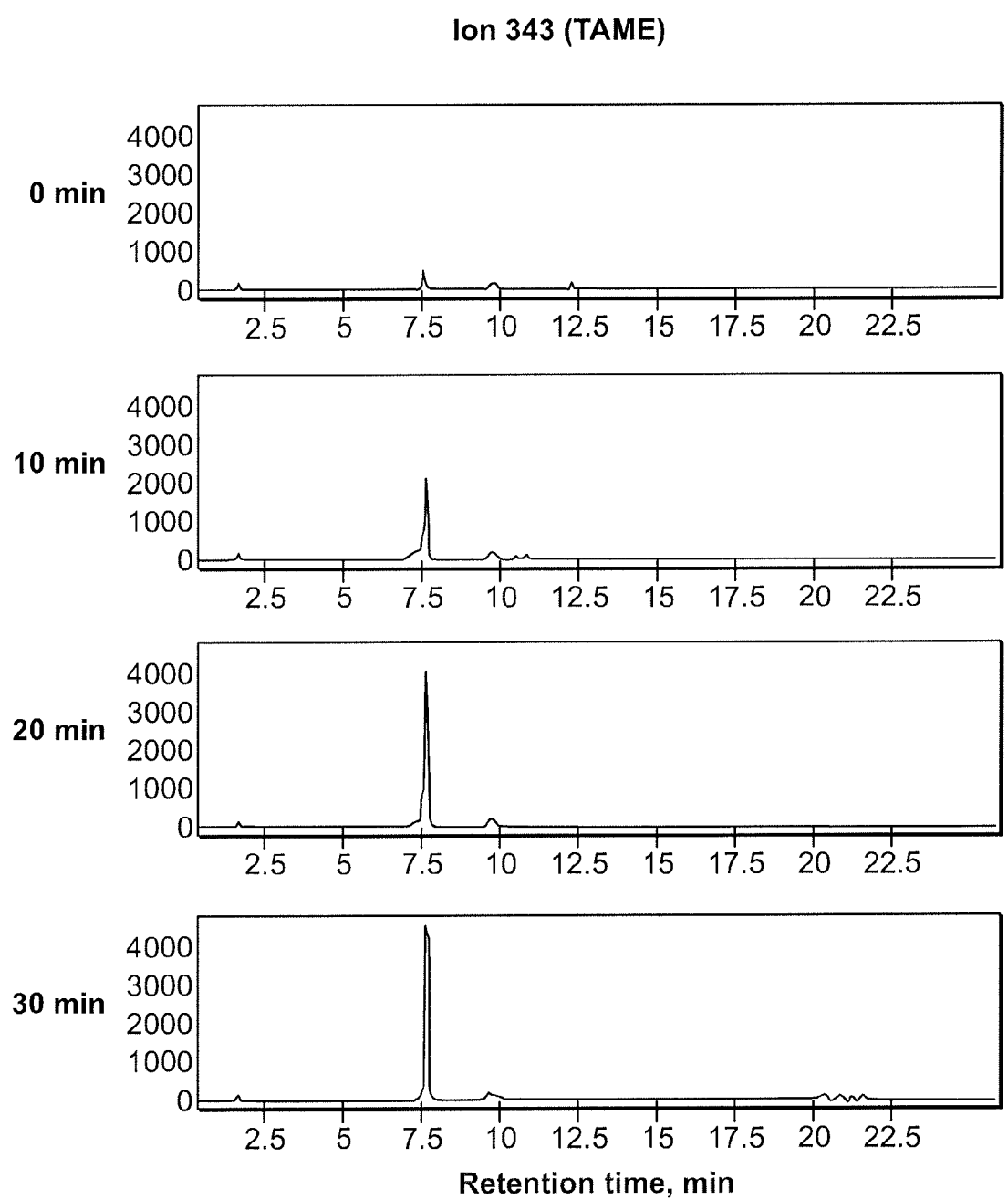
FIG. 2A is a chromatogram and accompanying graph. 50 μM proTAME was added to interphase Xenopus extract and samples were collected at indicated time points. Ethyl acetate extraction was performed, and samples analyzed by liquid-chromatography-mass spectrometry (LC/MS). Chromatograms and quantitation of the abundance of TAME and proTAME ion are shown.
Figure 2A:
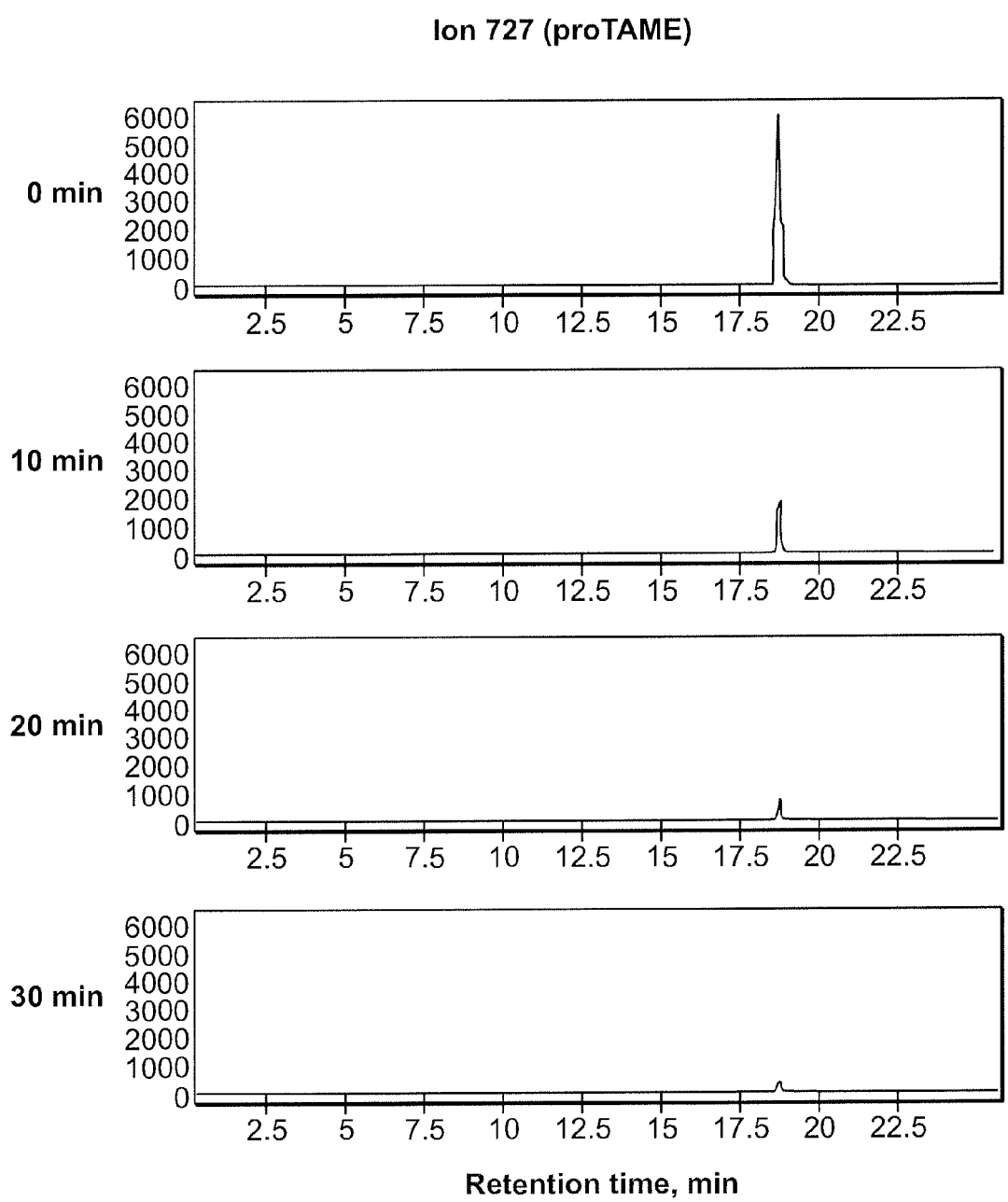
Figure 2A:
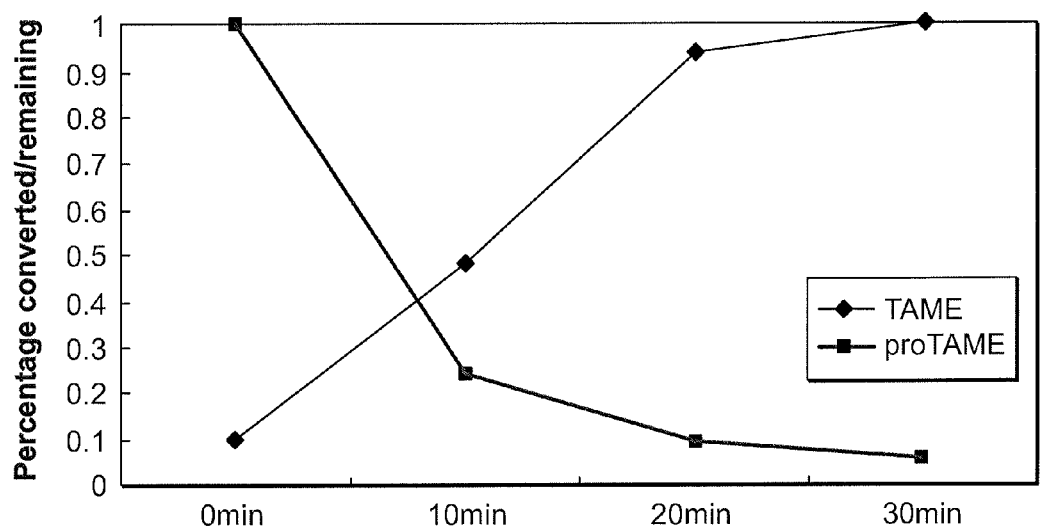
Figure 2B:
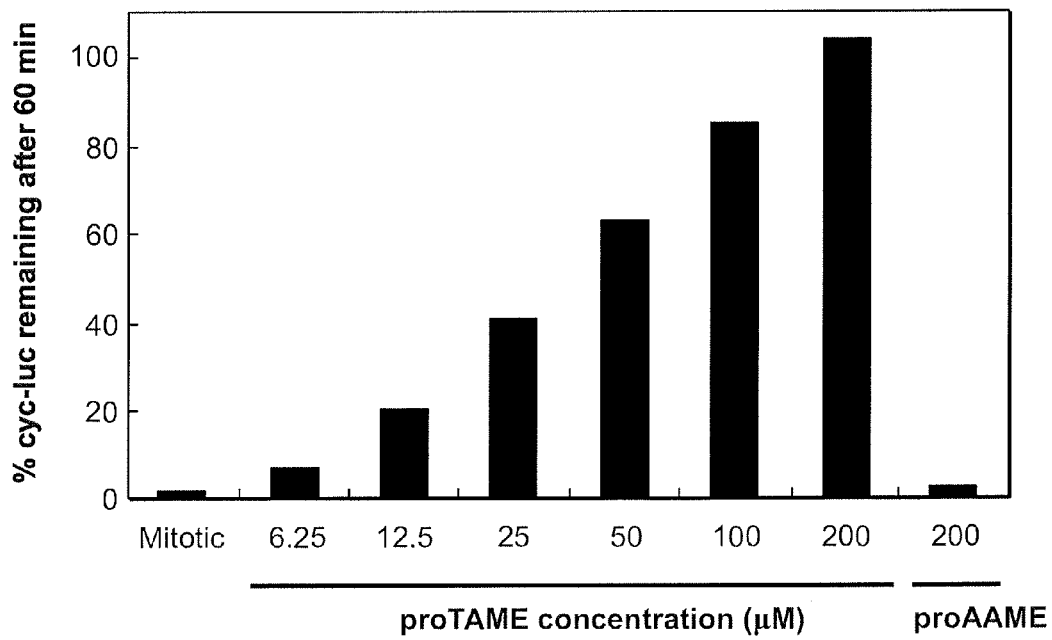
FIG. 2B is a graph showing that proTAME inhibits cyclin B-luciferase degradation in mitotic extract. Different concentrations of proTAME or proAAME were added to mitotic Xenopus extract containing cyclin B-luciferase reporter. Samples were collected at 60 min and the remaining reporter level was measured by luminescence.
Figure 2C:
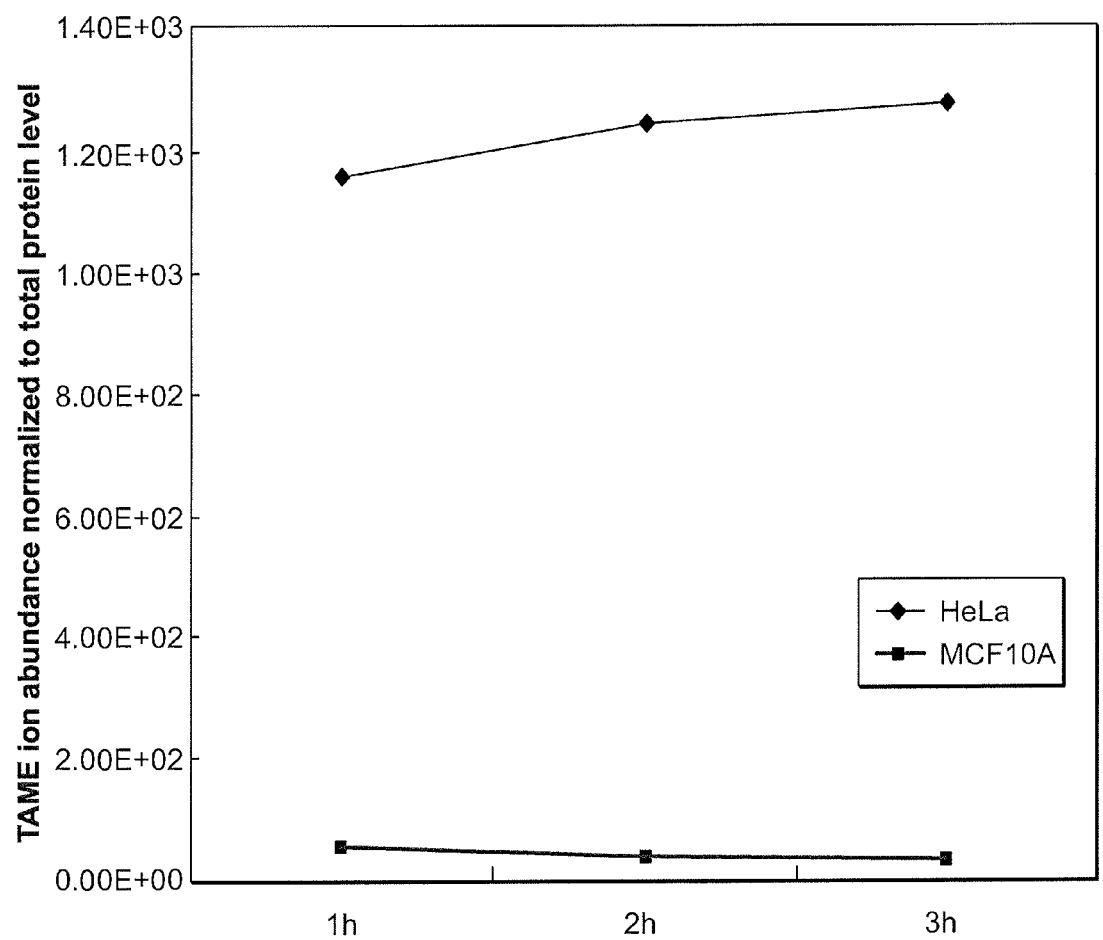
FIG. 2C is a chromatogram and accompanying graph showing that proTAME is efficiently activated in HeLa cells but not MCF10A cells. HeLa and MCF10A cells were treated with 20 μM proTAME. Cells were collected at indicated time points and lysed. Ethyl acetate extraction was performed prior to LC/MS analysis. Chromatograms and quantitation of the abundance of TAME ion normalized to total protein level are shown. Notice that the scale in the top panels is different for HeLa cells (maximum value 140,000) and MCF10A cells (maximum value 14,000).
Figure 3:
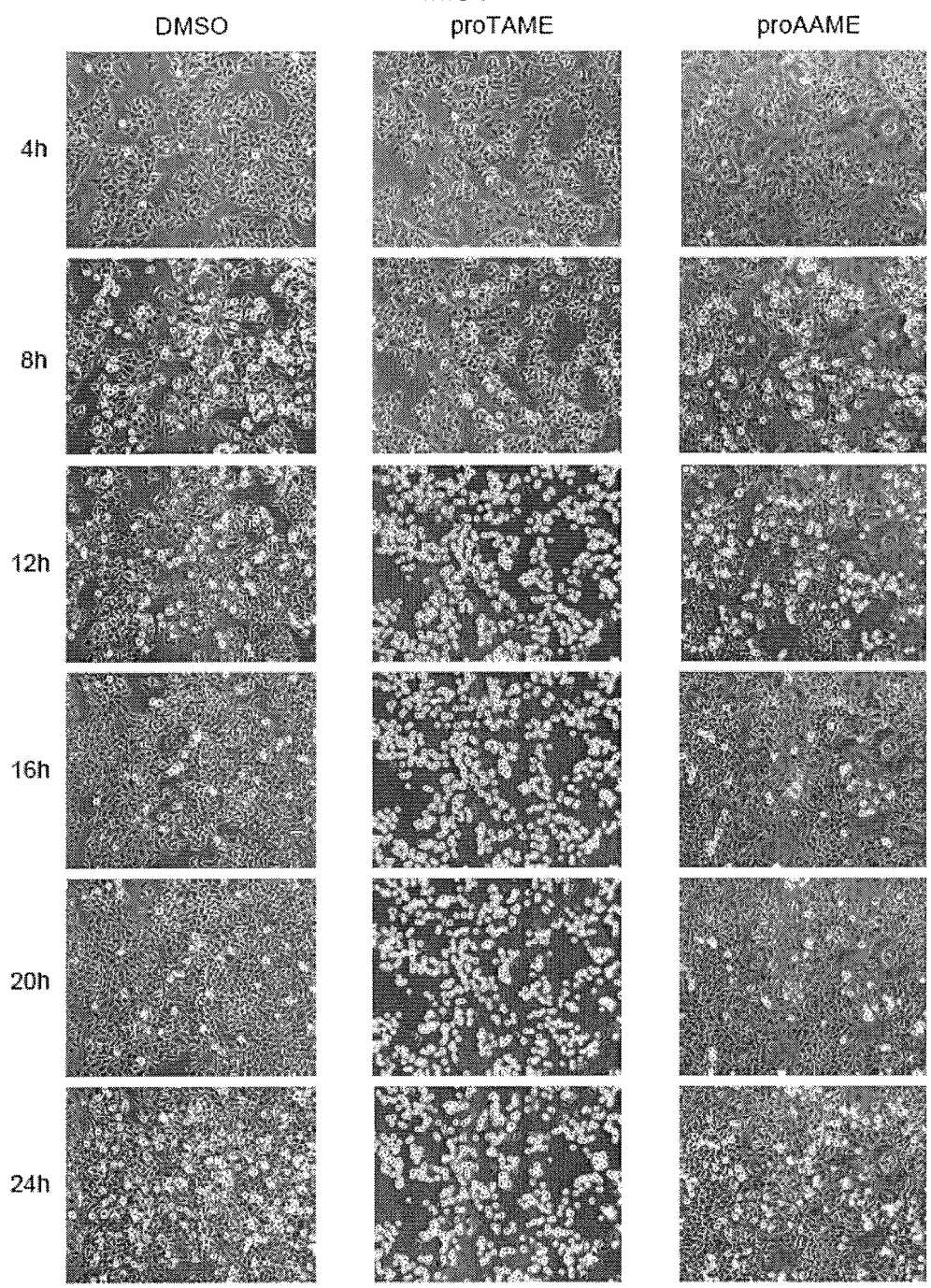
FIG. 3 is a series of photographs showing that proTAME induces mitotic arrest in synchronized HeLa cells. HeLa cells were synchronized with double thymidine block and released into 0.06% DMSO, 12 μM proTAME or 12 μM proAAME after the second block. Phase contrast images were taken every 4 h after release.

The ability of proTAME to stabilize cyclin A and other APC substrates suggested that proTAME inhibits APC activation in human cells. To test whether this effect is a consequence of inhibiting Cdc20 binding to the APC, HeLa cells were released from a double thymidine block for 10 hours, and then treated with MG132 plus proTAME or proAAME for 2 hours. Mitotic cells were collected by shakeoff, lysed, and the APC was isolated by immunoprecipitation. A 30% reduction was observed in Cdc20 binding to the APC after proTAME treatment (FIG. 1G). To test if this modest reduction of APC-bound Cdc20 resulted in inhibition of APC activity, an in vitro ubiquitination assay was performed with APC isolated as described above and it was found that proTAME treatment indeed inhibited APC activity, especially the ability of APC to catalyze formation of higher molecular weight ubiquitin conjugates (FIG. 1H).

ProTAME may induce a sustained mitotic arrest in HeLa cells despite the incomplete blockade of Cdc20 association. In addition to Cdc20, Apc10/Doc1 also has an IR tail, and Doc1 has been implicated in substrate recognition and processivity of the APC. However, it is not yet clear whether the IR tail of Doc1 is required for APC association or its ability to activate the APC. Alternatively, proTAME may interfere with substrate recruitment, such as the interaction of the MR-tail of Nek2A with the APC.

Example 3

ProTAME-Induced Mitotic Arrest is Partially Dependent on SAC Activity

The ability of proTAME to induce a prolonged mitotic arrest and inhibit APC activation in cells, despite producing only a partial reduction of Cdc20 association with the APC, suggested that the SAC may be important for the proTAME-induced mitotic arrest. One possibility is that in addition to its ability to directly bind to the APC, proTAME may nonspecifically perturb microtubules, resulting in SAC activation. Mitotic spindle and kinetochore morphology was therefore examined in HeLa cells arrested in mitosis with proTAME or microtubule inhibitors for 2 h.

Figure 4A:
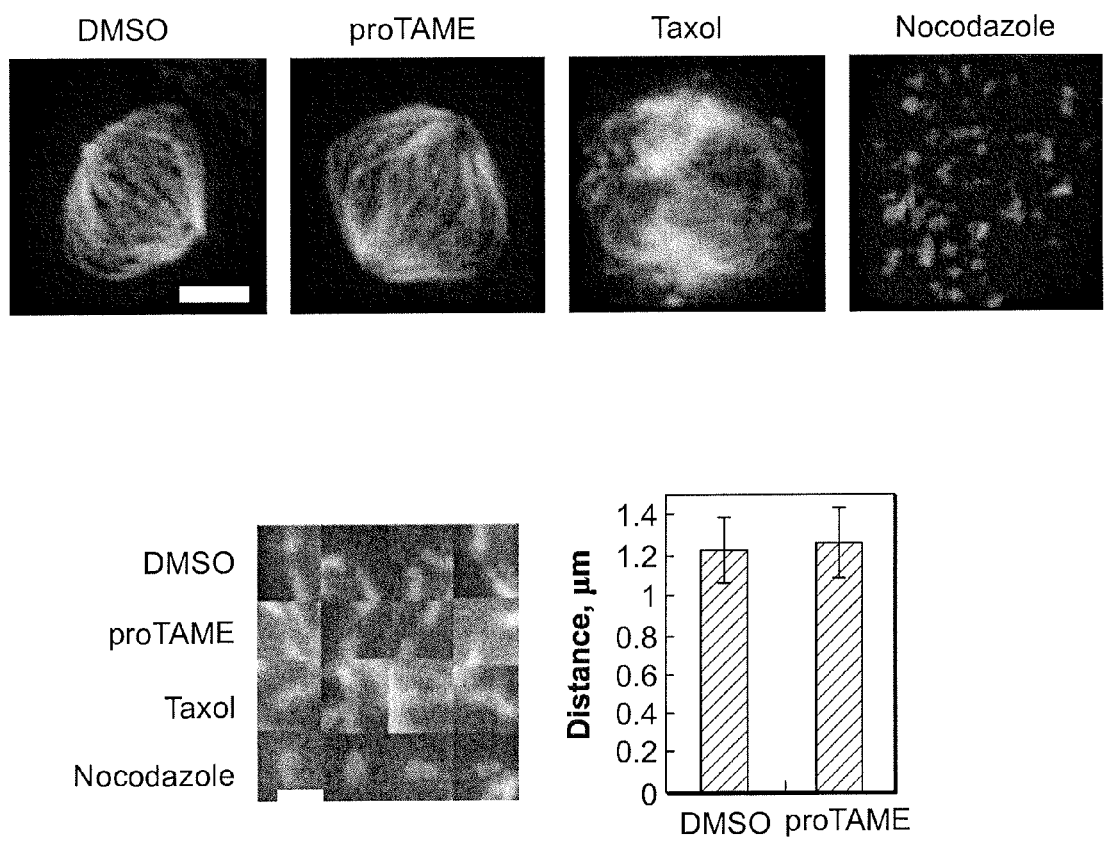
FIG. 4A is a series of photographs and accompanying graph showing that proTAME does not disrupt mitotic spindles. HeLa cells were treated with DMSO, proTAME (12 μM), Taxol™ or nocodazole (300 nM) for 2 h, and then stained with tubulin (green) and CREST (red) antibody. Representative images are shown. Bar: 3 mm. Representative images of kinetochore pairs are shown. Bar: 1.2 μm. Inter-kinetochore distance was measured in DMSO or proTAME treated cells and no statistically significant difference was found (n=55, P=0.3, paired t-test). Error bars represent standard deviation.

Whereas nocodazole and taxol strongly perturbed spindle organization, proTAME had no measurable effects on spindle morphology, spindle-kinetochore attachment, or tension across kinetochores compared to the DMSO control (FIG. 4A), suggesting that the mitotic arrest observed with proTAME treatment is not a consequence of microtubule perturbation.

Figure 4B:
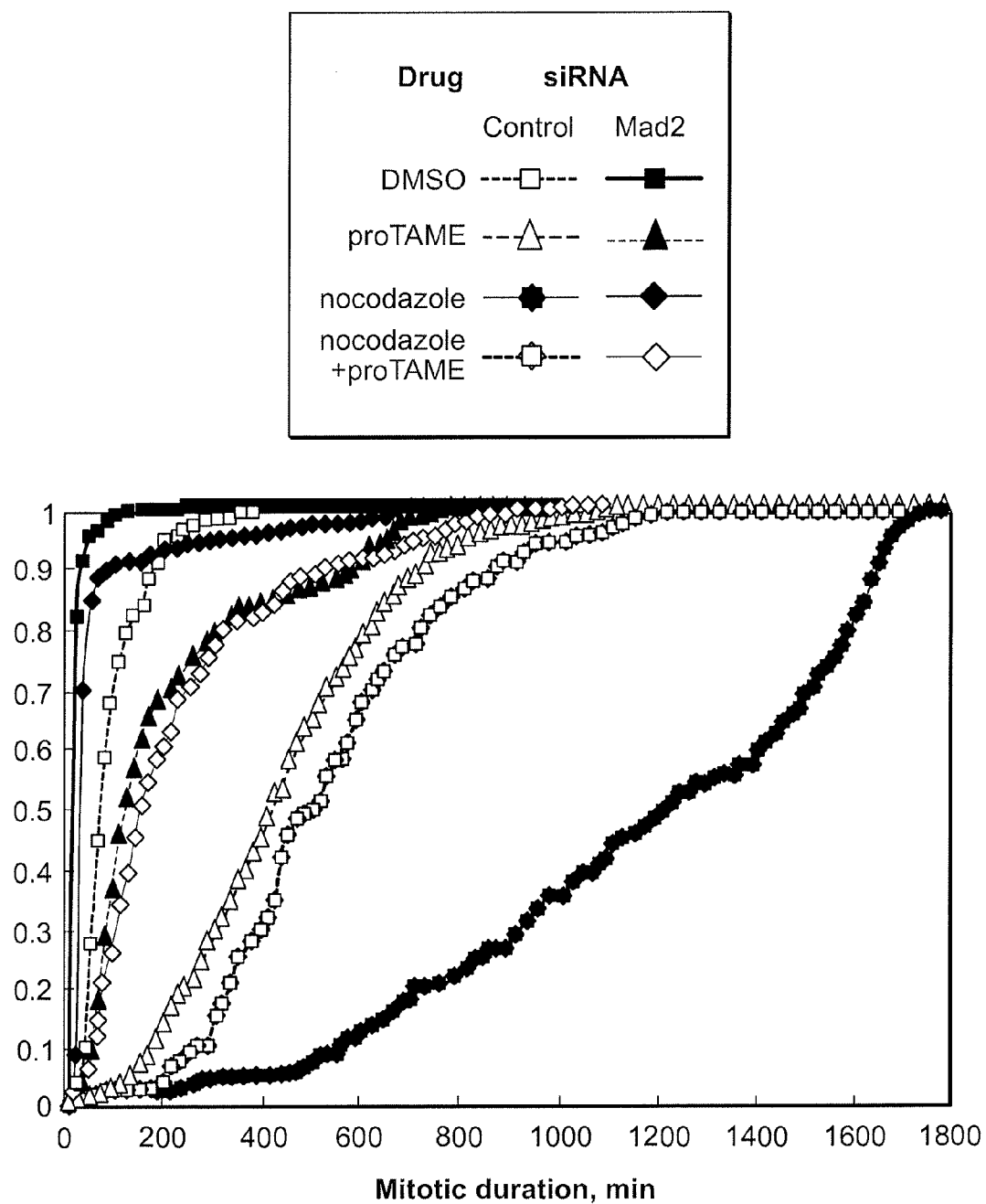
FIG. 4B is a graph showing that proTAME-induced mitotic arrest is partially Mad2-dependent. Synchronized HeLa cells were transfected with Mad2/control siRNA followed by drug treatments. Cumulative frequency curves of mitotic duration were plotted.
Figure 4C:
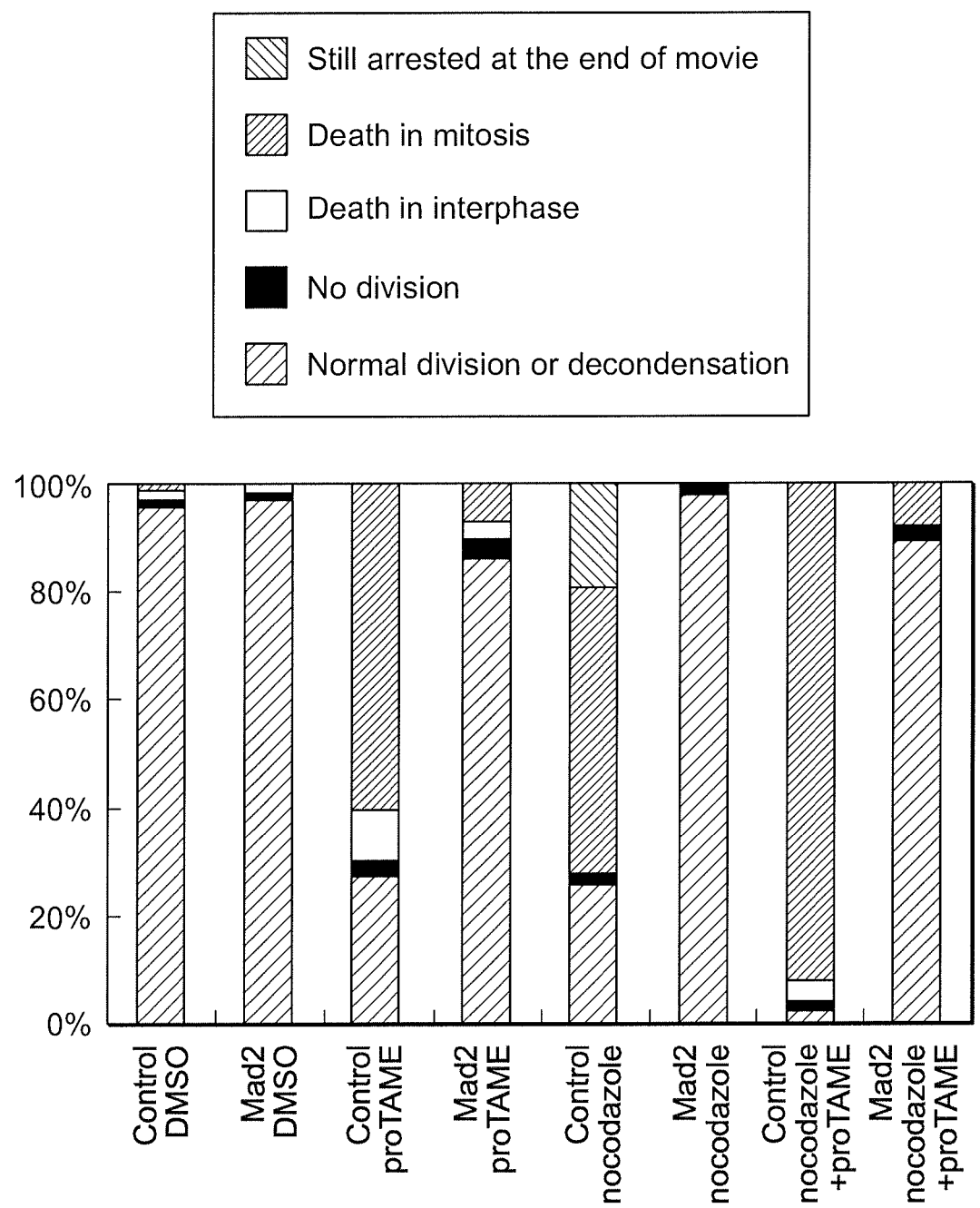
FIG. 4C is a graph of the cell fate distribution of the experiments in 4B.

To determine whether proTAME induced-arrest is SAC-dependent, Mad2 expression was knocked down with siRNA in synchronized cells, and the effects of proTAME or nocodazole on mitosis were analyzed by live cell fluorescence imaging. Mad2 knockdown shortened median mitotic duration from 75 minutes to 15 minutes in DMSO-treated cells (FIG. 4B), and shortened nocodazole-induced mitotic arrest from 1230 minutes to 30 minutes (FIG. 4B), indicating that the SAC was fully inactivated. Mad2 knockdown also shortened the duration of proTAME-induced arrest, from 420 minutes to 120 minutes, suggesting that proTAME-induced arrest is partially dependent on the SAC. However, Mad2 knockdown cells remained in mitosis for 2 hours in the presence of proTAME, indicating that a significant portion of the arrest is also SAC-independent (FIG. 4B). In support of earlier observations, the arrest in Mad2-knockdown cells cannot be a consequence of nonspecific microtubule disruption by proTAME, because nocodazole-induced microtubule disruption arrested Mad2 knockdown cells for only 30 minutes rather than 2 hours. Furthermore, addition of proTAME to nocodazole-treated Mad2 knockdown cells extended mitotic arrest from 30 minutes to 150 minutes, showing that microtubules are not a direct target of proTAME (FIG. 4B). A replicate experiment by DIC imaging of asynchronous cells produced similar results (FIG. 7A, B).

Figure 4D:
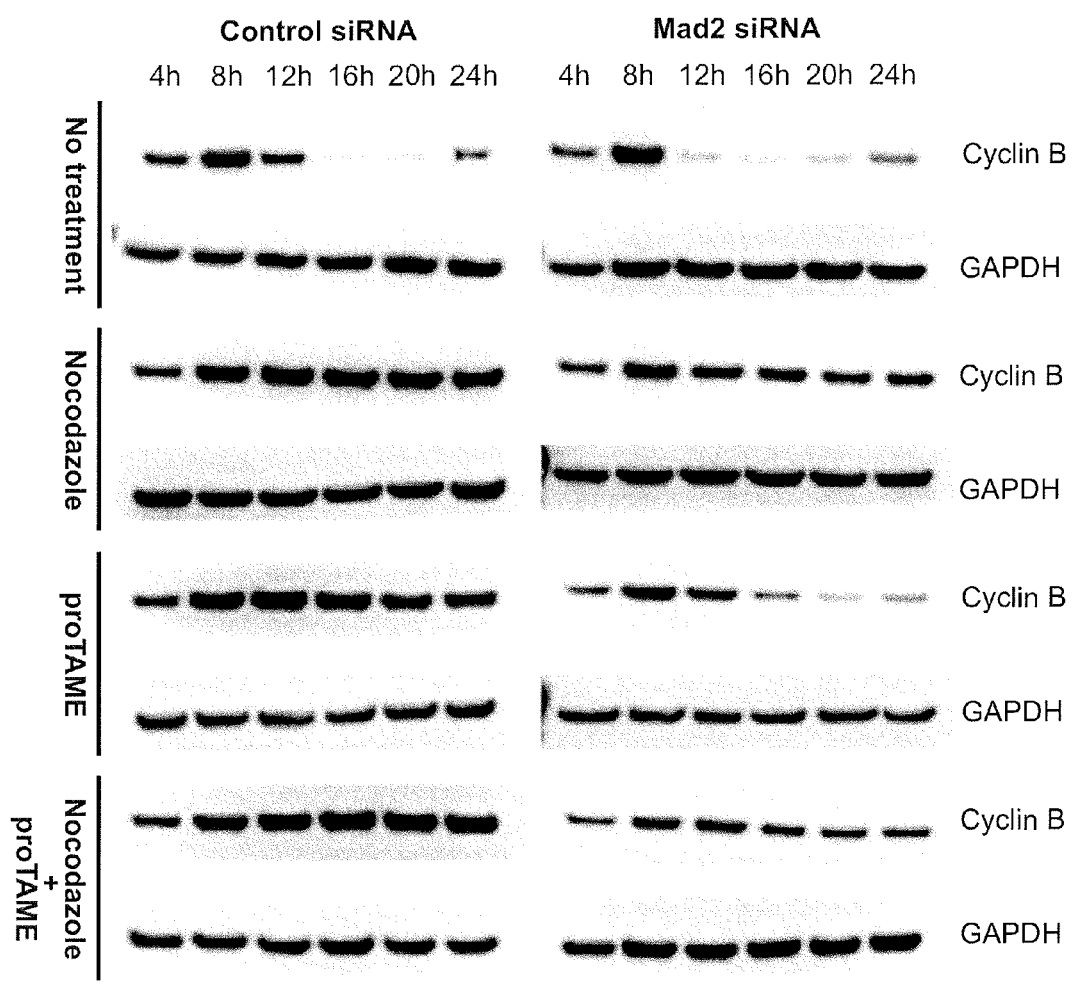
FIG. 4D is a series of photographs of gel electrophoresis analysis showing that proTAME-induced mitotic arrest is partially Mad2-dependent. HeLa cells were treated as in 4B. Protein levels were measured every 4 h by Western blot.
Figure 5A:
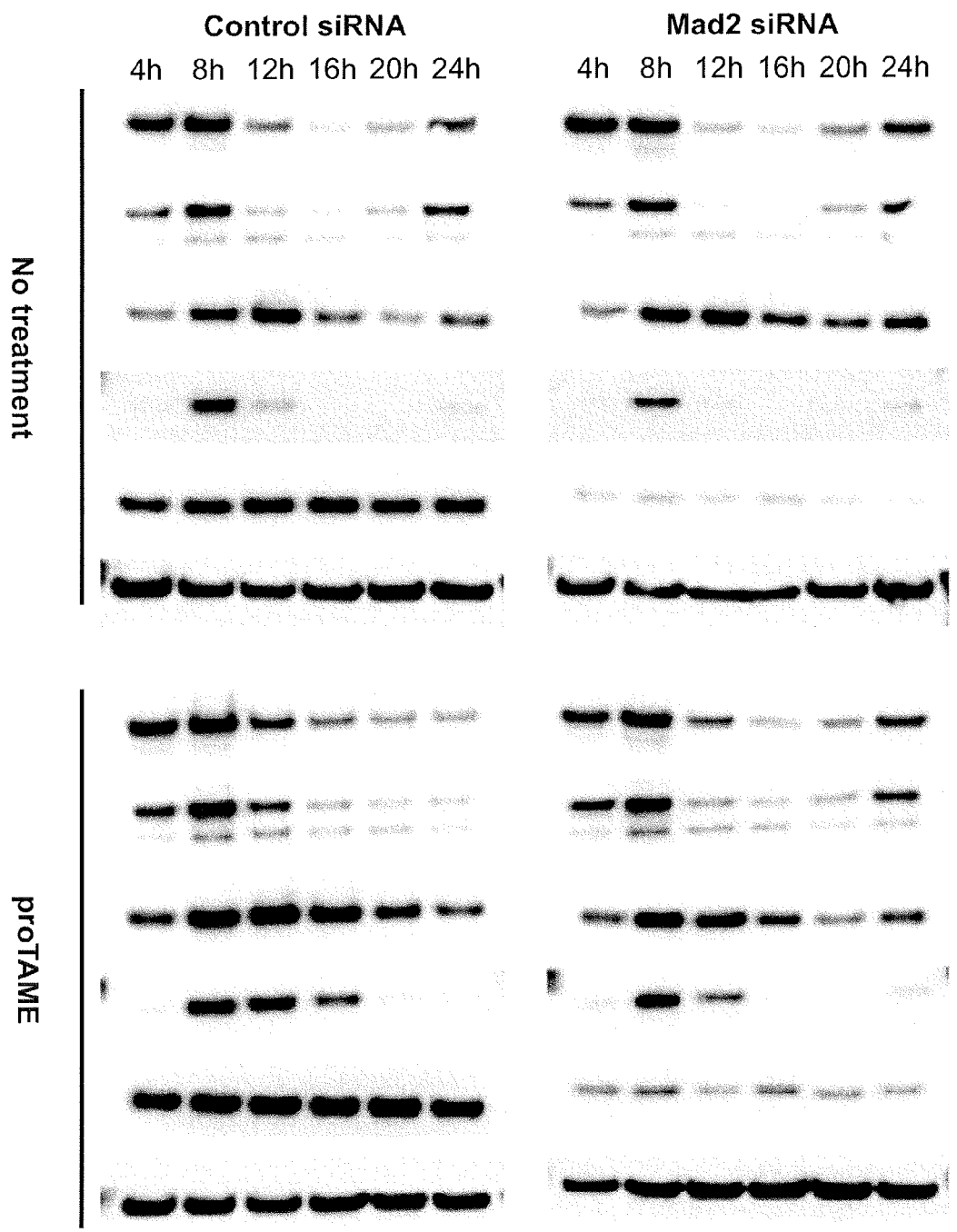
FIG. 5A is a series of photographs showing that proTAME induced mitotic arrest is partially Mad2-dependent. HeLa cells were synchronized with double thymidine block and released into 0.06% DMSO, 12 μM proTAME, 300 nM nocodazole or 12 μM proTAME plus 300 nM nocodazole after the second block. Samples were collected every 4 h and protein level was measure by Western blot.
Figure 5A:
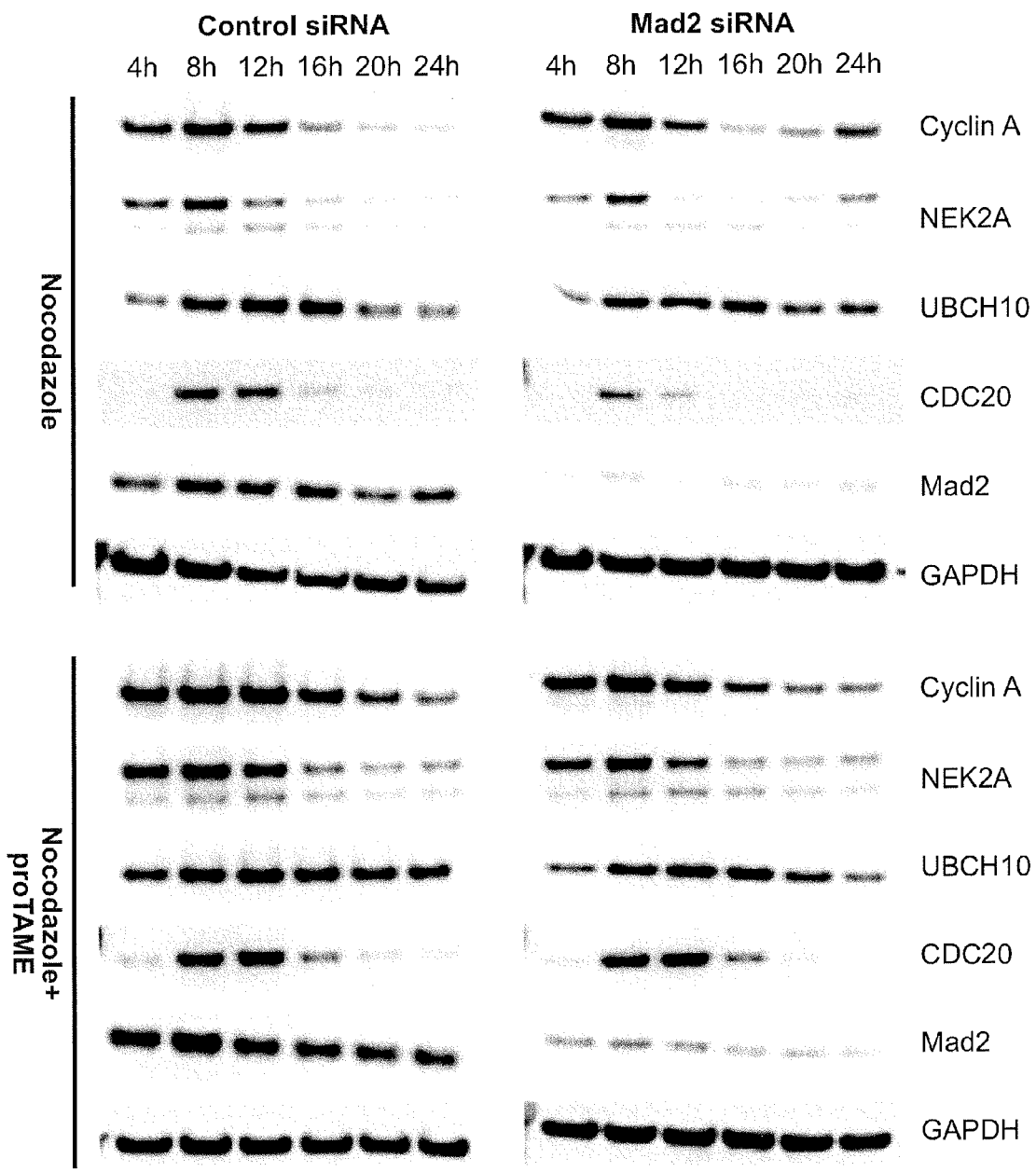
Figure 5B:
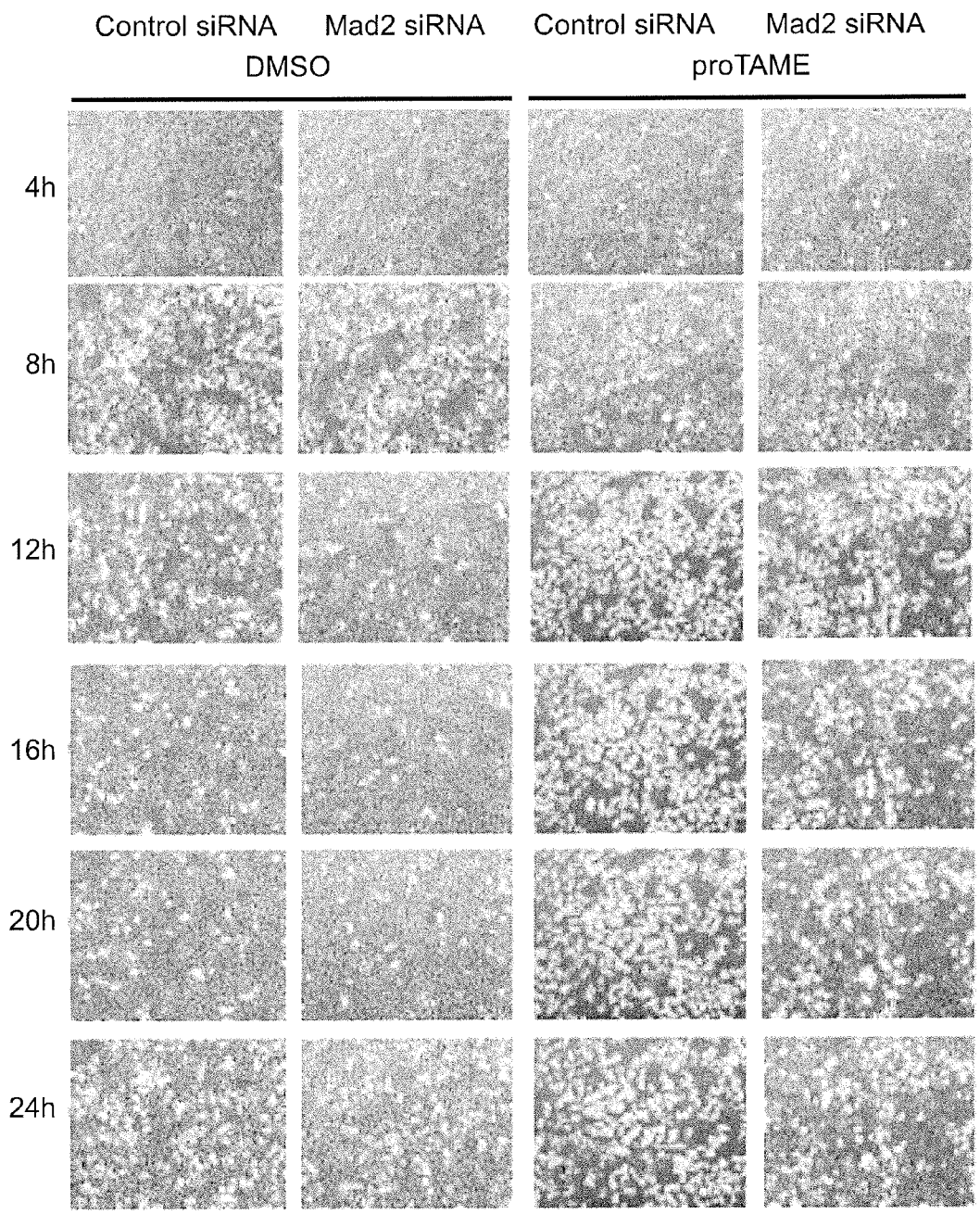
FIG. 5B is a series of photographs showing that proTAME induced mitotic arrest is partially Mad2-dependent. HeLa cells were treated as in FIG. 5A. Phase contrast images were taken every 4 h after release.
Figure 5B:
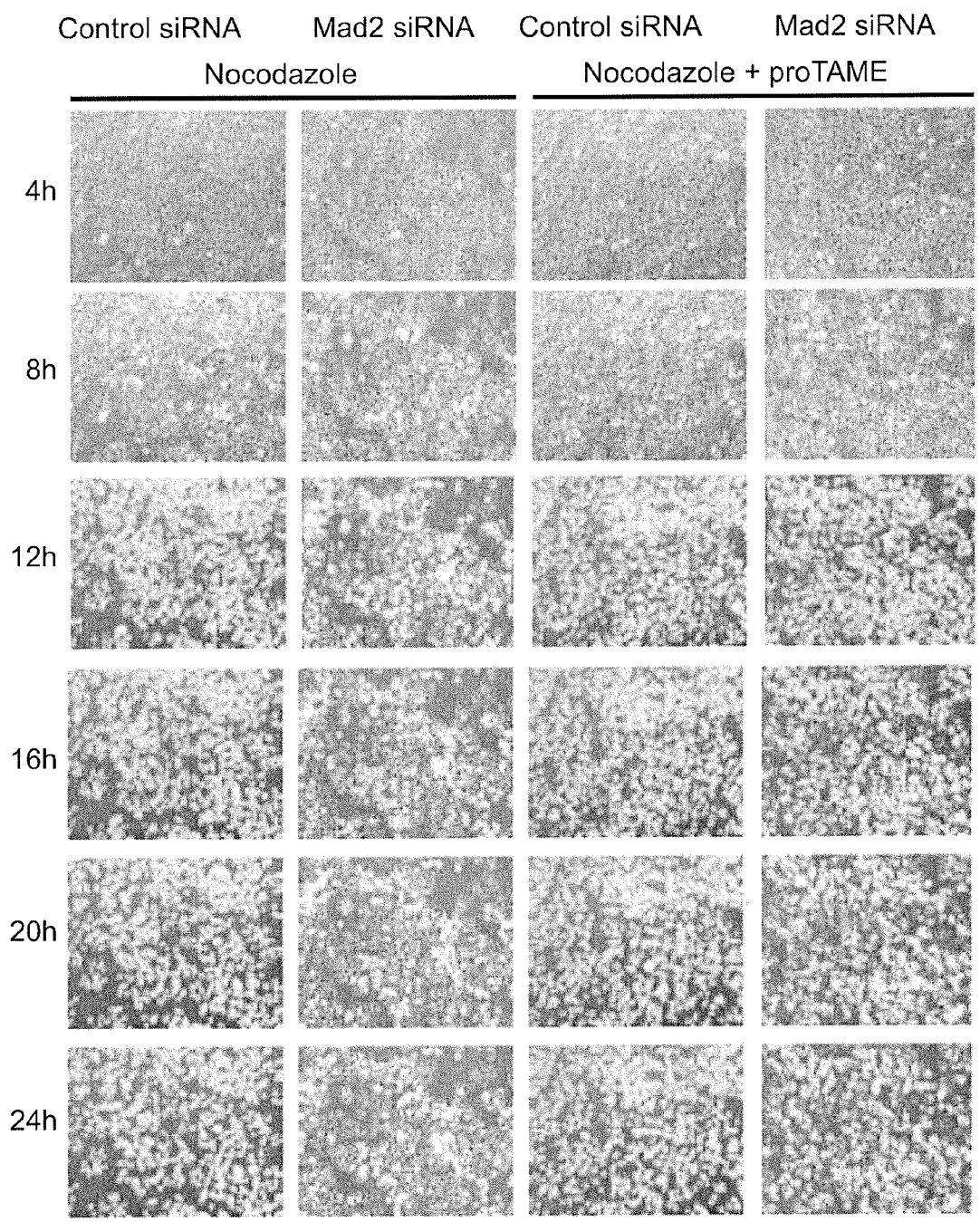

The Mad2-dependence of proTAME arrest was also confirmed by measurement of APC substrate levels in synchronized cells by western blotting (FIG. 4D). RNAi-mediated knockdown reduced Mad2 levels by 80% (FIG. 5A). This was sufficient to inactivate the SAC as measured by phase-contrast imaging (FIG. 5B). Although Mad2 knockdown resulted in efficient override of the mitotic arrest induced by nocodazole, cyclin was not efficiently degraded, as noted by other investigators (Michel, L. S. et al. Nature 409(6818): 355 (2001)), suggesting that microtubules may be required for efficient cyclin B proteolysis in human cells. In contrast, cyclin B was degraded more efficiently when proTAME-treated cells exited mitosis as a consequence of Mad2 depletion (FIG. 4D). These findings indicate that the mechanisms of mitotic exit in the presence of proTAME and nocodazole are distinct. Other APC substrates were efficiently degraded following Mad2 knockdown in the presence of either nocodazole or proTAME (FIG. 5A).

Figure 4E:
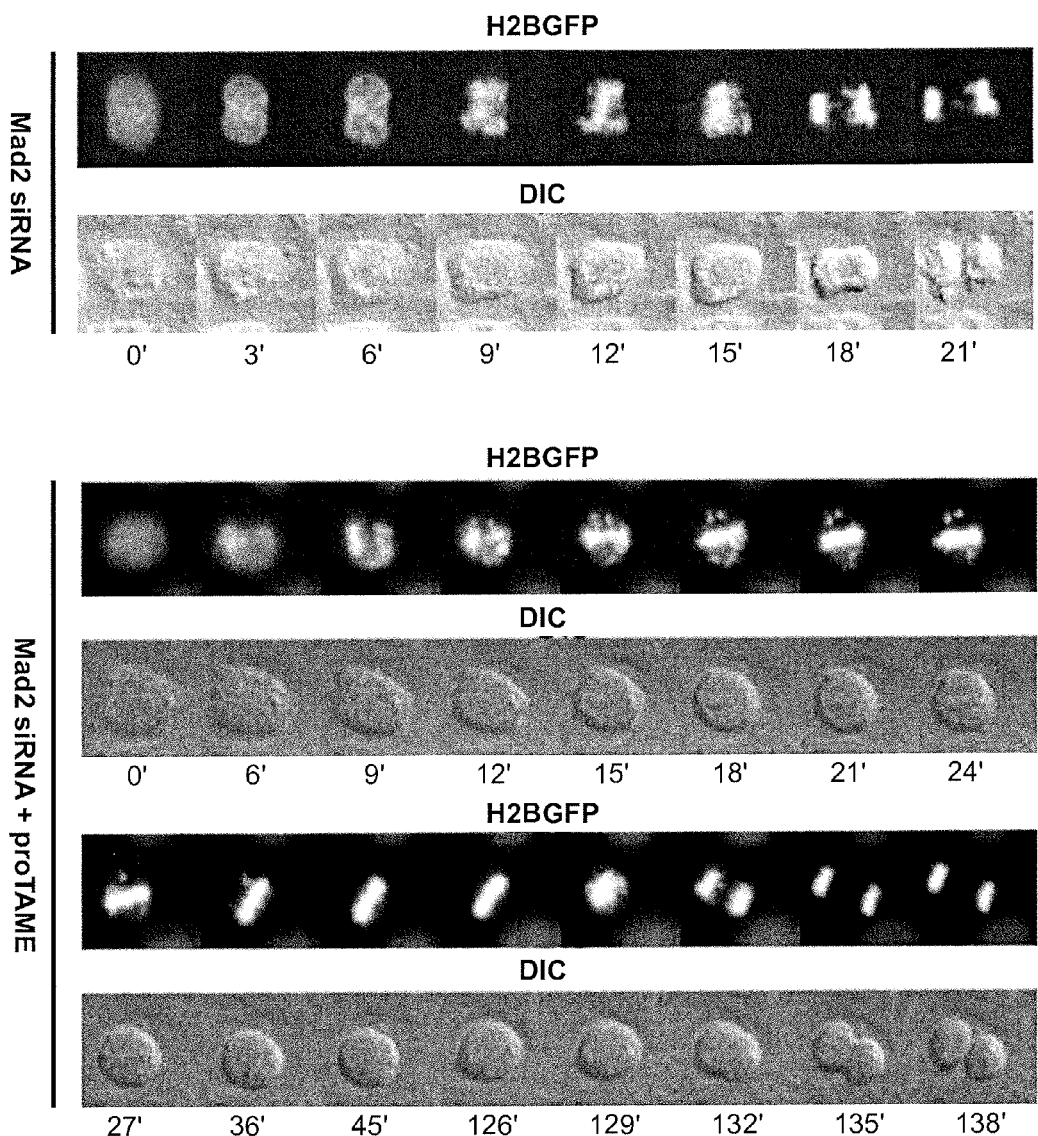
FIG. 4E is a series of photographs showing that proTAME rescues the mitotic defect induced by Mad2 knockdown. HeLa cells expressing H2B-GFP were treated with Mad2 siRNA 24 h prior to addition of DMSO or proTAME (12 μM). Cells were imaged every 3 minutes using a 40× objective.
Figure 8:
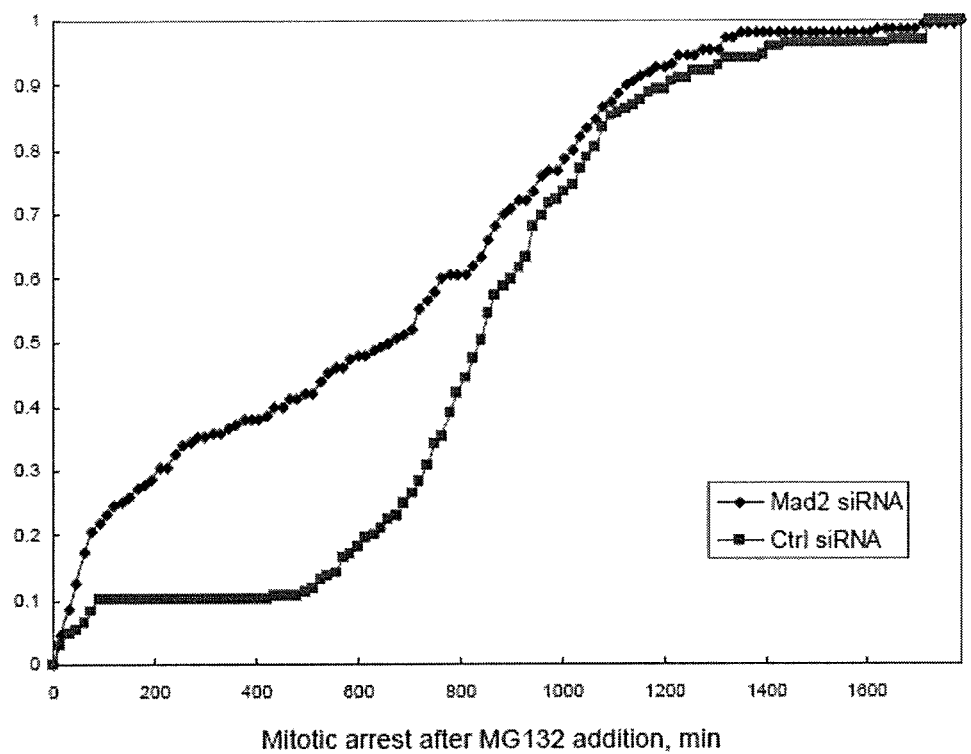
FIG. 8 is a showing that proteasome inhibitor-induced mitotic arrest is partially Mad2-dependent. HeLa cells were synchronized with double thymidine block, transfected with Mad2 or control siRNA after the first block, and released. 3 μM MG132 was added to Mad2 knockdown cells at 8.5 h post release and to control cells at 9.5 h post release because Mad2 knockdown cells enter mitosis faster than control cells. Live imaging was performed for 48 h at 15 min interval. Mitotic arrest of each division was determined as the time between anaphase and the addition of MG132 and cumulative frequency curves were plotted.

To confirm that proTAME directly inhibits APC activation, it was determined that the compound restores a normal mitosis in cells lacking Mad2. Thus, the effects of proTAME in Mad2 knockdown cells were analyzed in more detail by live cell imaging. Unlike control cells, Mad2 knockdown cells initiate anaphase before establishing a metaphase plate because of unconstrained APC activity (FIG. 4E), and slip out of mitosis quickly in the presence of nocodazole (FIG. 6). In striking contrast, the addition of proTAME allowed Mad2 knockdown cells sufficient time to build a normal metaphase plate followed by initiation of cytokinesis, fully rescuing the mitotic defect caused by Mad2 knockdown (FIG. 4E). Taken together, the data indicate that proTAME is capable of inducing a mitotic arrest with a duration of approximately 2 hours in the absence of Mad2, but sustained mitotic arrest requires the presence of an intact SAC. The data indicate that APC-dependent ubiquitination or proteolysis may be required for inactivation of the SAC. This idea is further supported by the finding that mitotic arrest induced by 3 µM MG132 is also partially dependent on Mad2 (FIG. 8).

The Mad2-dependence of proTAME-induced mitotic arrest in HeLa cells suggests that IR tail binding sites may be important for inactivation of the SAC. Recent work suggests that Cdc20 ubiquitination may be important for inducing dissociation of Cdc20 from Mad2. Given that elimination of the IR tail stabilizes Cdc20 in budding yeast, it is possible that association of the IR tail with the APC is required to trigger Cdc20 ubiquitination. The IR tail of Cdc20 may be especially critical for the ability of the APC to capture Mad2-Cdc20 complexes, ubiquitinate them, and induce their dissociation. By blocking IR-binding sites on the APC, proTAME may prevent APC from capturing Mad2-Cdc20 complexes and thereby inhibit SAC inactivation. In addition, APC-dependent proteolysis may also contribute to SAC inactivation, as it was observed that the mitotic arrest induced by MG132 is also partially Mad2 dependent. Candidate substrates could include Mps1, which is a target of the APC in budding yeast.

Example 4

ProTAME in Mammalian Cells versus *Xenopus* Extracts proTAME is less effective at inhibiting Cdc20 association with the APC in mammalian cells than in *Xenopus* extracts. Although it is possible that the APC-Cdc20 dissociation pathway may not be as active in mammalian cells, an active SAC in mammalian cells may counter the ability of TAME to induce Cdc20 dissociation. For example, SAC complexes, such as the MCC, may provide an alternative pathway for loading Cdc20 onto the APC that does not require the Cdc20 IR tail. It is also possible that the binding of checkpoint proteins to Cdc20 may shield it from factors that promote Cdc20 dissociation. Because the SAC is not active in *Xenopus* egg extract, such alternative loading or shielding mechanisms would not be operative, explaining why TAME is capable of inducing complete dissociation of Cdc20 from APC in the *Xenopus* system but not in mammalian cells.

Example 5

Pharmacologic Inhibition of the Anaphase-promoting Complex (APC) Induces a Spindle Checkpoint Dependent Mitotic Arrest in the Absence of Spindle Damage Microtubule inhibitors are important cancer drugs that induce mitotic arrest by activating the spindle assembly checkpoint (SAC), which in turn inhibits the ubiquitin ligase activity of the Anaphase-Promoting Complex (APC). This disclosure is based, at least in part, upon the discovery of a small molecule, Tosyl-L-Arginine Methyl Ester (TAME), which binds to the APC and prevents its activation by Cdc20 and Cdh1. The disclosure provides a prodrug of TAME that arrests cells in metaphase without perturbing the spindle. Nonetheless, this arrest is dependent on the SAC. Metaphase arrest induced by a proteasome inhibitor is also SAC-dependent, suggesting that APC-dependent proteolysis is required to inactivate the SAC. The mutual antagonism between the APC and the SAC yields a positive feedback loop that amplifies the ability of TAME to induce mitotic arrest.

The Anaphase-Promoting Complex (APC) is required for mitotic exit, making the APC a potential new target for antimitotic chemotherapy. TAME is the first small molecule inhibitor of the APC. The methods of the disclosure are used to develop and therapeutic uses for a cell-permeable derivative, proTAME. Treatment of cells with proTAME causes a surprisingly robust mitotic arrest because APC-dependent proteolysis is required for inactivation of the spindle assembly checkpoint (SAC). In contrast, SAC-activating compounds, such as microtubule inhibitors, do not suppress APC activity as completely. As a result, cells rely on continued protein synthesis to maintain mitotic arrest, providing an explanation for the known variability in cellular response to microtubule inhibitors. Thus, direct APC inhibitors may provide a more uniform and specific method for inducing mitotic arrest.

TAME is a small molecule that inhibits APC activation by preventing Cdc20 binding. A cell-permeable prodrug (proTAME) induces mitotic arrest and cell death. APC-dependent proteolysis is required for spindle-assembly checkpoint inactivation. ProTAME exploits mutual antagonism between the SAC and APC to block mitotic exit.

Microtubule inhibitors such as taxanes and the *vinca* alkaloids represent one of the most important classes of cancer drugs, used in the treatment of breast, ovarian, and lung cancer (Montero, A., et al. (2005). Lancet Oncol 6, 229-239). However, the response of cells to microtubule inhibitors is highly variable (Brito, D. A., et al. (2008). J Cell Biol 182, 623-629; Gascoigne, K. E., and Taylor, S. S. (2008). Cancer Cell 14, 111-122; Orth, J. D., et al. (2008). Mol Cancer Ther 7, 3480-3489; Shi, J., et al. (2008). Cancer Res 68, 3269-3276), potentially compromising clinical efficacy. How these drugs cause cell death remains unclear, but induction of mitotic arrest appears to be a key aspect of the mechanism (Bekier, M. E., et al. (2009). Mol Cancer Ther 8, 1646-1654; Huang, H. C., et al. (2009). Cancer Cell 16, 347-358). By perturbing the mitotic spindle, these drugs activate the Spindle Assembly Checkpoint (SAC), which delays mitotic exit by inhibiting the ubiquitin ligase activity of the Anaphase-Promoting Complex/Cyclosome (APC). In principle, a compound that directly inhibits APC-dependent proteolysis should arrest cells in mitosis without causing side effects that result from microtubule inhibition, such as peripheral neuropathy.

The APC is the most complex ubiquitin ligase known, consisting of more than 11 subunits. The activator proteins Cdh1 and Cdc20 bind to the APC at different cell cycle stages to stimulate APC-dependent ubiquitination of substrates and their subsequent destruction by the 26S proteasome (Peters, J. M. (2006). Nat Rev Mol Cell Biol 7, 644-656). The activators assist in recruitment of APC substrates and may also stimulate the catalytic activity of the ligase (Burton, J. L., et al. (2005). Mol Cell 18, 533-542; Kimata, Y., et al. (2008). Mol Cell 32, 576-583; Pfleger, C. M., et al. (2001). Genes Dev 15, 2396-2407). During G1, Cdh1 binds to the APC to promote degradation of APC substrates to keep mitotic cyclin-dependent kinase activity low. The initiation of anaphase and exit from mitosis instead require Cdc20-dependent ubiquitination of APC substrates such as securin and mitotic cyclins (Kraft, C., et al. (2003). EMBO J 22, 6598-6609; Kramer, E. R., et al. (2000). Mol Biol Cell 11, 1555-1569; Yu, H. (2007). Mol Cell 27, 3-16). Prior to anaphase, the ability of APC-Cdc20 to ubiquitinate certain substrates is inhibited by the SAC (Musacchio, A., and Salmon, E. D. (2007). Nat Rev Mol Cell Biol 8, 379-393). Unattached kinetochores catalyze the formation of an inhibitory protein complex, containing the proteins Mad2, BubR1 and Bub3 (Sudakin, V., et al. (2001). J Cell Biol 154, 925-936), that sequesters Cdc20 or interferes with its ability to activate the APC. Attachment of kinetochores to the mitotic spindle diminishes their ability to generate an inhibitory signal. Subsequently, the SAC-inhibited APC-Cdc20 complex is activated, through a process that may require APC-dependent ubiquitination (Reddy, S. K., et al. (2007). Nature 446, 921-925; Stegmeier, F., et al. (2007). Nature 446, 876-881), though the mechanism remains incompletely understood (Nilsson, J., et al. (2008). Nat Cell Biol 10, 1411-1420).

Because the APC regulates multiple cell cycle events, it is not clear whether pharmacological inhibition of its activity will lead to selective or prolonged arrest in mitosis as is the case with microtubule inhibitors. Proteasome inhibitors can block APC-dependent proteolysis without perturbing the mitotic spindle (Famulski, J. K., and Chan, G. K. (2007). Curr Biol 17, 2143-2149), but they also inhibit the degradation of many other substrates of the ubiquitin-proteasome system, and therefore also cause cell cycle arrest during interphase (Wojcik, C., et al. (1996). Eur J Cell Biol 70, 172-178). It may be difficult to achieve mitotic arrest by pharmacologic APC inhibition, as RNAi approaches indicate that Cdc20 expression must be reduced to a very low level to induce a mitotic arrest (Huang, H. C., et al. (2009). Cancer Cell 16, 347-358; Wolthuis, R., et al. (2008). Mol Cell 30, 290-302). Even when the SAC is strongly activated by a dose of microtubule inhibitor that completely depolymerizes microtubules, a fraction of cells escape mitotic arrest due to residual APC activity (Brito, D. A., and Rieder, C. L. (2006). Curr Biol 16, 1194-1200) suggesting that the SAC cannot fully inhibit the APC during mitosis. For this reason, microtubule inhibitors may suffer from limited effectiveness because some cells escape mitotic arrest before dying (Bekier, M. E., et al. (2009). Mol Cancer Ther 8, 1646-1654; Huang, H. C., et al. (2009). Cancer Cell 16, 347-358). Whether an APC inhibitor can better extinguish APC activity and induce a more persistent mitotic arrest is therefore an important question in contemplating development of APC inhibitors as a therapeutic strategy for cancer. Here the first small molecule inhibitor of the APC is described and the compound is used as a tool to reveal reciprocal antagonism between the APC and the SAC. The existence of this regulatory relationship makes direct APC inhibition a particularly effective approach for inducing mitotic arrest.

Figure 11A:
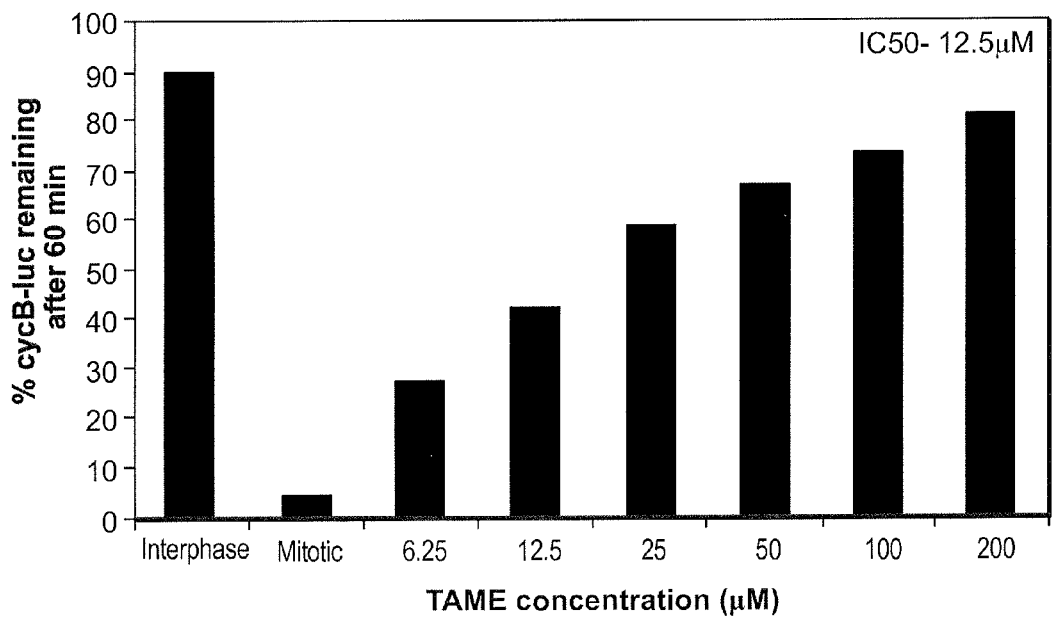
FIG. 11A is a graph showing that TAME stabilizes cyclin B-luciferase (cycB-luc) reporter in mitotic *Xenopus* extract. Different concentrations of TAME were added to the extract containing the reporter. Samples were collected at 60 min and the remaining reporter level was measured by luminescence. Interphase extract was used as a negative control.
Figure 11B:
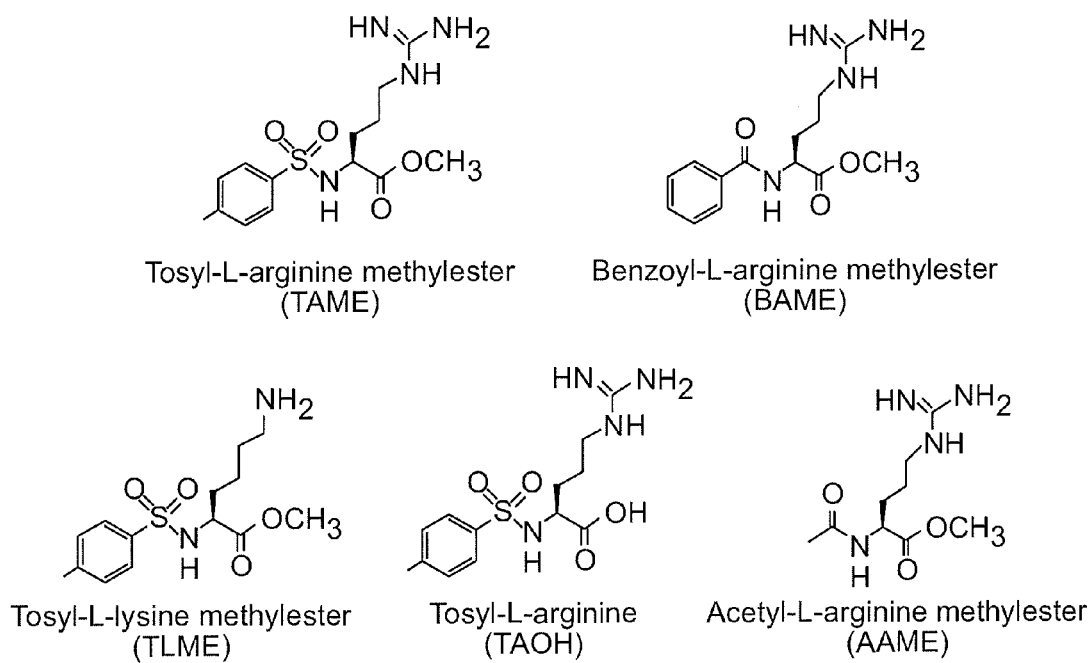
FIG. 11B is a series of schematic diagrams depicting the structures of TAME derivatives.
Figure 11C:
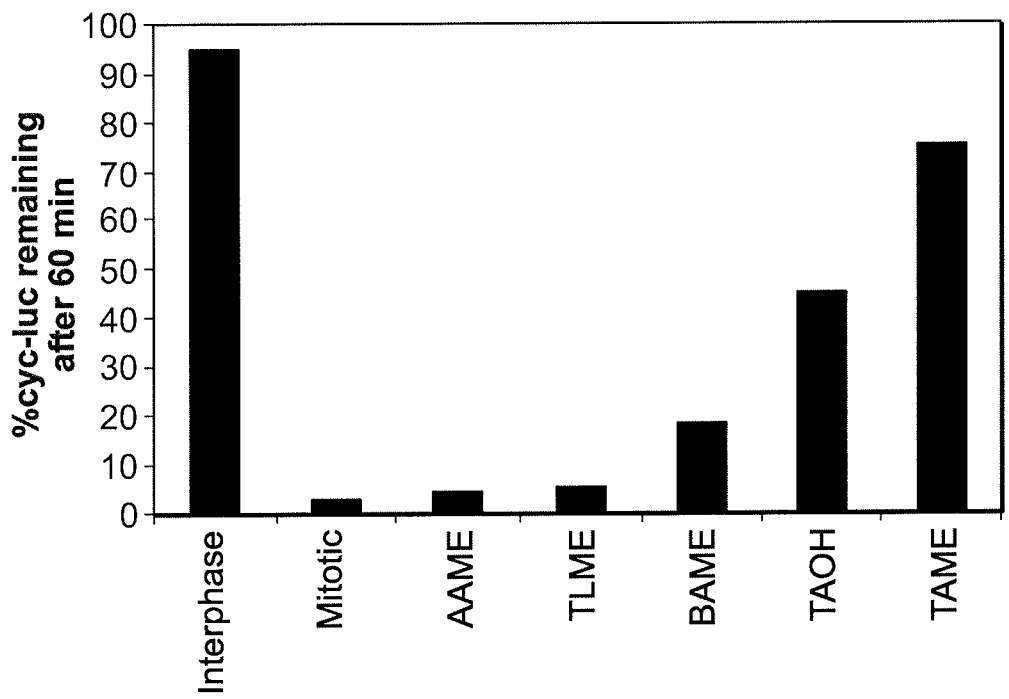
FIG. 11C is a graph depicting the results of a luciferase assay. The derivatives shown in (A) were tested in the luciferase assay at 200 μM.
Figure 11D:
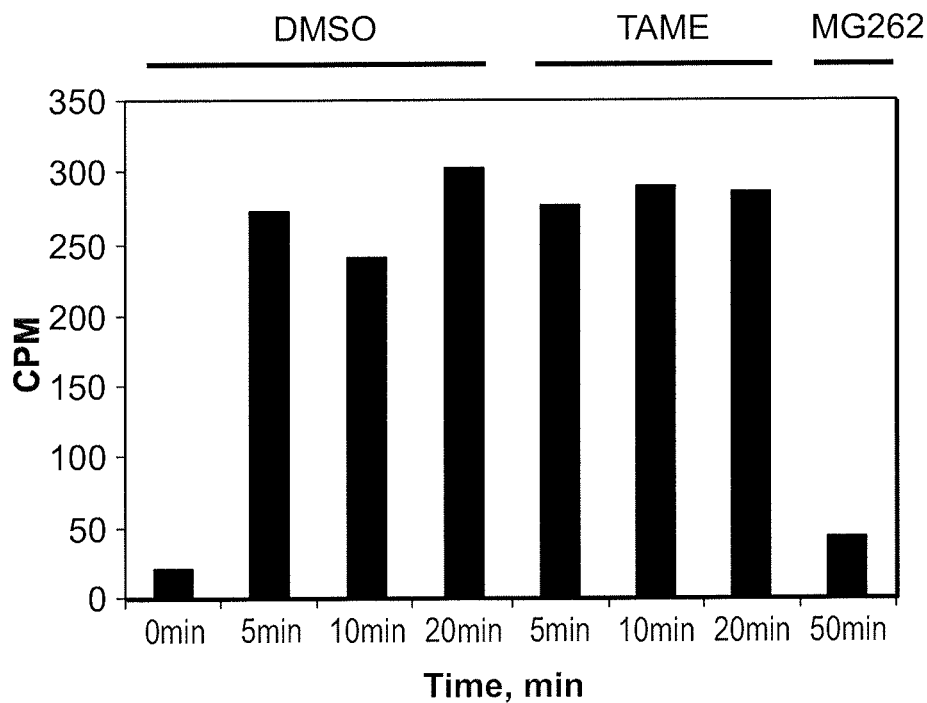
FIG. 11D is a graph showing that TAME does not inhibit degradation of pre-ubiquitinated cyclin B. Baculovirus-expressed and purified $^{35}$S-labeled cyclin B bound to unlabeled Cdk1 was first ubiquitinated by APC in an in vitro ubiquitination system and then added into *Xenopus* extract supplemented with DMSO, 200 μM TAME or 200 μM proteasome inhibitor MG262. At indicated time points, protein was precipitated and the level of radioactivity in supernatant was measured by scintillation counting.

TAME Inhibits APC Activation by Perturbing Activator Protein Binding. TAME (FIG. 10A) was identified as an inhibitor of cyclin proteolysis in mitotic Xenopus egg extract ($IC_{50}$ of 12 µM; FIG. 11A), but its mechanism of action has remained unknown. TAME also inhibited cyclin degradation in interphase extract activated by exogenous Cdh1, but had no effect on SCF-dependent proteolysis of β-catenin-luciferase (Verma, R., et al. (2004). Science 306, 117-120), indicating that it is not a general inhibitor of the ubiquitin-proteasome system. Testing of TAME derivatives indicated that the tosyl group, arginine, and the methyl ester are each important for activity (FIGS. 11B and 11C). A derivative, Acetyl-L-Arginine Methyl Ester (AAME; FIG. 10A) showed only low activity, and was therefore used as a negative control in subsequent experiments. When added to interphase extract treated with recombinant cyclin B1/cdc2 complex, TAME, but not AAME, arrested the extract in mitosis, with stable cyclin B1 and phosphorylated Cdc27 (FIG. 10B). Another APC substrate, cyclin A, was also stabilized by TAME in Xenopus extract. TAME had no effect on the ability of Xenopus extract to degrade cyclin B1 that had been preubiquitinated in vitro (FIG. 11D), indicating that TAME does not inhibit the proteasome or its ability to recognize ubiquitinated substrates.

Figure 11E:
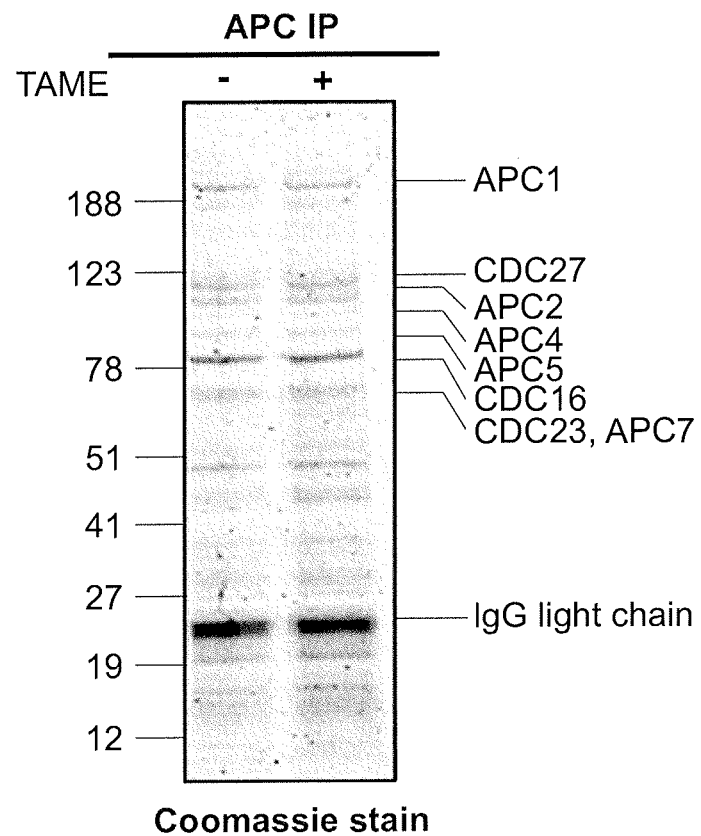
FIG. 11E is a photograph of an immunoprecipitation product analyzed using gel electrophoresis. The results demonstrate that TAME does not affect APC composition of APC core subunits. Mitotic extract was treated with DMSO or 200 μM TAME. APC was immunoprecipitated and the subunits were resolved by SDS-PAGE and visualized by coomassie stain. Identity of subunits was confirmed by mass spectrometry.

Because the SAC is not active in Xenopus extracts (Minshull, J., et al. (1994). Cell 79, 475-486), these findings suggested that TAME might inhibit cyclin proteolysis by directly inhibiting the APC. Indeed, when TAME was added to mitotic Xenopus extract during APC isolation, the APC showed a dramatic loss of activity in a reconstituted ubiquitination reaction (FIG. 10C). These results suggested that adding TAME to extract might alter APC composition, inactivating the complex. Consistent with this hypothesis, TAME addition to extract reduced Cdc20 association with the APC in a dose-dependent manner (FIG. 10D), but did not otherwise affect APC composition (FIG. 11E). TAME also inhibited the binding of Cdh1 to APC when Cdh1 and TAME were added together to interphase extract (FIG. 10E). The reduction in Cdh1 binding was accompanied by a reduction in APC activation (FIG. 10F). These findings suggested that TAME might block APC activation by perturbing the interaction between APC and its activator proteins Cdc20 or Cdh1.

Figure 12A:
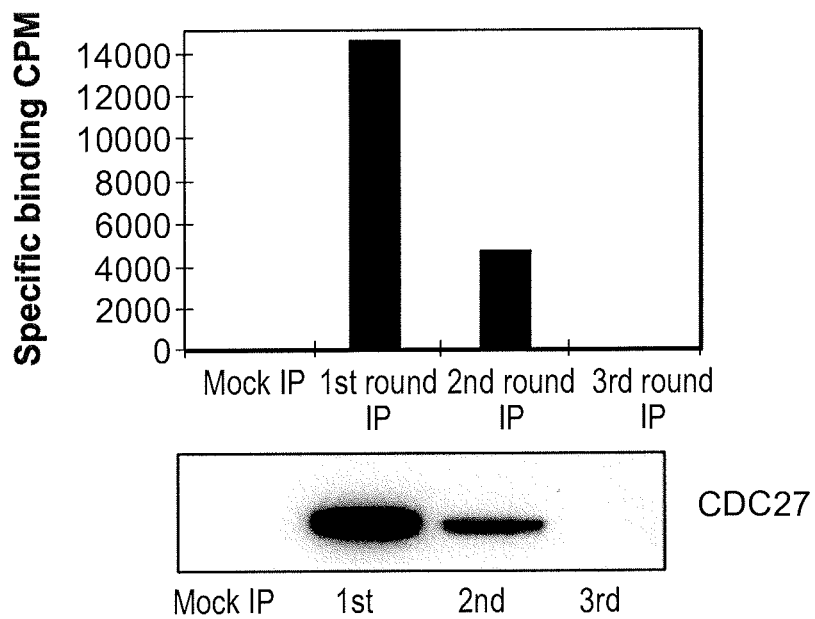
FIG. 12A is a paired graph and immunoblot showing that TAME binds to the APC and inhibits binding of the IR tail of activator proteins. TAME binds *Xenopus* APC. $^3$H-TAME was added to interphase extract or to extract that had been partially or completely immunodepleted of APC. Remaining APC was then immunoprecipitated and the associated radioactivity was measured by scintillation counting. Residual APC levels were measured by immunoblot with Cdc27 antibody. Specific binding was calculated as described in the methods.
Figure 12B:
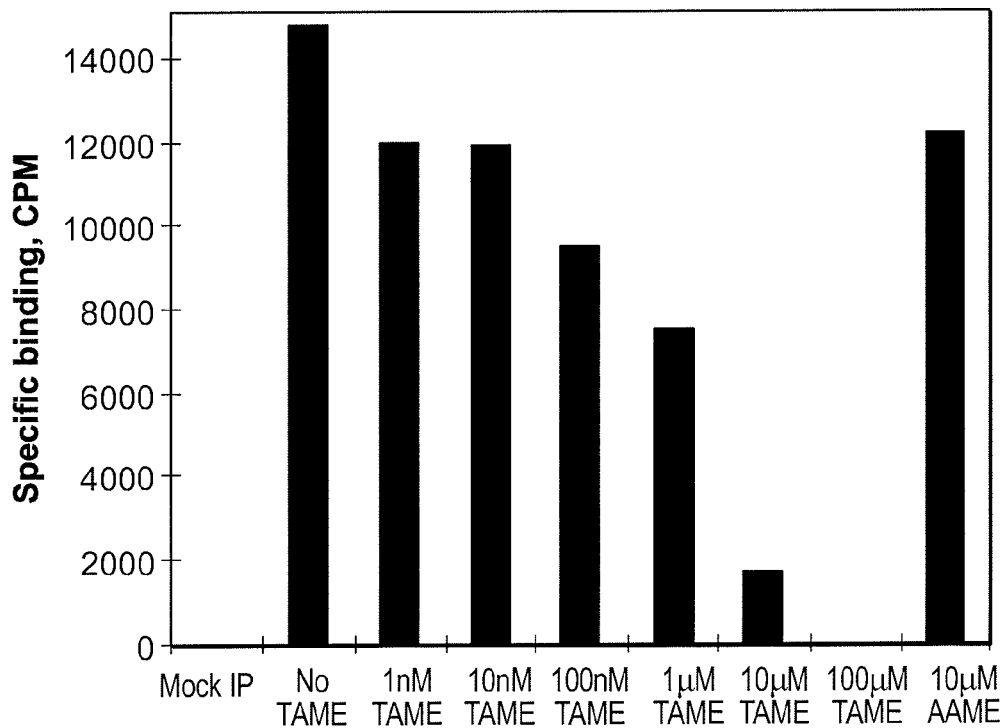
FIG. 12B is a graph showing that unlabeled TAME competes with $^3$H-TAME for binding to *Xenopus* APC. $^3$H-TAME was added to interphase extract with unlabeled TAME or AAME prior to APC immunoprecipitation.
Figure 12C:
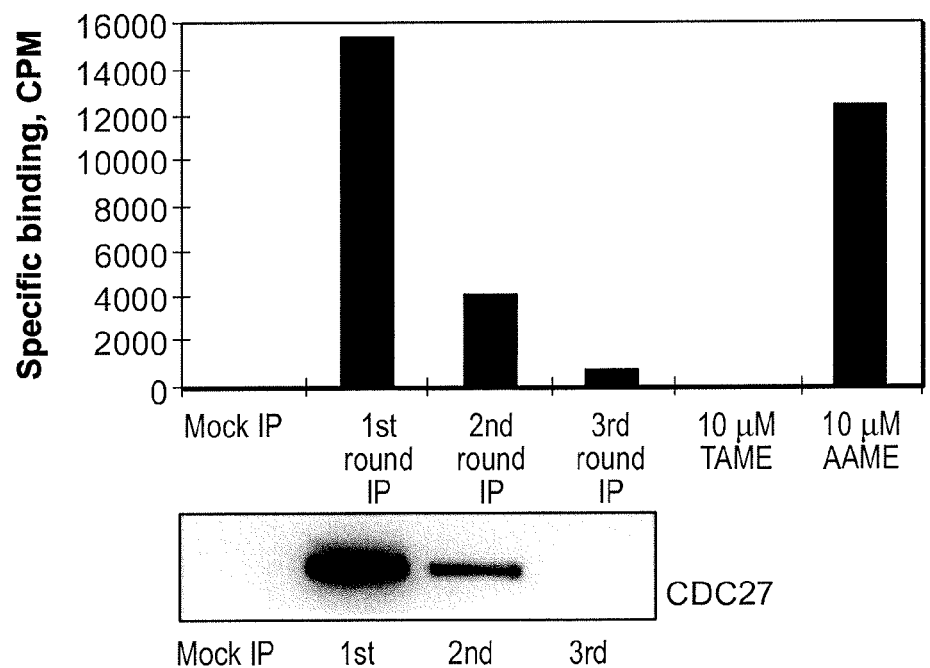
FIG. 12C is a paired graph and immunoblot showing that $^3$H-TAME binds to human APC. The experiment in FIG. 12A was repeated with lysate from asynchronous HeLa cells.

To understand how TAME disrupts the interaction between the activator proteins and the APC, it was first determined whether TAME binds to the APC. $^3$H-TAME was added to interphase Xenopus extract, or to extract immunodepleted of APC, and then isolated residual APC with Cdc27 antibodies and measured the amount of radioactivity associated with the beads. Binding of $^3$H-TAME correlated with the amount of immunoprecipitated Cdc27 (FIG. 12A). Unlabeled TAME competitively inhibited the binding of $^3$H-TAME, whereas AAME did not (FIG. 12B). Other TAME derivatives competed with $^3$H-TAME for APC binding in a manner that correlated with their ability to inhibit cyclin-luciferase proteolysis in Xenopus extract (FIG. 13A). A similar approach demonstrated that TAME binds to human APC isolated from HeLa cells (FIG. 12C). Together these findings indicate that the binding of TAME to the APC might explain the ability of TAME to perturb activator protein association.

To understand how TAME disrupts activator binding to the APC, it was determined whether TAME could inhibit the interaction of APC with motifs of the activator proteins that have been implicated in APC binding, including the C-box (Schwab, M., et al. (2001). EMBO J 20, 5165-5175) and the C-terminal isoleucine-arginine (IR) tail (FIG. 12D) (Burton, J. L., et al. (2005). Mol Cell 18, 533-542; Vodermaier, H. C., et al. (2003). Curr Biol 13, 1459-1468). Because TAME structurally resembles the IR tail of Cdc20 and Cdh1 (FIG. 12D), it was hypothesized that TAME might bind to the APC in the same site normally occupied by the IR tail. Previous work has demonstrated that a C-terminal 20 amino acid peptide derived from Cdh1 ("IR peptide") is sufficient to isolate Xenopus APC from interphase extract (Vodermaier, H. C., et al. (2003). Curr Biol 13, 1459-1468). This finding was confirmed and it was further discovered that TAME, but not AAME, was sufficient to block APC recruitment by the IR peptide (FIG. 12E). In contrast, TAME had no effect on recruitment of APC from mitotic extract by an N-terminal fragment of Cdc20 containing only the C-box interaction motif (FIG. 12F), indicating that TAME specifically inhibits the IR-tail-dependent interaction.

Figure 12G:
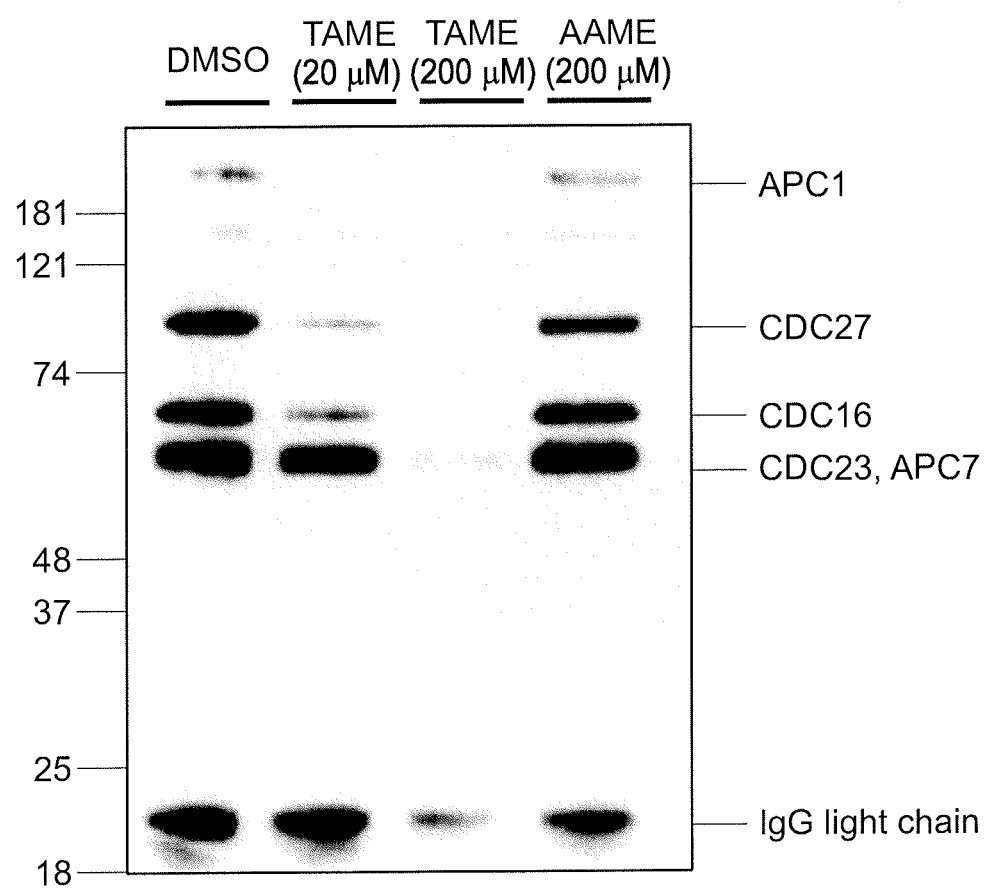
FIG. 12G is an immunoblot showing that TAME inhibits IR-peptide crosslinking to APC subunits. Purified interphase *Xenopus* APC was incubated with an IR peptide coupled to a biotin-containing label-transfer reagent, in the presence or absence of compounds, prior to photocrosslinking. Reaction products were detected by streptavidin-HRP.

The APC subunits Cdc27 and APC7 have been implicated in binding of the IR tail of Cdh1 to the APC (Matyskiela, M. E., and Morgan, D. O. (2009). Mol Cell 34, 68-80; Vodermaier, H. C., et al. (2003). Curr Biol 13, 1459-1468). To determine whether TAME could competitively inhibit the binding of the IR-tail to these proteins, the IR peptide was conjugated to a photo-affinity reagent and performed crosslinking studies with APC immunopurified from interphase Xenopus extract. Four proteins known to exist in an APC subcomplex, namely Cdc27, Cdc16, Cdc23 and Apc7, were crosslinked in an IR-dependent manner that could be competed by excess unlabeled IR peptide (FIGS. 13B and 13C). At low concentration (20 µM), TAME efficiently inhibited crosslinking of the IR peptide to Cdc27 and Cdc16 but only slightly reduced crosslinking to Cdc23 and Apc7 (FIG. 12G). At high concentration (200 µM), TAME strongly inhibited crosslinking to all APC subunits (FIG. 12G). Together these findings support the hypothesis that TAME binds to APC subunits that recruit the IR tail, thereby preventing activator proteins from associating with the APC.

Figure 14:
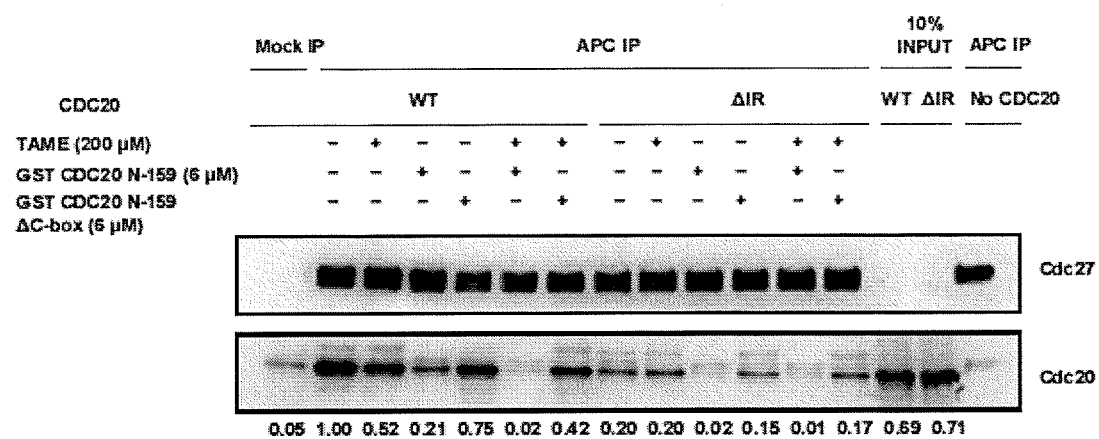
FIG. 14 is an immunoblot showing that TAME inhibits binding of wild type Cdc20 to the APC, but not binding of a ΔIR mutant. Mitotic APC immunoprecipitated from Xenopus extract was washed with XB high salt (500 mM KCl) and XB to remove endogenous Cdc20 prior to incubation with in vitro translated wild type Xenopus Cdc20 or the ΔIR mutant. Various competitors were added during incubation as indicated. Unbound proteins were washed away and bound Cdc20 was analyzed by immunoblot. Numbers represent the amount of Cdc20 normalized to Cdc27.

To confirm that TAME specifically antagonizes IR-tail dependent interactions between Cdc20 and the APC, the ability of TAME to inhibit the binding of Cdc20 to the APC was tested in a reconstituted system. APC was purified from mitotic Xenopus extracts and washed with high salt to remove most Cdc20. Purified mitotic APC was then incubated in reticulocyte lysate expressing wild-type or mutant Cdc20, and Cdc20 binding to APC was measured by co-immunoprecipitation. It was determined that efficient binding of Cdc20 to the APC under these conditions indeed requires the IR-tail, as a mutant lacking these two residues (Cdc20ΔIR) did not bind as efficiently to the APC (FIG. 14). TAME also strongly reduced Cdc20 binding to the APC under these conditions (FIG. 14). Importantly, addition of TAME had no further effect on binding of the Cdc20ΔIR mutant, confirming that TAME does not perturb other interactions between Cdc20 and the APC.

TAME addition or IR-tail deletion was not sufficient to fully inhibit Cdc20 association under these conditions. It was hypothesized that other interactions, such as C-box-dependent binding, might promote Cdc20 association with the APC, thereby masking the effect of TAME addition or IR-tail deletion. Consistent with this hypothesis, the results indicated that addition of a C-box-containing N-terminal fragment of Cdc20 could competitively inhibit binding of full-length Cdc20 to the APC (FIG. 14). In the presence of the C-box fragment, addition of TAME or deletion of the IR-tail was sufficient to completely suppress Cdc20 association with the APC. These results indicate that both C-box-dependent and IR-tail-dependent interactions are important for Cdc20 binding in these conditions, and that TAME specifically disrupts the IR-dependent interaction. Thus, the target of TAME is the APC, and it inhibits APC activation by interfering specifically with IR-tail dependent interactions between Cdc20 or Cdh1 and the APC.

Figure 15C:
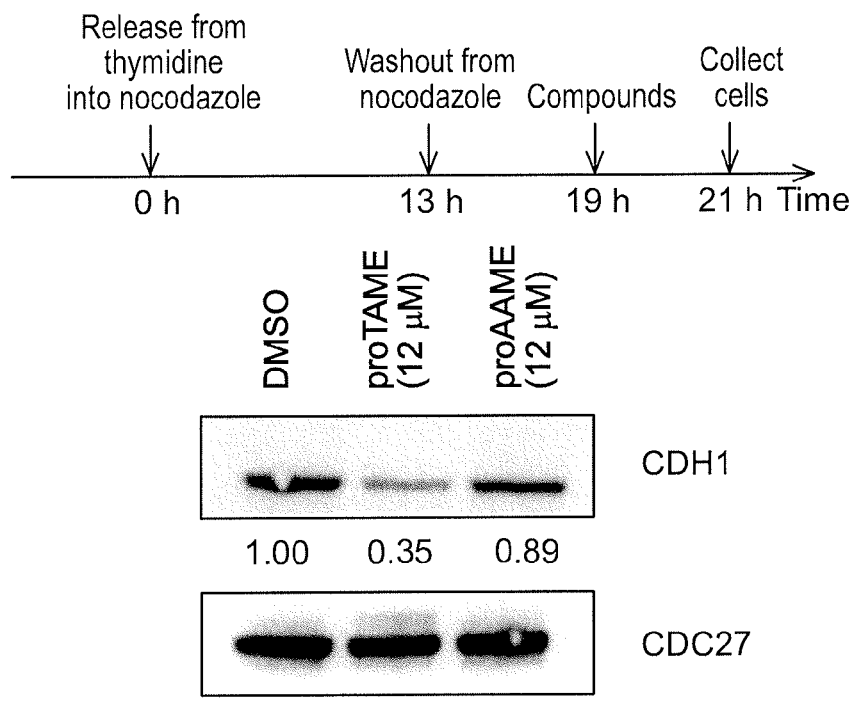
FIG. 15C is a series of immunoblots showing that proTAME blocks Cdh1 association with the APC. HeLa cells were released from nocodazole and treated with proTAME in G1. APC was immunoprecipitated from cell lysates and the amount of Cdc27 and Cdh1 was analyzed by immunoblot.
Figure 16A:
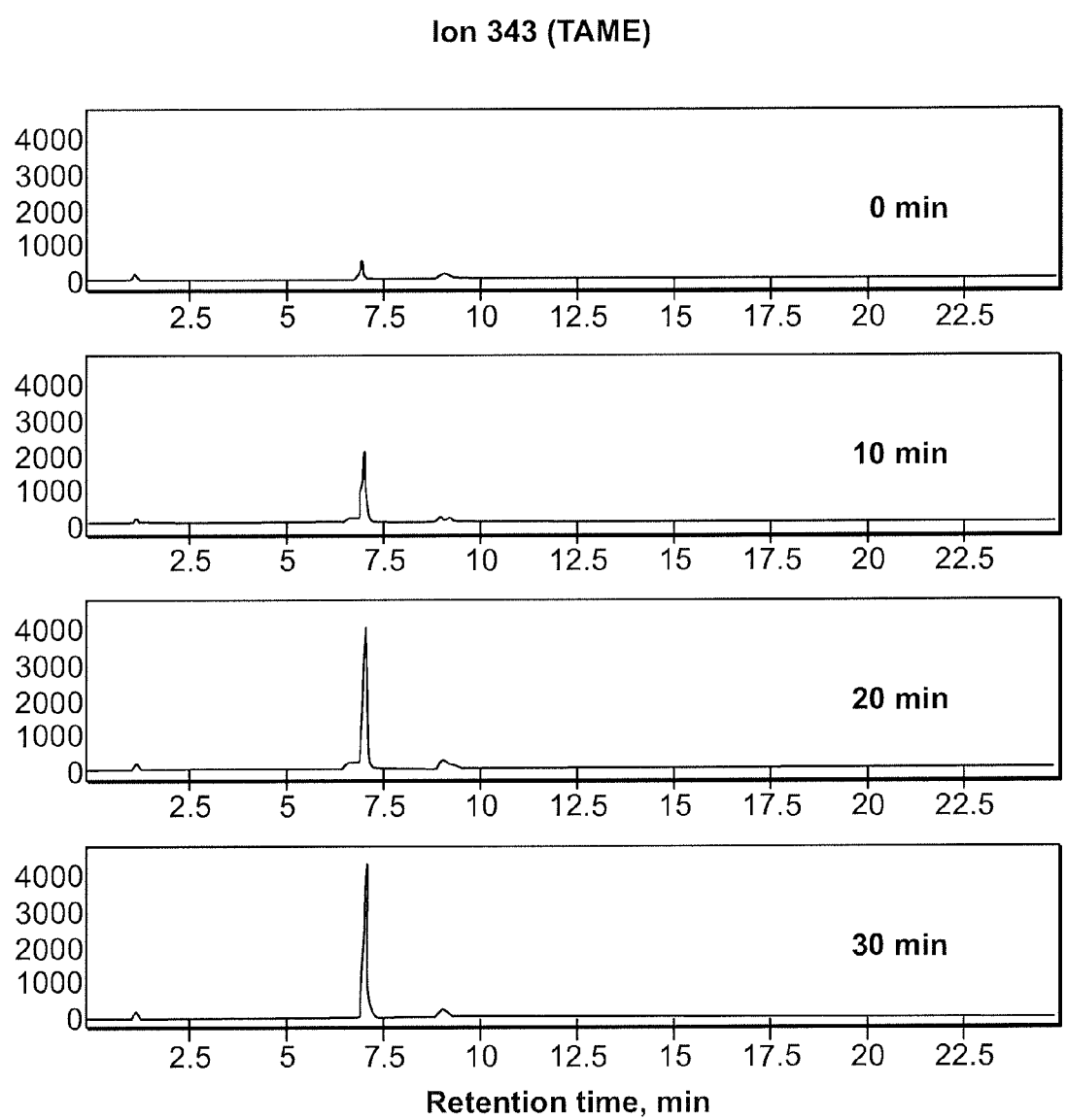
FIG. 16A is a series of graphs depicting the results of liquid-chromatography-mass spectrometry (LC/MS) analysis. ProTAME is converted to TAME in Xenopus extract. Fifty µM proTAME was added to interphase Xenopus extract and samples were collected at indicated time points. Ethyl acetate extraction was performed, and samples analyzed by liquid-chromatography-mass spectrometry (LC/MS). Chromatograms of the abundance of TAME and proTAME ion are shown.
Figure 16A:
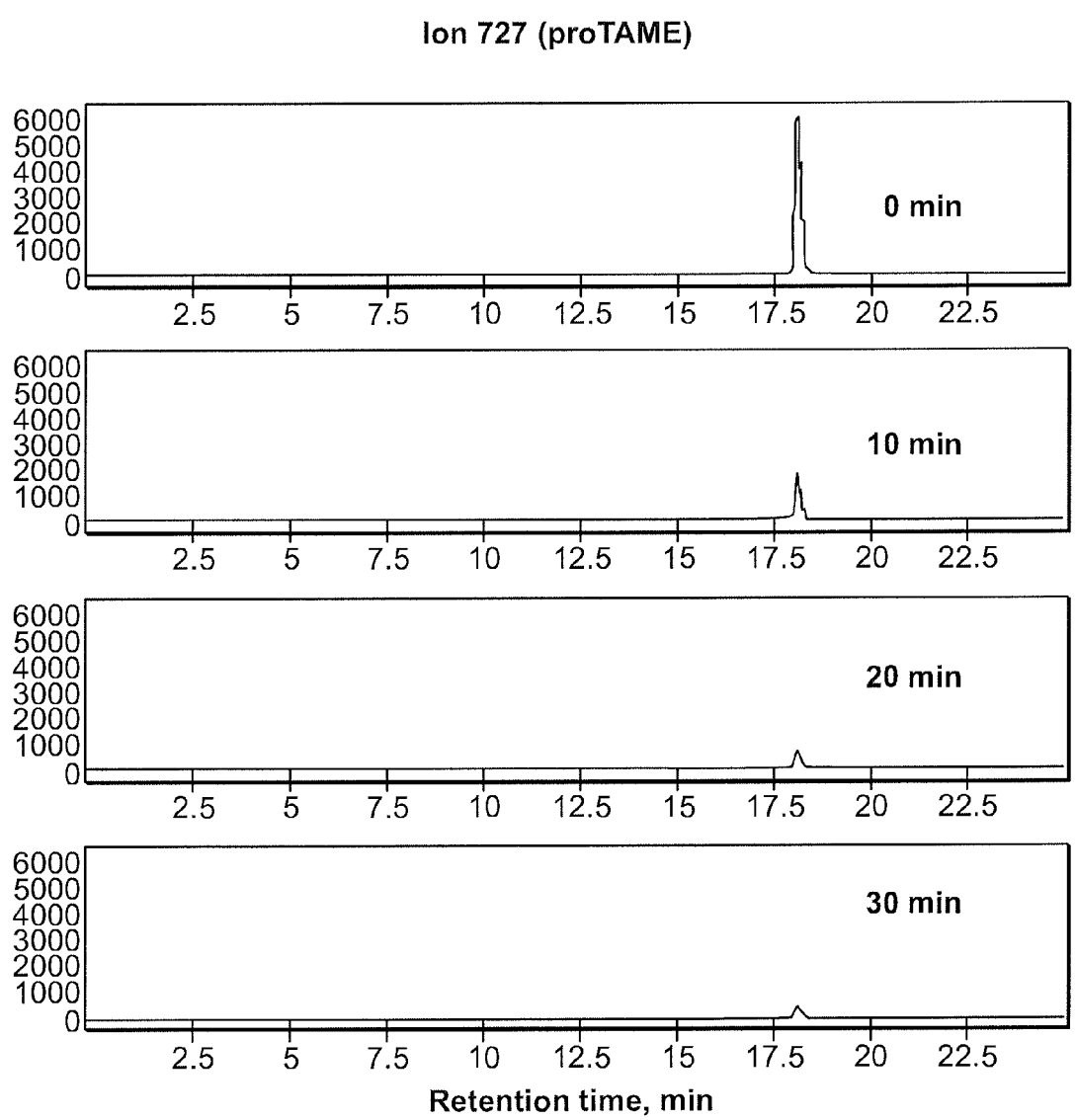
Figure 16B:
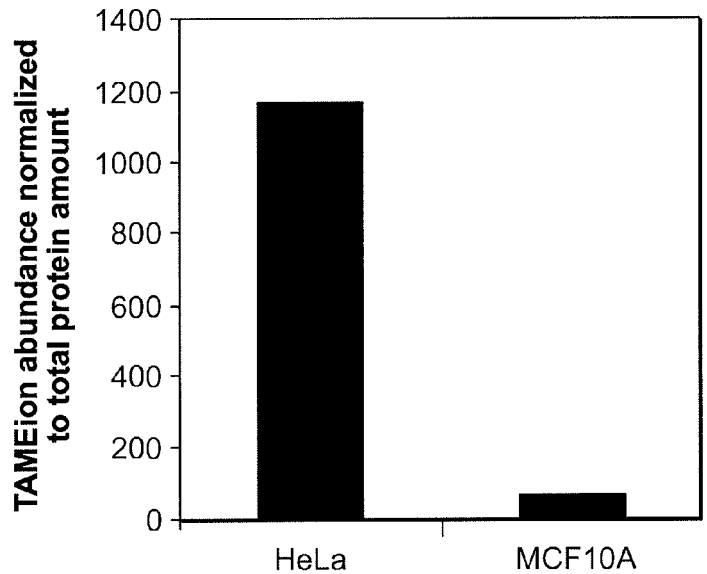
FIG. 16B is a graph showing that ProTAME is efficiently activated in HeLa cells but not MCF10A cells. HeLa and MCF10A cells were treated with 20 µM proTAME. Cells were collected after 1 h and lysed. Ethyl acetate extraction was performed prior to LC/MS analysis. Quantitation of the abundance of TAME ion normalized to total protein level is shown.

A TAME Prodrug Inhibits APC-Cdh1 Activation in Cells. Having established the mechanism by which TAME inhibits APC activation in Xenopus extract, it was next determined whether TAME inhibits APC activation in human cells. Because TAME is not cell permeable, a TAME prodrug (proTAME) was synthesized, and its control compound proAAME, by modifying the guanidino group to produce an N,N'-bis(acyloxymethyl carbamate) derivative (FIG. 15A). Such prodrugs can be processed by intracellular esterases to yield the parent compound. In Xenopus extract, proTAME was indeed rapidly converted to TAME (FIG. 16A), which efficiently inhibited cyclin B-luciferase proteolysis (FIG. 15B). ProTAME was also activated efficiently in HeLa cells, but not in MCF10A cells (FIG. 16B).

Figure 15D:
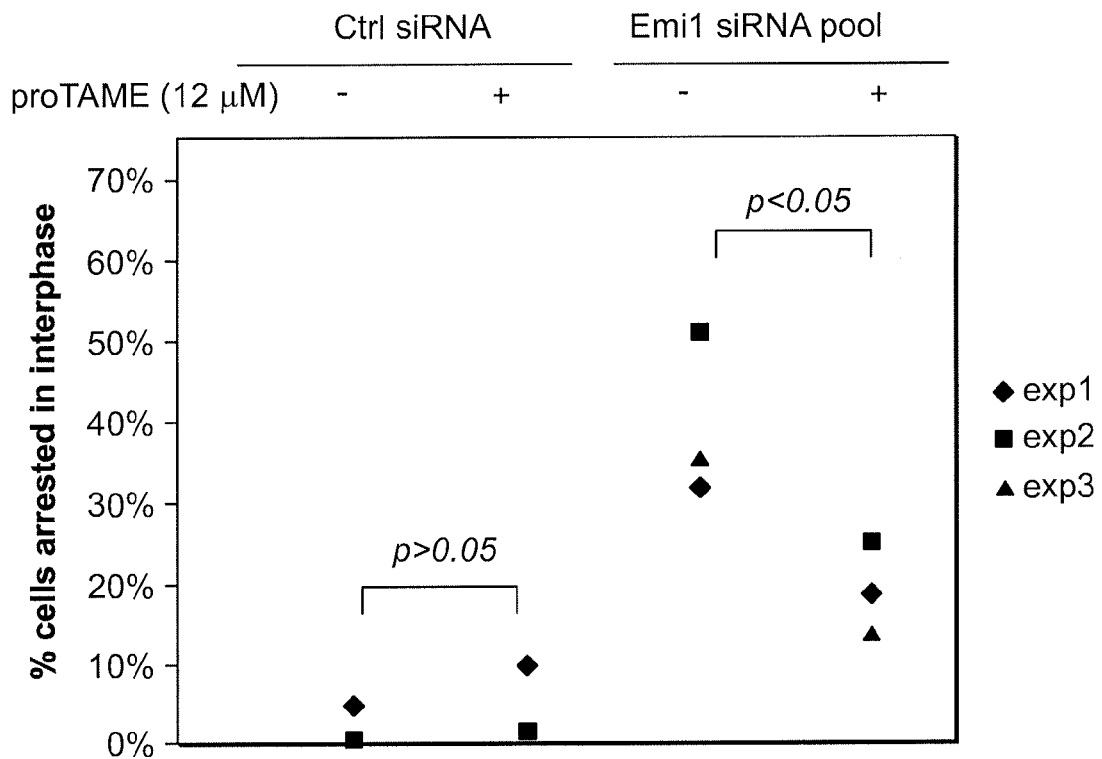
FIG. 15D is a graph showing that proTAME restores mitotic entry in Emi1-depleted cells. HeLa cells were transfected with control siRNA or Emi1 siRNA and treated with DMSO or proTAME 24 h after transfection and then imaged for 48 h. About 400 cells were analyzed in each experiment, and the proportion that failed to enter mitosis during the 48 h of imaging was calculated. Results of 3 independent experiments are shown. Statistical significance was calculated using an unpaired t-test.
Figure 16C:
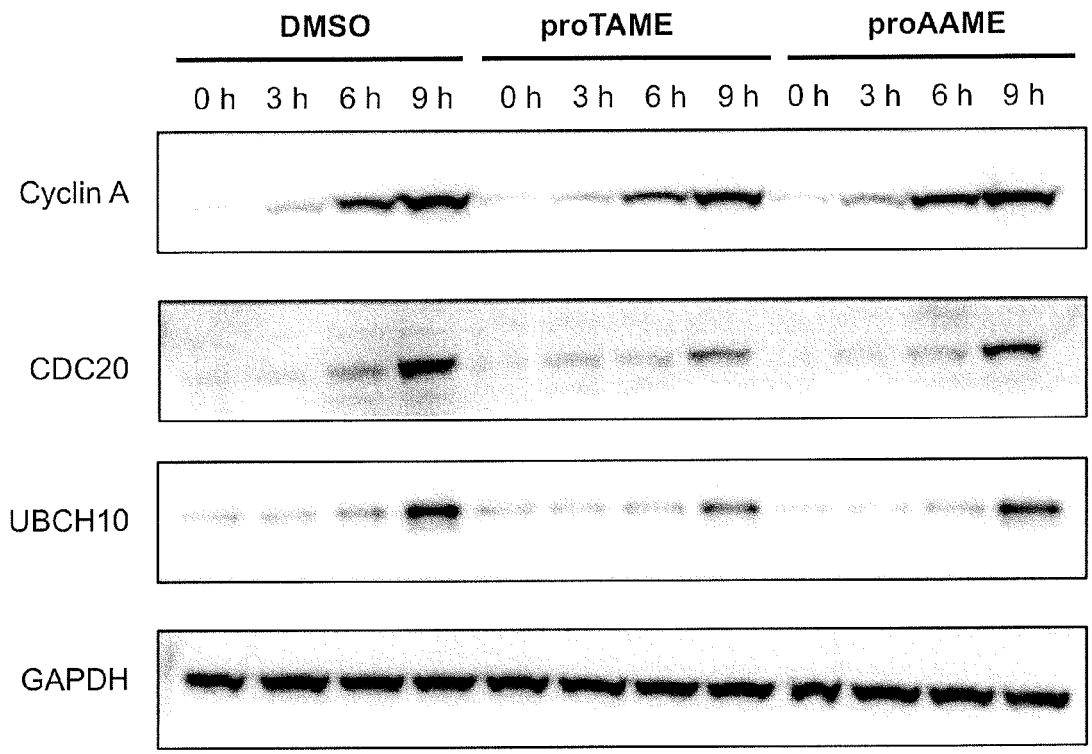
FIG. 16C is a series of immunoblots showing that proTAME does not induce premature accumulation of APC substrates in G1 cells. HeLa cells were synchronized by double thymidine block, released into nocodazole for 13 h and washed out of nocodazole for 6 h. Cells were then treated with DMSO (0.06%), proTAME or proAAME (12 µM). Samples were collected at indicated time points and protein level was measured by immunoblot.

It was next examined whether proTAME could inhibit association of Cdh1 with the APC in cells. HeLa cells expressing H2B-GFP were released from a nocodazole block and 12 µM of proTAME were added after cells had entered G1, when the APC is activated by Cdh1. Addition of proTAME inhibited Cdh1 association with the APC (FIG. 15C) but proAAME did not. However, proTAME was not sufficient to cause premature accumulation of endogenous APC substrates in G1 or S phase (FIG. 16C). During S phase, when APC substrates are known to be expressed, the effect of proTAME may be masked by Emi1-dependent inhibition of APC-Cdh1 (Hsu, J. Y., et al. (2002). Nat Cell Biol 4, 358-366). To test this idea, cells were depleted of Emi1, which leads to degradation of APC substrates and prevents mitotic entry (Hsu, J. Y., et al. (2002). Nat Cell Biol 4, 358-366). It was confirmed that Emi1 depletion prevents mitotic entry, and found that addition of 12 µM proTAME substantially rescued the mitotic entry defect caused by depletion of Emi1 (FIG. 15D). Therefore, proTAME is capable of inhibiting APC-Cdh1 function in cells.

Figure 15E:
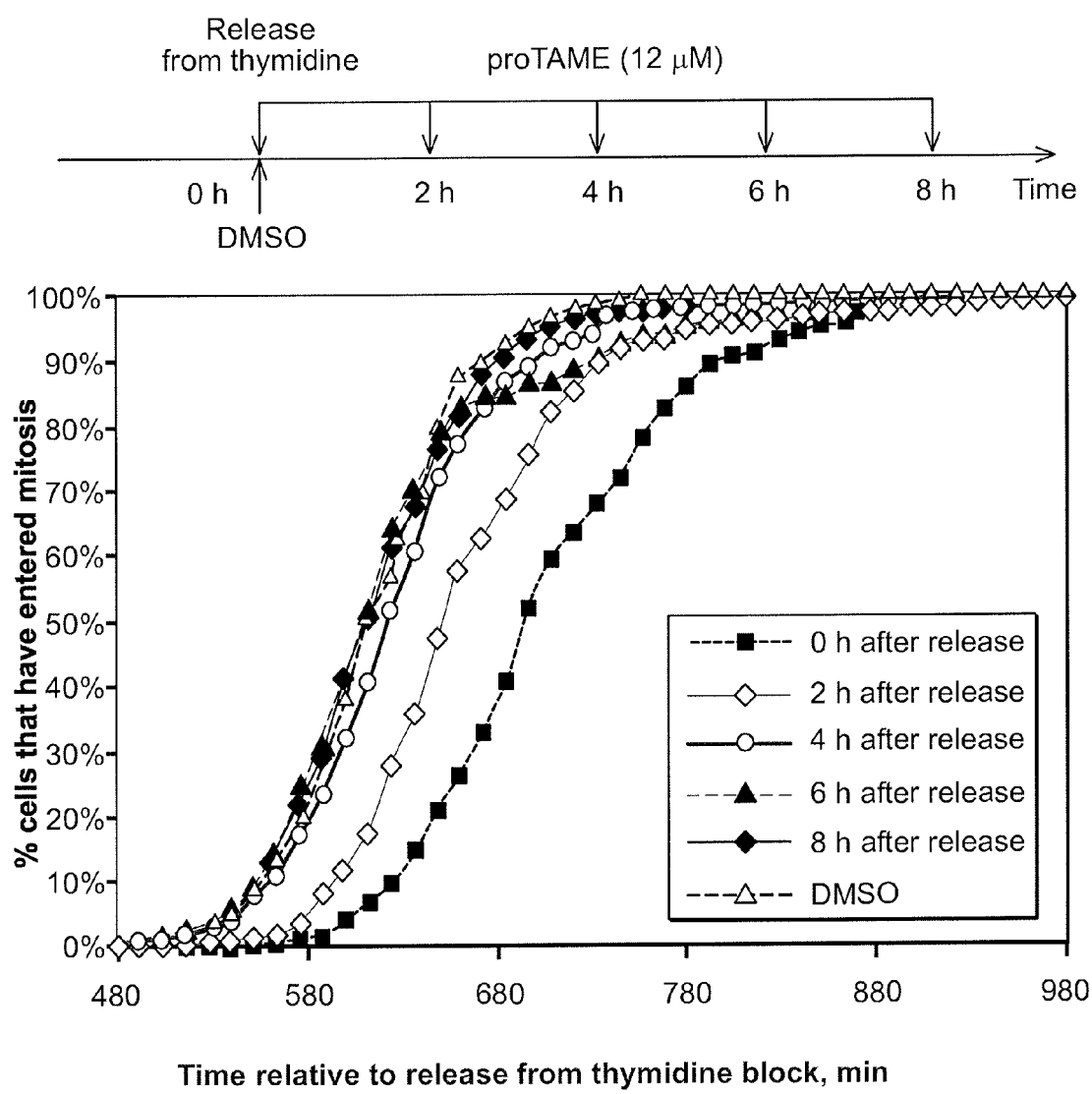
FIG. 15E is a graph showing that proTAME causes a mitotic entry delay if added during S-phase. HeLa H2B-GFP cells were released from a double thymidine block and proTAME (12 nM) was added at different time points as indicated. Mitotic entry was monitored by time-lapse imaging. Cumulative frequency curves of the time of mitotic entry are shown. Statistical analysis, including mean, median, statistical significance and number of cells analyzed per condition for all experiments is included in Table 1.

Previous studies have shown that knockdown of Cdh1 induces prolonged S-phase and mitotic entry delay in human cells (Engelbert, D., et al. (2008). Oncogene 27, 907-917; Sigl, R., et al. (2009). J Cell Sci 122, 4208-4217). Consistent with these findings, proTAME caused a 2 hour delay in mitotic entry when added during release from a double thymidine block (FIG. 15E). However, adding proTAME 6 hour or later after release did not delay mitotic entry (FIG. 15E), suggesting the delay may be a consequence of inhibiting APC-Cdh1 in S-phase. These findings indicate that although proTAME can inhibit APC-Cdh1 activation, it has only modest effects on cell cycle progression during interphase.

ProTAME Induces Mitotic Arrest in the Absence of Spindle Damage. To examine effects of proTAME treatment on mitosis, HeLa H2B-GFP cells were released from a double thymidine block and added proTAME 8 h after release, a time at which proTAME addition does not delay mitotic entry (FIG. 15E). Mitotic duration was then measured by time-lapse imaging. Cells treated with low doses of proTAME (780 nM or 3 µM) remained in metaphase for up to several hours, but then proceeded through a normal anaphase, whereas cells treated with 12 µM proTAME arrested in metaphase and subsequently died (FIG. 17A). In contrast, treatment of cells with 12 µM proAAME had no effect. ProTAME greatly increased mitotic duration in asynchronous hTERT-RPE1 cells as well, as 6 μM proTAME increased median mitotic duration to over 8 h, compared to 24 min in proAAME-treated cells (FIG. 18A). ProTAME had no effect at similar doses in MCF10a cells, because the prodrug was not efficiently activated (FIG. 16B).

Figure 17B:
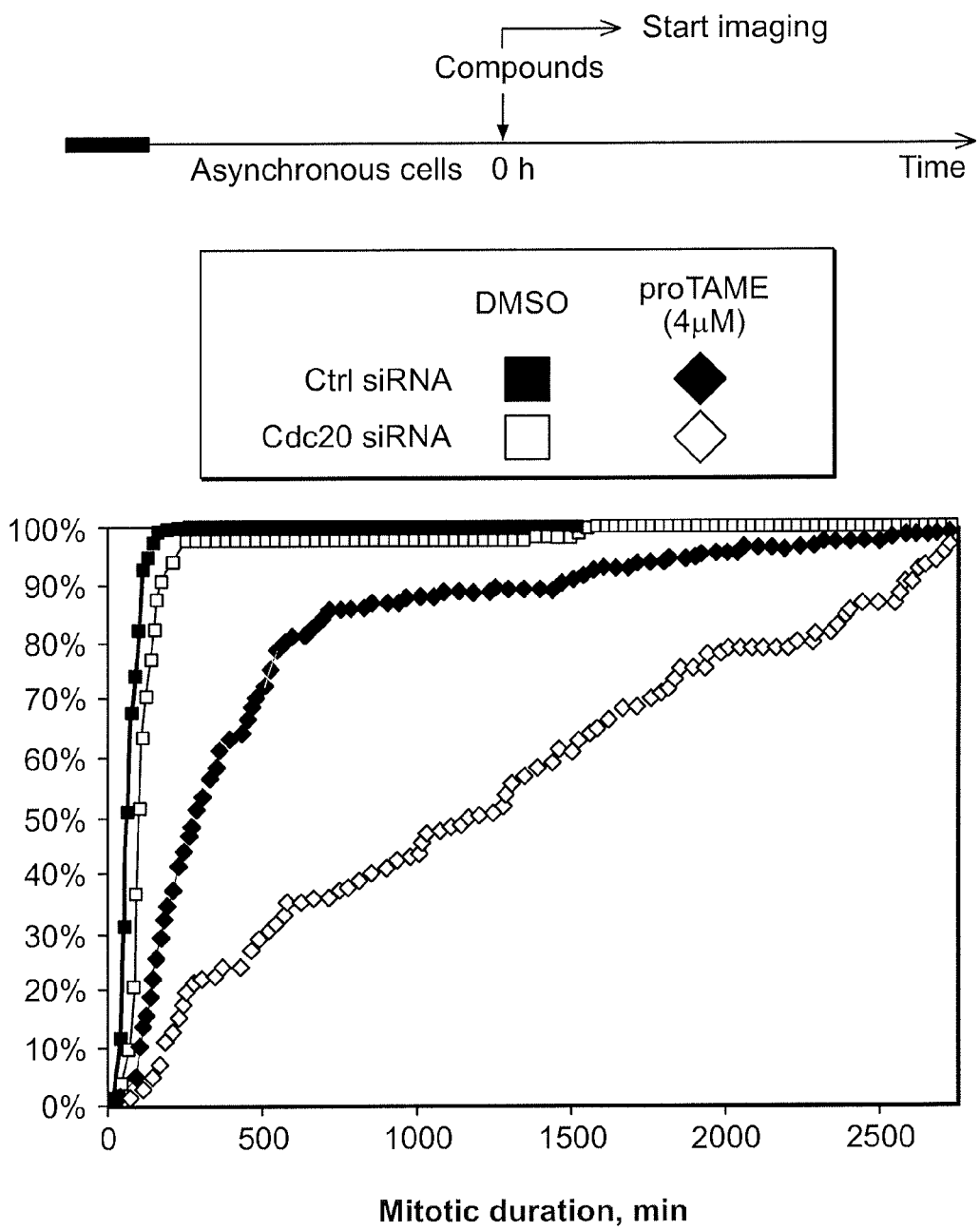
FIG. 17B is a schematic diagram depicting the experimental timeline and a graph showing that proTAME induces mitotic arrest without disrupting the mitotic spindle. Partial Cdc20 knockdown sensitizes cells to proTAME treatment. Asynchronous HeLa H2B-GFP cells were transfected with control or Cdc20 siRNA 24 h prior to treatment with compounds.

If proTAME blocks mitotic progression by disrupting the APC-Cdc20 interaction, then reducing Cdc20 expression should enhance the mitotic exit delay induced by proTAME treatment. In control-transfected cells, 4 μM proTAME increased mitotic duration from 1.0 h to 4.8 h (FIG. 17B). However, when Cdc20 levels were reduced by 50% using siRNA-mediated knockdown (FIG. 18B), proTAME prolonged mitotic duration to 19.4 h (FIG. 17B). This effect was synergistic, because Cdc20 knockdown by itself only increased mitotic duration to 1.6 hours. These results show that reducing the expression of Cdc20 strongly sensitizes cells to the effect of proTAME, consistent with the APC-Cdc20 interaction as the relevant target of the compound.

Figure 17C:
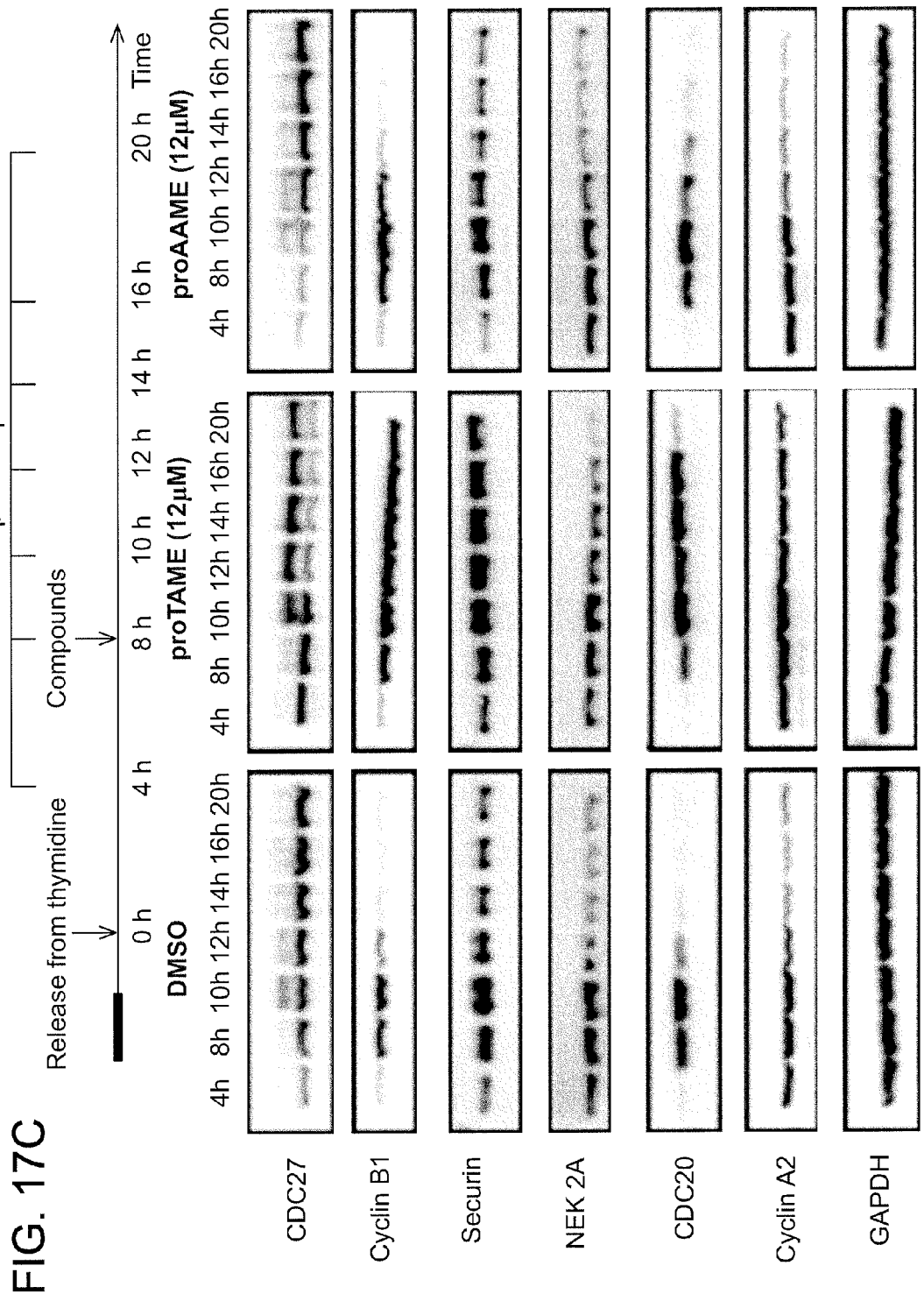
FIG. 17C is a series of immunoblots showing that proTAME stabilizes endogenous APC substrates. Double thymidine synchronized HeLa cells were treated with compounds.

The effect of proTAME treatment on degradation of APC substrates was investigated. Because the SAC does not stabilize all APC substrates during mitosis, some substrates such as cyclin A2, Cdc20, and Nek2A are degraded in cells treated with microtubule inhibitors (den Elzen, N., and Pines, J. (2001). J Cell Biol 153, 121-136; Hayes, M. J., et al. (2006). Nat Cell Biol 8, 607-614; Nilsson, J., et al. (2008). Nat Cell Biol 10, 1411-1420). In contrast, substrates such as cyclin B1 and securin are stabilized by SAC activation. If proTAME directly inhibits APC activation, then it would stabilize all APC substrates during mitosis, not just those whose stability depends on the SAC. Consistent with this hypothesis, cells treated with proTAME accumulated cyclin A2, Cdc20 and Nek2A in addition to cyclin B1 and securin (FIG. 17C). These results were confirmed in live cell imaging experiments, where proTAME stabilized cyclinA2-GFP but the microtubule depolymerizer nocodazole did not (FIG. 17D). Interestingly, proTAME treatment led to greater accumulation of cyclin B1-GFP than nocodazole treatment, suggesting that proTAME inhibited APC activation more effectively than a SAC-activating compound, consistent with the ability of proTAME to directly inhibit APC activation.

The effects of proTAME treatment on mitotic spindle morphology and chromosome congression were assessed and compared to the effects of treatment of cells with microtubule inhibitors. Compared to DMSO-treated cells, treatment of asynchronous HeLa cells with 12 μM proTAME for 2 h yielded no measurable differences in mitotic spindle morphology or inter-kinetochore distance, which reflects development of proper kinetochore tension (FIG. 17E). In contrast, treatment of cells with nocodazole or taxol for 2 h strongly perturbed spindle organization (FIG. 17E). In live cell imaging experiments, treatment of cells with 3 μM proTAME or 10 μM MG132 caused no delay in chromosome congression (FIG. 18C). Treatment of cells with 10 nM nocodazole or 12 μM proTAME caused a similar mild congression delay of 6 min (FIG. 18C), but these treatments produced contrasting effects on the metaphase plate. In cells treated with 10 nM nocodazole, the metaphase plate appeared loose and was prone to bending, whereas in cells treated with 12 μM proTAME the metaphase plate appeared tight and did not bend. Importantly, 10 nM nocodazole prolonged mitosis by only 20 min (data not shown), whereas 12 μM proTAME induced a mitotic arrest of over 28 h (FIG. 17A). Thus, the mild delay in congression is not sufficient to explain the ability of proTAME to arrest cells in mitosis. ProTAME induces a mitotic arrest by perturbing the APC-Cdc20 interaction rather than by stimulating the SAC through interfering with chromosome attachment to the mitotic spindle.

Figure 19A:
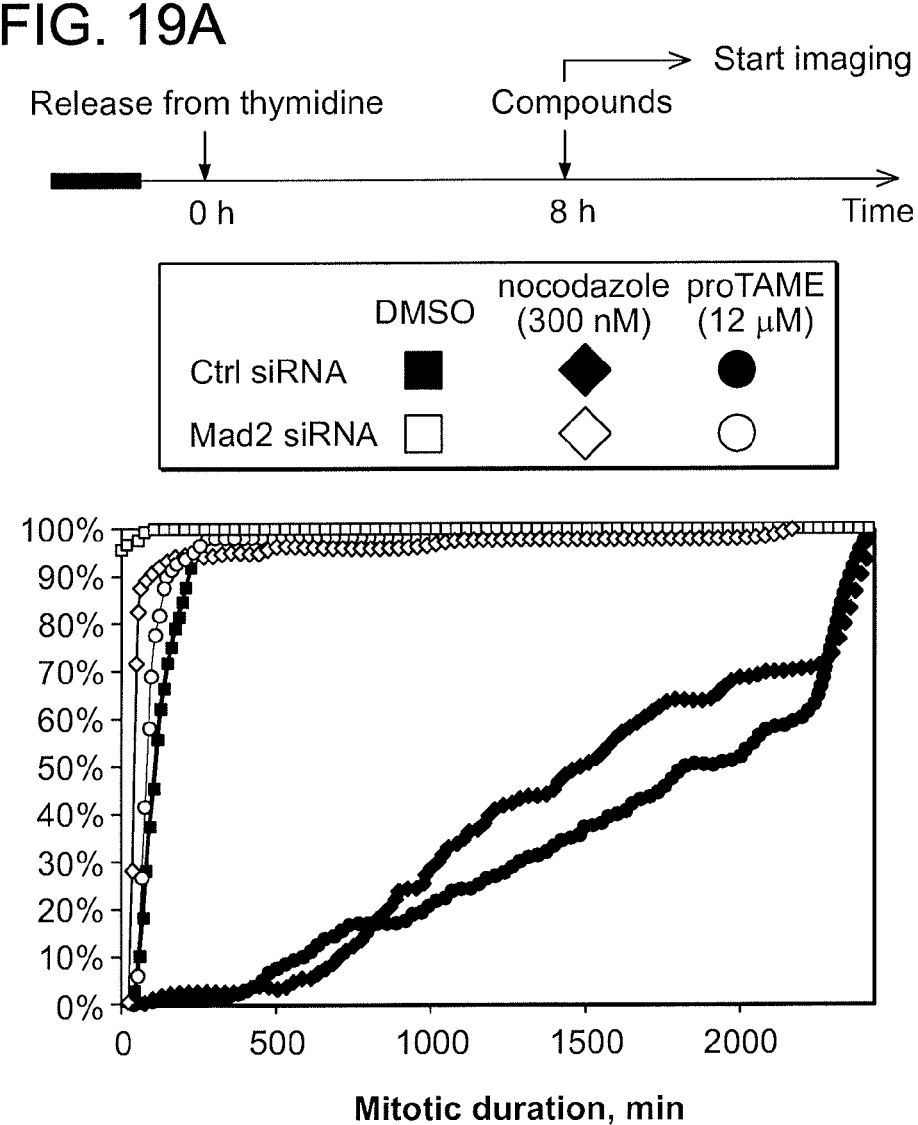
FIG. 19A is a schematic diagram depicting the experimental timeline and a graph showing that proTAME-induced mitotic arrest is SAC-dependent. ProTAME-induced mitotic arrest is Mad2-dependent. HeLa H2B-GFP cells were transfected with indicated siRNAs between rounds of thymidine treatment. Following release, cells were treated with compounds and analyzed by time-lapse imaging. A graph of the same data with an expanded x-axis is shown in FIG. 20A.
Figure 20:
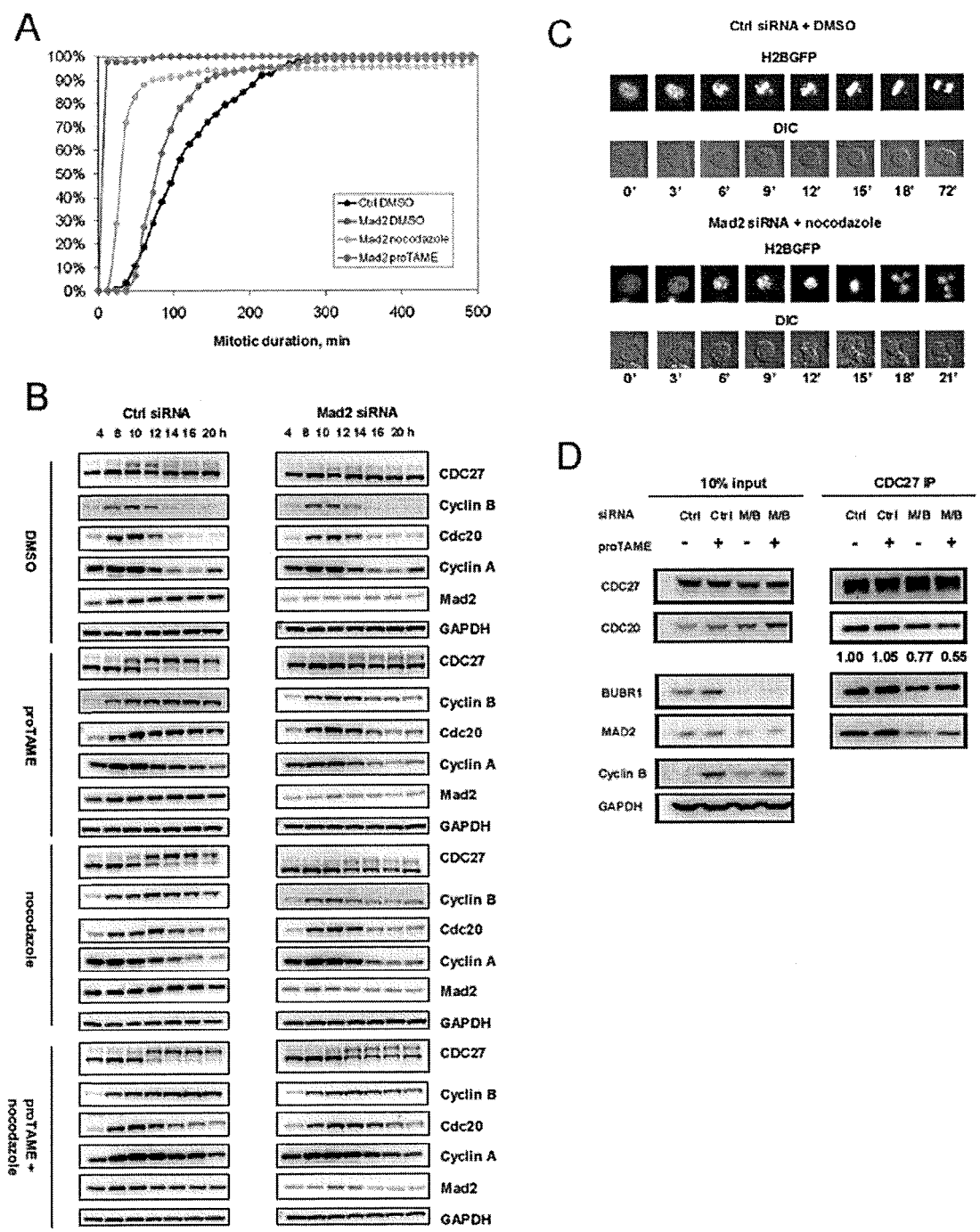
FIG. 20A is a graph showing the same experiment as shown in FIG. 19A but with an expanded x-axis to better show the difference between short mitotic durations.
FIG. 20B is a series of immunoblots from the experiment shown in FIG. 19A.
FIG. 20C is a series of photographs showing that Mad2 knockdown efficiently overrides the spindle assembly checkpoint in the presence of nocodazole. Above: Control-siRNA-treated cells were treated with 0.06% DMSO. Below: Mad2 knockdown cells were treated with 300 nM nocodazole. Live imaging was done at 40× magnification and 3 min interval.
FIG. 20D is a series of immunoblots showing that proTAME inhibits Cdc20 association with human APC if the SAC is inactivated. Double thymidine synchronized HeLa cells were transfected with Mad2 and BubR1 siRNA, and infected with cyclin BΔ107 adenovirus. At 10.5 h after release from thymidine, cells were treated with indicated drugs for 2 h. M/B: Mad2/BubR1 siRNA. Numbers indicate the relative Cdc20 band intensity normalized to Cdc27.

ProTAME-induced Mitotic Arrest is SAC-Dependent. Because TAME directly inhibits the APC, and causes arrest in metaphase with kinetochores that develop tension, it was hypothesized that the proTAME-induced mitotic arrest in human cells would be independent of the SAC. Therefore, unexpectedly, it was determined that the SAC is in fact essential for the prolonged mitotic arrest of cells treated with proTAME. In double-thymidine synchronized cells, Mad2 knockdown greatly shortened the duration of proTAME-induced arrest, from 24.6 h to 1.4 h (FIGS. 19A and 20A). As expected, Mad2 knockdown abrogated nocodazole-induced arrest, shortening the average mitotic duration from 30 h to 0.6 h. The Mad2-dependence of the proTAME-induced arrest was confirmed by measurement of APC substrate levels in synchronized cells (FIG. 20B). These findings indicate that prolonged mitotic arrest induced by proTAME depends strongly on the SAC.

Figure 19B:
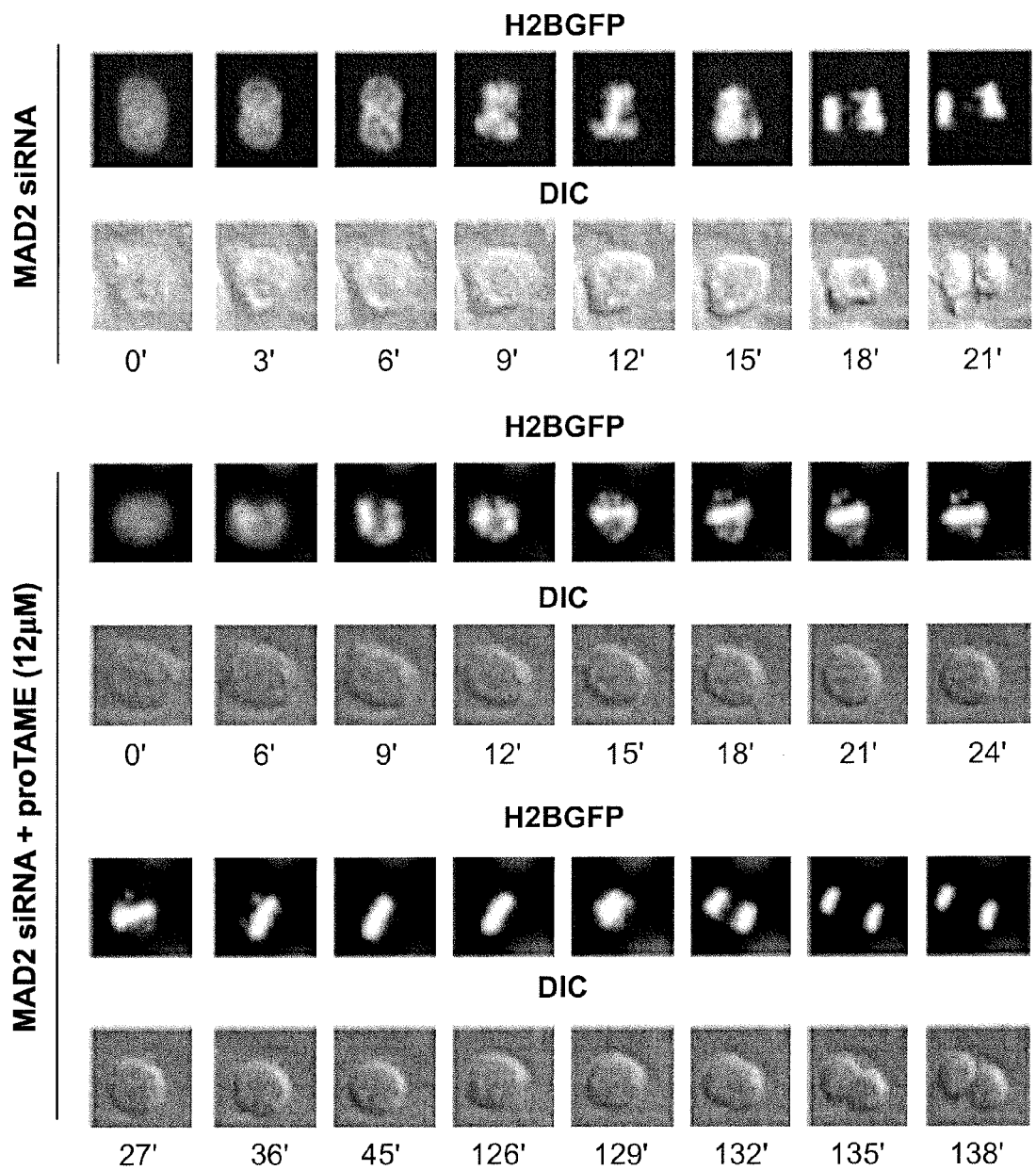
FIG. 19B is a series of photographs showing that proTAME rescues the mitotic defect induced by Mad2 knockdown. Asynchronous HeLa H2B-GFP cells were treated with Mad2 siRNA 24 h prior to addition of compound.

These experiments also revealed the ability of proTAME to delay mitotic exit independent of Mad2, as expected based on TAME's ability to directly inhibit APC activation. In Mad2 knockdown cells, proTAME treatment increased median mitotic duration from 12 min to 84 min (FIGS. 19A and 20A). Strikingly, this mitotic delay was sufficient to give Mad2 knockdown cells enough time to build a normal metaphase plate before initiating anaphase, rescuing the chromosome segregation defect caused by Mad2 knockdown (FIGS. 19B and 20C). The ability of proTAME to restore normal mitotic division in cells depleted of Mad2 highlights the ability of proTAME to directly inhibit APC activation, and further demonstrates that proTAME is unlikely to perturb microtubules or interfere with kinetochore function.

Whereas TAME caused substantial reduction of Cdc20 binding to the APC in *Xenopus* extracts, proTAME treatment did not cause substantial dissociation of Cdc20 from APC during mitotic arrest in HeLa cells. This might be a consequence of an active SAC pathway that may promote IR-tail independent binding of Cdc20 to the APC. Therefore, the effect of depleting SAC proteins on the ability of proTAME to disrupt the APC-Cdc20 interaction was examined. Indeed, when HeLa cells were arrested in mitosis by expression of nondegradable cyclin B, proTAME induced significant dissociation of Cdc20 from the APC, but only if SAC proteins were depleted by RNAi (FIG. 20D). These results show that a proTAME-induced mitotic arrest occurs without substantial dissociation of Cdc20 from the APC, as a consequence of persistent activity of the SAC.

Figure 19D:
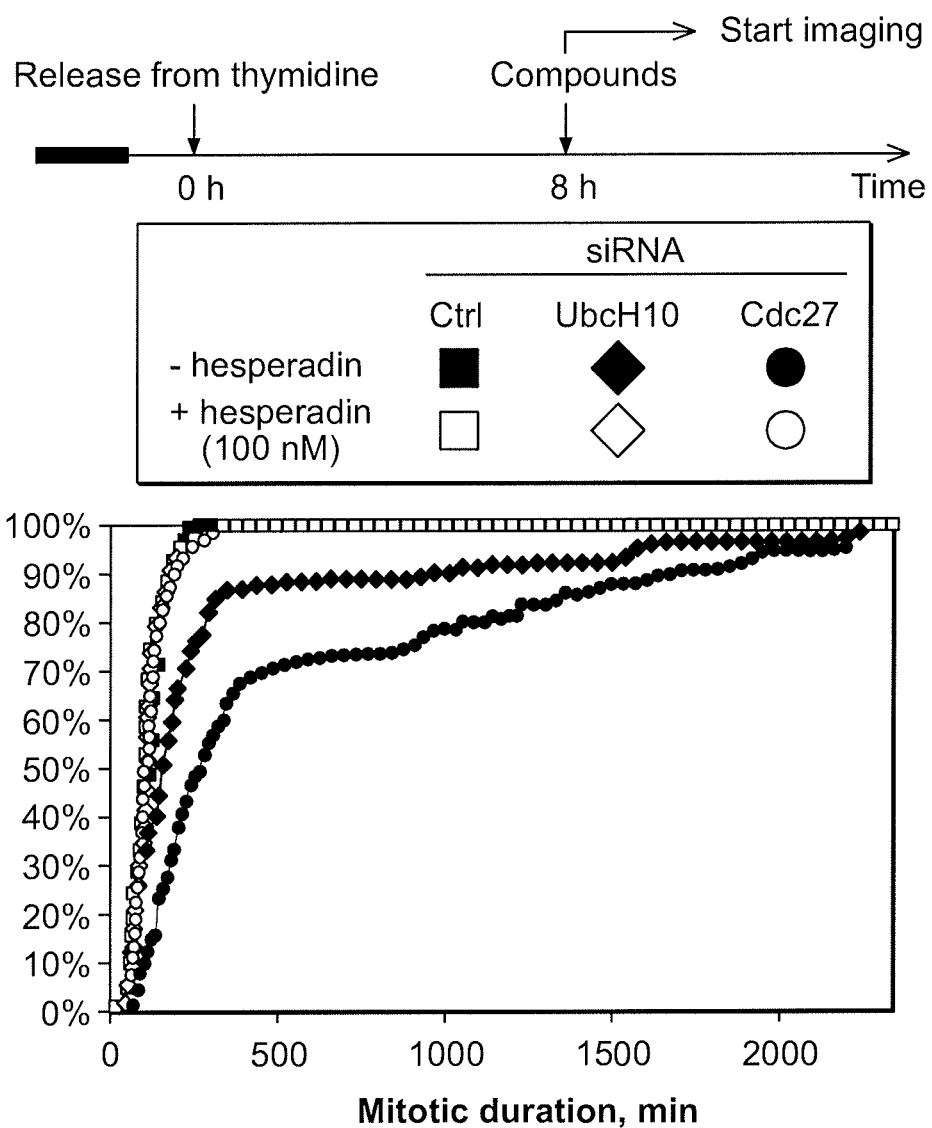
FIG. 19D is a schematic diagram depicting the experimental timeline and a graph showing that UbcH10 or Cdc27 knockdown induces a hesperadin-sensitive mitotic delay. HeLa H2B-GFP cells were transfected with indicated siRNA between rounds of thymidine synchronization and treated with hesperadin 8 h following release.
Figure 21:
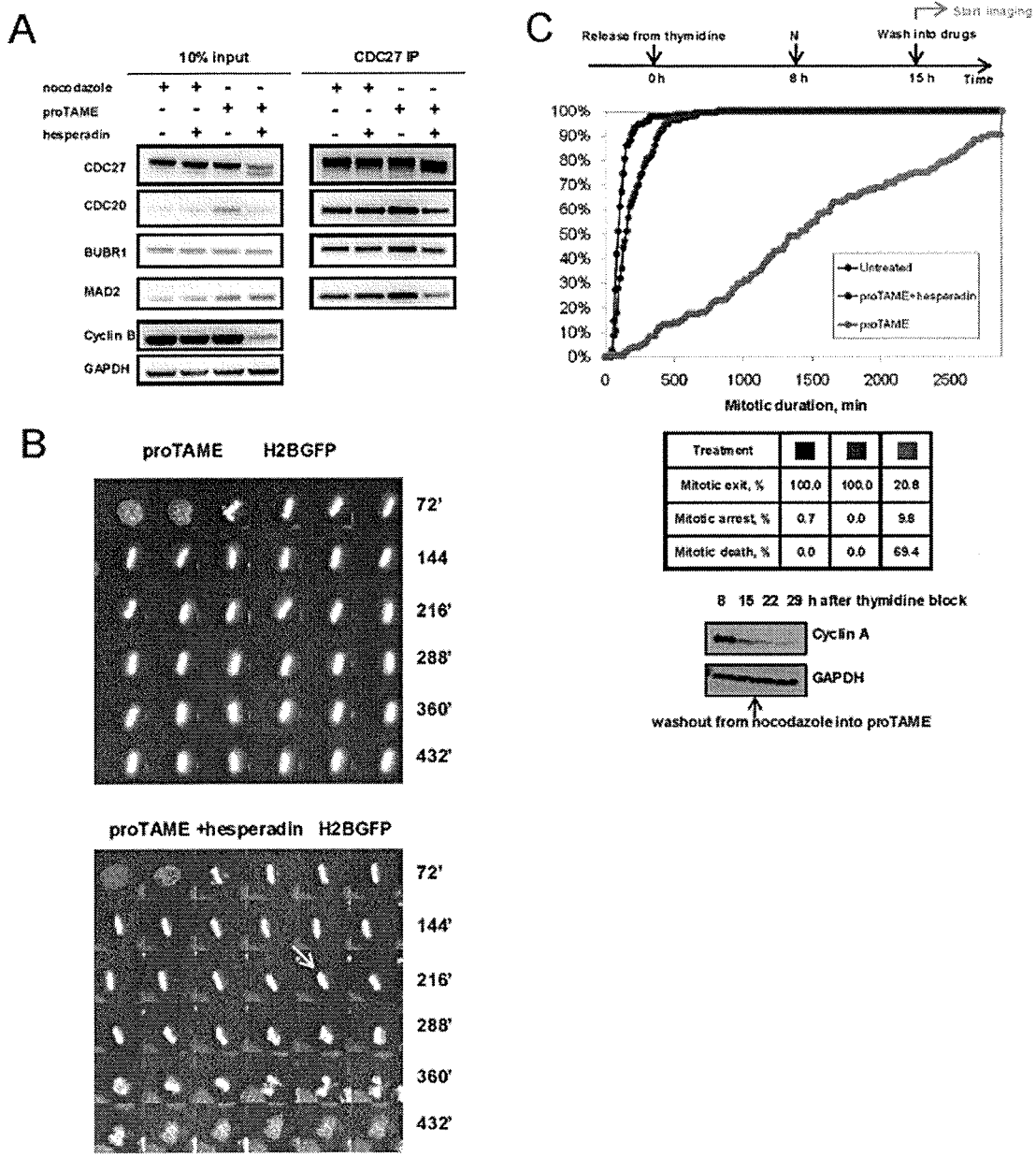
FIG. 21A is a series of immunoblots showing that hesperadin overrides a proTAME-induced mitotic arrest. HeLa cells were synchronized with double thymidine block and treated with indicated drugs at 10 h after release for 1 h. Mitotic cells were collected and APC was immunoprecipitated from cell lysate. Protein levels were measured by Western blot.
FIG. 21B is a series of photographs showing that hesperadin induces deformation of the metaphase plate in proTAME-arrested cells. HeLa H2B-GFP cells were synchronized with double thymidine block and treated with 12 μM proTAME at 8 h after release and with 100 nM hesperadin at 10 h after release. For cells that have entered metaphase prior to hesperadin treatment, changes in the morphology of metaphase plate were analyzed and one representative cell is shown. The yellow arrow denotes the time of hesperadin addition. A representative cell arrested with proTAME alone is also shown for comparison.
FIG. 21C is a graph, table, and accompanying immunoblot showing that hesperadin overrides proTAME-induced mitotic arrest of cells released from nocodazole-induced arrest. HeLa H2B-GFP cells were synchronized with double thymidine block and treated with 300 nM nocodazole at 8 h after release from thymidine block. Cells were washed out of nocodazole at 15 h after release from thymidine block into growth medium, or 12 μM proTAME, or 12 μM proTAME and 100 nM hesperadin. Cells were imaged at 12 min interval. Cumulative frequency curves of mitotic duration and cell fate distribution are shown. Cell samples were collected at different time points as indicated and protein levels were measured by immunoblot. The top diagram shows timing of treatments. N: nocodazole.

To further understand the SAC-dependence of the proTAME arrest, SAC signaling was pharmacologically inactivated by treating cells with hesperadin (Hauf, S., et al. (2003). J Cell Biol 161, 281-294), an inhibitor of Aurora B kinase. This kinase phosphorylates proteins at kinetochores that are not under tension, leading to destabilization of microtubule-kinetochore interactions and activation of the SAC (Biggins, S., and Murray, A. W. (2001). Genes Dev 15, 3118-3129; Cheeseman, I. M., et al. (2006). Cell 127, 983-997; DeLuca, J. G., et al. (2006). Cell 127, 969-982). However, recent work using phosphospecific antibodies that recognize Aurora B substrates indicates that kinetochore proteins remain phosphorylated at a basal rate during metaphase (Welburn, J. P., et al. (2010). Mol Cell 38, 383-392). It was hypothesized that this basal rate of Aurora B-dependent phosphorylation may produce a persistent SAC signal during metaphase that may contribute to the proTAME-induced arrest. Three observations supported this hypothesis. First, hesperadin treatment dramatically shortened proTAME-induced mitotic arrest (FIG. 19C), and led to dissociation of Mad2 and BubR1 from the APC in proTAME-arrested cells (FIG. 21A). As expected, hesperadin also substantially shortened taxol-induced mitotic arrest, with a less pronounced effect on nocodazole-induced arrest (FIG. 19C). Second, treatment of proTAME-arrested metaphase cells with hesperadin caused deformation of the metaphase plate before cells exited mitosis, suggesting that ongoing Aurora B-dependent phosphorylation is required to maintain proper kinetochore-microtubule attachment in metaphase (FIG. 21B). Third, knockdown of the APC component Cdc27 or the APC-specific E2 UbcH10 caused a mitotic delay that could be completely suppressed by hesperadin treatment (FIG. 19D). Together, these experiments support the idea that the SAC remains active in metaphase, despite the presence of properly attached chromosomes, and that SAC signaling is important for the prolonged mitotic arrest induced by APC inhibition.

One possible explanation for the SAC-dependence of the proTAME arrest is that proTAME stabilizes APC substrates such as Nek2A or cyclin A that are normally degraded in early mitosis. For example, overexpression of cyclin A has been reported to delay chromosome congression (den Elzen, N., and Pines, J. (2001). J Cell Biol 153, 121-136). To test whether stabilization of these substrates is important for the proTAME-induced arrest, HeLa cells were released from double thymidine block into nocodazole for 15 h to allow degradation of cyclin A and other APC substrates that are not efficiently stabilized by the SAC. Cells were then washed out of nocodazole into proTAME. Under this condition, proTAME remained capable of inducing a prolonged mitotic arrest that was highly hesperadin-sensitive (FIG. 21C). This result indicates that the SAC-dependence of proTAME-induced mitotic arrest is unlikely to be caused by stabilization of APC substrates that are normally degraded in a SAC-independent fashion.

Figure 22A:
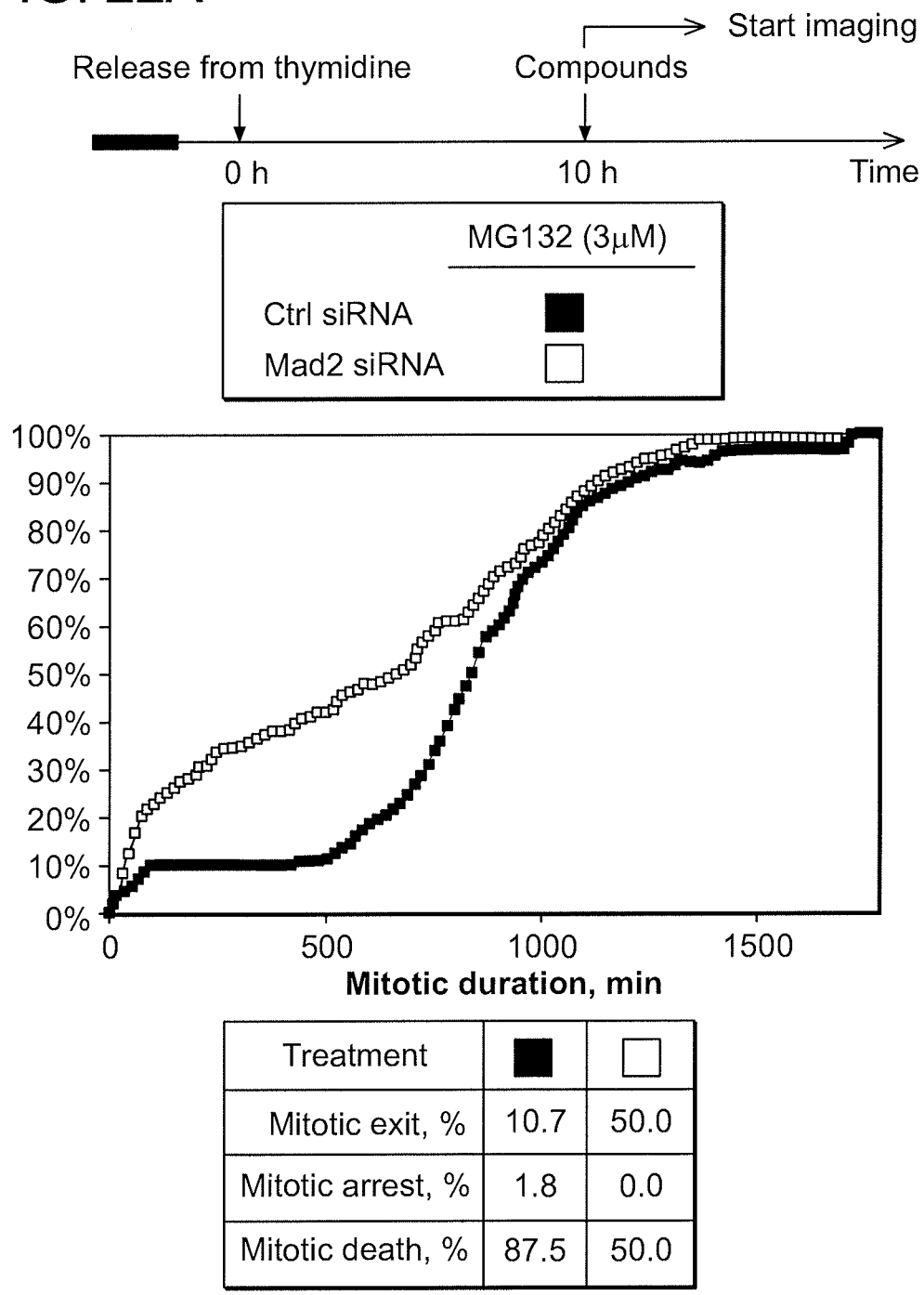
FIG. 22A is a schematic diagram depicting the experimental timeline, graph, and accompanying table showing that MG132-induced mitotic arrest is SAC-dependent. MG132-induced arrest is Mad2-dependent. HeLa H2B-GFP cells were transfected with indicated siRNAs between rounds of thymidine synchronization, treated with compounds, and followed by time-lapse imaging.

Metaphase Arrest Induced by a Proteasome Inhibitor is SAC-Dependent. Previous work has indicated that APC-dependent ubiquitination promotes SAC inactivation in cell lysates (Reddy, S. K., et al. (2007). Nature 446, 921-925), potentially explaining why the proTAME arrest is SAC-dependent. In the cell lysate system, APC-dependent ubiquitination of Cdc20, but not APC-dependent proteolysis, was suggested to be important for release of Cdc20 from SAC proteins (Reddy, S. K., et al. (2007). Nature 446, 921-925). Proteasome activity may be required for dissociation of the Mad2-Cdc20 complex (Visconti, R., et al. (2010). Cell Cycle 9, 564-569). Moreover, the data presented herein demonstrate that APC-dependent proteolysis could be important for SAC inactivation. A prediction of this model is that mitotic arrest induced by treatment with a proteasome inhibitor should be SAC-dependent. To test this idea, cells were treated with a low dose of proteasome inhibitor (3 µM) that was sufficient to arrest cells in mitosis (median duration of 15 h). At this concentration, the duration of arrest was limited by cell death rather than mitotic exit, as only 10% of cells exited mitosis during the 30 h duration of the experiment (FIG. 22A). In MG132-treated cells depleted of Mad2 by RNAi, 50% of the cells exited mitosis (FIG. 22A), indicating that the SAC is required to prevent mitotic exit.

Figure 22B:
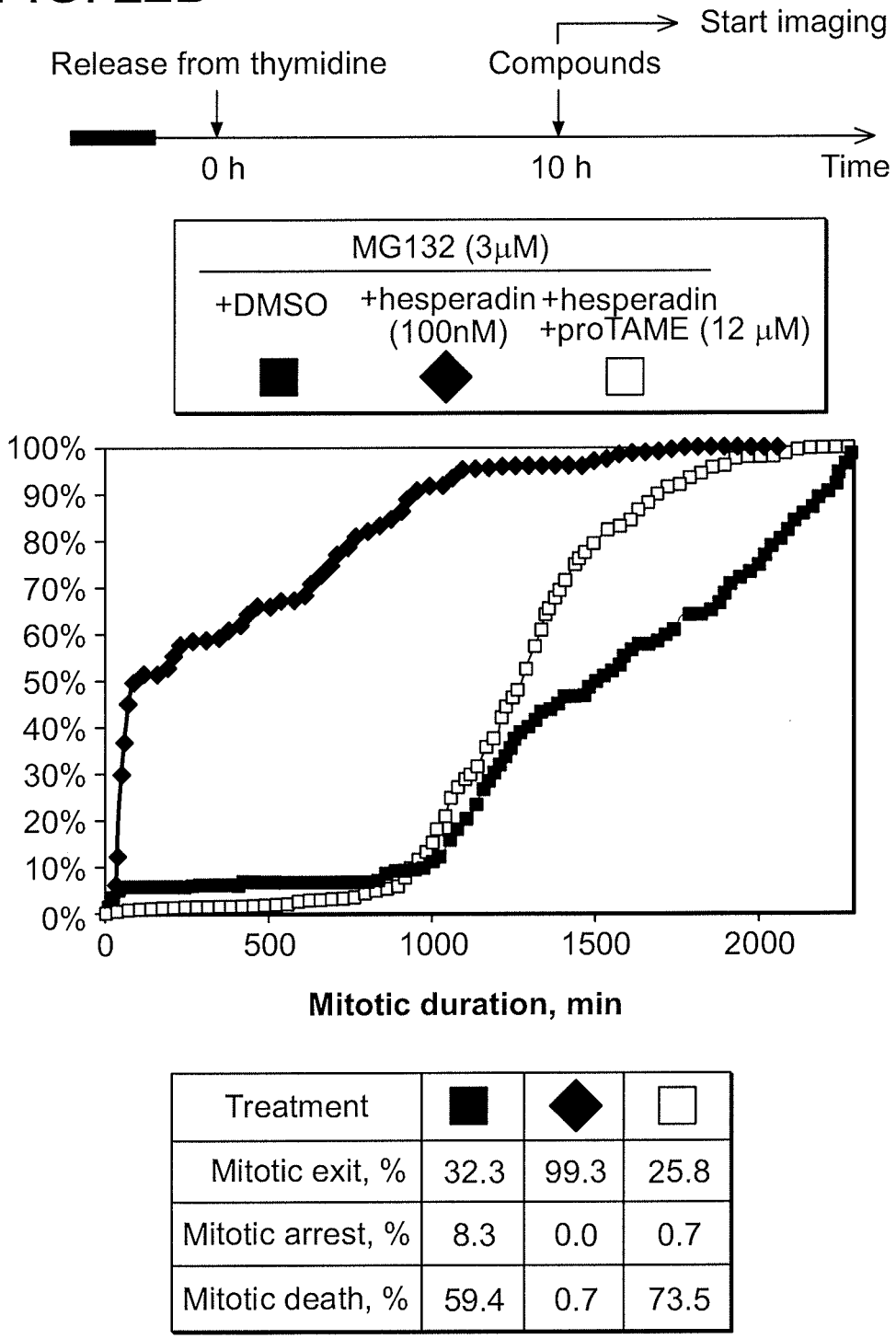
FIG. 22B is a schematic diagram depicting the experimental timeline, graph, and accompanying table showing that MG132-induced arrest is hesperadin-sensitive, but mitotic exit can be suppressed by proTAME. Double thymidine synchronized HeLa cells were treated with compounds.
Figure 22C:
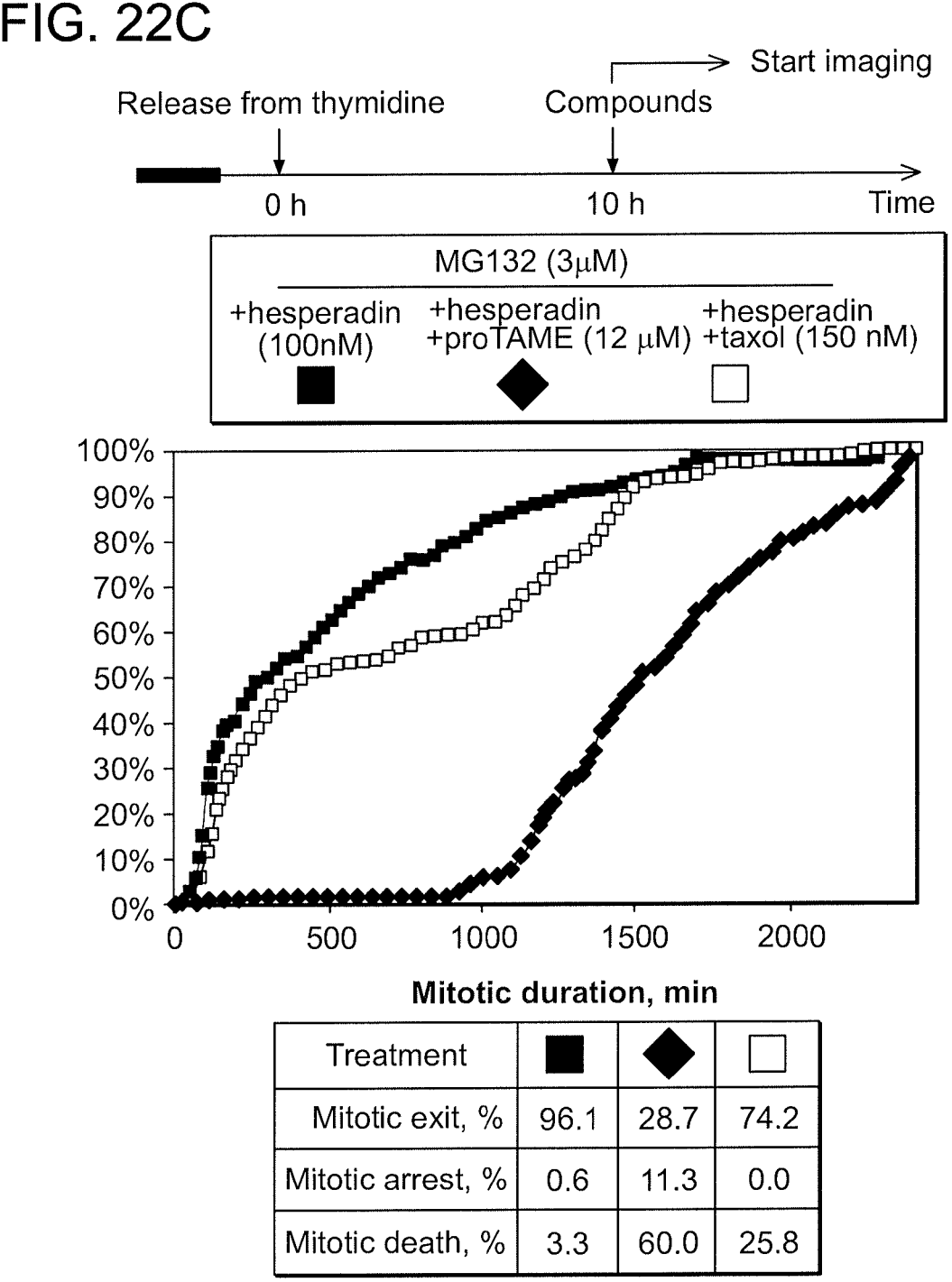
FIG. 22C is a schematic diagram depicting the experimental timeline, graph, and accompanying table showing that Taxol™ cannot restore mitotic arrest in the presence of MG132 and hesperadin. Double thymidine synchronized HeLa cells were treated with compounds.
Figure 22D:
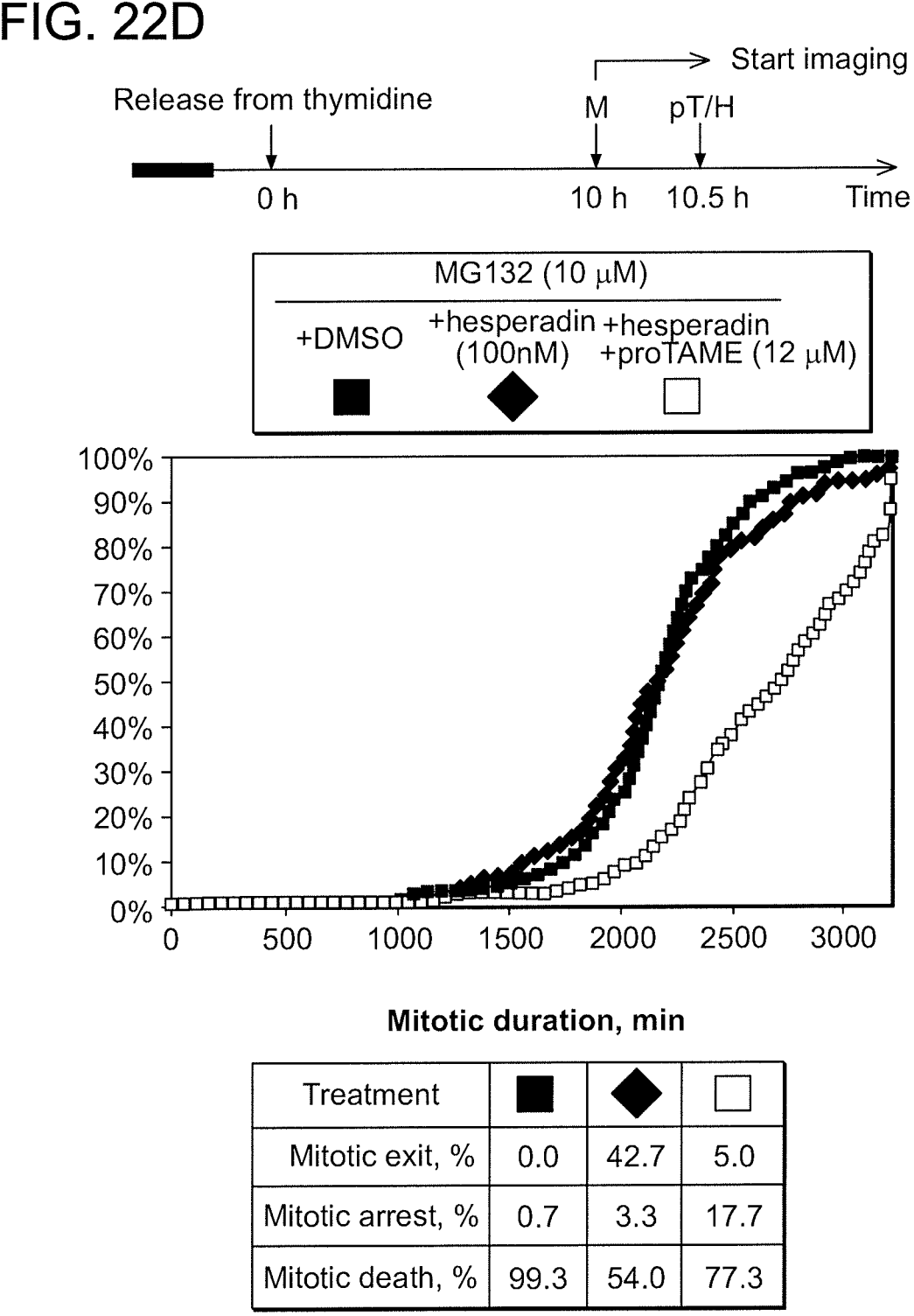
FIG. 22D is a schematic diagram depicting the experimental timeline, graph, and accompanying table showing that mitotic arrest induced by a higher concentration of MG132 remains hesperadin-sensitive. Double thymidine synchronized HeLa cells were treated with compounds. M: MG132; pT: proTAME; H: hesperadin.
Figure 23:
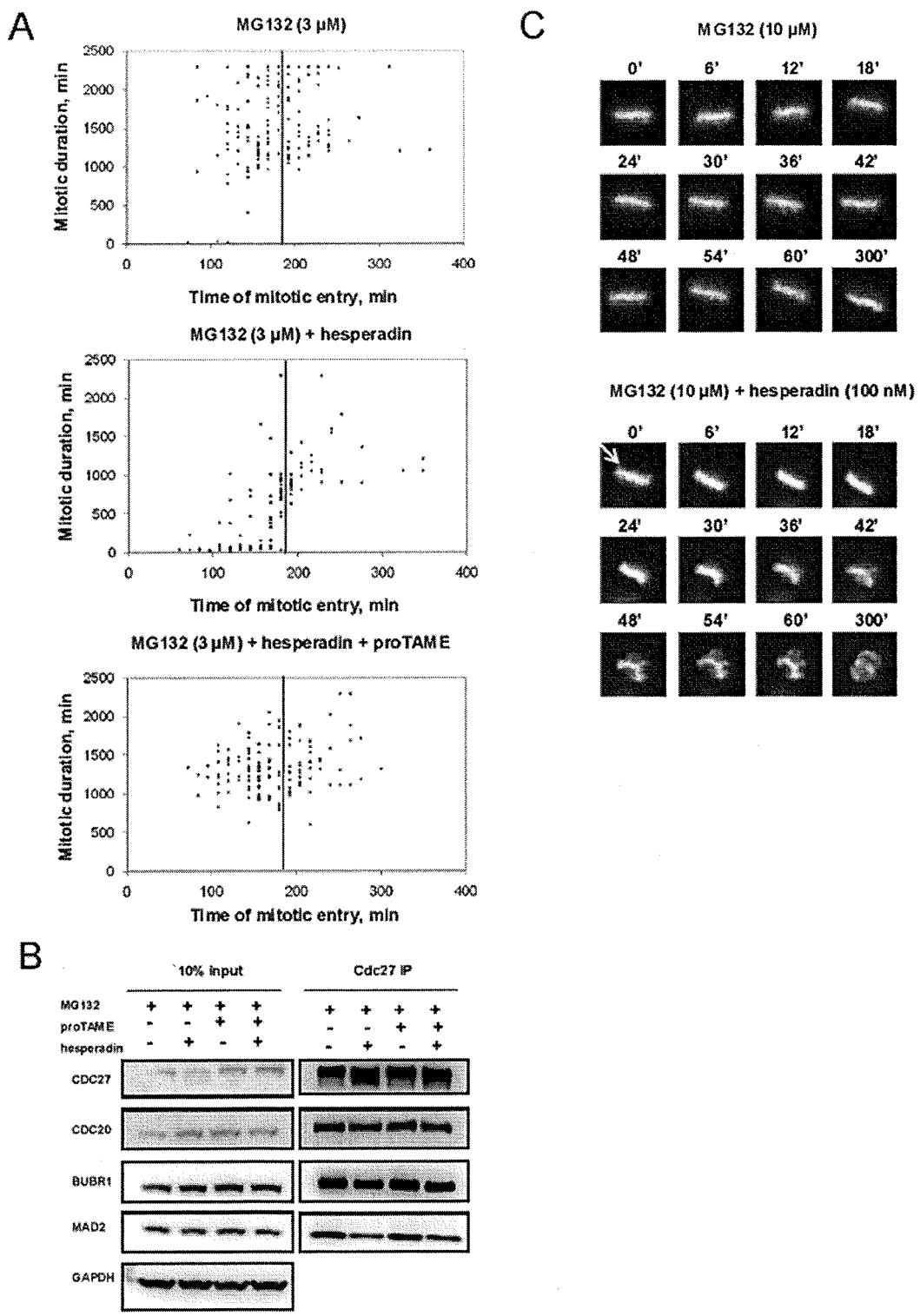
FIG. 23A is a series of graphs showing that hepseradin overrides MG132-induced mitotic arrest. HeLa H2B-GFP cells were synchronized with double thymidine block and treated with indicated drugs at 10 h after release. Mitotic duration of each individual cell is plotted against its mitotic entry time point. The red line denotes the time of addition of MG132.
FIG. 23B is a series of immunoblots showing that HeLa cells were synchronized with double thymidine block and treated with indicated drugs at 10 h after release for 2 h. Mitotic cells were collected and APC was immunoprecipitated from cell lysate. Protein levels were measured by immunoblot.
FIG. 23C is a series of photographs showing that hesperadin induces deformation of the metaphase plate in MG132-arrested cells. HeLa H2B-GFP cells were synchronized with double thymidine block and treated with 10 μM proTAME at 10 h after release, and with 100 nM hesperadin at 11 h after release. For cells that have entered metaphase prior to hesperadin treatment, changes in the morphology of metaphase plate after hesperadin treatment were analyzed and one representative cell is shown. The yellow arrow denotes the time of hesperadin addition. A representative cell arrested with MG132 alone is also shown for comparison.

Like proTAME-treated cells, MG132-treated cells also arrest in metaphase with apparently normal kinetochore attachment (Famulski, J. K., and Chan, G. K. (2007). Curr Biol 17, 2143-2149). Given that the MG132-induced arrest is Mad2-dependent, it was next determined whether the arrest is also hesperadin-sensitive. To test this idea, ten hours following thymidine release, HeLa H2B-GFP cells were treated with 3 µM MG132 in the presence or absence of hesperadin. Strikingly, hesperadin induced rapid mitotic exit in half of the cells, with the remainder exiting mitosis more slowly (FIG. 22B). These distinct behaviors correlated with the timing of drug administration: cells that encountered drug while in mitosis exited mitosis quickly, whereas cells that encountered drug before mitosis exited slowly (FIG. 23A). Hesperadin treatment induced dephosphorylation of Cdc27 and reduced levels of Mad2 and BubR1 bound to the APC compared to cells treated with MG132 alone (FIG. 23B). Co-addition of proTAME to MG132 abrogated the ability of hesperadin to drive mitotic exit (FIG. 22B), indicating that mitotic exit under these conditions requires APC-dependent ubiquitination. In contrast, co-addition of taxol to MG132 did not efficiently suppress hesperadin-induced mitotic exit (FIG. 22C), underscoring the distinct mechanisms underlying taxol and proTAME-induced mitotic arrests. Even when the proteasome was more fully inhibited by increasing the MG132 concentration to 10 µM (FIG. 22D), addition of hesperadin caused 40% of cells to exit mitosis (FIG. 22D), implying that sufficient proteasome activity remains in these cells to permit mitotic exit if the SAC is inactivated. Addition of proTAME suppressed the ability of hesperadin to induce mitotic exit, indicating that mitotic exit remains dependent on APC-dependent ubiquitination. Together these results indicate that the mitotic arrest induced by a proteasome inhibitor is not simply a consequence of direct inhibition of the proteasome, but also requires inhibition of APC-dependent ubiquitination by the SAC.

The hesperadin sensitivity of the MG132-induced arrest indicated that Aurora B activity is important for maintaining the metaphase plate, as shown in proTAME treated cells. Consistent with this idea, treatment of MG132-arrested metaphase cells with hesperadin induced deformation of the metaphase plate within 30 min, whereas cells arrested with MG132 alone maintained a normal-appearing metaphase plate for over 5 h (FIG. 23C). These results suggest that an Aurora B-dependent process is required for maintaining the metaphase plate in MG132-treated cells. Inhibitors of APC-dependent proteolysis produce a metaphase arrest that is SAC-dependent because Aurora B-dependent pathways remain active in metaphase.

Figure 24A:
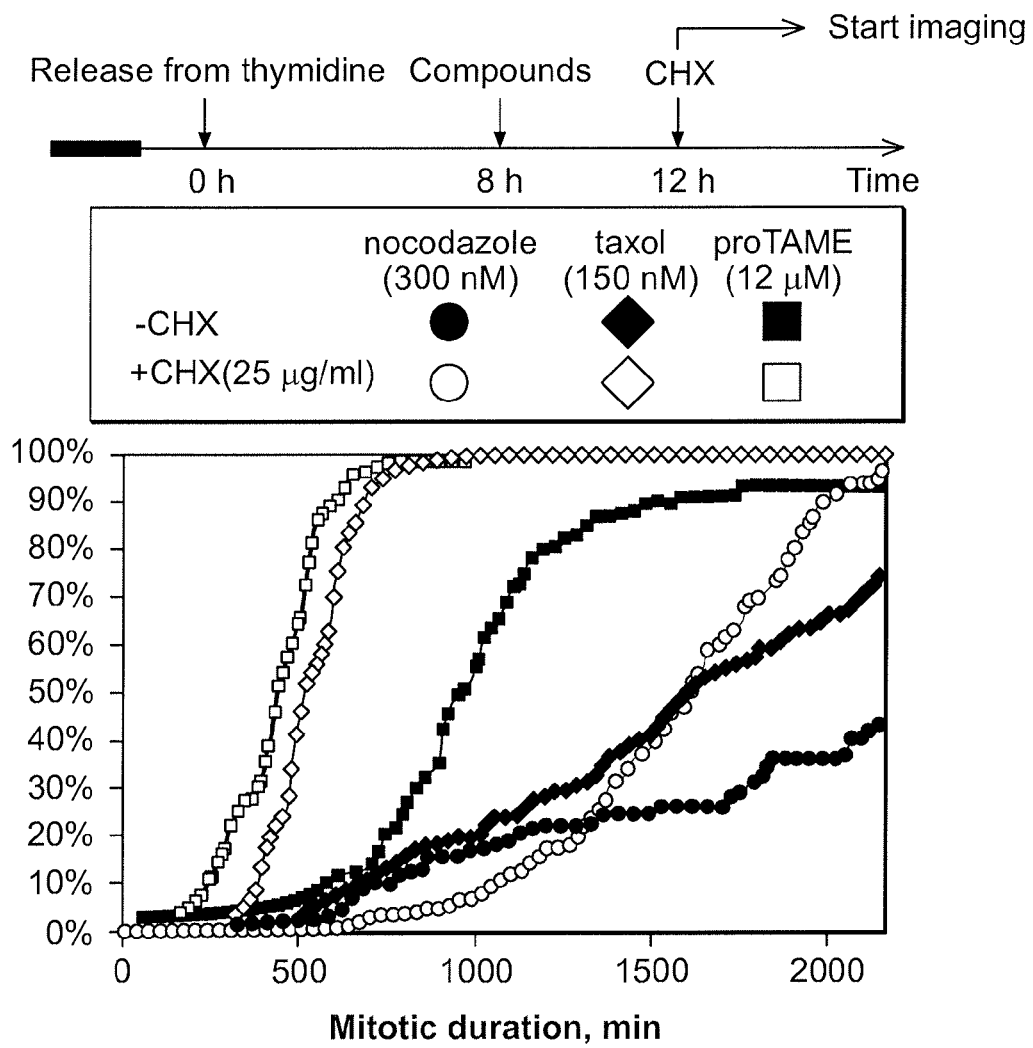
FIG. 24A is a schematic diagram depicting the experimental timeline, graph, and accompanying table showing that microtubule inhibitors require protein synthesis for mitotic arrest whereas proTAME and MG132 do not. Mitotic arrest induced by microtubule inhibitors requires protein synthesis but proTAME-induced arrest does not. Double thymidine synchronized HeLa-H2B-GFP cells were treated with compounds and followed by time-lapse imaging. CHX: cycloheximide.
Figure 24B:
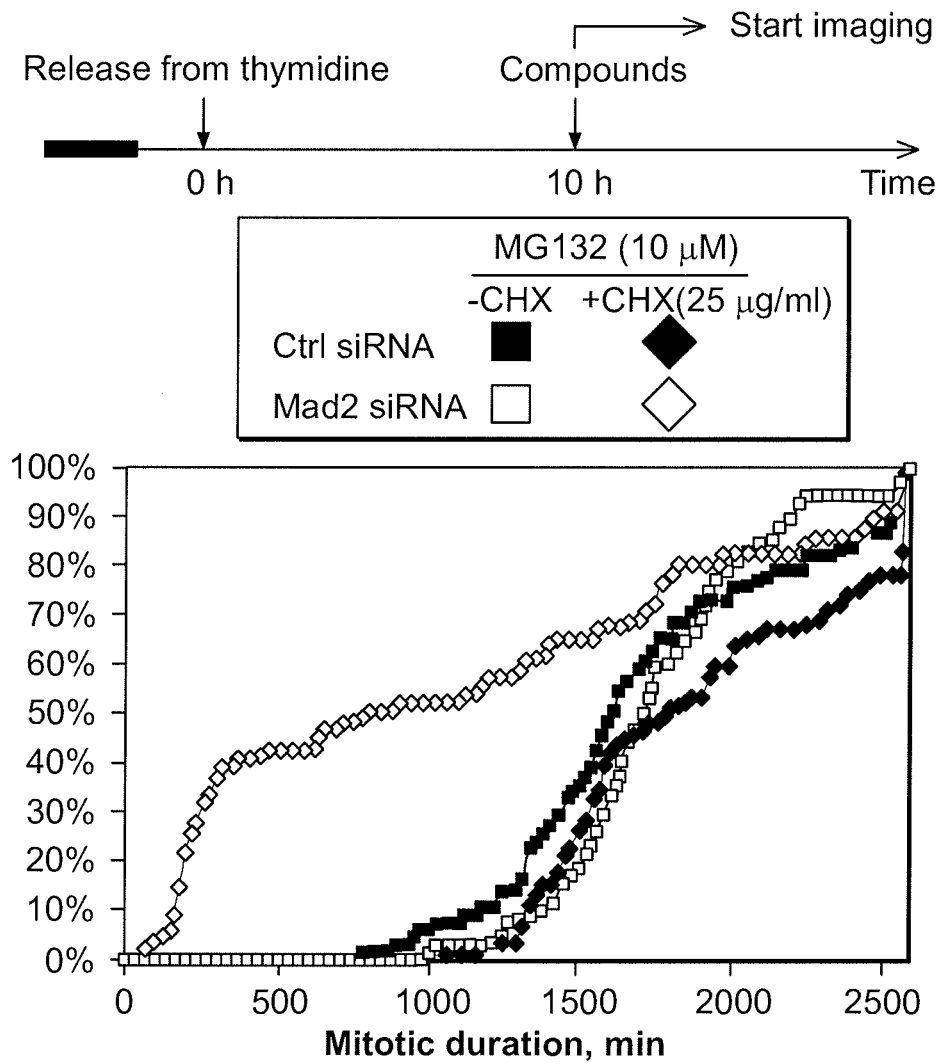
FIG. 24B is a schematic diagram depicting the experimental timeline, graph, and accompanying table showing that MG132 (10 μM)-induced arrest is cycloheximide-resistant but Mad2-dependent. HeLa cells were transfected with indicated siRNAs between rounds of thymidine synchronization.
Figure 25:
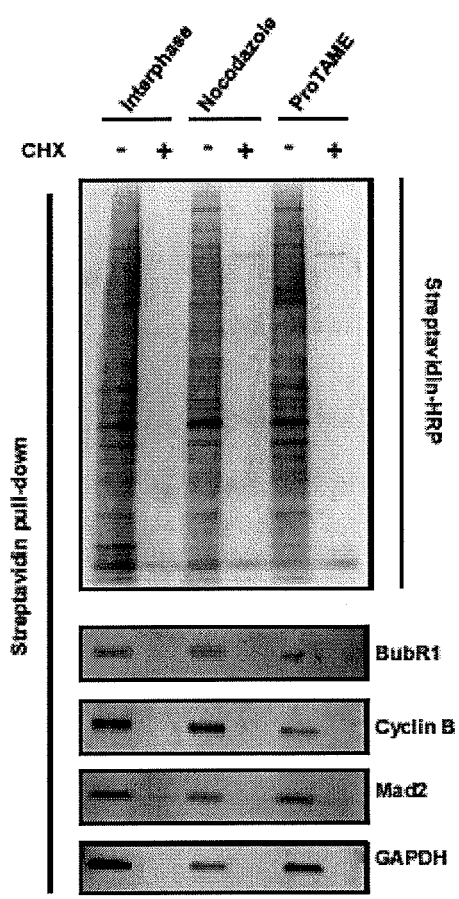
FIG. 25 is a series of immunoblots showing proteins required for maintenance of the SAC are synthesized during prolonged mitotic arrest. HeLa H2B-GFP cells were arrested in interphase by a 24-hour thymidine block (2 mM) and released in growth medium. To identify newly translated proteins in interphase cells, cells were switched to methionine-free labeling medium 3 hrs after release and de novo translated proteins were labeled by adding the methionine analog L-azidohomoalanine (AHA) at 250 μM for 3 hrs and collected by trypsinization. For labeling of proteins newly translated during mitosis, cells were released from thymidine block and nocodazole (300 nM) or proTAME (12 μM) was added 5 hrs after release. Seven hours later, mitotic cells were collected by shakeoff and switched to the labeling medium and incubated with 250 μM AHA for 12 hours. A majority of cells remained in mitosis based on morphology. Following the labeling period, mitotic cells were collected by shake off A labeling reaction including cycloheximide 25 μg/mL as negative control was carried in parallel for each condition. Cells in nocodazole+cycloheximide slipped out of mitosis after the 12 hrs incubation and were collected by trypsinization. Protein lysates were generated for each labeling condition, and newly synthesized proteins were labeled using biotin azide and purified with neutravidin-agarose resin as described in the Methods section. Purified proteins from equivalent amounts of total protein were eluted by boiling in SDS sample buffer, separated on SDS-PAGE gels and indicated proteins were detected by western blotting.

Protein Synthesis is Required for Mitotic Arrest Induced by Microtubule Inhibitors but not for APC or Proteasome Inhibitors. The data support a model in which APC-dependent proteolysis is required to inactivate the SAC. However, this model yields a paradox: How could the APC initiate SAC inactivation if it is fully inhibited by the SAC? One possibility is that SAC inhibition of APC is never complete, with residual APC remaining active to initiate SAC inactivation. Indeed, it has been shown that cyclin B1 and securin are slowly degraded even in the presence of a fully active SAC (Brito, D. A., and Rieder, C. L. (2006). Curr Biol 16, 1194-1200; Nilsson, J., et al. (2008). Nat Cell Biol 10, 1411-1420). Prolonged arrest in mitosis might therefore require the continued synthesis of APC substrates during mitosis. Consistent with this model, cycloheximide promoted mitotic exit of nocodazole- or taxol-arrested cells (FIG. 24A). In striking contrast, cycloheximide did not accelerate mitotic exit in proTAME-treated cells, but rather extended mitotic arrest by delaying cell death (FIG. 24A). Cycloheximide addition produced similar effects in MG132-treated cells, suppressing cell death without promoting mitotic exit (FIG. 24B). Consistent with these findings, labeling experiments demonstrated that known APC substrates such as cyclin B1 and BubR1 are translated during mitotic arrest (FIG. 25). Together these findings indicate that ongoing mitotic protein synthesis is essential to maintain a SAC-dependent mitotic arrest, perhaps by replenishing components that are degraded by residual APC-dependent proteolysis.

Figure 24C:
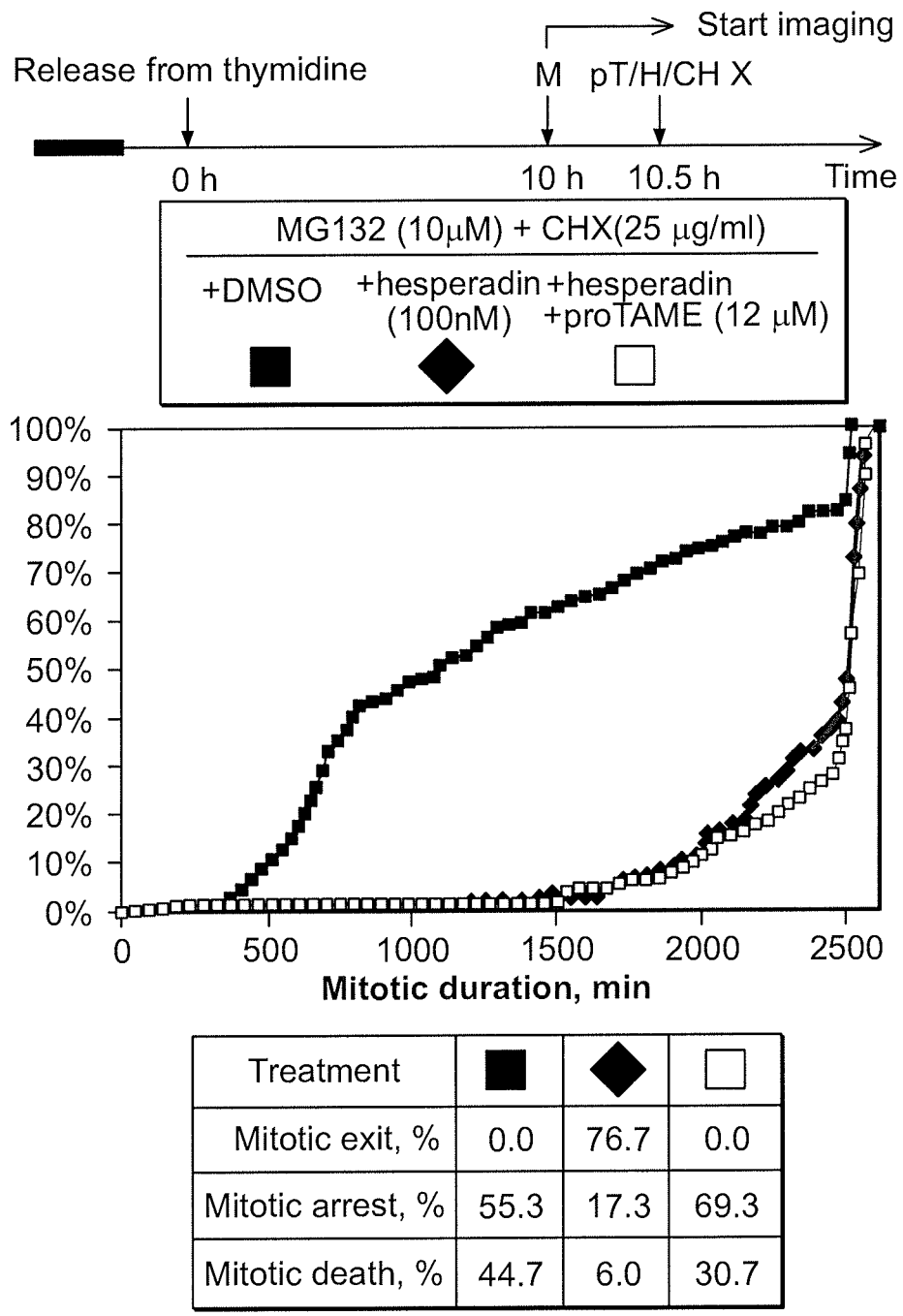
FIG. 24C is a schematic diagram depicting the experimental timeline, graph, and accompanying table showing that MG132 (10 μM)-induced arrest is cycloheximide-resistant but hesperadin-sensitive. Double thymidine synchronized HeLa cells were treated with compounds.

Studies were carried out to understand why the MG132-induced arrest is resistant to cycloheximide. It was hypothesized that persistent SAC activity cooperates with direct pharmacologic inhibition of the proteasome to slow the rate of APC-dependent proteolysis to such a great extent that mitotic arrest no longer depends upon protein synthesis. If this hypothesis is correct, then inactivating the SAC should make the MG132-induced arrest sensitive to cycloheximide, as protein synthesis would now be required to balance the increased rate of APC-dependent degradation. This was indeed the case, as depletion of Mad2 (FIG. 24B) or inactivation of the SAC with hesperadin (FIG. 24C) led to mitotic exit in cells treated with cycloheximide and high dose MG132. Addition of proTAME suppressed the effect of hesperadin (FIG. 24C), indicating that mitotic exit remains dependent on APC-mediated ubiquitination. Together these results indicate that the ability of proTAME or proteasome inhibitors to induce a prolonged mitotic arrest independent of protein synthesis requires persistent inhibition of the APC by the SAC.

The mechanism of the first small molecule inhibitor of the APC has been identified. TAME binds to the APC and displaces the IR tail of Cdc20 or Cdh1, preventing efficient APC activation. In human cells, proTAME treatment causes arrest in metaphase without perturbing the mitotic spindle. Despite development of normal kinetochore tension that should silence the SAC, the SAC is required for proTAME to induce mitotic arrest. Similar results were obtained using a proteasome inhibitor. Kinetochore-dependent SAC signaling persists at a low rate in metaphase, and is inactivated by residual APC-dependent proteolysis, creating a positive feedback loop between the APC and the SAC (FIG. 8D). The ability of low doses of proTAME or MG132 to induce metaphase arrest is strongly enhanced by this feedback loop, enabling mitotic arrest to be achieved at drug concentrations below those necessary to fully inhibit the APC or the proteasome.

TAME interferes with IR-tail dependent APC activation. TAME prevents APC activation by perturbing the binding of the IR-tail of Cdc20 and Cdh1 to the APC. The importance of the IR motif in promoting Cdh1 association with yeast and human APC is well-established (Burton, J. L., et al. (2005). Mol Cell 18, 533-542; Kraft, C., et al. (2005). Mol Cell 18, 543-553; Matyskiela, M. E. and Morgan, D. O. (2009). Mol Cell 34, 68-80; Vodermaier, H. C., et al. (2003). Curr Biol 13, 1459-1468). However, the role of the Cdc20 IR motif is less clear, because the Cdc20 IR tail is not essential in budding yeast (Thornton, B. R., et al. (2006). Genes Dev 20, 449-460) and a Cdc20ΔIR mutant can support APC-dependent degradation of Nek2A in Xenopus extract (Kimata, Y., et al. (2008). Mol Cell 32, 576-583). The data show that the IR motif of Cdc20 indeed contributes significantly to APC-association in vitro, as Cdc20ΔIR binds the APC with lower affinity than the wild type protein, and TAME competes with wild type Cdc20 for APC association. Moreover, TAME induces significant dissociation of Cdc20 from the APC in Xenopus extract, and proTAME can antagonize Cdc20 binding in human cells if the SAC is inactivated. Functionally, TAME stabilizes APC substrates in Xenopus extract and proTAME inhibits both Cdc20 and Cdh1-dependent degradation in HeLa cells. Taken together, these data show that proper engagement of the IR motif of Cdc20 or Cdh1 is critical for APC activation.

TAME Exploits a Positive Feedback Loop between the SAC and the APC. ProTAME-induced mitotic arrest requires sustained SAC activity. This finding was unexpected, because proTAME-treated cells arrest in metaphase with kinetochores that develop normal tension, a condition that should inactivate the SAC. In principle, the requirement for the SAC in the proTAME arrest could be explained in one of two ways. First, proTAME treatment could produce defects in microtubule-kinetochore interactions that generate an abnormally high degree of checkpoint signal compared to normal metaphase kinetochores. Alternatively, proTAME may hamper SAC inactivation, despite normal microtubule-kinetochore interactions. The latter model is favored because the degree of checkpoint dependence far exceeds the observed degree of kinetochore-microtubule perturbation.

Defects in microtubule-kinetochore attachment are either an off-target effect of TAME on microtubules or a consequence of specific APC inhibition. Knockdown of Cdc27 or UbcH10 each produced a mitotic exit delay that was SAC-dependent. Furthermore, treatment of cells with a proteasome inhibitor yielded a SAC-dependent mitotic arrest, consistent with a recent study showing that MG132-treated mitotic cells show persistent Mad2-Cdc20 interaction (Visconti, R., et al. (2010). Cell Cycle 9, 564-569), and work in S. pombe showing that Mad2 and Mad3 remain APC-bound in proteasome mutants (Ohi, M. D., et al., (2007). Mol Cell 28, 871-885). Together these findings indicate that if defective microtubule kinetochore interactions are indeed present in proTAME-treated cells, they are likely to result from specific inhibition of APC-dependent proteolysis rather than from nonspecific effects of proTAME on microtubules.

If defective microtubule-kinetochore interactions exist in proTAME-treated cells, they must be subtle. Cells treated with 12 μM proTAME arrest in mitosis until they die, yet form a normal-appearing metaphase plate and develop normal kinetochore tension. Furthermore, cells treated with 12 μM proTAME undergo a normal-appearing anaphase when the SAC is inactivated, indicating that the mitotic spindle functions properly in the presence of proTAME. The only change in chromosome behavior caused by this dose of proTAME is a slight delay in chromosome congression. A lower dose of proTAME (3 μM) causes no delay in chromosome congression, yet still extends mitotic duration to 5 hours. Although subtle defects in microtubule-kinetochore interactions in proTAME-treated cells cannot be completely ruled-out, such defects are not of sufficient magnitude to explain the strong dependence of the proTAME arrest on the SAC.

The alternative explanation for the SAC-dependence of the proTAME arrest is that APC-dependent ubiquitination or proteolysis is required to inactivate the SAC. Such mutual antagonism between the APC and the SAC is predicted to create a positive feedback loop that would amplify the inhibitory effects of proTAME or a proteasome inhibitor in a SAC-dependent manner. This is what occurred. If the SAC is inactivated by Mad2 depletion, 12 μM proTAME extends mitotic duration by only 72 minutes, indicating that this dose only partially inhibits APC activation (consistent with the measured $IC_{50}$ of 12 μM in Xenopus extract). However, when the same dose of proTAME is used in cells with an intact SAC, proTAME extends mitotic duration by 23 hours, indicating that the effect of proTAME is greatly amplified by the SAC. This degree of amplification cannot be explained by the mild effect of proTAME on chromosome congression, because a dose of nocodazole (10 nM) that causes a similar delay in chromosome congression extends mitotic duration by only 20 minutes in SAC-proficient cells. Because similar results were obtained with a proteasome inhibitor, this amplification is best explained by a requirement for APC-dependent proteolysis to inactivate the SAC.

APC substrates play an important role in mediating the mutual antagonism between the APC and the SAC. APC-dependent ubiquitination of Cdc20 has been proposed to release the APC from the inhibitory effects of the SAC (Reddy, S. K., et al. (2007). Nature 446, 921-925; Stegmeier, F., et al. (2007). Nature 446, 876-881). However, this process does not require proteasome activity in cell lysates (Reddy, S. K., et al. (2007). Nature 446, 921-925), and others argue that Cdc20 ubiquitination targets Cdc20 for proteasomal degradation in a manner that sustains the SAC (Ge, S., et al. (2009). Cell Cycle 8, 167-171; Nilsson, J., et al. (2008). Nat Cell Biol 10, 1411-1420). Alternatively, many SAC proteins are APC substrates, and may need to be degraded to inactivate the SAC. Consistent with this possibility, expression of a stable BubR1 mutant induces a mitotic arrest (Choi, E., et al. (2009). EMBO J 28, 2077-2089). Another candidate is cyclin B, because it is degraded prior to anaphase (Clute, P., and Pines, J. (1999). Nat Cell Biol 1, 82-87) and cyclin-dependent kinase activity is required to maintain the SAC (Chung, E. and Chen, R. H. (2003). Nat Cell Biol 5, 748-753; D'Angiolella, V., et al. (2003). Genes Dev 17, 2520-2525). Other SAC proteins, including Mps1, Bub1, and Aurora B are also APC substrates, but their bulk population is not degraded until after anaphase (Palframan, W. J., et al. (2006). Science 313, 680-684; Qi, W. and Yu, H. (2007). J Biol Chem 282, 3672-3679; Stewart, S. and Fang, G. (2005). Cancer Res 65, 8730-8735). It is possible that degradation of these proteins prior to anaphase is masked by their resynthesis. The mutual antagonism between the APC and the SAC may reflect a system-level behavior that is regulated by small changes in the abundance of multiple SAC proteins prior to anaphase. If so, confirmation of this model will require quantitative measurements of the relative rates of synthesis and degradation of APC substrates that regulate SAC activity.

Results indicate that it is possible to induce mitotic arrest without fully inhibiting the APC or the proteasome pharmacologically. This result was unexpected, because RNAi-based experiments indicated that Cdc20 must be reduced to very low levels to induce mitotic arrest (Wolthuis, R., et al. (2008). Mol Cell 30, 290-302). Unlike the proTAME-induced arrest, the mitotic arrest induced by Cdc20 knockdown does not depend on the SAC (Huang, H. C., et al. (2009). Cancer Cell 16, 347-358). One possible explanation for the lack of SAC-dependence in the context of Cdc20 depletion is that Cdc20 is the target of the SAC (Yu, H. (2007). Mol Cell 27, 3-16). Therefore, when Cdc20 levels are reduced, the SAC is no longer required to inhibit Cdc20 function. In contrast, other methods of perturbing APC function, including knockdown of core APC subunits or the E2 enzyme UbcH10, or proTAME treatment, all produce an arrest that is SAC-dependent. This is likely a consequence of the fact that Cdc20 remains present under each of these conditions.

Figure 24D:
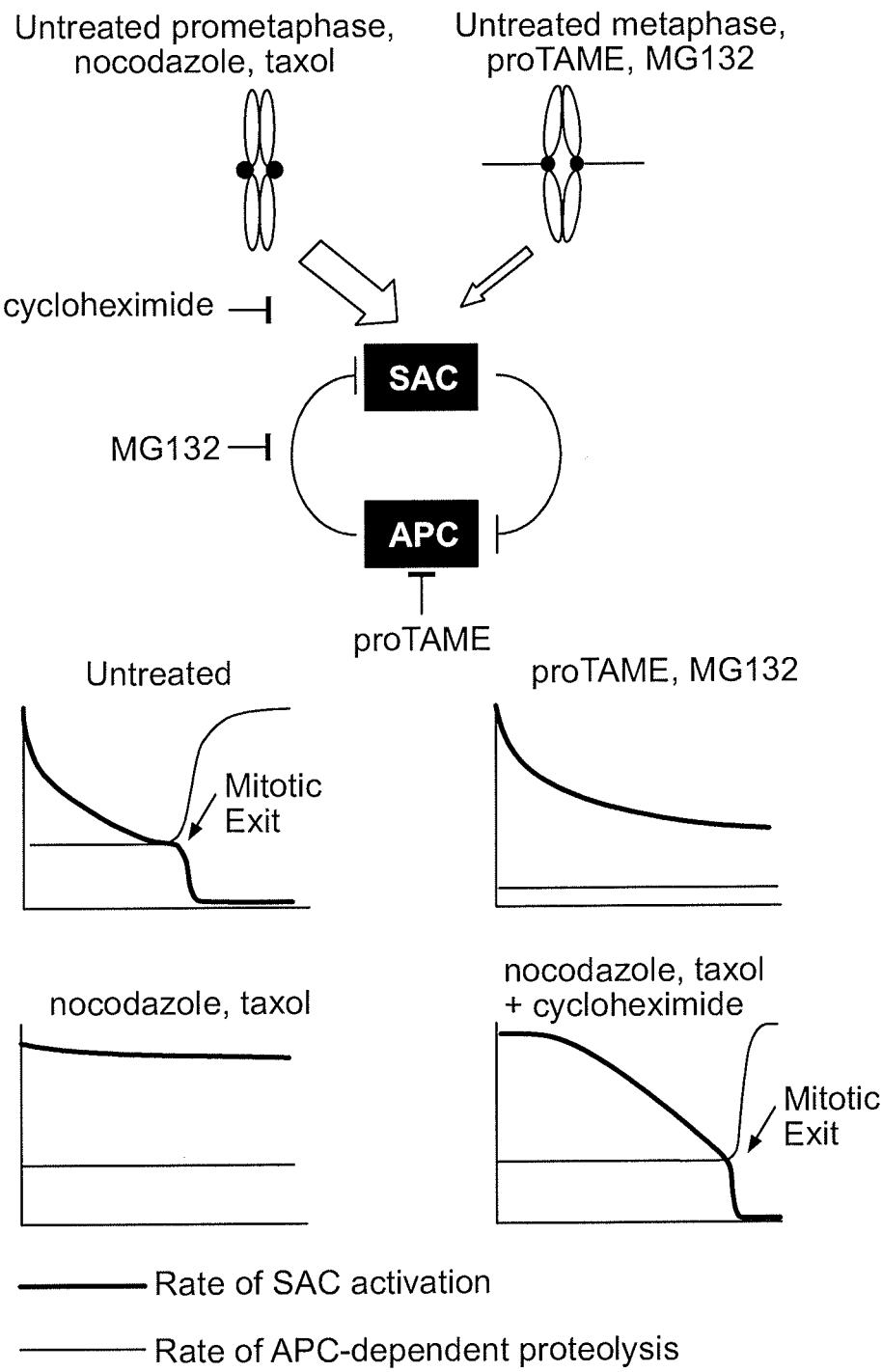
FIG. 24D is a schematic diagram depicting a model summarizing the mutual antagonism between the SAC and the APC. In the bottom panels, the x-axis indicates time from mitotic entry.

A Model for Regulation of Mitotic Exit. A model is shown in FIG. 24D. A positive feedback loop between the SAC and the APC has the potential to adopt one of two stable states: high SAC activity (mitotic arrest) or high APC activity (mitotic exit). During normal division, it is important that cells do not become permanently arrested in mitosis. The SAC does not fully inhibit the APC during mitosis because residual APC activity must be preserved to prevent cells from becoming locked in mitosis. This residual APC activity may explain why cyclin B1 is degraded prior to the initiation of anaphase (Clute, P., and Pines, J. (1999). Nat Cell Biol 1, 82-87) and during prolonged SAC-dependent mitotic arrest (Brito, D. A. and Rieder, C. L. (2006). Curr Biol 16, 1194-1200; Gascoigne, K. E. and Taylor, S. S. (2008). Cancer Cell 14, 111-122; Huang, H. C., et al. (2009). Cancer Cell 16, 347-358; Huang, H. C., et al. (2009). Cancer Cell 16, 347-358; Nilsson, J., et al. (2008). Nat Cell Biol 10, 1411-1420). To remain in mitosis for a prolonged period, a cell may need to continue to resynthesize APC substrates that are degraded by residual APC-dependent proteolysis.

During normal mitosis, the development of kinetochore tension reduces the rate of SAC activation, but SAC activation is unlikely to be completely suppressed during metaphase. Anaphase is triggered when the rate of SAC activation falls below the rate at which APC-dependent proteolysis inactivates the SAC, tipping the feedback loop toward rapid APC activation and mitotic exit. The timing of anaphase initiation therefore depends not only on how kinetochore attachment controls SAC activation, but also on the level of residual APC activity.

During nocodazole or taxol treatment, the rate of SAC activation remains above the rate at which the APC inactivates the SAC, tipping the loop in the direction of APC inhibition thereby preventing mitotic exit. Because APC-dependent proteolysis is not fully inhibited by the SAC, mitotic arrest is dependent on protein synthesis to resupply APC substrates. If the rate of protein synthesis is not sufficient, the rate of SAC signal production will fall below the rate at which it is inactivated by the APC, leading to rapid APC activation and mitotic slippage. Therefore, the rate of protein synthesis in mitosis may be an important determinant of the duration of mitotic arrest in cells treated with microtubule inhibitors.

In contrast to microtubule inhibitors, proTAME and MG132 induce mitotic arrest by inhibiting residual APC-dependent proteolysis rather than by stimulating SAC activation. The rate of SAC signal production by kinetochores may decline normally in proTAME- or MG132-treated cells because kinetochores develop proper tension. However, because the rate of residual APC-dependent proteolysis is lowered by proTAME or MG132, the rate of SAC signal production cannot fall below the rate at which it is inactivated by APC-dependent proteolysis, leading to mitotic arrest. The strong hesperadin sensitivity of both proTAME and MG132-induced arrests indicates the importance of metaphase kinetochores in generating a SAC signal to sustain mitotic arrest. Compared to microtubule inhibitors, this mechanism of mitotic arrest shows reduced dependence on protein synthesis because the rate of residual APC activity is lower in proTAME and MG132-treated cells, yielding a lower requirement for protein synthesis to replenish APC substrates.

Antimitotic Cancer Therapy. The results of the study described here provide an explanation for the variability in cellular responses to microtubule inhibitors that could limit their therapeutic effectiveness. Because the SAC does not completely inhibit the APC, mitotic arrest induced by microtubule inhibition depends on protein synthesis. As a result, variation in the rates of protein synthesis among cells may be one factor that explains the highly variable response of cells to microtubule inhibitors. In contrast, cells treated with an APC inhibitor are less prone to mitotic slippage because residual APC activity is inhibited. APC inhibitors may therefore be more effective in promoting mitotic arrest, inducing a greater pro-apoptotic effect. Furthermore, low doses of an APC inhibitor are useful in combination with microtubule inhibitors to sustain mitotic arrest and enhance cell death.

Example 6

ProTAME Synergy

To determine whether proTAME treatment can enhance mitotic arrest and cell death induced by taxol or a proteasome inhibitor (MG132), HeLa H2B-GFP cells were co-treated with low doses of the microtubule poison Taxol or the proteasome inhibitor MG132 in combination with a low dose of proTAME.

Figure 26:
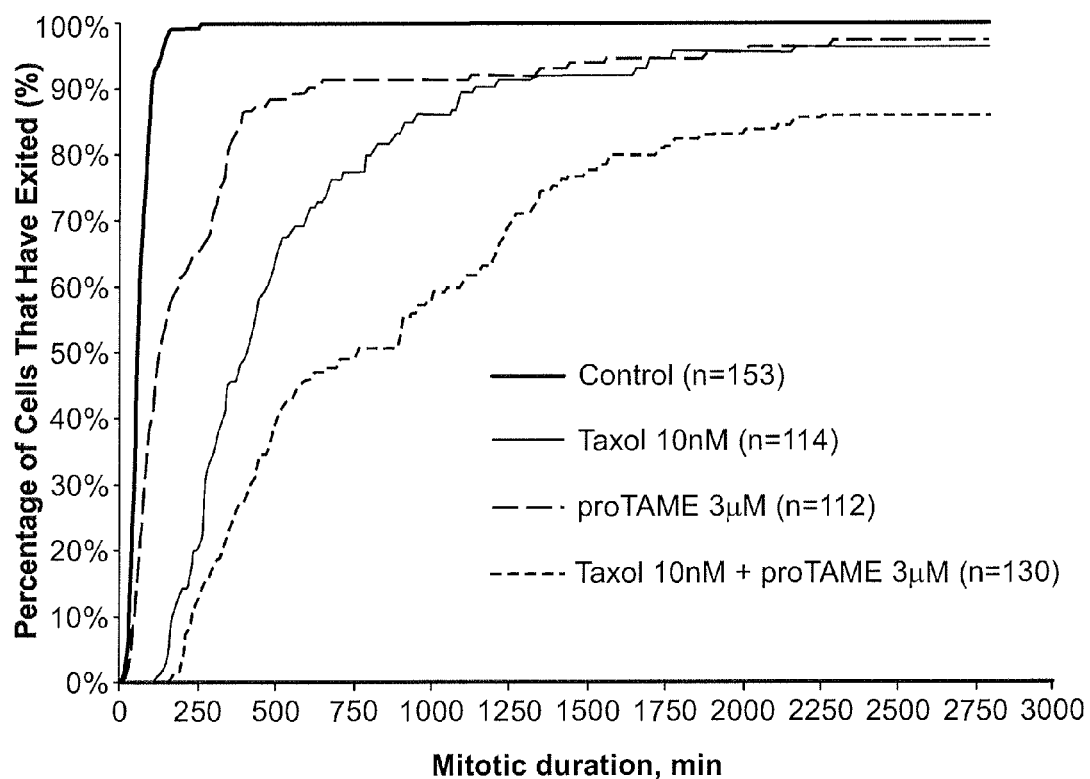
FIG. 26 is a pair of graphs depicting the percentage of cells that have exited the cell cycle versus the mitotic duration for cells treated with either control (top trace), Taxol, proTAME, or a combination of Taxol and proTAME (bottom trace). The table correlates to the top graph. The bottom graph depicts the mitotic fate of cells treated to each condition.
Figure 26:
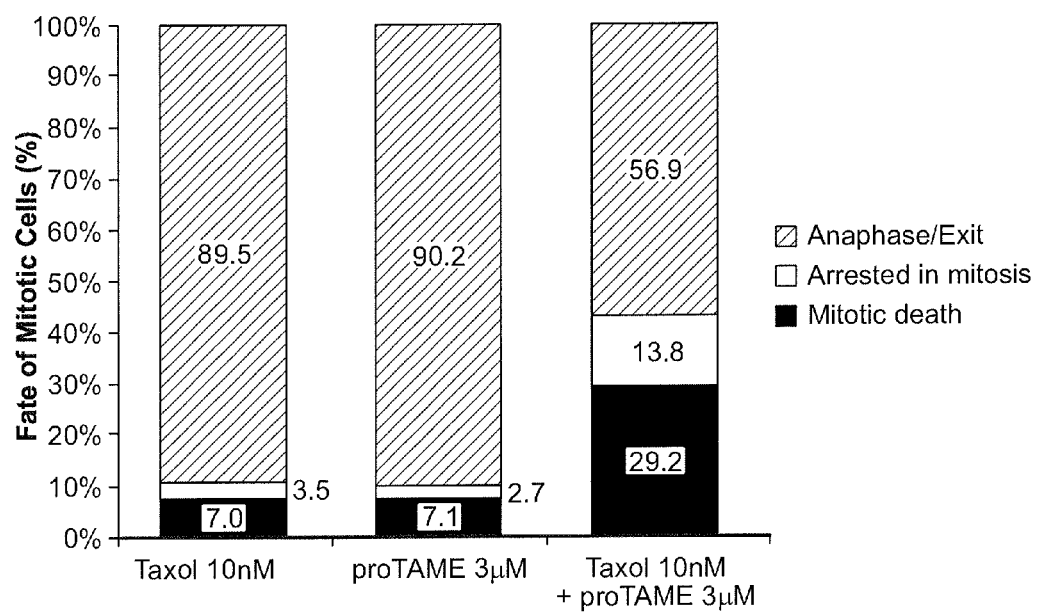

Unsynchronized HeLa H2B-GFP cells were treated with DMSO (control), taxol 10 nM or proTAME 3 µM or a combination of Taxol 10 nM and proTAME 3 µM (FIG. 26). The cells were imaged by FITC fluorescence microscopy to monitor the cell cycle and mitotic events. Duration of mitotic events, initiated during the first 21 hours of imaging, was manually determined for indicated number of cells and the cumulative percentage of cells was plotted as a function of mitotic duration. Individual chemicals induced a mitotic delay with a median of 414 min for Taxol alone and 132 min for proTAME alone as compared to a median mitotic duration of 60 min for control-treated cells. The combination resulted in a synergistic increase in mitotic duration to 768 min median mitotic duration. Single treatments resulted in about 10% of cells that remained arrested or died in mitosis throughout the 48 hrs movie while most cells exited mitosis. In contrast, 43% cells stayed arrested or died in mitosis in the co-treatment, therefore indicating synergism in inducing mitotic arrest and mitotic cell death.

Figure 27:
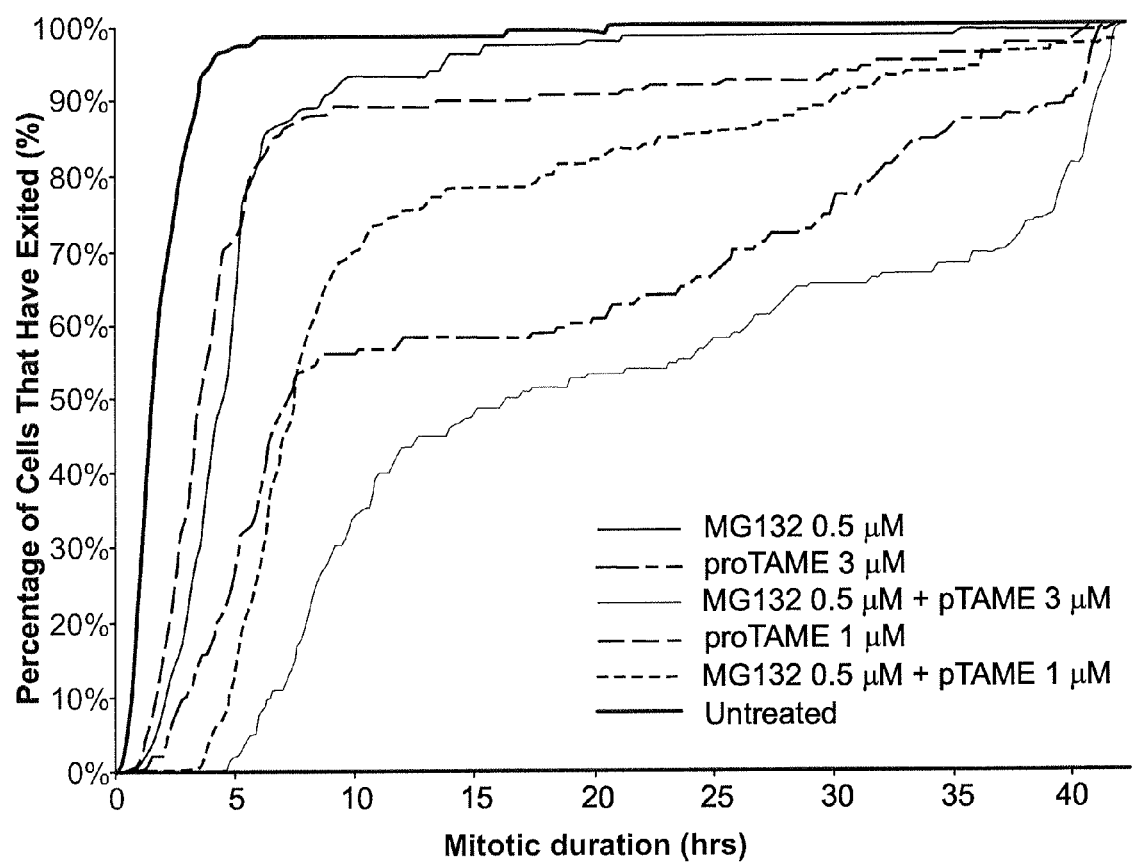
FIG. 27 is a pair of graphs depicting the percentage of cells that have exited the cell cycle versus the mitotic duration for cells that are untreated (top trace), or alternatively, treated with proTAME, MG132, or a combination of MG132 and proTAME, each at varying concentrations. The table correlates to the top graph. The bottom graph depicts the mitotic fate of cells treated to each condition.
Figure 27:
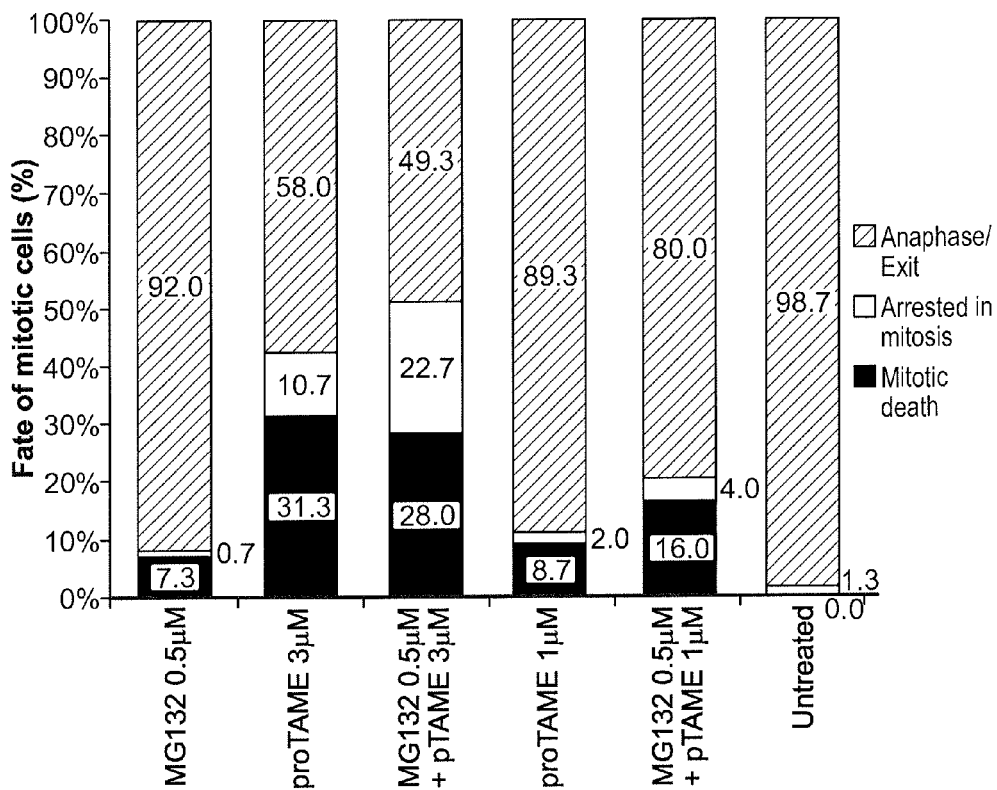

To analyze interactions between proTAME and a proteasome inhibitor (FIG. 27), HeLa H2B-GFP cells were synchronized by double thymidine block (2 mM thymidine block for 18 hrs, release in medium for 8 hrs 2 mM thymidine block for 18 hrs), and treated with the drugs 10 hrs after release from the block as the cells just entered mitosis. In cells treated with a single drug, MG132 induced a mitotic delay of 276 min (median) while proTAME (3 µM) induced a delay of 438 minutes. The effect of co-treatment was synergistic, resulting in a median mitotic arrest of more than 1000 min. The synergistic effect in duration of mitotic arrest was also observed with a lower dose of proTAME (1 µM) where the cells arrested for a median time of 216 min while the combination with MG132 0.5 µM resulted in a median arrest of 456 min. The co-treatments resulted in an increase in the percentage of cells indefinitely arrested in mitosis or dying in mitosis during the movie, as compared to single treatments, indicating a benefit in terms of mitotic phenotype of the combination.

These data demonstrate that co-treatment of cells with the APC/C inhibitor, proTAME, and drugs that stimulate the spindle assembly checkpoint (taxol) or inhibit proteasome-dependent degradation (MG132) results in prolonged mitotic arrest associated with increased mitotic cell death. These co-treatments are beneficial in terms of increased mitotic duration and potency to induce cell death in mitosis in development of anticancer co-treatment regimens.

Example 7

Cyclinal is a Small Molecule Antagonist of the D-box/Cdc20 Interaction that Stabilizes APC Substrates but Overrides the Spindle Assembly Checkpoint Cyclinal is a Competitive Inhibitor of $APC^{Cdc20}$ Cyclinal (FIG. 28A) was identified in an earlier study as an inhibitor of cyclin proteolysis in mitotic Xenopus egg extract (IC50 of 20 µM; FIG. 28B), but its mechanism of action has remained unknown (Verma, R., et al. Science 306, 117-120 (2004)). Cyclinal also inhibited cyclin degradation in interphase extract activated by exogenous Cdh1, but had little effect on SCF-dependent proteolysis of β-catenin-luciferase, indicating that it is not a general inhibitor of the ubiquitin-proteasome system (Verma, R., et al. Science 306, 117-120 (2004)). Testing of cyclinal derivatives indicated that the pyrimidine moiety but not the nitro-imidazole moiety is essential for activity (FIG. 28C). Cyclinal was also able to stabilize full length recombinant cyclin B1, which was added to interphase extract in the form of Maturation Promoting Factor (MPF, a complex of cyclin B1/Cdk1) (FIG. 28D). These data suggest that cyclinal acts as an APC inhibitor. Therefore, the effect of cyclinal was tested in an in vitro reconstituted APC ubiquitination assay with a cyclin B1 N-terminal fragment (CycB-NT) as the substrate. Consistent with cyclinal being an APC inhibitor, cyclinal reduced the ubiquitin conjugates mass on CycB-NT under this condition (FIG. 28E). To gain insight into the inhibitory mechanism, the effect of cyclinal treatment on the $k_{cat}$ and $K_m$ of the APC was measured. An assay was performed to measure the initial rate of APC-dependent mono-ubiquitination on CycB-NT that has been previously established to satisfy the assumptions of the Michaelis-Menton equation. The results showed that cyclinal causes a significant increase in the $K_m$ but has little effect on the $k_{cat}$ (FIG. 28F), which is the typical behavior of a competitive inhibitor. Together these results indicate that cyclinal inhibits the APC by competing with substrates for APC binding.

Cyclinal Competes with the D-box for Cdc20 Binding

The discovery that cyclinal acts as a competitive APC inhibitor suggests that cyclinal binds to the same site on the APC as the substrate does. Electron microscopy structure of the APC revealed that a co-receptor for the D-box on APC substrates form between the APC activator and a core subunit Apc10 (Buschhorn, B. A., et al. Nat Struct Mol Biol 18, 6-13 (2011); da Fonseca, P. C., et al. Nature 470, 274-278 (2011)). Since the D-box is the critical signal for $APC^{Cdc20}$-driven degradation of cyclin B1, cyclinal may either bind to Cdc20 or the core APC via Apc10. To identify the binding target of cyclinal, the amino cyclinal derivative (FIG. 28C) was coupled to Affigel resin and incubated the resin with Xenopus extracts. The level of Cdc20 and Cdc27 remaining in the extract after cyclinal resin incubation was measured. The results showed that Cdc20 but not Cdc27 was significantly depleted from both interphase and mitotic extracts by cyclinal resin (FIG. 29A), indicating that cyclinal directly binds to Cdc20 instead of the core APC. Because Cdc20 is a sub-stoichiometric component of the APC in these extracts, even if the $APC^{Cdc20}$ complex may also be pulled down by the resin, the change in the total soluble pool of the APC should be insignificant. As expected, the mitotic extract depleted of Cdc20 by cyclinal resin was not able to support degradation of the cyclin-luciferase reporter, which could be rescued by adding in vitro-translated Cdc20 (FIG. 29B), confirming that the target of cyclinal is Cdc20.

It was determined whether cyclinal competes with the D-box for Cdc20 binding taking advantage of the ability of the cyclinal resin to pull down Cdc20. The pull down of in vitro-translated Cdc20 to the resin can be competed by addition of free cyclinal in a dose-dependent manner, but not by addition of the inactive morpholino derivative (FIG. 29C). A WT cyclin B N-terminal fragment also reduced Cdc20 binding to the cyclinal resin in a dose-dependent manner but the same fragment with a mutated or deleted D-box had a severely compromised ability to reduce Cdc20 binding to the resin (FIG. 29D). Moreover, a stapled D-box peptide is also capable of reducing Cdc20 binding to the cyclinal resin (FIG. 29E). Taken together, these data suggested that cyclinal directly binds to Cdc20 which prevents Cdc20 from interacting with the D-box. One possible model is cyclinal and the D-box compete for the same binding site on Cdc20 but the data are also consistent with cyclinal binding to an allosteric site on Cdc20 which in turn affects D-box binding. A definitive answer to this question relies on structural analysis of the Cdc20/cyclinal or the Cdc20/D-box complex.

APC substrates promote Cdc20 binding to the APC even if the IR-tail binding site is blocked by TAME presumably because the formation of the co-receptor between Cdc20 and Apc10 for the D-box in substrates offers one additional contact point between Cdc20 and the APC. Co-addition of cyclinal and TAME should inhibit Cdc20 binding the APC even in the presence of substrates, because both the Cdc20/APC and the Cdc20/D-box interactions will be disrupted. To confirm this hypothesis, various combinations of TAME, cyclinal and CycB-NT were added to mitotic extract and steady-state Cdc20 binding to the APC was measured. As expected, in the absence of CycB-NT, TAME caused a strong reduction in Cdc20 level bound to the APC whereas cyclinal only had a modest effect (FIG. 29F). Addition of CycB-NT alone enhanced Cdc20 binding to the APC both in the absence and presence of TAME. Addition of cyclinal with CycB-NT largely abrogated CycB-NT's ability to enhance Cdc20 binding (FIG. 29F). Importantly, co-addition of TAME and cyclinal with CycB-NT resulted in strong inhibition of Cdc20 binding similar to what was observed with adding TAME alone (FIG. 29F). These results demonstrate that cyclinal antagonizes CycB-NT's ability to promote Cdc20 binding to the APC, providing further evidence that cyclinal is a D-box antagonist.

Because cyclinal and TAME synergize to strongly inhibit Cdc20 binding to the APC in the presence of substrates, it was determined whether both compounds could also synergize to inhibit the APC. Because both compounds are very effective on their own in stabilizing APC substrates in the extract, a condition was used that desensitizes the extract to drug inhibition. Adding high concentrations of the E2 enzymes UbcH10 and UBE2S strongly rescues degradation of the cyclin B1-luciferase reporter in the presence of TAME as a consequence of enhanced processivity during single substrate binding cycle. Adding UbcH10 and UBE2S also promoted degradation of the reporter in cyclinal-treated extract (FIG. 29G). However, co-addition of TAME and cyclinal significantly stabilized the reporter in the presence of high concentrations of UbcH10 and UBE2S (FIG. 29G). This result can be explained by the fact that TAME and cyclinal synergize to inhibit Cdc20 binding to the APC so that even a single substrate binding cycle becomes impossible.

Figure 30:
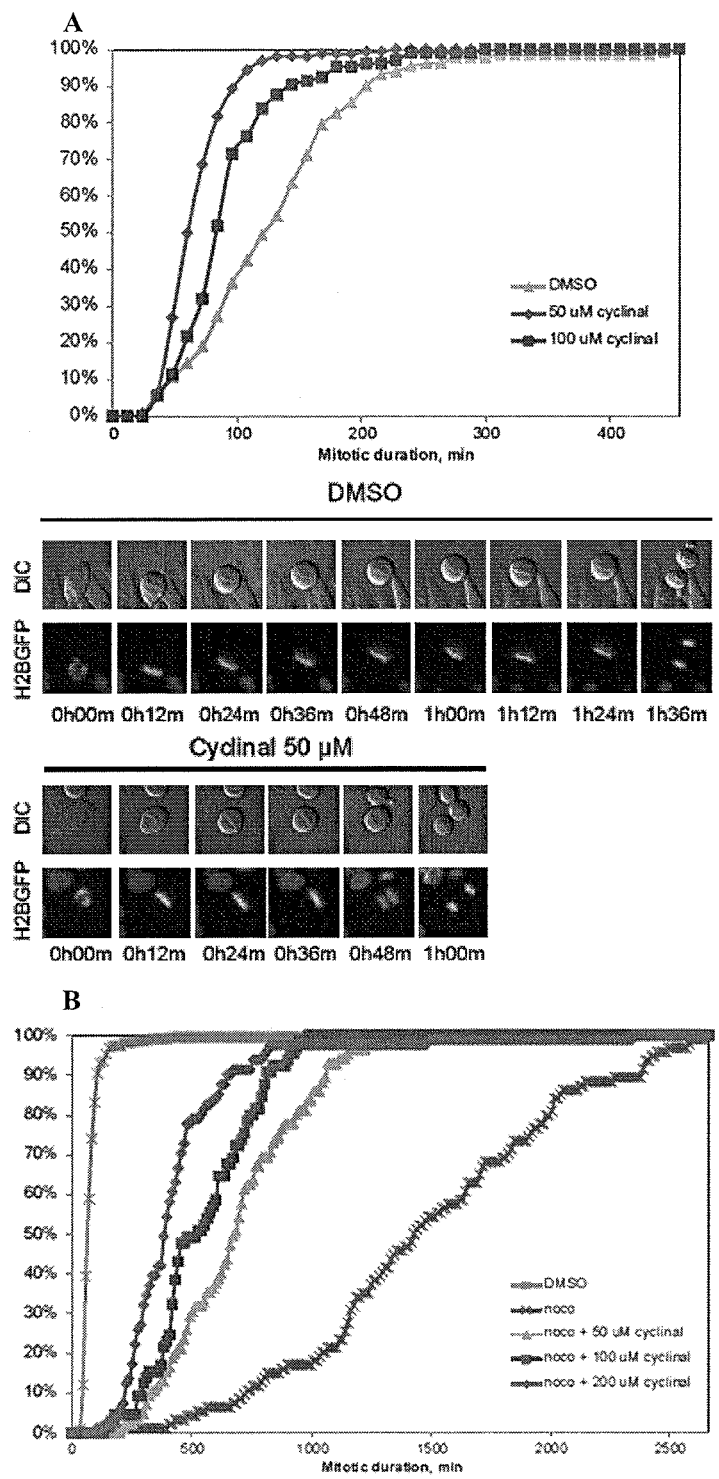
FIG. 30A is a graph and corresponding images of live cells showing that cyclinal accelerates normal mitosis. Double thymidine synchronized HeLa cells were treated with cyclinal after release from thymidine. Cumulative frequency curves of mitotic duration were plotted. Representative frames from live cell imaging are shown.
FIG. 30B is a graph showing that cyclinal overrides nocodazole-induced mitotic arrest. Double thymidine synchronized HeLa cells were treated with nocodazole (300 nM) and cyclinal after release from thymidine. Cumulative frequency curves of mitotic duration were plotted.
FIG. 30C is a graph and corresponding images of live cells showing that cyclinal delays mitotic exit in SAC-deficient cells. Double thymidine synchronized HeLa cells were transfected with Mad2 siRNA between the thymidine blocks and treated with cyclinal at 8 h after release from thymidine. Cumulative frequency curves of mitotic duration were plotted. Representative frames from live cell imaging are shown.
FIG. 30D is a photograph of a Western blot showing that cyclinal delays cyclin B1 degradation in checkpoint lysate. Checkpoint lysate was prepared from nocodazole-arrested HeLa cells and incubated at RT with or without cyclinal. Samples were taken at indicated time points and protein levels were analyzed by Western blot.

Cyclinal overrides mitotic arrest induced by microtubule inhibitors but delays mitotic exit in the absence of the SAC. The effect of cyclinal on tissue culture cells was examined. As opposed to what is expected for an APC inhibitor, cyclinal slightly accelerated an otherwise unperturbed mitosis (FIG. 30A). Interestingly, the acceleration effect becomes weaker as the dose of cyclinal increases. Thus, cyclinal may have two opposing effects on mitosis: one is to delay mitotic exit by stabilizing cyclin B1 (as observed in Xenopus extract) and the other one is to accelerate mitosis. As cyclinal concentration increases, the mitotic delay effect may start to outcompete the acceleration effect. Consistent with the acceleration effect, cyclinal also induced premature exit from mitosis in cells arrested with nocodazole (FIG. 30B). These results suggest that cyclinal compromises the SAC. However, cyclinal treatment has different effects from other methods of inactivation of the SAC. First, when the SAC is inactivated by Mad2 knockdown, mitotic duration becomes so short that there is not enough time for the cell to congress chromosomes before anaphase onset. Cyclinal-treated cells spend significantly longer time in mitosis than Mad2 knockdown and they only initiate anaphase after completion of chromosome congression (FIG. 30A). Second, cells co-treated with taxol and cyclinal still display a transient mitotic arrest (above 10 h) before they exit from mitosis, whereas inhibition of Aurora B kinase and kinetochore-dependent SAC signaling by hesperadin induces rapid mitotic exit in the presence of taxol (~2 h mitotic duration). Taken together, these results suggest that cyclinal prevents the SAC from persistently arresting the cell in mitosis but cyclinal unlikely to interfere with the initial establishment of the SAC by kinetochore-dependent signaling.

The dominant effect of cyclinal in cells seems to be compromising the SAC, which is different from its behavior as an APC inhibitor in Xenopus extracts that lacks an active SAC pathway. Thus, if the SAC is inactivated in cells, then the cell system resemble the extract system and the effect of cyclinal as an APC inhibitor may be manifested. Two lines of evidence suggest that this is the case. First, when Mad2 knockdown cells were treated with cyclinal, a dose-dependent delay in mitotic exit was observed (FIG. 30C). In this case, Mad2 knockdown cells are allowed sufficient time to build a normal-looking metaphase plate before anaphase onset (FIG. 30C). Second, when cyclinal was added to the lysates from cells arrested in mitosis with nocodazole (checkpoint lysate), a clear delay in cyclin B1 degradation was observed (FIG. 30D). The checkpoint lysate does not contain chromosomes and therefore can no longer generate new SAC signal. Together these data demonstrate that the effect of cyclinal as an APC inhibitor can be revealed in cells when active SAC signaling is absent.

Cyclinal Inhibits the Assembly of the Mitotic Checkpoint Complex

The effect of cyclinal on the SAC suggests that a D-box/Cdc20 interaction is critical for prolonged SAC-dependent mitotic arrest but dispensable for a transient mitotic delay. The effector of the SAC is the Mitotic Checkpoint Complex (MCC) consisting of Mad2, Cdc20, BubR1 and Bub3 (Sudakin, V., et al. J Cell Biol 154, 925-936 (2001)). Direct binding between Cdc20 and Mad2 or BubR1 has been observed (Fang, G., et al. Genes Dev 12, 1871-1883 (1998); Tang, Z., et al. Dev Cell 1, 227-237 (2001)), whereas Bub3 is thought to associate with BubR1 (Taylor, S. S., et al. J Cell Biol 142, 1-11 (1998)). Although Mad2 and BubR1 can separately form complexes with Cdc20 and inhibits APC-$^{Cdc20}$ in vitro (Fang, G., et al. Genes Dev 12, 1871-1883 (1998); Tang, Z., et al. Dev Cell 1, 227-237 (2001)), the SAC requires both proteins to be present for proper function as knockdown of either one results in total inactivation of the SAC (Meraldi, P., et al. Dev Cell 7, 45-60 (2004)). Because human Mad2 does not contain a D-box and the Mad2-interaction motif on Cdc20 lies out of the WD40 domain, the Mad2/Cdc20 interaction is unlikely to be perturbed by cyclinal. However, budding yeast Mad3 (BubR1 homolog) does contain a C-terminal D-box that has been shown to contribute to Mad3/Cdc20 binding (Burton, J. L. & Solomon, M. J. Genes Dev 21, 655-667 (2007)).

Furthermore, mutation of this D-box compromises the SAC, although the phenotype is not as severe as Mad3 deletion or mutation in the N-terminal KEN-boxes (Burton, J. L. & Solomon, M. J. Genes Dev 21, 655-667 (2007)). This D-box is also conserved in BubR1 of higher organisms but its relevance for the SAC has never been directly evaluated. In mouse embryonic fibroblasts, expressing an N-terminal fragment of BubR1 containing the KEN-boxes in place of endogenous BubR1 supports a transient mitotic delay in the presence of nocodazole but is insufficient for the prolonged mitotic arrest observed in normal cells (Malureanu, L. A., et al. Dev Cell 16, 118-131 (2009)), suggesting certain elements, most likely the D-box, downstream of the KEN-boxes of BubR1 are required for a persistent SAC-induced arrest. Because the phenotype of cyclinal treatment is very similar to replacing WT BubR1 with the N-terminal fragment, it is hypothesized that by selectively perturbing the D-box-dependent interaction between BubR1 and Cdc20, cyclinal induces a partial compromise of the SAC.

To test this hypothesis, the assembly of the MCC was examined in cells treated with cyclinal. Cdc20 was immunoprecipitated from checkpoint lysates prepared from mitotic cells treated with nocodazole or nocodazole plus cyclinal and measured the amount of BubR1 and Mad2 bound to Cdc20. Cyclinal treatment caused a partial reduction in the amount of BubR1 and Mad2 bound to Cdc20, which is consistent with a selective perturbation of the D-box but not the KEN-box dependent interaction between BubR1 and Cdc20 (FIG. 31A).

The formation of MCC promotes Cdc20 auto-ubiquitination and proteolysis during a SAC-induced arrest (Reddy, S. K., et al. Nature 446, 921-925 (2007); Nilsson, J., et al. Nat Cell Biol 10, 1411-1420 (2008); Ge, S., et al. Cell Cycle 8, 167-171 (2009); Pan, J. & Chen, R. H. Genes Dev 18, 1439-1451 (2004)). If cyclinal inhibits the assembly of the MCC, Cdc20 auto-ubiquitination should be suppressed and its stability should be enhanced in a SAC-induced arrest. Synchronized cells were treated with nocodazole+/−cyclinal and collected samples before the +cyclinal cells exited mitosis to analyze the level of Cdc20. Whereas Cdc20 was highly unstable in nocodazole treated cells, co-treatment of cyclinal had a clear effect of enhancing its stability (FIG. 31B). It has been proposed that one essential function of the SAC is to limit Cdc20 levels via promoting its degradation, as cells expressing a non-ubiquitinatable Cdc20$^{K\text{-less}}$ rapidly exit from mitosis even in the presence of nocodazole (Nilsson, J., et al. Nat Cell Biol 10, 1411-1420 (2008)). Therefore stabilization of Cdc20 by cyclinal may be a contributing factor for the compromised SAC response.

In vitro ubiquitination assay. Interphase Xenopus egg extract was driven into mitosis by a non-degradable cyclin B fragment (MBP-cyclin BΔ90, added to the extract at 70 μg/ml). APC was then immunoprecipitated from the extract with Cdc27 antibody (Santa Cruz, sc-9972, AF3.1) covalently coupled to protein A beads at 4° C. for 1 h (Bio-Rad, 156-0006). For a single immunoprecipitation (IP), 2 μg antibody was bound to 5 μl beads and mixed with 100 μl extract. For experiments with endogenous Cdc20, the beads were washed with ubiquitin chain buffer (UCB, 20 mM Tris, 100 mM KCl, 2 mM ATP and 2.5 mM MgCl$_2$, pH 7.7)+0.1% IGEPAL CA-630 (Sigma I-8896) 3 times. The ubiquitination mixture was prepared by adding 250 nM E1 (Boston Biochem, E-304), 2 μM UbcH10, 150 μM ubiquitin (Boston Biochem, U-100H), 500 nM cycB-NT and 0.1% IGEPAL CA-630 to the ubiquitin chain buffer 30 min prior to the reaction. The reaction was started by mixing 5 μl beads with 10 μl of the ubiquitination mixture and left on a shaker at RT for 10 min. The supernatant was then separated from the beads and Cdc20 remaining on the beads or dissociated into the supernatant was analyzed separately by Western blot. Cdc20 antibody was from Santa Cruz (sc-53399, BA8). Ubiquitinated cycB-NT was detected with the HA-HRP antibody from Roche Applied Science (12013819001, 3F-10). All Western blot images were taken with a Fuji LAS3000 CCD-camera based imaging system.

Kinetic analysis of APC$^{Cdc20}$ reactions. Endogenous APC$^{Cdc20}$ was isolated from Xenopus extract as described above. The ubiquitination mixture was prepared as described in Cdc20 ubiquitination assay with the exception that 60 μM methylated ubiquitin was used in place of WT ubiquitin. CycB-NT was diluted into the mixture to final concentrations of 1 μM, 500 nM, 250 nM, 125 nM and 62.5 nM prior to the reaction. For each reaction, 2.5 μl beads were mixed with 20 μl ubiquitination mixture and left on a shaker at RT for 30 seconds. The reaction was stopped by adding 7 μl hot 4×LDS sample buffer (Invitrogen NP0007)+100 μM DTT. Band intensity of the mono-, di-, and tri-ubiquitinated cycB-NT was quantitated with Image J and fitted to a hyperbolic equation by nonlinear regression.

Coupling of amino-cyclinal to Affigel-10 resin. Affigel-10 resin (Bio-Rad) was washed twice with DMSO and dried. The resin was then mixed with 5 mM amino-cyclinal dissolved in DMSO (2× volume of dry resin). N,N-Diisopropylethylamine was diluted 50-fold into the solution. The resin was rotated at RT for 2 h and the reaction was quenched with ⅕ resin volume of ethanolamine. The resin was then washed sequentially with isopropanol, water and XB+0.05% tween. The resin was stored at 4° C. as 50% slurry in XB+0.05% Tween.

Cdc20 pull down assay by amino-cyclinal resin. For a single pull down assay, 5 μl amino-cyclinal resin was incubated with 30 μl diluted in vitro-translated Cdc20 (5 μl reticulocyte lysate diluted to 30 μl with XB+0.05% Tween) and various competitors at 4 C for 1 h.

Cdc20 depletion and rescue. To deplete Cdc20, mitotic Xenopus extract was incubated with amino-cyclinal affigel resin at a volume ratio of 2:1 and left on a rotator at 4° C. for 45 min and the same process was repeated again. To rescue degradation in the depleted extract, reticulocyte lysates containing in vitro-translated Cdc20 was added to the extract at 1/10$^{th}$ extract volume.

Live cell imaging experiments. Cell synchronization, knockdown of Cdc20 or Mad2 by siRNA, setup of the live imaging experiments and analysis of the movie were performed as described previously (Zeng, X., et al. Cancer Cell 18, 382-395 (2010)). Nocodazole, taxol, proTAME, cyclinal and hesperadin were added to cells at 8 h after release. MG132 was added to cells at 10 h after release to allow mitotic entry. Roscovitine was added to cells at 12 h after release.

Preparation of checkpoint lysate. HeLa cells were synchronized by double thymidine block and treated with 300 nM nocodazle at 8 h after second release from thymidine-.Mitotic cells were collected at around 12.5 h after treatment.

Cells were frozen in liquid nitrogen and stored at −80° C. until the experiment. Cells were lysed in 1× pellet volume of lysis buffer (20 mM Hepes, KOH to pH 7.6; 5 mM KCl; 1 mM DTT; 1× protease inhibitor cocktail (from 1000× stock: leupeptin, pepstatin, chymostatin, all 10 mg/ml, dissolved in DMSO); 20 µg/ml cytochalasin B; 1× energy mix (from 20× stock: 150 mM creatine phosphate, 20 mM ATP, 2 mM EGTA, 20 mM $MgCl_2$, 2 mg/ml creatine phosphokinase, NaOH to pH 7.7) on ice for 15 min and vortexed vigorously every 5 min. The mixture was then centrifuged at 12,000 rpm for 30 min and the supernatant was collected as the checkpoint lysate. Protein concentration of the lysate was typically between 15-20 mg/ml.

Example 8

Cyclinal Synergizes with proTAME to Robustly Induce Mitotic Arrest

Figure 32A:
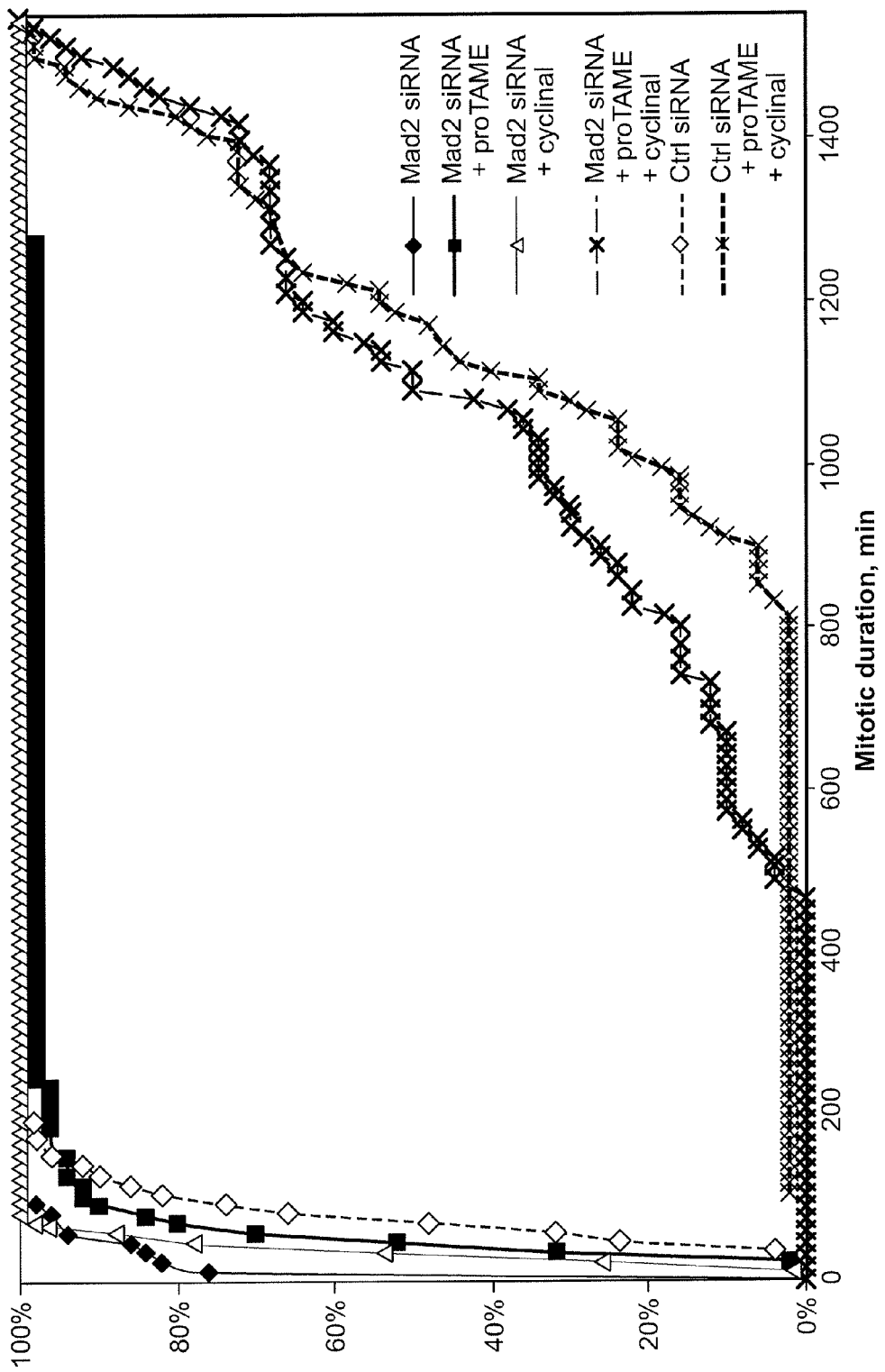
FIG. 32A is a graph, table, and corresponding live cell images showing that cyclinal and proTAME-induced mitotic arrest is Mad2-independent. Double thymidine synchronized HeLa cells were transfected with Control or Mad2 siRNA between the thymidine blocks and treated with proTAME (12 µM) and cyclinal (100 µM) at 8 h after release from thymidine. Cumulative frequency curves of mitotic duration were plotted. Cell fate distribution is shown in the table. Representative frames from live cell imaging are shown.
Figure 32A:
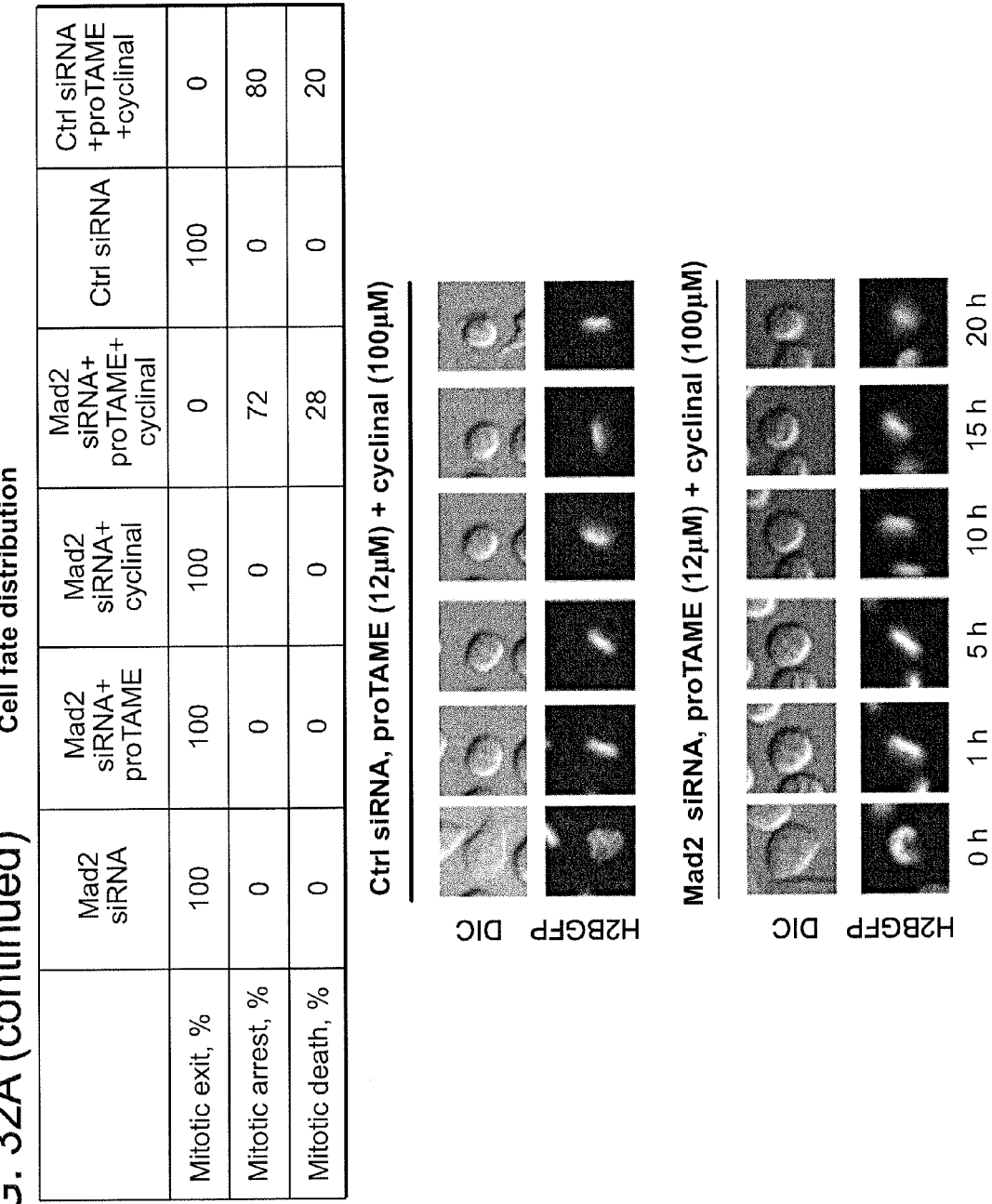
Figure 32B:
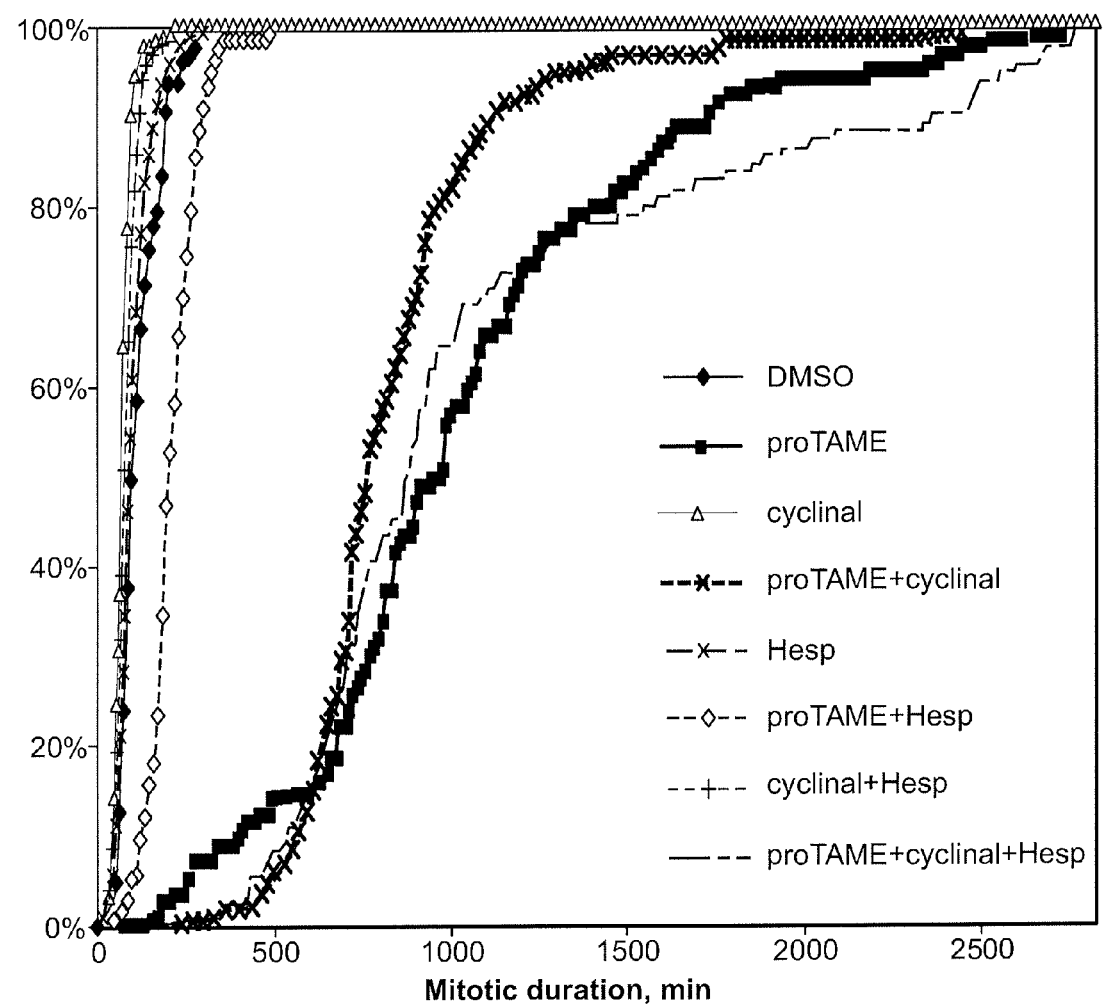
FIG. 32B is a graph, table, and corresponding live cell images showing that cyclinal and proTAME-induced mitotic arrest is hesperadin-insensitive. Double thymidine synchronized HeLa cells were treated with drugs as indicated at 8 h after release. Cumulative frequency curves of mitotic duration were plotted. Cell fate distribution is shown in the table. Representative frames from live cell imaging are shown.
Figure 32B:
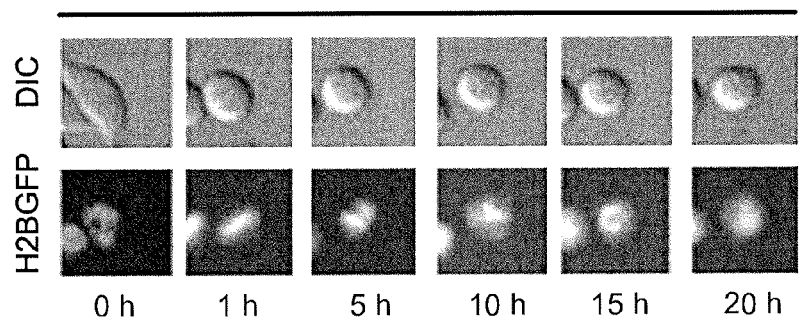

Whereas proTAME induces a persistent mitotic arrest in SAC-proficient cells, it only transiently delays mitotic exit once the SAC is inactivated, suggesting that the major effect of proTAME is prevention of SAC inactivation, but its ability to directly inhibit non-SAC inhibited APC in the context of the cell is rather weak (Zeng, X., et al. Cancer Cell 18, 382-395 (2010)). Because cyclinal and TAME synergize to strongly inhibit APC activation by Cdc20 in Xenopus extracts, it was further determined whether cyclinal and proTAME also synergize in cells. For this experiment, Mad2-knockdown cells were treated with proTAME or cyclinal or the combination of the two. Whereas proTAME or cyclinal alone only transiently delayed mitotic exit in Mad2-knockdown cells, co-addition of both compounds induced a persistent mitotic arrest in these cells (FIG. 32A). Notably proTAME/cyclinal arrested cells were able to build a normal-looking metaphase plate (FIG. 32A), suggesting that the combination of the compounds does not perturb microtubule function. The Aurora B inhibitor hesperadin was also used as an alternative method to inactivate the SAC. In this case, proTAME only transiently delayed mitotic exit in the presence of hesperadin whereas cyclinal even accelerated a hesperadin-treated mitosis (FIG. 32B). Unlike Mad2 knockdown, hesperadin does not accelerate an otherwise unperturbed mitosis, which is consistent with the idea that the mitotic timer is set by a kinetochore-independent pathway (FIG. 32B). As observed with Mad2-knockdown cells, co-addition of cyclinal and proTAME induced a persistent mitotic arrest in cells in the presence of hesperadin (FIG. 32B). In contrast to Mad2 knockdown cells, hesperadin treatment prevented the mitotically arrested cells from maintaining the metaphase plate (FIG. 32B). Together these data demonstrate that cyclinal and proTAME synergize with each other to induce strong direct inhibition of the APC so that the mitotic arrest is completely independent on the SAC.

Because the mitotic arrest induced by cyclinal/proTAME was extremely robust, it was determined whether any method can possibly override the effect of both drugs to induce mitotic exit. Direct Cdk1 inhibition has been shown to induce mitotic exit in cells arrested in mitosis with nocodazole (D'Angiolella, et al. Genes Dev 17, 2520-2525 (2003)). If Cdk1 activity can be fully inhibited, then it is no longer necessary for the APC to degrade cyclin B1, which should result in mitotic exit even if the APC remains strongly inhibited by cyclinal/proTAME. Therefore, cells arrested in mitosis were treated with different methods with a high concentration of a Cdk1 inhibitor roscovitine (100 µM). Consistent with earlier reports, roscovitine induced instantaneous mitotic exit in cells arrested with nocodazole (FIG. 32C) and taxol (data not shown). Roscovitine also induces rapid mitotic exit in the presence of proTAME (FIG. 32C). Interestingly, Cdc20 knockdown cells remained resistant to roscovitine. When treated with roscovitine, these cells attempted cytokinesis by elongating the cell body and initiating furrow ingression. However, the elongated cell quickly reversed to the original round state and the furrow regressed (FIG. 32C). The cells then arrested permanently in mitosis (FIG. 32C). Similarly, MG132 or cyclinal/proTAME arrested cells showed complete resistance to roscovitine (FIG. 5C) and they also went through the process of cell elongation/reversion upon roscovitine treatment. These data demonstrate that roscovitine-induced mitotic exit still depends on $APC^{Cdc20}$-dependent proteolysis. As a result, strong inhibition of the proteasome by MG132 or the APC by cyclinal/proTAME abrogates the ability of roscovitine to drive mitotic exit.

Example 9

Demonstration of Synergy between TAME and R7 in Xenopus Cell Cycle Extract

Figure 34:
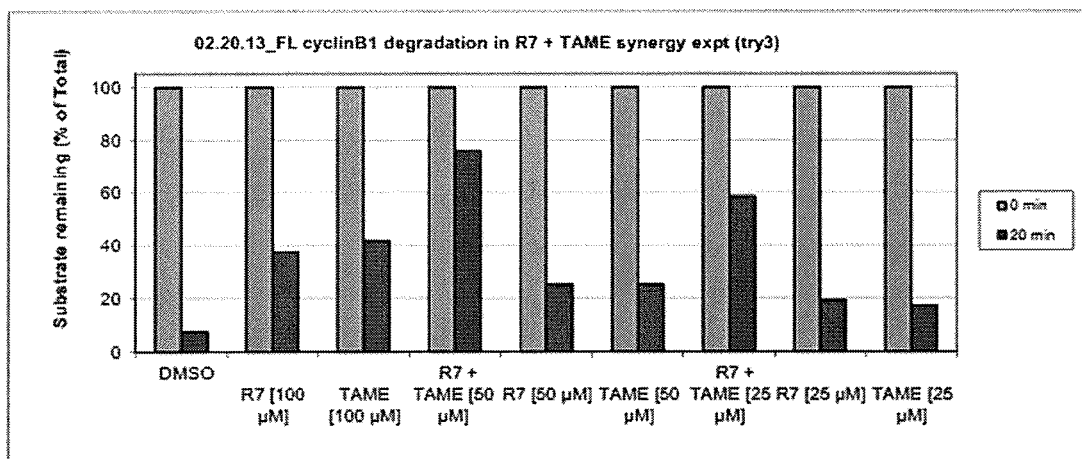
FIG. 34 is a graph demonstrating synergy between TAME and R7 in *Xenopus* cell cycle extract. The percent of total substrate remaining is plotted as a function of concentration(s) of R7 and/or TAME.

A 35S-labeled cyclin B1 protein was expressed in reticulocyte lysate, and a 10% volume of this material was added to mitotically arrested Xenopus egg extract, in the presence of DMSO or different concentrations of inhibitors. Aliquots were taken at 0 and 20 minutes, and samples separated by SDS-PAGE and radioactivity measured by quantitative phosphorimager analysis. In the presence of DMSO, the majority of this substrate is degraded by 20 minutes. Synergy is demonstrated by the fact that the combination of 50 µM R7 plus 50 uM TAME has more inhibitory activity than either 100 uM TAME or R7 alone. Similar results were observed at concentrations of 25 uM R7 plus 25 uM TAME, which had more activity than 50 uM of each drug on its own. See FIG. 34.

Example 10

Apcin Binds to Cdc20 and Competitively Inhibits APC/C-dependent Ubiquitination

Analysis of the structure-activity relationship of apcin (FIG. 40a) revealed that elimination of a single nitrogen in the pyrimidine ring of apcin (apcin-P) reduced activity, but replacement with a morpholino group (apcin-M) eliminated activity (FIG. 40b). Elimination of the nitro-imadazole moiety (apcin-A) also reduced activity (FIG. 40b). To identify the target of apcin, apcin-A was coupled to beads via its free amino group, the beads were incubated with mitotic Xenopus extract, and then the beads were removed. It was determined that Cdc20 but not Cdc27 was substantially depleted from the extracts (FIG. 40c). A cyclin B-luciferase reporter protein was stabilized in the depleted extract, and proteolysis could be rescued by adding in vitro-translated Cdc20 (FIG. 40d). Cdc20 expressed in reticulocyte lysate interacted with apcin-A beads in a manner that could be competed by free apcin (FIG. 40e) but not by the inactive analog apcin-M or the APC/C inhibitor TAME (FIG. 35a). Among a panel of WD40-containing proteins, Cdc20 binding to apcin-A beads was most robust, followed by Cdh1, with much less binding of other WD40-containing proteins observed (FIG. 40f and FIG. 35b). A cyclin B1 N-terminal fragment also competed for Cdc20 binding to the apcin-A resin, but the same fragment with a mutated D-box did not (FIG. 40g). Kinetic analysis of APC/C-dependent ubiquitination of an N-terminal fragment of cyclin B1 using a previously established method (Zeng, X. & King, R. W. Nat Chem Biol 8, 383-392, (2012)) showed that apcin caused a significant increase (p=0.0039) in the Km (Ki=23 µM) of the reaction but no reduction in kcat (FIG. 40h and FIG. 35c). Together these results suggest that apcin competitively inhibits APC/C-dependent ubiquitination by binding to Cdc20 and preventing substrate recognition.

Example 11

Apcin Binds to the D-box Binding Site of Cdc20

To identify the site on Cdc20 that binds apcin, apcin was soaked into Cdc20 protein crystals and the structure of the Cdc20-apcin complex was resolved to 2.1 Å resolution (Table 2). Apcin bound a small pocket on the side of the WD40 domain that has been implicated in binding the D-box (FIG. 41a and FIG. 36a). Compared to the apo-Cdc20 structure, apcin did not cause noticeable changes in Cdc20 conformation. The binding orientation of the small molecule is consistent with the structure-activity relationship, as the required pyrimidine ring and neighboring aminal nitrogen make potential hydrogen bonds with backbone atoms from D177: the aminal NH of apcin is positioned to act as a hydrogen bond donor with the backbone carbonyl oxygen of D177, and one of the pyrimidine nitrogens of apcin is positioned to serve as a hydrogen bond acceptor with the backbone NH group of D177. The hydrophobic trichloromethyl group is buried in the pocket occupied by leucine of the D-box (FIG. 41b and FIG. 36a). The nitro-imidazole moiety of apcin, which is not required for activity, is positioned facing solvent, explaining why apcin-A retains some activity and can be used to isolate Cdc20 protein when coupled to beads.

TABLE 2

Data collection and refinement statistics for Cdc20-apcin structure.

| Data collection | |
| --- | --- |
| Space group | $P2_1$ |
| Cell dimensions | |
| a, b, c (Å) | 41.041, 87.177, 48.043 |
| α, β, γ (°) | 90.00, 112.72, 90.00 |
| Resolution range (Å) | 44.3-1.95 (1.98-1.95) |
| $R_{merge}$ (%)$^a$ | 9.80 (55.0) |
| I/σ(I) | 11.8 (0.75) |
| Data completeness (%) | 82.3 (24.4) |
| Redundancy | 3.3 (1.2) |
| Energy (eV) | 12,684.1 |
| Unique reflections | 18,376 (280) |
| Wilson B-value (Å$^2$) | 27.7 |
| Refinement statistics | |
| Resolution range (Å) | 28.6-2.10 (2.23-2.10) |
| No. of reflections $R_{work}/R_{free}$ | 16,859/857 (1,915/100) |
| Data completeness (%) | 92.4 (67.0) |
| Atoms (non-H protein/solvent/inhibitor) | 2,430/81/27 |
| $R_{work}$ (%) | 16.5 (21.4) |
| $R_{free}$ (%) | 21.3 (29.1) |
| R.m.s.d. bond length (Å) | 0.002 |
| R.m.s.d. bond angle (°) | 0.73 |
| Mean B-value (Å$^2$) (protein/solvent/inhibitor) | 29.8/30.0/51.1 |
| Ramachandran plot (%) (favored/additional/disallowed)$^b$ | 97.4/2.3/0.3 |

TABLE 2-continued

Data collection and refinement statistics for Cdc20-apcin structure.

| Maximum likelihood coordinate error | 0.20 |
| --- | --- |
| Missing residues, by chain | A: 161-164 |

Data for the outermost shell are given in parentheses.
$^b$As defined by the validation suite MolProbity.

It was determined whether mutations in the presumptive binding site affect the binding of Cdc20 to apcin-A containing beads (FIG. 41c). V200 is located at the base of the hydrophobic pocket (FIG. 41b), and mutation to methionine strongly blocked binding of Cdc20 (FIG. 41c), and also inactivated the ability of Cdc20 to rescue cyclin degradation in a Cdc20-depleted extract (FIG. 41c). D177 and P179 line the binding pocket and make potentially critical interactions with apcin; mutation of either residue to alanine also strongly reduced binding to apcin and function of Cdc20 (FIG. 41c). I216 also lines the pocket, and mutation to serine perturbed binding to apcin (FIG. 41c). The effect of mutating charged surface residues that are more distant from the apcin-binding site was also investigated. E465 makes an ionic interaction with the conserved arginine of the D-box. Mutation of this residue decreased the ability of Cdc20 to rescue degradation in a Cdc20-depleted extract, but had little effect on apcin binding. E180 lies nearby and may also interact with the D-box arginine, but mutation to alanine had no effect on apcin binding or rescue activity. Finally, R174 lies near the pyrimidine ring of apcin, and mutation to serine strongly reduced apcin binding and blocked Cdc20 rescue activity, consistent with a potential role of this residue in interacting with negatively charged amino acids in the D-box (FIG. 41c and FIG. 36a). Although the guanidino group of R174 does not interact with apcin, its aliphatic segment packs against V176, which lines the binding pocket. Overall, a strong correlation was observed between effects on apcin binding and Cdc20 function, particularly for residues that line the apcin-binding pocket.

Example 12

Effects of Apcin on Cdc20 Binding to APC/C and Stability of APC/C Substrates in Mitotic *Xenopus* Extract Because apcin occupies the leucine-binding pocket of Cdc20 but appears not to obscure other D-box interacting residues, it provides a useful tool for assessing the role of the leucine pocket in stabilizing ternary interactions between APC/C, Cdc20, and substrate. Structural and biochemical studies suggest that Cdc20 is recruited to the APC/C through multiple, weak interactions. These include the C-terminal isoleucine-arginine (IR)-tail of Cdc20, which interacts with Cdc27, and the C-box, which is thought to interact with APC2. Additionally, substrates can promote cooperative Cdc20 binding to the APC/C through a co-receptor interaction in which the substrate is simultaneously recognized by Cdc20 and the APC/C. To assess the importance of the leucine pocket in co-receptor-dependent binding, it was determined whether apcin could block substrate-induced binding of Cdc20 to the APC/C in *Xenopus* extract. Substrate increased Cdc20 loading onto APC/C in a concentration- and D-box-dependent manner (FIG. 42a and FIG. 37a) and that this loading could be blocked by addition of apcin, indicating that the leucine pocket is critical for co-receptor-mediated Cdc20 binding to APC/C. The small molecule TAME, which antagonizes the IR-tail interaction between Cdc20 and the APC/C, also antagonized Cdc20 loading.

Interestingly, at high concentrations of substrate, the combined use of apcin and TAME was more effective at blocking Cdc20 binding to APC/C than either compound used alone, suggesting that simultaneous disruption of multiple interactions between substrate, Cdc20 and the APC/C may be an effective strategy for inhibiting APC/C function.

Figure 37:
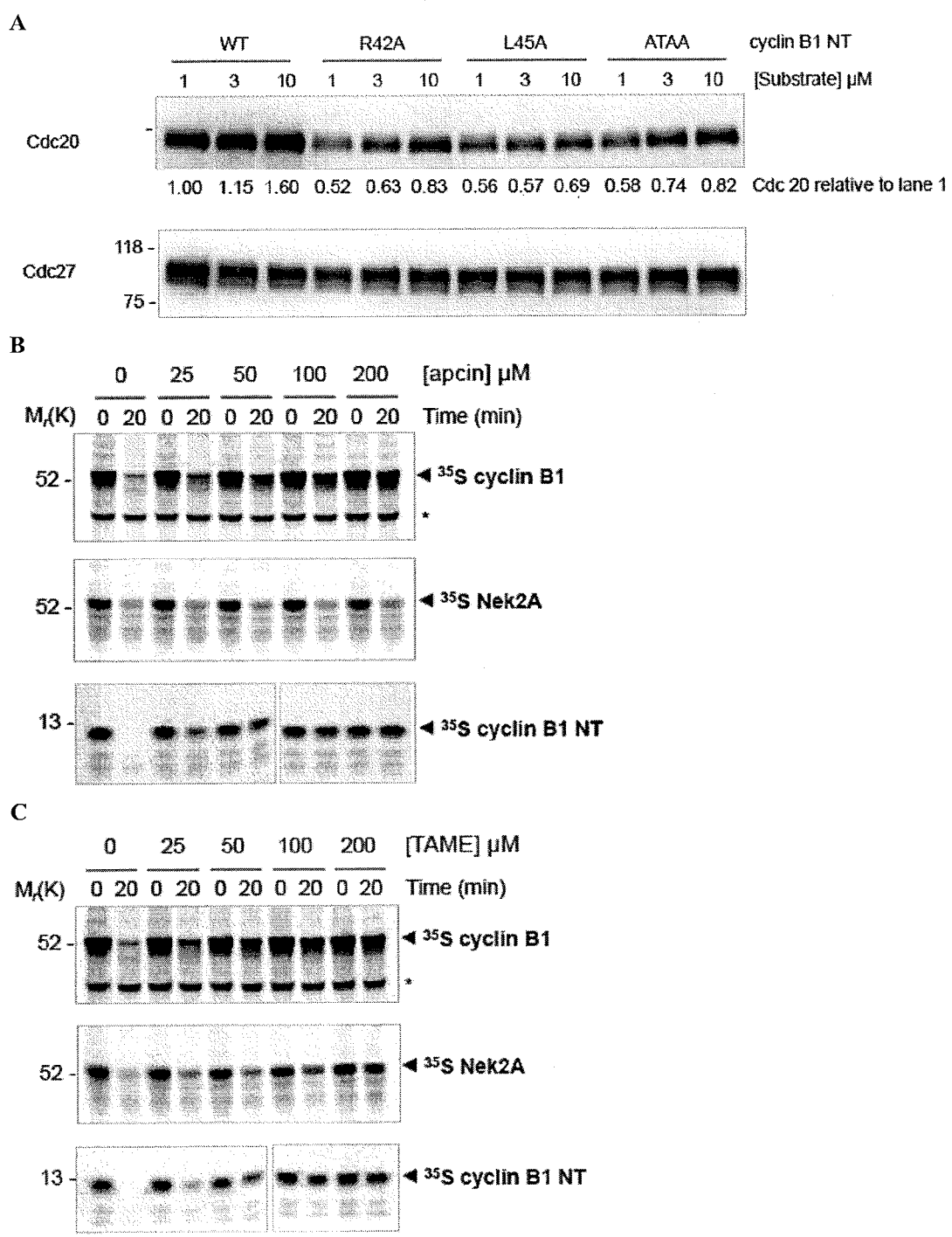
FIG. 37A is a pair of photographs showing that substrate-mediated recruitment of Cdc20 to APC/C in Xenopus extract is dependent on the D-box motif. Increasing concentrations of wild-type or different D-box mutants of cyclin B1 NT were introduced into mitotically-arrested Xenopus extract and the APC/C was isolated with anti-Cdc27 antibodies by immunoprecipitation for 1 hour at 4° C. The immunoprecipitate was separated by SDS-PAGE and analyzed by western blotting against Cdc20 and Cdc27. Levels of Cdc20 were quantitated using Image J and normalized to APC/C subunit Cdc27.
FIG. 37B is a series of photographs showing that apcin inhibits degradation of APC/C substrates in Xenopus extract differentially. $^{35}$S-labeled substrates were introduced into mitotically-arrested Xenopus extract that had been pre-treated with protein-synthesis inhibitor cycloheximide (to prevent further incorporation of $^{35}$S-labeled amino acids) and DMSO or increasing concentrations of apcin for 10 min. Stability of the exogenous substrates at 20 min was assessed by SDS-PAGE and phosphorimaging. Levels of substrates were quantitated using Quantity One and plotted as percent of input radiolabeled protein. This experiment corresponds to the graph in FIG. 42B.
FIG. 37C is a series of photographs showing that apcin inhibits degradation of APC/C substrates in Xenopus extract differentially. $^{35}$S-labeled substrates were introduced into mitotically-arrested Xenopus extract that had been pre-treated with protein-synthesis inhibitor cycloheximide (to prevent further incorporation of $^{35}$S-labeled amino acids) and DMSO or increasing concentrations of apcin for 10 min. Stability of the exogenous substrates at 20 min was assessed by SDS-PAGE and phosphorimaging. Levels of substrates were quantitated using Quantity One and plotted as percent of input radiolabeled protein. This experiment corresponds to the graph in FIG. 42C.
FIG. 37D is a series of photographs showing that apcin inhibits degradation of APC/C substrates in Xenopus extract differentially. $^{35}$S-labeled substrates were introduced into mitotically-arrested Xenopus extract that had been pre-treated with protein-synthesis inhibitor cycloheximide (to prevent further incorporation of $^{35}$S-labeled amino acids) and DMSO or increasing concentrations of apcin for 10 min. Stability of the exogenous substrates at 20 min was assessed by SDS-PAGE and phosphorimaging. Levels of substrates were quantitated using Quantity One and plotted as percent of input radiolabeled protein. This experiment corresponds to the graph in FIG. 42D.
FIG. 37E is a photograph and corresponding graph showing that apcin and TAME synergize in stabilizing cyclin A in Xenopus extract. $^{35}$S-labeled cyclin A was introduced into mitotically-arrested Xenopus extract that had been pre-treated with apcin or TAME, at indicated concentrations, or DMSO and cycloheximide for 10 min. Degradation was allowed to proceed for 20 min before analysis by SDS-PAGE and phosphorimaging. Substrate levels were quantitated using Quantity One, and presented in a bar graph as percent of input radiolabeled protein.
FIG. 37F is a photograph and corresponding graph showing that apcin and TAME synergize in stabilizing securin in Xenopus extract. $^{35}$S-labeled securin was introduced into mitotically-arrested Xenopus extract that had been pre-treated with apcin or TAME, at indicated concentrations, or DMSO and cycloheximide for 10 min. Degradation was allowed to proceed for 20 min before analysis by SDS-PAGE and phosphorimaging. Substrate levels were quantitated using Quantity One, and presented in a bar graph as percent of input radiolabeled protein.
Figure 37:
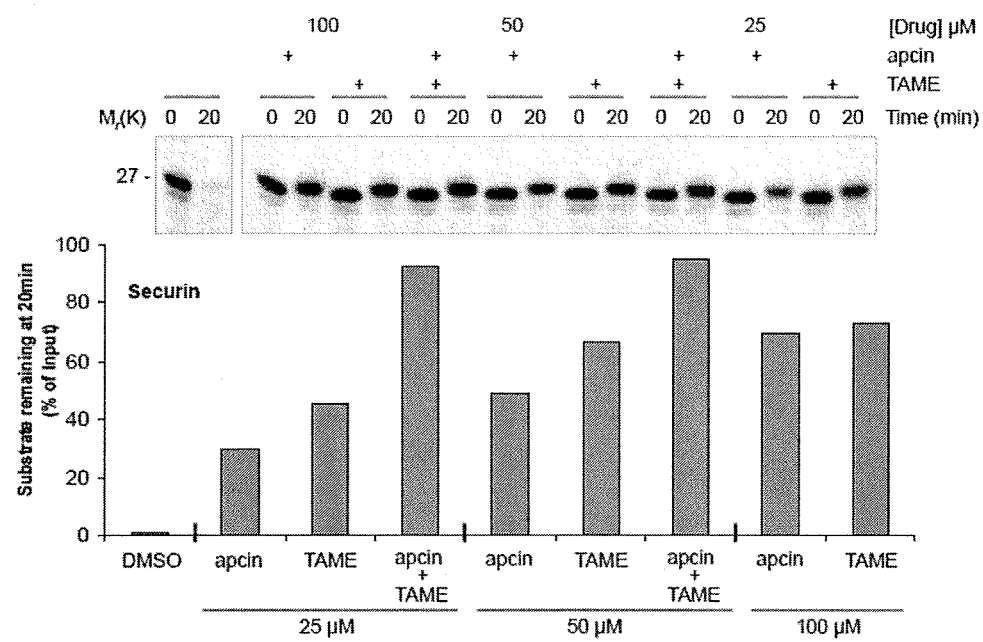

Because substrates can be recruited to the APC/C through both D-box-dependent and D-box-independent mechanisms, the ability of apcin to stabilize different APC/C substrates in mitotic *Xenopus* extract was compared. Apcin stabilized an N-terminal fragment of cyclin B1 and securin most effectively (FIG. 42*b* and FIG. 37*f*), with somewhat weaker effects against full-length cyclin B1 (FIG. 42*b*). Interestingly, even high concentrations of apcin failed to stabilize cyclin A2 or Nek2A (FIG. 42*b* and FIG. 37*e*). In contrast, TAME inhibited the degradation of all APC/C substrates (FIG. 42*c* and FIGS. 37*c*, 37*e*, 37*f*), consistent with TAME's ability to directly block recruitment of Cdc20 to the APC/C. These results indicate that the leucine pocket of Cdc20 plays an essential role in recruiting the D-boxes of securin and the N-terminal fragment of cyclin B1, and that apcin can effectively compete with these interactions. The ability of full-length cyclin B1 to bind Cks1 via Cdk1 may facilitate its recruitment to the APC/C independent of the D-box, helping the substrate to partially overcome the effects of apcin. A similar phenomenon may explain the insensitivity of cyclin A2 proteolysis to apcin. Furthermore, the N-terminal region of cyclin A2 appears to bind Cdc20 with higher affinity than cyclin B125, which may further reduce the effectiveness of apcin. In contrast to all of these substrates whose degradation is D-box-dependent, Nek2A is thought to be recruited directly to the APC/C via a Cdc20-independent mechanism that requires its MR-tail rather than a canonical D-box, explaining why apcin fails to stabilize the protein (FIG. 42*b* and FIG. 37). The sensitivity of APC/C substrates to apcin parallels their sensitivity to APC/C inhibition by the spindle assembly checkpoint (SAC), as cyclin A2 and Nek2A are also unique in their ability to evade stabilization by the SAC.

Because apcin and TAME inhibit APC/C-dependent proteolysis by distinct mechanisms, and the combined compounds showed a greater effect in blocking substrate-dependent binding of Cdc20 to the APC/C, the effect of combining the inhibitors on the proteolysis of APC/C substrates in *Xenopus* extracts was determined. Combining the compounds led to synergistic stabilization of full length cyclin B1, the N-terminal cyclin B1 fragment, securin, and cyclin A2, with a much weaker effect for Nek2A (FIG. 42*d* and FIGS. 37*d*, 37*e*, and 37*f*). For example, combining TAME and apcin at 25 µM each was more effective at stabilizing cyclin B1 than using either compound alone at 100 µM. Apcin was able to strongly potentiate the effect of TAME in stabilizing cyclin A2, despite having no effect by itself. This finding indicates that engagement of the D-box binding site by cyclin A2 may be particularly important when other interactions in the substrate-Cdc20-APC/C complex are weakened. Apcin slightly enhanced the ability of TAME to stabilize Nek2A (FIG. 42*d*), indicating that the leucine pocket on Cdc20 may bind Nek2A, even though this interaction is not essential for proteolysis if the APC/C is not otherwise perturbed.

Example 13

Apcin Synergizes with proTAME to Prolong Mitotic Duration

To determine whether this synergistic inhibition of APC/C-dependent proteolysis would translate into a similar effect on mitotic exit in mammalian cells, the effect of apcin, proTAME[9] (a cell-permeable TAME prodrug), and the combination, on mitotic duration in different human cell lines was determined. In order to quantitatively assess interactions between the inhibitors, a high-throughput image-based assay was used to determine the mitotic index (FIG. 38*a*). As determined by comparison to a Bliss-independence model, apcin and proTAME showed a strongly synergistic ability to increase the mitotic fraction in all cell lines examined (FIG. 43*a* and FIG. 38*b*). Apcin-M was inactive in this assay whereas apcin-P retained activity (FIG. 38*c*), consistent with effects on Cdc20 binding and APC/C substrate stability in *Xenopus* extract.

To confirm these results, the effect of these inhibitors on mitotic duration was evaluated by live cell imaging in RPE1 cells (FIG. 43*b*, Tables 3-6). On its own, 25 µM apcin showed a non-significant trend to decrease the rate of mitotic exit (to 88.8% of that in control (DMSO) treated cells, $p=0.279$, Cox proportional hazards model) but apcin-M did not ($p=0.201$). The ability of apcin to slow mitotic exit was much more apparent ($p=0.0001$) when mitotic duration was shortened by inactivation of the SAC by depletion of Mad2 by RNAi. These data indicate that apcin slows mitotic exit.

TABLE 3

| Treatment | Cells (Fates Observed) | Median |
| --- | --- | --- |
| DMSO, control siRNA | 200 (200) | 24 |
| DMSO, mad2 siRNA | 103 (103) | 18 |
| apcin-M, control siRNA | 180 (180) | 24 |
| apcin-M, mad2 siRNA | 105 (105) | 18 |
| apcin, control siRNA | 173 (173) | 24 |
| apcin, mad2 siRNA | 105 (105) | 19 |
| proTAME, control siRNA | 115 (103) | 120 |
| proTAME, mad2 siRNA | 77 (74) | 114 |
| proTAME + apcin-M, control siRNA | 127 (118) | 132 |
| proTAME + apcin-M, mad2 siRNA | 80 (78) | 84 |
| proTAME + apcin, control siRNA | 109 (86) | 942 |
| proTAME + apcin, mad2 siRNA | 76 (64) | 810 |

TABLE 4 control siRNA, DMSO control (n = 904)

| Effect | % rate of mitotic exit | P-value relative to DMSO | P-value for pairwise comparison |
| --- | --- | --- | --- |
| apcin-M | 115.18 | 0.20 | |
| apcin | 82.87 | 0.28 | |
| proTAME | 2.32 | <2E−16 | |
| apcin-M + proTAME | 2.54 | <2E−16 | 0.68 |
| apcin + proTAME | 1.30 | <2E−16 | |

TABLE 5

Mad2 siRNA, DMSO control (n = 546)

| Effect | % rate of mitotic exit | P-value relative to DMSO | P-value for pairwise comparison |
| --- | --- | --- | --- |
| apcin-M | 114.34 | 0.34 | |
| apcin | 57.38 | 1.27E−04 | |

TABLE 5-continued

Mad2 siRNA, DMSO control (n = 546)

| Effect | % rate of mitotic exit | P-value relative to DMSO | P-value for pairwise comparison |
|---|---|---|---|
| proTAME | 0.22 | <2E−16 | }  0.70 |
| apcin-M + proTAME | 0.25 | <2E−16 | |
| apcin + proTAME | 0.05 | <2E−16 | |

TABLE 6

Synergy between apcin & proTAME

| Treatment | % rate of mitotic exit | P-value |
|---|---|---|
| control siRNA, DMSO control | 63.3 | 0.016 |
| Mad2 siRNA, DMSO control | 38.3 | 8.92E−05 |

In contrast, in the presence of proTAME, the addition of apcin dramatically slowed the rate of mitotic exit in a synergistic manner (FIG. 43b, Tables 3-6): the rate of mitotic exit was 63% of that predicted by a multiplicative combination of the single compound effects (p=0.016, Cox proportional hazards model). Significant synergy was also observed in U2OS cells (p=2.0×10$^{-8}$) (FIG. 38e, 38f and Tables 7-9). Addition of the inactive derivative apcin-M had no effect on the rate of mitotic exit in the presence of proTAME (p=0.68). The effect of proTAME alone was biphasic, because prolongation of metaphase can cause cohesion fatigue in a subpopulation of cells, which can in turn reactivate the SAC to block mitotic exit. Notably, in addition to prolonging mitotic duration, the addition of apcin eliminated the biphasic response. Furthermore, the combined effect of apcin and proTAME was largely preserved even when the SAC was inactivated by Mad2 depletion. When modeled quantitatively, the degree of synergy between apcin and proTAME was enhanced in the absence of Mad2, as the rate of mitotic exit was reduced to 38% of the rate predicted by a multiplicative combination of the single compound effects (p=8.92×10$^{-5}$; Tables 4-6). The increase in synergy arose because inactivating the SAC had a proportionately greater effect on proTAME treatment alone compared to the combined effect of apcin and proTAME. Together these findings suggest that the synergistic effect on mitotic exit does not rely on the SAC, but instead likely reflects direct APC/C inhibition.

TABLE 7

U2OS

| Treatment | Cells (Fates Observed) | Median |
|---|---|---|
| DMSO | 137 (137) | 20 |
| apcin | 191 (191) | 24 |
| proTAME | 311 (304) | 180 |
| proTAME + apcin-M | 170 (168) | 120 |
| proTAME + apcin | 169 (163) | 660 |

TABLE 8

| Compound | % rate of mitotic exit | P-value relative to DMSO | P-value for pairwise comparison (n = 410) |
|---|---|---|---|
| apcin | 109.64 | 0.418 | |
| proTAME | 3.63 | <2E−16 | } 0.108 |
| apcin-M + proTAME | 4.90 | <2E−16 | |
| apcin + proTAME | 1.70 | <2E−16 | |

DMSO control (n = 978)

TABLE 9

| Synergy | % rate of mitotic exit | P-value |
|---|---|---|
| apcin & proTAME | 42.88 | 2.01E−08 |

Example 14

Figure 39:
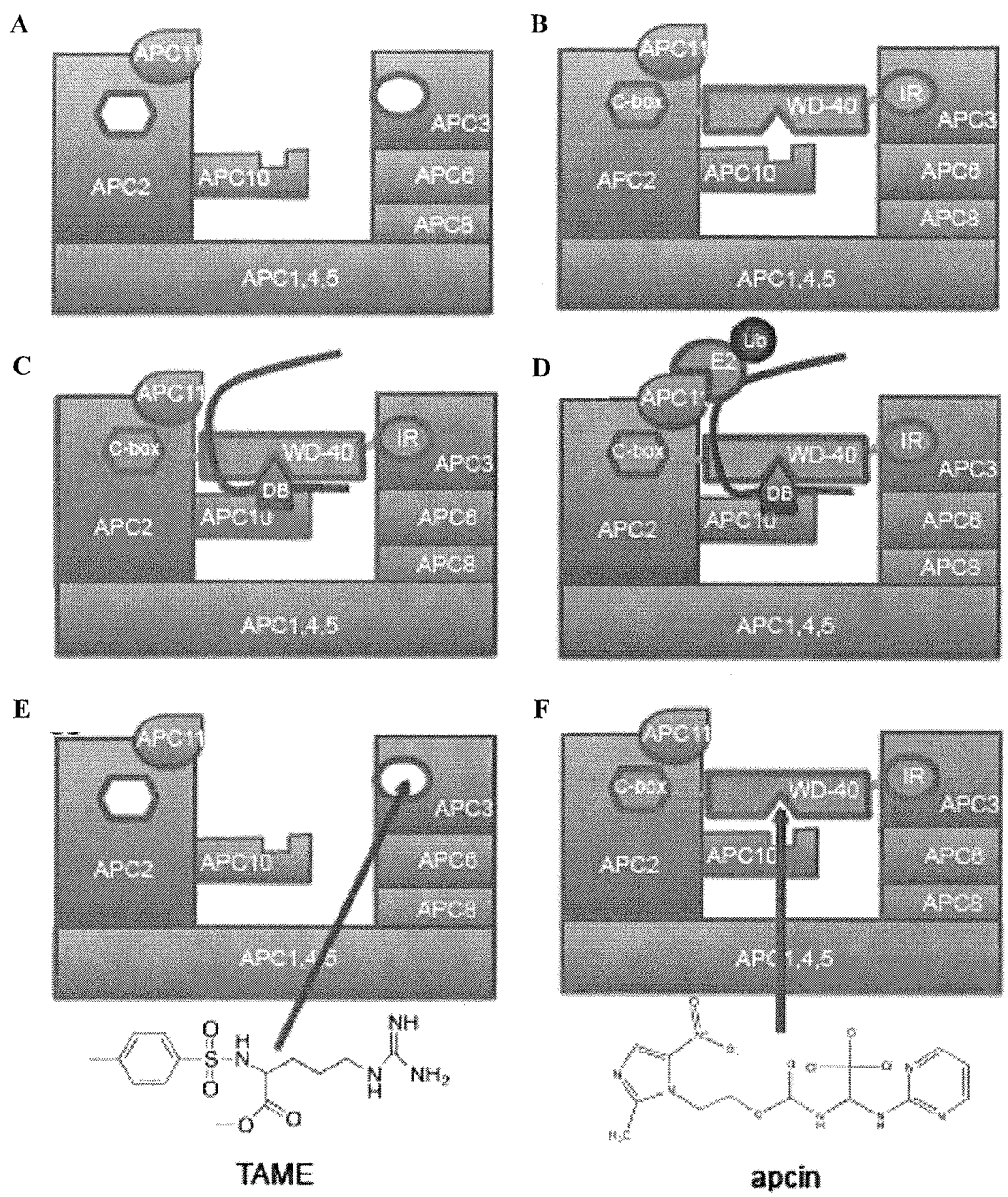
Figure 39:
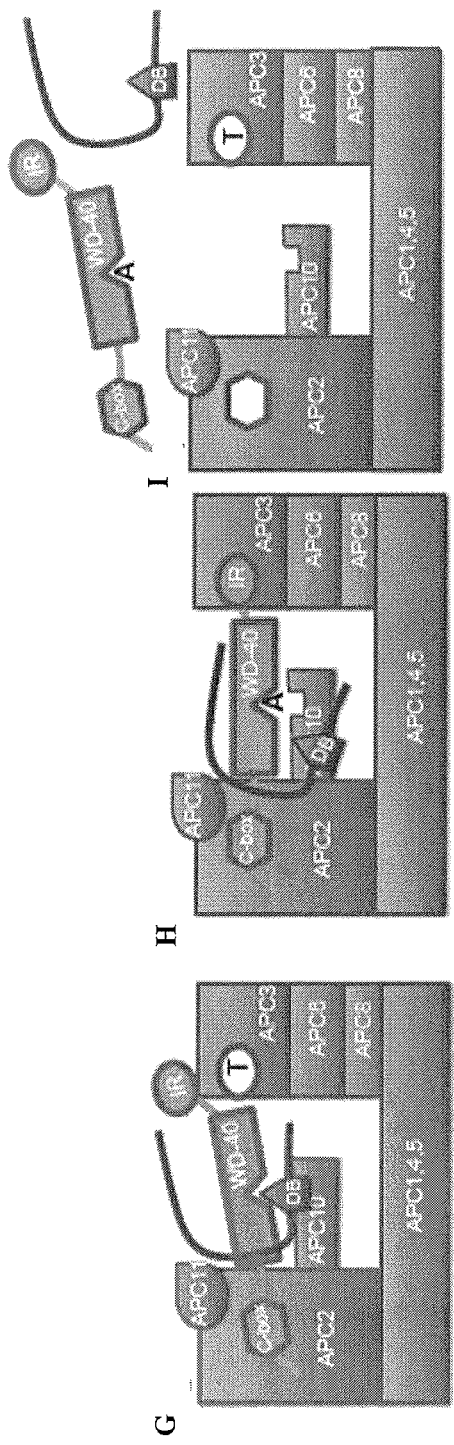

Effects of Apcin and TAME on Formation of the APC/C-Cdc20-substrate Ternary Complex Apcin preferentially stabilizes APC/C substrates whose degradation is D-box dependent. However, on its own, apcin does not effectively block mitotic exit, either because substrates can outcompete apcin binding to the leucine pocket, or because substrates can be recruited to the APC/C through other mechanisms. The effectiveness of apcin can be dramatically enhanced by the addition of TAME, which blocks Cdc20 loading through a distinct mechanism, highlighting the importance of multiple weak protein-protein interactions in promoting activator binding and efficient substrate ubiquitination (FIG. 39). Interestingly, these weak interactions are mediated by binding of Cdc20 to three distinct subunits of the APC/C, perhaps explaining why APC/C composition is so complex. In addition to identifying a new druggable site on Cdc20, this work highlights the possibility of disrupting the function of a protein machine by simultaneously inhibiting multiple protein-protein interactions. Because dynamic protein complexes regulate virtually all aspects of cell biology, simultaneously targeting of multiple weak interactions may represent a new opportunity for therapeutic targeting of protein complexes that may otherwise be difficult to inhibit with a single compound.

Other Embodiments

The patent and scientific literature referred to herein establishes the knowledge that is available to those with skill in the art. All United States patents and published or unpublished United States patent applications cited herein are incorporated by reference. All published foreign patents and patent applications cited herein are hereby incorporated by reference. All other published references, documents, manuscripts and scientific literature cited herein are hereby incorporated by reference.

While this disclosure has been particularly shown and described with references to preferred embodiments thereof, it will be understood by those skilled in the art that various changes in form and details may be made therein without departing from the scope of the invention encompassed by the appended claims.

What is claimed is:

1. A synergistic composition comprising a prodrug of tosyl-L-arginine methylester (TAME) and apcin or an analog or derivative thereof,
wherein the prodrug of TAME is proTAME:

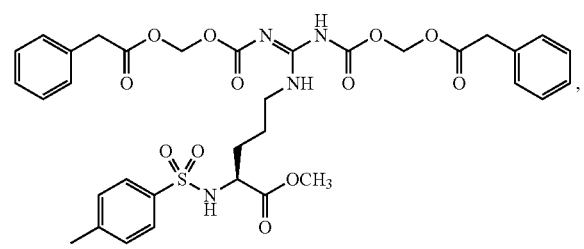 [SMILES: COC(=O)[C@H](CCCN/C(=N\C(=O)OCOC(=O)Cc1ccccc1)NC(=O)OCOC(=O)Cc1ccccc1)NS(=O)(=O)c1ccc(C)cc1]

and
wherein the apcin comprises

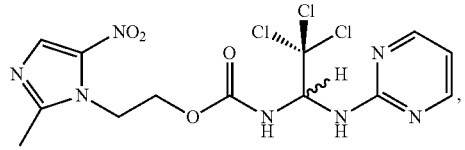

wherein said composition diffuses across the plasma membrane of a cell.

2. The composition of claim 1, wherein said prodrug is characterized as having a eukaryotic cell permeability level at least 20% greater than that of TAME.

3. A pharmaceutical composition comprising the composition of claim 1 and a pharmaceutical carrier.

4. The composition of claim 1, wherein said cell is eukaryotic, mammalian, or human.

5. The composition of claim 1, wherein said prodrug of TAME inhibits an activity of an anaphase promoting complex (APC).

6. A synergistic formulation comprising an amount of:
a) a prodrug of tosyl-L-arginine methylester (TAME), and
b) apcin,
that is sufficient to inhibit the degradation of a substrate of an anaphase-promoting complex/cyclosome (APC) for arresting the mitotic cycle of a cell,
wherein said prodrug of TAME is proTAME:

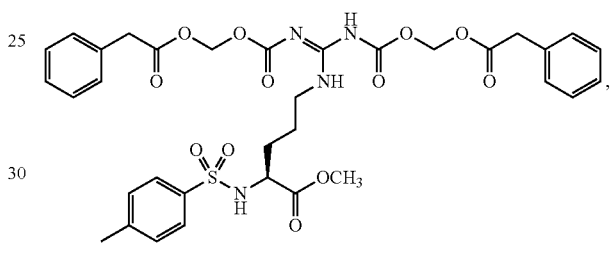

and
wherein said apcin is

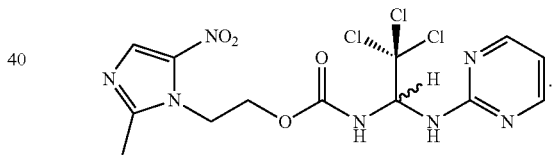

7. The formulation of claim 6, further comprising a pharmaceutical carrier.

8. The formulation of claim 6, further comprising an additional therapeutic agent.

9. The formulation of claim 8, wherein the therapeutic agent comprises a chemotherapy agent, a radiation therapy agent, an immunotherapy agent, or a hormone therapy agent.

10. The formulation of claim 9, wherein the radiation therapy agent is actinium-225 ($Ac^{225}$), bismuth-213 ($Bi^{213}$), boron-10 ($B^{10}$)+neutron therapy, holmium-166 ($Ho^{166}$), iodine-125 ($I^{125}$), iodine-131 ($I^{133}$), iridium-192 ($Ir^{192}$), lead-212 ($Pb^{212}$), lutetium-177 ($Lu^{177}$), rhenium-186 ($Re^{186}$), samarium-153 ($Sm^{153}$), strontium-89 ($Sr^{89}$), or yttrium-90 ($Y^{90}$).

11. The formulation of claim 9, wherein the immunotherapy agent is an antibody selected from the group consisting of rituximab, trastuzumab, gemtuzumab ozogamicin, alemtuzumab, ibritumomab tiuxetan, tositumomab, cetuximab, bevacizumab, panitumumab, ofatumumab, denosumab, ipilimumab, and brentuximab vedotin.

12. The formulation of claim 9, wherein the hormone therapy agent is tamoxifen, an aromatase inhibitor, anastrozole, letrozole, or fulvestrant.

13. The formulation of claim 9, wherein the chemotherapy agent is carboplatin, cisplatin, cyclophosphamide, doxorubicin, etoposide, fluorouracil, gemcitabine, irinotecan, methotrexate, paclitaxel, topotecan, vincristine, or vinblastine.

14. The formulation of claim 9, wherein the chemotherapy agent is a nutlin, sirolimus (rapamycin), or MG132.

15. The formulation of claim 6, wherein said cell is eukaryotic, mammalian, or human.

16. The formulation of claim 6, wherein said cell is characterized by a proliferative disorder.

17. The formulation of claim 16, wherein the cell proliferative disorder is cancer, Castleman Disease, Gestational Trophoblastic Disease, or myelodysplastic syndrome.

18. The formulation of claim 17, wherein the cancer is adrenal cortical cancer, anal cancer, bile duct cancer, bladder cancer, bone cancer, brain or a nervous system cancer, breast cancer, cervical cancer, colon cancer, rectal cancer, colorectal cancer, endometrial cancer, esophageal cancer, Ewing family of tumor, eye cancer, gallbladder cancer, gastrointestinal carcinoid cancer, gastrointestinal stromal cancer, Hodgkin Disease, intestinal cancer, Kaposi Sarcoma, kidney cancer, large intestine cancer, laryngeal cancer, hypopharyngeal cancer, laryngeal and hypopharyngeal cancer, leukemia, acute lymphocytic leukemia (ALL), acute myeloid leukemia (AML), chronic lymphocytic leukemia (CLL), chronic myeloid leukemia (CML), chronic myelomonocytic leukemia (CMML), liver cancer, lung cancer, non-small cell lung cancer, small cell lung cancer, lung carcinoid tumor, lymphoma, lymphoma of the skin, malignant mesothelioma, multiple myeloma, nasal cavity cancer, paranasal sinus cancer, nasal cavity and paranasal sinus cancer, nasopharyngeal cancer, neuroblastoma, non-Hodgkin lymphoma, oral cavity cancer, oropharyngeal cancer, oral cavity and oropharyngeal cancer, osteosarcoma, ovarian cancer, pancreatic cancer, penile cancer, pituitary tumor, prostate cancer, retinoblastoma, rhabdomyosarcoma, salivary gland cancer, sarcoma, adult soft tissue sarcoma, skin cancer, basal cell skin cancer, squamous cell skin cancer, basal and squamous cell skin cancer, melanoma, stomach cancer, small intestine cancer, testicular cancer, thymus cancer, thyroid cancer, uterine sarcoma, uterine cancer, vaginal cancer, vulvar cancer, Waldenstrom Macroglobulinemia, or Wilms Tumor.

19. The formulation of claim 18, wherein the cancer is primary or metastatic.

20. The formulation of claim 18, wherein the cancer occurs in a child or an adult.

* * * * *